US012268753B2

(12) United States Patent
Shehata et al.

(10) Patent No.: US 12,268,753 B2
(45) Date of Patent: Apr. 8, 2025

(54) NANOMATERIALS COMPRISING A BIODEGRADABLE FEATURE

(71) Applicant: Beam Therapeutics Inc., Cambridge, MA (US)

(72) Inventors: Mina Fawzy Shehata, Spartanburg, SC (US); Neeraj Narendra Patwardhan, Medford, MA (US); Gregory Lawrence Hamilton, Atlanta, GA (US); Cory Dane Sago, Boston, MA (US); Milloni Balwantkumar Chhabra, Dunwoody, GA (US)

(73) Assignee: Beam Therapeutics Inc., Cambridge, MA (US)

( * ) Notice: Subject to any disclaimer, the term of this patent is extended or adjusted under 35 U.S.C. 154(b) by 353 days.

(21) Appl. No.: 17/579,150

(22) Filed: Jan. 19, 2022

(65) Prior Publication Data

US 2022/0249694 A1 Aug. 11, 2022

Related U.S. Application Data

(60) Provisional application No. 63/139,731, filed on Jan. 20, 2021.

(51) Int. Cl.

| | |
|---|---|
| ***C07C 219/16*** | (2006.01) |
| ***A61K 9/00*** | (2006.01) |
| ***A61K 9/51*** | (2006.01) |
| ***A61K 31/7105*** | (2006.01) |
| ***A61K 31/711*** | (2006.01) |
| ***A61K 47/69*** | (2017.01) |
| ***A61K 48/00*** | (2006.01) |
| ***A61P 1/16*** | (2006.01) |
| ***C07D 207/08*** | (2006.01) |
| ***C07D 207/16*** | (2006.01) |
| ***C07D 211/22*** | (2006.01) |
| ***C07D 211/62*** | (2006.01) |
| ***C07D 295/15*** | (2006.01) |
| ***C07J 41/00*** | (2006.01) |

(52) U.S. Cl.

CPC ...... *A61K 47/6929* (2017.08); *A61K 31/7105* (2013.01); *A61K 31/711* (2013.01); *A61P 1/16* (2018.01); *C07C 219/16* (2013.01); *C07D 211/22* (2013.01)

(58) Field of Classification Search

CPC ................ C07C 219/16; C07D 211/22; C07D 207/16; C07D 211/62; C07D 295/15; C07D 207/08; A61K 9/0019; A61K 9/5123; A61K 48/0033; A61K 31/7105; A61K 31/711; C07J 41/0055

See application file for complete search history.

(56) References Cited

U.S. PATENT DOCUMENTS

| | | | |
|---|---|---|---|
| 3,686,238 A | 8/1972 | Alejandro | |
| 8,058,069 B2 | 11/2011 | Yaworski et al. | |
| 9,364,435 B2 | 6/2016 | Yaworski et al. | |
| 9,840,699 B2 | 12/2017 | Liu et al. | |
| 10,113,163 B2 | 10/2018 | Liu et al. | |
| 10,124,065 B2 | 11/2018 | Baryza et al. | |
| 10,167,457 B2 | 1/2019 | Liu et al. | |
| 2003/0083272 A1 | 5/2003 | Wiederholt et al. | |
| 2016/0311759 A1 | 10/2016 | Brito et al. | |
| 2017/0210698 A1 | 7/2017 | Benenato et al. | |
| 2018/0147166 A1 | 5/2018 | Dong et al. | |
| 2018/0290965 A1 | 10/2018 | Brito et al. | |
| 2019/0002393 A1 | 1/2019 | Beckwith et al. | |
| 2019/0076462 A1 | 3/2019 | Dong et al. | |
| 2019/0358170 A1 | 11/2019 | Brito et al. | |
| 2021/0113365 A1 | 4/2021 | Kim | |
| 2021/0130805 A1 | 5/2021 | Gaudelli et al. | |
| 2021/0169804 A1 | 6/2021 | Patwardhan et al. | |
| 2021/0230112 A1* | 7/2021 | Hamilton | A61K 47/24 |
| 2022/0096381 A1 | 3/2022 | Endo et al. | |
| 2022/0249694 A1 | 8/2022 | Shehata et al. | |
| 2022/0273566 A1 | 9/2022 | Dahlman et al. | |

FOREIGN PATENT DOCUMENTS

| | | | |
|---|---|---|---|
| AU | 2020369940 A1 | 5/2022 | |
| CN | 108368028 A | 8/2018 | |
| CN | 110520409 A | 11/2019 | |
| EP | 1164125 A1 | 12/2001 | |
| EP | 3733211 A1 | 11/2020 | |
| EP | 3842538 A1 | 6/2021 | |
| EP | 4069675 A1 | 10/2022 | |
| GB | 968849 A | 9/1964 | |
| JP | 2005-181734 A | 7/2005 | |
| WO | WO-02/44321 | 6/2002 | |
| WO | WO-03/101952 A2 | 12/2003 | |
| WO | WO-2008/155141 A2 | 12/2008 | |
| WO | WO-2011/153493 A2 | 12/2011 | |
| WO | WO-2013/086354 A1 | 6/2013 | |
| WO | WO-2014/136086 A1 | 9/2014 | |

(Continued)

OTHER PUBLICATIONS

U.S. Appl. No. 18/220,874, filed Jul. 12, 2023, Shehata et al.

Adams, D. et al., Patisiran, an RNAi Therapeutic, for Hereditary Transthyretin Amyloidosis, N. Engl. J. Med., 379(1):11-21 (2018).

Augustin, H.G. and Koh, G.Y., Organotypic vasculature: From descriptive heterogeneity to functional pathophysiology, Science, 357(6353):eaal2379 (2017).

Brown et al., Organic Chemistry, Second Edition, Saunders College Publishing, p. 169, 3 page, (1995).

CAS Registry No. 751440-44-5, 3-octyl-6-[7-oxo-7-[[2-[(1-oxooctadecyl)oxy]-1-[[(oxooctadecyl)oxy]methyl]ethoxy]heptyl]-4-Cyclohexene-1,2-dicarboxylic acid, 1 page, (2004).

(Continued)

*Primary Examiner* — Samantha L Shterengarts
*Assistant Examiner* — Sagar Patel
(74) *Attorney, Agent, or Firm* — Proskauer Rose LLP

(57) ABSTRACT

The present disclosure describes compositions, preparations, nanoparticles (such as lipid nanoparticles), and/or nanomaterials and methods of their use.

14 Claims, 9 Drawing Sheets

(56) References Cited

FOREIGN PATENT DOCUMENTS

| | | | | |
|---|---|---|---|---|
| WO | WO-2015/095340 A1 | | 6/2015 | |
| WO | WO-2015/095346 A1 | | 6/2015 | |
| WO | WO-2016/187531 A1 | | 11/2016 | |
| WO | WO-2017/173054 A1 | | 10/2017 | |
| WO | WO-2018/220553 A1 | | 12/2018 | |
| WO | WO-2019/008441 A1 | | 1/2019 | |
| WO | WO-2019/089561 A1 | | 5/2019 | |
| WO | WO-2019/099501 A1 | | 5/2019 | |
| WO | WO-2019/126378 A1 | | 6/2019 | |
| WO | WO-2020/028787 A1 | | 2/2020 | |
| WO | WO-2020/072605 A1 | | 4/2020 | |
| WO | WO-2020/118041 A1 | | 6/2020 | |
| WO | WO-2020/150320 A1 | | 7/2020 | |
| WO | WO-2020/152037 A1 | | 7/2020 | |
| WO | WO-2020/176856 A1 | | 9/2020 | |
| WO | WO-2020/176859 A1 | | 9/2020 | |
| WO | WO-2020/176868 A1 | | 9/2020 | |
| WO | WO-2020219876 A1 | * | 10/2020 | ......... A61K 31/7105 |
| WO | WO-2020/246581 A1 | | 12/2020 | |
| WO | WO-2020/247382 A1 | | 12/2020 | |
| WO | WO-2021/021634 A1 | | 2/2021 | |
| WO | WO-2021/021636 A1 | | 2/2021 | |
| WO | 2021/080847 A1 | | 4/2021 | |
| WO | WO-2021/113365 A1 | | 6/2021 | |
| WO | WO-2021/141969 A1 | | 7/2021 | |
| WO | WO-2022/140238 A1 | | 6/2022 | |
| WO | WO-2022/140239 A1 | | 6/2022 | |
| WO | WO-2022/140252 A1 | | 6/2022 | |
| WO | WO-2022/159421 A1 | | 7/2022 | |
| WO | WO-2022/159463 A1 | | 7/2022 | |
| WO | WO-2022/159472 A1 | | 7/2022 | |
| WO | WO-2022/159475 A1 | | 7/2022 | |
| WO | WO-2023056917 A1 | * | 4/2023 | ......... A61K 38/1808 |
| WO | 2023121971 A1 | | 6/2023 | |
| WO | 2023121975 A1 | | 6/2023 | |
| WO | WO-2023/121964 A1 | | 6/2023 | |
| WO | WO-2023/121965 A1 | | 6/2023 | |
| WO | WO-2023/121970 A1 | | 6/2023 | |
| WO | 2024019936 A1 | | 1/2024 | |

OTHER PUBLICATIONS

Cheng, Z. et al., Multifunctional nanoparticles: cost versus benefit of adding targeting and imaging capabilities, Science, 338(6109):903-910 (2012).
Cullis, P.R. and Hope, M.J., Lipid Nanoparticle Systems for Enabling Gene Therapies, Mol. Ther., 25(7):1467-1475 (2017).
Dahlman, J.E. et al., In vivo endothelial siRNA delivery using polymeric nanoparticles with low molecular weight, Nat. Nanotechnol., 9(8):648-655 (2014).
Dang, C.V. et al., Drugging the 'undruggable' cancer targets, Nat. Rev. Cancer, 17(8):502-508 (2017).
Diab, H.M. et al., ZnO-Nanoparticles-Catalyzed Synthesis of Poly(tetrahydrobenzimidazo[2,1-b]quinazolin-1(2H)-ones) as Novel Multi-armed Molecules, Synlett, 29(12):1627-1633 (2018).
Dixon, S.J. and Stockwell, B.R., Identifying druggable disease-modifying gene products, Curr. Opin. Chem. Biol., 13(5-6):549-555 (2009).
Elbashir, S.M. et al., Duplexes of 21-nucleotide RNAs mediate RNA interference in cultured mammalian cells, Nature, 411(6836):494-498 (2001).
Funakoshi, Y. et al., Effect of Alkyl Chain Length and Unsaturation of the Phospholipid on the Physicochemical Properties of Lipid Nanoparticles, Chem. Pharm. Bull (Tokyo), 63(9):731-736 (2015).
Gelsema, W.J. et al., Benzoolysis of diacylglycerophosphocholines: dephosphorylation and sequential formation of isomeric reaction products, J. Lipid Res., 37(6):1224-1233 (1996).
International Search Report for PCT/US2020/043512, filed Jul. 24, 2020, 7 pages, (mailed Sep. 23, 2020).
International Search Report for PCT/US2020/062893, filed Dec. 2, 2020, 7 pages, (mailed Feb. 19, 2021).
International Search Report for PCT/US2022/012867, filed Jan. 19, 2022, 5 pages, (mailed Jun. 8, 2022).
International Search Report for PCT/US2022/053193, filed Dec. 16, 2022, 4 pages, (mailed May 3, 2023).
International Search Report for PCT/US2022/053209, filed Dec. 16, 2022, 5 pages, (mailed Mar. 24, 2023).
International Search Report for PCT/US22/12951, filed Jan. 19, 2022, 5 pages, (mailed May 23, 2022).
Jenkins, R.W. et al., Mechanisms of resistance to immune checkpoint inhibitors, Br. J. Cancer, 118:9-16 (2018).
Kedmi, R. et al., A modular platform for targeted RNAi therapeutics, Nat. Nanotechnol., 13(3):214-219 (2018).
Khalil, D.N. et al., The future of cancer treatment: immunomodulation, CARs and combination immunotherapy, Nat. Rev. Clin. Oncol., 13(5):273-290 (2016).
Kumar, P. et al., T cell-specific siRNA delivery suppresses HIV-1 infection in humanized mice, Cell, 134(4):577-586 (2008).
Lokugamage, M.P. et al., Constrained Nanoparticles Deliver siRNA and sgRNA to T Cells In Vivo without Targeting Ligands (with supporting information), Adv. Mater., 31(41):e1902251 (2019).
Lokugamage, M.P. et al., Testing thousands of nanoparticles in vivo using DNA barcodes, Curr. Opin. Biomed. Eng., 7:1-8 (2018).
Lorenzer, C. et al., Going beyond the liver: progress and challenges of targeted delivery of siRNA therapeutics, J. Control Release, 203:1-15 (2015).
MacParland, S.A. et al., Phenotype Determines Nanoparticle Uptake by Human Macrophages from Liver and Blood, ACS Nano, 11(3):2428-2443 (2017).
Paunovksa, K. et al., Analyzing 2000 in Vivo Drug Delivery Data Points Reveals Cholesterol Structure Impacts Nanoparticle Delivery, ACS Nano, 12(8):8341-8349 (2018).
Paunovska, K. et al., A Direct Comparison of in Vitro and in Vivo Nucleic Acid Delivery Mediated by Hundreds of Nanoparticles Reveals a Weak Correlation, Nano. Lett., 18(3):2148-2157 (2018).
Platt, R.J. et al., CRISPR-Cas9 knockin mice for genome editing and cancer modeling, Cell, 159(2):440-455 (2014).
Pollastri, M.P. et al., Synthesis, structure, and thermal properties of 1,2-dipalmitoylgalloylglycerol (DPGG), a novel self-adhering lipid, Chem. Phys. Lipids, 104(1):67-74 (2000).
PubChem SID 274013917, Tris(deoxycholic acid) 1,3,5-benzenetriyltris(methylene) ester, 2 pages, deposit available Dec. 18, 2015, deposit modified Nov. 21, 2016.
PUBCHEM-SID-46481541, 5 pages, (2007).
Ramishetti, S. et al., Systemic Gene Silencing in Primary T Lymphocytes Using Targeted Lipid Nanoparticles, ACS Nano, 9(7):6706-6716 (2015).
Sharma, P. and Allison, J.P., The future of immune checkpoint therapy, Science, 348(6230):56-61 (2015).
Tavares, A.J. et al., Effect of removing Kupffer cells on nanoparticle tumor delivery, PNAS USA, 114(51):E10871-E10880 (2017).
Tsoi, K.M. et al., Mechanism of hard-nanomaterial clearance by the liver, Nat. Mater., 15(11):1212-1221 (2016).
Ui-Tei, K. et al., Sensitive assay of RNA interference in Drosophila and Chinese hamster cultured cells using firefly luciferase gene as target, FEBS Lett., 479(3):79-82 (2000).
U.S. Appl. No. 16/938,104, filed Jul. 24, 2020, Dahlman et al.
U.S. Appl. No. 17/579,115, filed Jan. 19, 2022, Sago et al.
Belliveau, N.M. et al., Microfluidic Synthesis of Highly Potent Limit-size Lipid Nanoparticles for In Vivo Delivery of siRNA, Mol. Ther. Nucleic Acids, 1(8):e37 (2012).
Chen, D. et al., Rapid discovery of potent siRNA-containing lipid nanoparticles enabled by controlled microfluidic formulation, J. Am. Chem. Soc., 134(16):6948-6951 (2012).
Heidenreich, O. et al., High activity and stability of hammerhead ribozymes containing 2'-modified pyrimidine nucleosides and phosphorothioates, J. Biol. Chem., 269(3):2131-2138 (1994).
International Search Report for PCT/US2021/012282, filed Jan. 6, 2021, 5 pages, (mailed Mar. 3, 2021).
Kariko, K. et al., Incorporation of pseudouridine into mRNA yields superior nonimmunogenic vector with increased translational capacity and biological stability, Mol. Ther., 16(11):1833-1840 (2008).

(56) References Cited

OTHER PUBLICATIONS

Kozak, M., An analysis of 5'-noncoding sequences from 699 vertebrate messenger RNAs, Nucleic Acids Res., 15(20):8125-8148 (1987).
Leung, A.K.K. et al., Lipid Nanoparticles Containing siRNA Synthesized by Microfluidic Mixing Exhibit an Electron-Dense Nanostructured Core, J. Phys. Chem. C. Nanomater. Interfaces, 116(34):18440-18450 (2012).
Makarova, K.S. et al., An updated evolutionary classification of CRISPR-Cas systems, Nat. Rev. Microbiol., 13(11):722-736 (2015).
Mathiowitz, E. and Langer, R., Polyanhydride Microspheres as Drug Carriers I. Hot-Melt Microencapsulation, J. Control. Release, 5:13-22 (1987).
Mathiowitz, E. et al., Novel Microcapsules for Delivery Systems, Reactive Polymers, 6:275-283 (1987).
Mathiowitz, E. et al., Polyanhydride microspheres as drug carriers. II. Microencapsulation by solvent removal, J. Applied Polymer Science, 35(3):755-774 (1988).
Partial Search Report for PCT/US2022/012867, filed Jan. 19, 2022, 3 pages, (mailed Mar. 28, 2022).
Partial Search Report for PCT/US22/12941, filed Jan. 19, 2022, 2 pages (mailed Mar. 21, 2022).
Partial Search Report for PCT/US22/12951, filed Jan. 19, 2022, 2 pages, (mailed Mar. 23, 2022).
Partial Search Report for PCT/US22/12954, filed Jan. 19, 2022, 2 pages, (mailed Mar. 23, 2022).
PUBCHEM-SID-402741750, 5 pages, (2020).
Sago, C.D. et al, High-throughput in vivo screen of functional mRNA delivery identifies nanoparticles for endothelial cell gene editing, Proc. Natl. Acad. Sci. USA, 115(42):E9944-E9952 (2018).
Sago, C.D. et al., Modifying a Commonly Expressed Endocytic Receptor Retargets Nanoparticles in Vivo, Nano. Lett., 18(12):7590-7600 (2018).
Sago, C.D. et al., Nanoparticles That Deliver RNA to Bone Marrow Identified by in Vivo Directed Evolution, J. Am. Chem. Soc., 140(49):17095-17105 (2018).
Shmakov, S. et al., Discovery and Functional Characterization of Diverse Class 2 CRISPR-Cas Systems, Mol. Cell., 60(3):385-397 (2015).
Yokoe, H. and Meyer, T., Spatial dynamics of GFP-tagged proteins investigated by local fluorescence enhancement, Nat. Biotechnol., 14(10):1252-1256 (1996).
Zetsche, B. et al., Cpf1 is a single RNA-guided endonuclease of a class 2 CRISPR-Cas system, Cell, 163(3):759-771, (with supporting information), (2015).
International Search Report for PCT/US2020/043512 dated Sep. 23, 2020 (7 pages).
International Search Report for PCT/US2020/062893 dated Feb. 19, 2021 (7 pages).
International Search Report for PCT/US2021/012282 dated Mar. 3, 2021 (5 pages).
International Search Report for PCT/US2023/027741 dated Oct. 13, 2023 (3 pages).
Chenthamara, et al., "Therapeutic efficacy of nanoparticles and routes of administration", Biomaterials Research, vol. 23, No. 20, Nov. 21, 2019 (29 pages).
Epand, et al., "Role of the position of unsaturation on the phase behavior and intrinsic curvature of phosphatidylethanolamines", Biophysical Journal, vol. 71, No. 4, pp. 1806-1810, Oct. 1996 (5 pages).
Fenton, et al., "Synthesis and Biological Evaluation of lonizable Lipid Materials for the In Vivo Delivery of Messenger RNA to B Lymphocytes", Advanced materials (Deerfield Beach, Fla.), vol. 29, No. 33, Sep. 2017 (7 pages).
Junquera, et al., "Recent progress in gene therapy to deliver nucleic acids with multivalent cationic vectors", Advances in Colloid and Interface Science, vol. 233, 2016, pp. 161-175, (15 pages).
Reichmuth, et al., "mRNA vaccine delivery using lipid nanoparticles", Therapeutic Delivery, vol. 7, No. 5, pp. 319-334, 2016 (16 pages).
Scheidt, et al., "The interaction of small molecules with phospholipid membranes studied by 1H NOESY NMR under magic-angle spinning", Acta Pharmacologica Sinica, vol. 29, No. 1, 2008, pp. 35-49 (15 pages).
Wang, et al., "Effects of various numbers and positions of cis double bonds in the sn-2 acyl chain of phosphatidylethanolamine on the chain-melting temperature", The Journal of Biological Chemistry, vol. 274, No. 18, pp. 12289-12299. Apr. 30, 1999 (11 pages).

* cited by examiner

NANOMATERIALS COMPRISING A BIODEGRADABLE FEATURE

CROSS REFERENCE TO RELATED APPLICATIONS

This application claims the benefit of U.S. Provisional Application No. 63/139,731, filed Jan. 20, 2021, the entire contents of which are hereby incorporated by reference.

BACKGROUND

Delivery of drug delivery systems poses challenges in fields of chemistry, biology, and medicine. For example, drug delivery systems are hindered due to poor understanding of how molecular properties of a system control delivery to tissues and confer drug efficacy.

SUMMARY

The present invention recognizes a need for compositions, preparations, nanoparticles, and/or nanomaterials and methods of their use. Among other things, the present disclosure recognizes that structural features of compositions, preparations, nanoparticles, and/or nanomaterials impact functional responses in vivo, in vitro, and ex vivo. For example, in some embodiments, the present disclosure describes compositions, preparations, nanoparticles, and/or nanomaterials that comprise a lipid containing a biodegradable tail feature. In some embodiments, lipids and/or compositions, preparations, nanoparticles and/or nanomaterials that include them are characterized by improved stability relative to certain comparable reference entities. In some embodiments, tail structures described herein degrade more easily once administered in vivo compared to other tail structures.

Moreover, the present disclosure describes, among other things, that selection and combination of one or more components described herein influence functional activity of lipid nanoparticles. In some embodiments, for example, functional activity can refer to desired tropisms, stabilization, and/or drug delivery efficacy. In some embodiments, among other things, the present disclosure describes that different ratios of one of more components influence one or more functional activities of compositions, preparations, nanoparticles, and/or nanomaterials described herein.

Moreover, among other things, the present disclosure recognizes that chemical structures of lipids confer improved characteristic(s) (e.g., efficacy, stability, biocompatibility, etc.) compared to traditional lipid structures known in the art.

In some embodiments, the present disclosure identifies the source of a problem with certain alternative lipid agents and/or compositions, preparations, nanoparticles, and/or nanomaterials that include them, for example providing an insight that certain tail structures may impart or contribute to one or more attributes whose improvement would be beneficial. In addition to such identification of a source of a problem, the present disclosure provides certain solutions to the problem, including lipid compound, and/or compositions, preparations, nanoparticles, and/or nanomaterials that include them, with different tail structures. In some embodiments, provided lipids and/or compositions, preparations, nanoparticles, and/or nanomaterials including them are characterized by improved stability, bioavailability, and/or degradation property(ies) relative to an appropriate comparable reference with a different tail structure. In some particular embodiments, provided lipids and/or compositions, preparations, nanoparticles, and/or nanomaterials including them are characterized by improved stability, bioavailability, and/or degradation property(ies) relative to an appropriate comparable reference with a linoleic acid tail feature (e.g., moiety).

Among other things, the present disclosure provides compounds of Formula I:

(I)

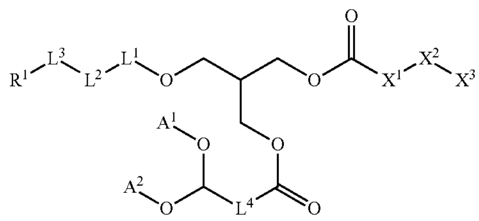

or a pharmaceutically acceptable salt thereof, wherein:

$L^1$ is a covalent bond, —C(O)—, or —OC(O)—;

$L^2$ is a covalent bond, an optionally substituted bivalent saturated or unsaturated, straight or branched $C_1$-$C_{12}$ hydrocarbon chain, or

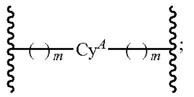

$Cy^A$ is an optionally substituted ring selected from phenylene and 3- to 7-membered saturated or partially unsaturated carbocyclene;

each m is independently 0, 1, or 2;

$L^3$ is a covalent bond, —C(O)—, —C(O)O—, —OC(O)—, —O—, or —OC(O)O—;

$R^1$ is

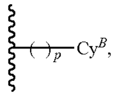

an optionally substituted saturated or unsaturated, straight or branched $C_1$-$C_{20}$ hydrocarbon chain wherein 1-3 methylene units are optionally and independently replaced with —O— or —NR—, or

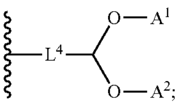

$Cy^B$ is an optionally substituted ring selected from 3- to 12-membered saturated or partially unsaturated carbocyclyl, 1-adamantyl, 2-adamantyl,

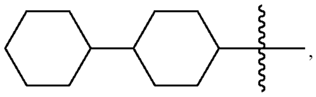

sterolyl, and phenyl;

p is 0, 1, 2, or 3;

each $L^4$ is independently a bivalent saturated or unsaturated, straight or branched $C_1$-$C_6$ hydrocarbon chain;

each $A^1$ and $A^2$ is independently an optionally substituted $C_1$-$C_{20}$ aliphatic or —$L^5$—$R^5$;

or $A^1$ and $A^2$, together with their intervening atoms, may form an optionally substituted ring:

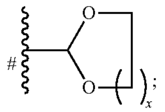

where x is selected from 1 or 2; and # represents the point of attachment to $L^4$;

each $L^5$ is independently a bivalent saturated or unsaturated, straight or branched $C_1$-$C_{20}$ hydrocarbon chain, wherein 1-3 methylene units are optionally and independently replaced with —O— or —NR—;

each $R^5$ is independently an optionally substituted group selected from a 5- to 10-membered aryl ring or a 3- to 8-membered carbocyclic ring;

$X^1$ is a covalent bond, —O—, or —NR—;

$X^2$ is a covalent bond or an optionally substituted, bivalent saturated or unsaturated, straight or branched, $C_1$-$C_{12}$ hydrocarbon chain, wherein 1-3 methylene units are optionally and independently replaced with —O—, —NR—, or —$Cy^C$—;

$Cy^C$ is an optionally substituted ring selected from 3- to 7-membered saturated or partially unsaturated carbocyclene, phenylene, 3- to 7-membered saturated or partially unsaturated heterocyclene having 1-3 heteroatoms independently selected from nitrogen, oxygen, and sulfur, and 5- to 6-membered heteroarylene having 1-3 heteroatoms independently selected from nitrogen, oxygen, and sulfur;

$X^3$ is hydrogen or an optionally substituted ring selected from 3- to 7-membered saturated or partially unsaturated carbocyclyl, phenyl, 3- to 7-membered saturated or partially unsaturated heterocyclyl having 1-3 heteroatoms independently selected from nitrogen, oxygen, and sulfur, or 5- to 6-membered heteroaryl having 1-3 heteroatoms independently selected from nitrogen, oxygen, and sulfur; and each R is independently hydrogen or an optionally substituted $C_1$-$C_6$ aliphatic group; provided that when $L^3$ is a covalent bond, then $R^1$ must be

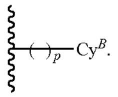

Among other things, the present disclosure recognizes that lipid nanoparticle (LNP) compositions comprising one or more ionizable lipids may display unexpected properties. For example, the present disclosure provides that LNP compositions and/or preparations comprising one or more of the disclosed ionizable lipids conferred unexpected tropisms.

In some embodiments, provided compositions, preparations, nanoparticles, and/or nanomaterials are for use in methods of treatment, delivery, producing polypeptides, or delaying/arresting progression of a disease or disorder.

In some embodiments, provided compositions, preparations, nanoparticles, and/or nanomaterials are for use in methods of manufacturing.

In some embodiments, provided compositions, preparations, nanoparticles, and/or nanomaterials are for use in methods of characterization.

Elements of embodiments involving one aspect of the invention (e.g., methods) can be applied in embodiments involving other aspects of the invention, and vice versa.

DEFINITIONS

Figure 1:
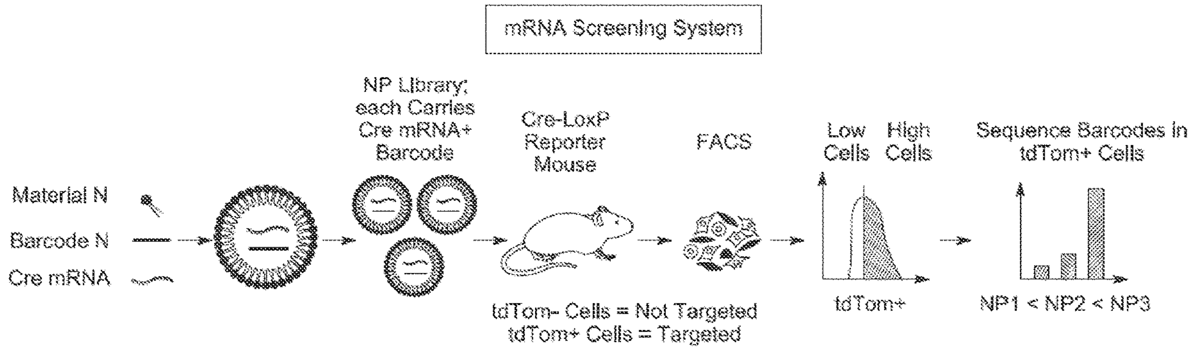
FIG. 1 depicts an exemplary mRNA screening system of LNP preparations, in accordance with an embodiment of the present disclosure.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intraarterial, intracerebral ventricular, intracisterna manga, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, by nebulization, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time. In some embodiments, a pharmaceutical composition comprising lipid nanoparticles can be formulated for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

Aliphatic: The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "carbocyclic", or "cycloaliphatic"), that has a single point of attachment to the rest of the molecule. Unless otherwise specified, aliphatic groups contain 1-6 aliphatic carbon atoms. In some embodiments, aliphatic groups contain 1-5 carbon atoms. In some embodiments, aliphatic groups contain 1-4 carbon atoms. In some embodiments, aliphatic groups contain 1-3 carbon atoms, and in some embodiments, aliphatic groups contain 1-2 carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: The term "alkenyl", used alone or as part of a larger moiety, refers to an optionally substituted straight or branched hydrocarbon chain having at least one double bond and having (unless otherwise specified) 2-20, 2-18, 2-16, 2-14, 2-12, 2-10, 2-8, 2-6, 2-4, or 2-3 carbon atoms (e.g., $C_{2-20}$, $C_{2-18}$, $C_{2-16}$, $C_{2-14}$, $C_{2-12}$, $C_{2-10}$, $C_{2-8}$, $C_{2-6}$, $C_{2-4}$, or $C_{2-3}$). Exemplary alkenyl groups include ethenyl, propenyl, butenyl, pentenyl, hexenyl, and heptenyl.

Alkenylene: The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, a cycloalkyl ring has from about 3-10 carbon atoms in their ring structure where such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkylenyl: The term "alkylenyl" refers to a bivalent alkyl group that is a straight-chain (i.e., unbranched) or branched, substituted or unsubstituted. An "alkylenyl" is a polymethylene group, i.e., $-(CH_2)_n-$, wherein n is a positive integer, preferably from 1 to 10, from 1 to 9, from 1 to 8, from 1 to 7, from 1 to 6, from 1 to 5, from 1 to 4, from 1 to 3, from 1 to 2, from 2 to 5, or from 4 to 8. A substituted alkylenyl is a polymethylene group in which one or more methylene hydrogen atoms are replaced with a substituent. Suitable substituents include those described below for a substituted aliphatic group.

Alkynyl: The term "alkynyl", used alone or as part of a larger moiety, refers to an optionally substituted straight or branched chain hydrocarbon group having at least one triple bond and having (unless otherwise specified) 2-20, 2-18, 2-16, 2-14, 2-12, 2-10, 2-8, 2-6, 2-4, or 2-3 carbon atoms (e.g., $C_{2-20}$, $C_{2-18}$, $C_{2-16}$, $C_{2-14}$, $C_{2-12}$, $C_{2-10}$, $C_{2-8}$, $C_{2-6}$, $C_{2-4}$, or $C_{2-3}$). Exemplary alkynyl groups include ethynyl, propynyl, butynyl, pentynyl, hexynyl, and heptynyl.

Amino acid: in its broadest sense, as used herein, refers to any compound and/or substance that can be incorporated into a polypeptidechain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Animal: as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In general, those skilled in the art, familiar with the context, will appreciate the relevant degree of variance encompassed by "about" or "approximately" in that context. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aptamer: As used herein, the term "aptamer" refers to a macromolecule composed of nucleic acid (e.g., RNA, DNA) that binds tightly to a specific molecular target (e.g., an umbrella topology glycan). A particular aptamer may be described by a linear nucleotide sequence and is typically about 15-60 nucleotides in length. Without wishing to be bound by any theory, it is contemplated that the chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers typically have very high affinities for their targets (e.g., affinities in the picomolar to low nanomolar range for proteins). In many embodiments, aptamers are chemically stable and can be boiled or frozen without loss of activity. Because they are synthetic molecules, aptamers are amenable to a variety of modifications, which can optimize their function for particular applications. For example, aptamers can be modified to dramatically reduce their sensitivity to degradation by enzymes in the blood for use in in vivo applications. In addition, aptamers can be modified to alter their biodistribution or plasma residence time.

Aryl: The term "aryl" refers to monocyclic and bicyclic ring systems having a total of six to fourteen ring members (e.g., $C_{6-14}$), wherein at least one ring in the system is aromatic and wherein each ring in the system contains three to seven ring members. The term "aryl" may be used interchangeably with the term "aryl ring". In some embodiments, "aryl" refers to an aromatic ring system which includes, but is not limited to, phenyl, naphthyl, anthracyl and the like, which may bear one or more substituents. Unless otherwise specified, "aryl" groups are hydrocarbons.

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Biodegradable: As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Bivalent: As used herein, the term "bivalent" refers to a chemical moiety with two points of attachment. For example, a "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Carbocyclyl: The terms "carbocyclyl," "carbocycle," and "carbocyclic ring" as used herein, refer to saturated or partially unsaturated cyclic aliphatic monocyclic, bicyclic, or polycyclic ring systems, as described herein, having from 3 to 14 members, wherein the aliphatic ring system is optionally substituted as described herein. Carbocyclic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, "carbocyclyl" (or "cycloaliphatic") refers to an optionally substituted monocyclic $C_3$-$C_8$ hydrocarbon, or an optionally substituted $C_7$-$C_{10}$ bicyclic hydrocarbon that is completely saturated or that contains one or more units of unsaturation, but which is not aromatic, that has a single point of attachment to the rest of the molecule. The term "cycloalkyl" refers to an optionally substituted saturated ring system of about 3 to about 10 ring carbon atoms. In some embodiments, cycloalkyl groups have 3-6 carbons. Exemplary monocyclic cycloalkyl rings include cyclopropyl, cyclobutyl, cyclopentyl, cyclohexyl, and cycloheptyl. The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentenyl, cyclohexenyl, and cycloheptenyl.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Encapsulated: The term "encapsulated" is used herein to refer to substances that are completely surrounded by another material.

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: As used herein, the term "expression" of a nucleic acid sequence refers to the generation of any gene product from the nucleic acid sequence. In some embodiments, a gene product can be a transcript. In some embodiments, a gene product can be a polypeptide. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Heteroaryl: The terms "heteroaryl" and "heteroar-", used alone or as part of a larger moiety, e.g., "heteroaralkyl", or "heteroaralkoxy", refer to monocyclic or bicyclic ring groups having 5 to 10 ring atoms (e.g., 5- to 6-membered monocyclic heteroaryl or 9- to 10-membered bicyclic heteroaryl); having 6, 10, or 14 $\pi$ electrons shared in a cyclic array; and having, in addition to carbon atoms, from one to five heteroatoms. Exemplary heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridonyl, pyridazinyl, pyrimidinyl, pyrazinyl, indolizinyl, purinyl, naphthyridinyl, pteridinyl, imidazo[1,2-a]pyrimidinyl, imidazo[1,2-a]pyridinyl, thienopyrimidinyl, triazolopyridinyl, and benzoisoxazolyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring (i.e., a bicyclic heteroaryl ring having 1 to 3 heteroatoms). Nonlimiting examples include indolyl, isoindolyl, benzothienyl, benzofuranyl, dibenzofuranyl, indazolyl, benzimidazolyl, benzothiazolyl, benzothiadiazolyl, benzoxazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, pyrido[2,3-b]-1,4-oxazin-3(4H)-one, and benzoisoxazolyl. The term "heteroaryl" may be used interchangeably with the terms "heteroaryl ring", "heteroaryl group", or "heteroaromatic", any of which terms include rings that are optionally substituted.

Heteroatom: The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

Heterocycle: The terms "heterocycle", "heterocyclyl", "heterocyclic radical", and "heterocyclic ring" are used interchangeably herein, and refer to a stable 3- to 8-membered monocyclic, a 7- to 12-membered bicyclic, or a 10- to 16-membered polycyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, azetidinyl, oxetanyl, tetrahydrofuranyl, tetrahydrothienyl, pyrrolidinyl, piperidinyl, decahydroquinolinyl, oxazolidinyl, piperazinyl, tetrahydropyranyl, dioxanyl, dioxolanyl, diazepinyl, oxazepinyl, thiazepinyl, morpholinyl, thiamorpholinyl, and

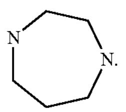

A heterocyclyl group may be mono-, bi-, tri-, or polycyclic, preferably mono-, bi-, or tricyclic, more preferably mono- or bicyclic. A bicyclic heterocyclic ring also includes groups in which the heterocyclic ring is fused to one or more aryl, heteroaryl, or cycloaliphatic rings. Exemplary bicyclic heterocyclic groups include indolinyl, isoindolinyl, benzodioxolyl, 1,3-dihydroisobenzofuranyl, 2,3-dihydrobenzofuranyl, and tetrahydroquinolinyl. A bicyclic heterocyclic ring can also be a spirocyclic ring system (e.g., 7- to 11-membered spirocyclic fused heterocyclic ring having, in addition to carbon atoms, one or more heteroatoms as defined above (e.g., one, two, three or four heteroatoms)). A bicyclic heterocyclic ring can also be a bridged ring system (e.g., 7- to 11-membered bridged heterocyclic ring having one, two, or three bridging atoms.

Inhibitory agent: As used herein, the term "inhibitory agent" refers to an entity, condition, or event whose presence, level, or degree correlates with decreased level or activity of a target). In some embodiments, an inhibitory agent may be act directly (in which case it exerts its influence directly upon its target, for example by binding to the target); in some embodiments, an inhibitory agent may act indirectly (in which case it exerts its influence by interacting with and/or otherwise altering a regulator of the target, so that level and/or activity of the target is reduced). In some embodiments, an inhibitory agent is one whose presence or level correlates with a target level or activity that is reduced relative to a particular reference level or activity (e.g., that observed under appropriate reference conditions, such as presence of a known inhibitory agent, or absence of the inhibitory agent in question, etc.).

In vitro: The term "in vitro" as used herein refers to events that occur in an artificial environment, e.g., in a test tube or reaction vessel, in cell culture, etc., rather than within a multi-cellular organism.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

In vivo: as used herein refers to events that occur within a multi-cellular organism, such as a human and a non-human animal. In the context of cell-based systems, the term may be used to refer to events that occur within a living cell (as opposed to, for example, in vitro systems).

Linker: as used herein, is used to refer to that portion of a multi-element agent that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polyptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

Nanoparticle: As used herein, the term "nanoparticle" refers to a particle having a diameter of less than 1000 nanometers (nm). In some embodiments, a nanoparticle has a diameter of less than 300 nm, as defined by the National Science Foundation. In some embodiments, a nanoparticle has a diameter of less than 100 nm as defined by the National Institutes of Health. In some embodiments, nanoparticles are micelles in that they comprise an enclosed compartment, separated from the bulk solution by a micellar membrane, typically comprised of amphiphilic entities which surround and enclose a space or compartment (e.g., to define a lumen). In some embodiments, a micellar membrane is comprised of at least one polymer, such as for example a biocompatible and/or biodegradable polymer. In some embodiments, lipid nanoparticles described herein can have an average hydrodynamic diameter from about 30 to about 170 nm. In some embodiments, lipid nanoparticles described herein can have an average hydrodynamic diameter that is about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, or any range having endpoints defined by any two of the aforementioned values. For example, in some embodiments, lipid nanoparticles described herein have an average hydrodynamic diameter from between 50 nm to 100 nm.

Nanoparticle composition: As used herein, the term "nanoparticle composition" refers to a composition that contains at least one nanoparticle and at least one additional agent or ingredient. In some embodiments, a nanoparticle composition contains a substantially uniform collection of nanoparticles as described herein.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide. In some embodiments, a nucleic acid has enzymatic activity.

Operably linked: as used herein, refers to a juxtaposition wherein the components described are in a relationship permitting them to function in their intended manner. A control element "operably linked" to a functional element is associated in such a way that expression and/or activity of the functional element is achieved under conditions compatible with the control element. In some embodiments, "operably linked" control elements are contiguous (e.g., covalently linked) with the coding elements of interest; in some embodiments, control elements act in trans to or otherwise at a from the functional element of interest.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other nontoxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenyl sulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refer to the multiple polypeptides that are physically associated and function together as the discrete unit. In some embodiments, proteins may include moieties other than amino acids (e.g., may be glycoproteins, proteoglycans, etc.) and/or may be otherwise processed or modified. Those of ordinary skill in the art will appreciate that in some embodiments the term "protein" may refer to a complete polypeptide chain as produced by a cell (e.g., with or without a signal sequence), and/or to a form that is active within a cell (e.g., a truncated or complexed form). In some embodiments where a protein is comprised of multiple polypeptide chains, such chains may be covalently associated with one another, for example by one or more disulfide bonds, or may be associated by other means.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term “sample” typically refers to an aliquot of material obtained or derived from a source of interest, as described herein. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a biological tissue or fluid may be or comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may be or comprise an intracellular fluid, an extracellular fluid, an intravascular fluid (blood plasma), an interstitial fluid, a lymphatic fluid, and/or a transcellular fluid. In some embodiments, a biological fluid may be or comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., bronchioalveolar, ductal, nasal, ocular, oral, uterine, vaginal, or other washing or lavage). In some embodiments, a biological sample is or comprises cells obtained from an individual. In some embodiments, a sample is a “primary sample” obtained directly from a source of interest by any appropriate means. In some embodiments, as will be clear from context, the term “sample” refers to a preparation that is obtained by processing (e.g., by removing one or more components of and/or by adding one or more agents to) a primary sample. For example, filtering using a semi-permeable membrane. Such a “processed sample” may comprise, for example nucleic acids or proteins extracted from a sample or obtained by subjecting a primary sample to one or more techniques such as amplification or reverse transcription of nucleic acid, isolation and/or purification of certain components, etc.

Stable Nanoparticle Composition: The term “stable,” when applied to compositions herein, means that the compositions maintain one or more aspects of their physical structure (e.g., size range and/or distribution of particles) over a period of time. In some embodiments, a stable nanoparticle composition is one for which the average particle size, the maximum particle size, the range of particle sizes, and/or the distribution of particle sizes (i.e., the percentage of particles above a designated size and/or outside a designated range of sizes) is maintained for a period of time under specified conditions. In some embodiments, a stable provided composition is one for which a biologically relevant activity is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. For example, if a population of nanoparticles is subjected to prolonged storage, temperature changes, and/or pH changes, and a majority of the nanoparticles in the composition maintain a diameter within a stated range, the nanoparticle composition is stable. In some embodiments, a stable composition is stable at ambient conditions. In some embodiments, a stable composition is stable under biologic conditions (i.e. 37° C. in phosphate buffered saline).

Sterolyl: The term “sterolyl”, as used herein, refers to a 17-membered fused polycyclic ring moiety, which is either saturated or partially unsaturated and substituted with at least one hydroxyl group, and has a single point of attachment to the rest of the molecule at any substitutable carbon or oxygen atom. In some embodiments, a sterolyl group is a cholesterolyl group, or a variant or derivative thereof. In some embodiments, a cholesterolyl group is modified. In some embodiments, a cholesterolyl group is an oxidized cholesterolyl group (e.g., oxidized on the beta-ring structure or on the hydrocarbon tail structure). In some embodiments, a cholesterolyl group is an esterified cholesterolyl group. In some embodiments, a sterolyl group is a phytosterolyl group. Exemplary sterolyl groups include but are not limited to 25-hydroxycholesterolyl (25-OH), 20α-hydroxycholesterolyl (20α-OH), 27-hydroxycholesterolyl, 6-keto-5α-hydroxycholesterolyl, 7-ketocholesterolyl, 7β-hydroxycholesterolyl, 7α-hydroxycholesterolyl, 7β-25-dihydroxycholesterolyl, beta-sitosterolyl, stigmasterolyl, brassicasterolyl, campesterolyl.

Subject: As used herein, the term “subject” refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term “substantially” refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term “substantially”

is therefore used herein to capture the potential lack of completeness inherent in many biological and chemical phenomena.

Substituted or optionally substituted: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

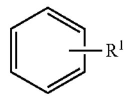

refers to at least

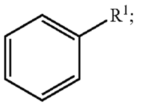

and

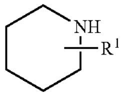

refers to at least

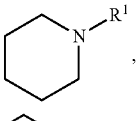

,

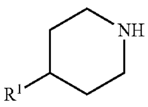

,

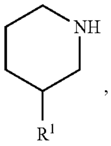

, or

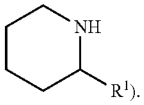

).

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Groups described as being "substituted" preferably have between 1 and 4 substituents, more preferably 1 or 2 substituents. Groups described as being "optionally substituted" may be unsubstituted or be "substituted" as described above.

Suitable monovalent substituents include halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}Ph$, which may be substituted with R°; $—(CH_2)_{0-4}O(CH_2)_{0-1}Ph$ which may be substituted with R°; —CH═CHPh, which may be substituted with R°; $—(CH_2)_{0-4}O(CH_2)_{0-1}$-pyridyl which may be substituted with R°; $—NO_2$; —CN; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ}C(O)NR^{\circ})_2$; $—N(R^{\circ})C(S)NR^{\circ}_2$; $—(CH_2)_{0-4}N(R^{\circ}C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)O$ SiR°3; $—(CH_2)_{0-4}OC(O)R^{\circ}$; $—OC(O)(CH_2)_{0-4}SR^{\circ}—$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ})_2$; $—C(O)N(OR^{\circ})R^{\circ}$; $—C(O)C(O)R^{\circ}$; $—C(O)CH_2C(O)R^{\circ}$; $—C(NOR^{\circ})R^{\circ}$; $—(CH_2)_{0-4}SSR^{\circ}$; $—(CH_2)_{0-4}S(O)_2R^{\circ}$; $—(CH_2)_{0-4}S(O)_2OR^{\circ}$; $—(CH_2)_{0-4}OS(O)_2R^{\circ}$; $—S(O)_2NR^{\circ}_2$; $—(CH_2)_{0-4}S(O)R^{\circ}$; $—N(R^{\circ})S(O)_2NR^{\circ})_2$; $—N(R^{\circ}S(O)_2R^{\circ}$; $—N(OR^{\circ})R^{\circ}$; $—C(NH)NR^{\circ}_2$; $—P(O)_2R^{\circ}$; $—P(O)R^{\circ}_2$; $—OP(O)R^{\circ}_2$; $—OP(O)(OR^{\circ})_2$; $—SiR^{\circ}_3$; $—OSiR^{\circ}_3$; $—(C_{1-4}$ straight or branched)alkylene) $O—N(R^{\circ}_2$; or $—(C_{1-4}$ straight or branched)alkylene)C(O) $O—N(R^{\circ}_2$, wherein each R° may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, $—(CH_2)_{0-2}R^{\bullet}$,-(halo$R^{\bullet}$), $—(CH_2)_{0-2}OH$, $—(CH_2)_{0-2}OR^{\bullet}$, $—(CH_2)_{0-2}CH(OR^{\bullet})_2$; —O(halo$R^{\bullet}$), —CN, $—N_3$, $—(CH_2)_{0-2}C(O)R^{\bullet}$, $—(CH_2)_{0-2}C(O)OH$, $—(CH_2)_{0-2}C(O)OR^{\bullet}$, $—(CH_2)_{0-2}SR^{\bullet}$, $—(CH_2)_{0-2}SH$, $—(CH_2)_{0-2}NH_2$, $—(CH_2)_{0-2}NHR^{\bullet}$, $—(CH_2)_{0-2}NR^{\bullet}_2$, $—NO_2$, $—SiR^{\bullet}_3$, —C(O)SR', $—(C_{1-4}$ straight or branched alkylene)C(O)O$R^{\bullet}$, or —SS$R^{\bullet}$ wherein each $R^{\bullet}$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents include the following: ═O, ═S, $═NNR^*_2$, ═NNHC(O)R*, ═NNHC(O)OR*, $═NNHS(O)_2R^*$, ═NR*, ═NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $—R^{\bullet}$,-(halo$R^{\bullet}$), —OH, $—OR^{\bullet}$, —O(halo$R^{\bullet}$), —CN, —C(O)OH, $—C(O)OR^{\bullet}$, $—NH_2$, $—NHR^{\bullet}$, $—NR^{\bullet}_2$, or $—NO_2$, wherein each $R^{\bullet}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

In some embodiments, suitable substituents on a substitutable nitrogen include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^•$,-(halo$R^•$), —OH, —OR', —O(halo$R^•$), —CN, —C(O)OH, —C(O)$OR^•$, —$NH_2$, —$NHR^•$, —$NR^•_2$, or —$NO_2$, wherein each R' is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Susceptible to: An individual who is "susceptible to" a disease, disorder, or condition is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition. In some embodiments, a risk of developing a disease, disorder, and/or condition is a population-based risk (e.g., family members of individuals suffering from the disease, disorder, or condition).

Systemic: The phrases "systemic administration," "administered systemically," "peripheral administration," and "administered peripherally" as used herein have their art-understood meaning referring to administration of a compound or composition such that it enters the recipient's system.

Tautomeric forms: The phrase "tautomeric forms," as used herein, is used to describe different isomeric forms of organic compounds that are capable of facile interconversion. Tautomers may be characterized by the formal migration of a hydrogen atom or proton, accompanied by a switch of a single bond and adjacent double bond. In some embodiments, tautomers may result from prototropic tautomerism (i.e., the relocation of a proton). In some embodiments, tautomers may result from valence tautomerism (i.e., the rapid reorganization of bonding electrons). All such tautomeric forms are intended to be included within the scope of the present disclosure. In some embodiments, tautomeric forms of a compound exist in mobile equilibrium with each other, so that attempts to prepare the separate substances results in the formation of a mixture. In some embodiments, tautomeric forms of a compound are separable and isolatable compounds. In some embodiments of the disclosure, chemical compositions may be provided that are or include pure preparations of a single tautomeric form of a compound. In some embodiments, chemical compositions may be provided as mixtures of two or more tautomeric forms of a compound. In certain embodiments, such mixtures contain equal amounts of different tautomeric forms; in certain embodiments, such mixtures contain different amounts of at least two different tautomeric forms of a compound. In some embodiments of the disclosure, chemical compositions may contain all tautomeric forms of a compound. In some embodiments of the disclosure, chemical compositions may contain less than all tautomeric forms of a compound. In some embodiments of the disclosure, chemical compositions may contain one or more tautomeric forms of a compound in amounts that vary over time as a result of interconversion. In some embodiments of the disclosure, the tautomerism is keto-enol tautomerism. One of skill in the chemical arts would recognize that a keto-enol tautomer can be "trapped" (i.e., chemically modified such that it remains in the "enol" form) using any suitable reagent known in the chemical arts in to provide an enol derivative that may subsequently be isolated using one or more suitable techniques known in the art. Unless otherwise indicated, the present disclosure encompasses all tautomeric forms of relevant compounds, whether in pure form or in admixture with one another.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, inhibit, alleviate, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount. The precise dosage will vary according to a variety of factors such as subject-dependent variables (e.g., age, immune system health, etc.), the disease, and the treatment being effected.

"Tissue" and/or "Organ": As used herein, the term, "tissue" and/or "organ" refers to viable cellular materials in an aggregate form, e.g., small portions of an organ, as well as dispersed cells, e.g., cells dispersed, isolated and/or grown from muscle, heart muscle, liver or kidney, including bone marrow cells and progeny cells, blood born stem cells and progeny, and the various other blood elements, unless otherwise specified. In some embodiments, the tissue and/or organ refers to kidney, heart liver, stomach, spleen, pancreas, lung, brain, eye, intestines, bladder, skin or dermal tissue, blood vessel, veins, arteries, heart valves, sperm, and oocyte(s). As used herein, the term "organ" encompasses both solid organs, e.g., kidney, heart, liver, lung, as well as functional parts of organs, e.g., segments of skin, sections of artery, veins, transplantable lobes of a liver, kidney, lung, and the like.

Treatment: As used herein, the term "treatment" (also "treat" or "treating") refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition. Thus, in some embodiments, treatment may be prophylactic; in some embodiments, treatment may be therapeutic.

DETAILED DESCRIPTION OF CERTAIN EMBODIMENTS

The present disclosure describes that selection and combination of one or more of the components as described herein impact functional activity of lipid nanoparticles such as desired tropisms, stabilization, and drug delivery efficacy. Among other things, the present invention provides compositions, preparations, nanoparticles, and/or nanomaterials for delivery of therapeutic and/or prophylactic agents to target cells and/or tissue. For example, the present disclosure describes lipid compounds for use in compositions, preparations, nanoparticles, and/or nanomaterials. In some embodiments, compositions, preparations, nanoparticles, and/or nanomaterials comprise LNPs carrying cargo to designated target cells, tissue, and/or organs.

I. Lipid Nanoparticles (LNPs)

The present invention provides for compositions, preparations, and/or nanomaterials that comprise lipid nanoparticles. In some embodiments, lipid nanoparticles comprise one or more components. In some embodiments, lipid nanoparticles comprise one or more components such as compounds, ionizable lipids, sterols, conjugate-linker lipids, and phospholipids. Among other things, the present disclosure describes that selection and combination of one or more of the components as described herein impacts characteristics of lipid nanoparticles such as diameter, pKa, stabilization, and ionizability.

Among other things, the present disclosure describes that selection and combination of one or more of the components as described herein impacts functional activity of lipid nanoparticles such as tropism, stabilization, and drug delivery efficacy. For example, the present disclosure describes that a combination of components may better suit delivery of siRNA. As another example, the present disclosure describes that a combination of components may better suit delivery of mRNA. As another example, the present disclosure describes that a combination of components may better suit delivery of DNA.

In some embodiments, lipid nanoparticles comprises one or more compounds as described herein. In some embodiments, lipid nanoparticles comprises one or more ionizable lipids as described herein. In some embodiments, lipid nanoparticles comprises one or more sterols as described herein. In some embodiments, lipid nanoparticles comprises one or more conjugate-linker lipids as described herein. In some embodiments, lipid nanoparticles comprises one or more phospholipids as described herein.

In some embodiments, the present disclosure provides ionizable lipids with improved chemical stability relative to an appropriate comparable reference; in some embodiments, such an appropriate comparable reference is a lipid (e.g., an ionizable lipid) with a linoleic acid tail feature (e.g., moiety). Without wishing to be bound by any theory, the present disclosure provides an insight that ionizable lipids containing a 1,4-diene motif (e.g., as seen in a linoleic acid moiety) may be prone to isomerization promoted by ambient oxygen, UV light, and high temperature. Moreover, the present disclosure provides an insight that such structural transformation (e.g., decomposition) may undesirably impact functional activities of corresponding compositions, preparations, nanoparticles, and/or nanomaterials. The present disclosure provides ionizable lipids that do not contain such 1,4-diene motif, and that display better chemical stability.

In some embodiments, the present disclosure provides ionizable lipids and/or compositions, preparations, nanoparticles, and/or nanomaterials with desirable degradation and tolerability properties in vivo. Without wishing to be bound by any theory, the present disclosure provides an insight that ionizable lipids and/or compositions, preparations, nanoparticles, and/or nanomaterials, possessing an ester moiety in the tail structures, may degrade more readily in vivo, e.g., due to action of esterase enzymes.

A. Compounds

Among other things, the present disclosure describes compositions, preparations, nanoparticles, and/or nanomaterials that comprise one or more compounds as described herein.

In some embodiments, the present disclosure provides a compound of Formula I:

(I)

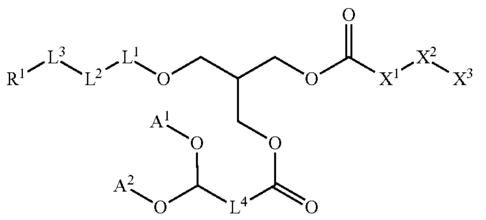

or a pharmaceutically acceptable salt thereof, wherein:

$L^1$ is a covalent bond, —C(O)—, or —OC(O)—;

$L^2$ is a covalent bond, an optionally substituted bivalent saturated or unsaturated, straight or branched $C_1$-$C_{12}$ hydrocarbon chain, or

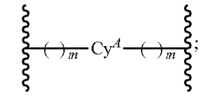

$Cy^A$ is an optionally substituted ring selected from phenylene and 3- to 7-membered saturated or partially unsaturated carbocyclene;

each m is independently 0, 1, or 2;

$L^3$ is a covalent bond, —C(O)—, —C(O)O—, —OC(O)—, —O—, or —OC(O)O—;

$R^1$ is

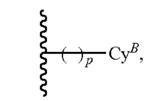

an optionally substituted saturated or unsaturated, straight or branched $C_1$-$C_{20}$ hydrocarbon chain wherein 1-3 methylene units are optionally and independently replaced with —O— or —NR—, or

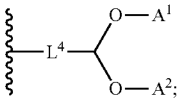

$Cy^B$ is an optionally substituted ring selected from 3- to 12-membered saturated or partially unsaturated carbocyclyl, 1-adamantyl, 2-adamantyl,

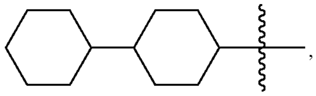 [SMILES: *C1CCC(C2CCCCC2)CC1]

sterolyl, and phenyl;

p is 0, 1, 2, or 3;

each $L^4$ is independently a bivalent saturated or unsaturated, straight or branched $C_1$-$C_6$ hydrocarbon chain;

each $A^1$ and $A^2$ is independently an optionally substituted $C_1$-$C_{20}$ aliphatic or —$L^5$—$R^5$;

or $A^1$ and $A^2$, together with their intervening atoms, may form an optionally substituted ring:

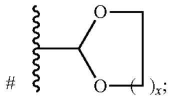

where x is selected from 1 or 2; and # represents the point of attachment to $L^4$;

each $L^5$ is independently a bivalent saturated or unsaturated, straight or branched $C_1$-$C_{20}$ hydrocarbon chain, wherein 1-3 methylene units are optionally and independently replaced with —O— or —NR—;

each $R^5$ is independently an optionally substituted group selected from a 5- to 10-membered aryl ring or a 3- to 8-membered carbocyclic ring;

$X^1$ is a covalent bond, —O—, or —NR—;

$X^2$ is a covalent bond or an optionally substituted, bivalent saturated or unsaturated, straight or branched, $C_1$-$C_{12}$ hydrocarbon chain, wherein 1-3 methylene units are optionally and independently replaced with —O—, —NR—, or —$Cy^C$—;

$Cy^C$ is an optionally substituted ring selected from 3- to 7-membered saturated or partially unsaturated carbocyclene, phenylene, 3- to 7-membered saturated or partially unsaturated heterocyclene having 1-3 heteroatoms independently selected from nitrogen, oxygen, and sulfur, and 5- to 6-membered heteroarylene having 1-3 heteroatoms independently selected from nitrogen, oxygen, and sulfur;

$X^3$ is hydrogen or an optionally substituted ring selected from 3- to 7-membered saturated or partially unsaturated carbocyclyl, phenyl, 3- to 7-membered saturated or partially unsaturated heterocyclyl having 1-3 heteroatoms independently selected from nitrogen, oxygen, and sulfur, or 5- to 6-membered heteroaryl having 1-3 heteroatoms independently selected from nitrogen, oxygen, and sulfur; and each R is independently hydrogen or an optionally substituted $C_1$-$C_6$ aliphatic group;

provided that when $L^3$ is a covalent bond, then $R^1$ must be

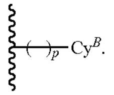

In some embodiments, the present disclosure provides a compound of Formula II:

(II)

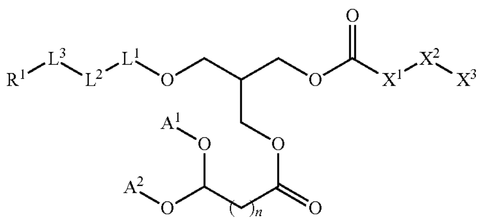

or a pharmaceutically acceptable salt thereof, wherein n is 1, 2, 3 or 4, and $L^1$, $L^2$, $L^3$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula III:

(III)

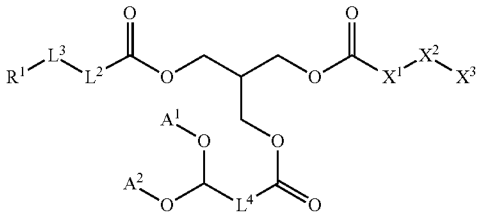

or a pharmaceutically acceptable salt thereof, wherein $L^2$, $L^3$, $L^4$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula IIIA:

(IIIA)

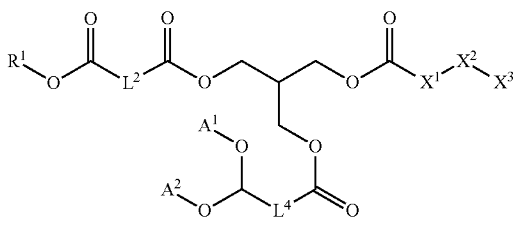

or a pharmaceutically acceptable salt thereof, wherein $L^2$, $L^4$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula (IIIB):

(IIIB)

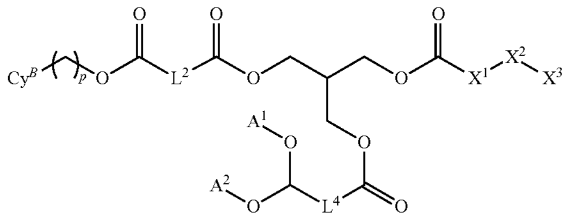

or a pharmaceutically acceptable salt thereof, wherein p, $Cy^B$, $L^2$, $L^4$, $A^1$, $A^2$, $A^2$, $X^1$, $X^2$, and $X^3$ are as defined above for Formula I and described in classes and subclasses herein, both singly and in combination.

In some embodiments, the present disclosure provides a compound of Formula IIIC:

(IIIC)

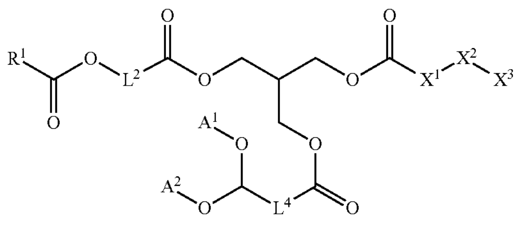

or a pharmaceutically acceptable salt thereof, wherein $L^2$, $L^4$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula (IV):

(IV)

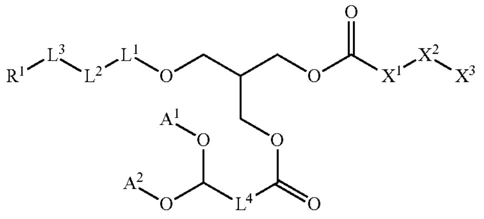

or a pharmaceutically acceptable salt thereof, wherein $L^1$, $L^2$, $L^3$, $L^4$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula (V):

(V)

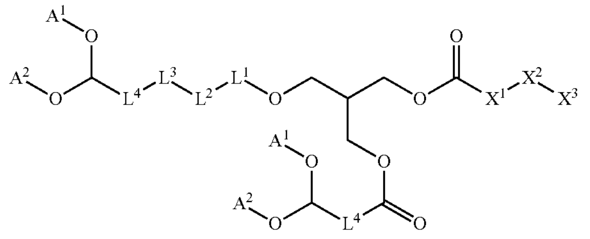

or a pharmaceutically acceptable salt thereof, wherein $L^1$, $L^2$, $L^3$, $L^4$, $A^1$, $A^2$, $X^1$, $X^2$, and $X^3$ are as defined above for Formula I and described in classes and subclasses herein, both singly and in combination.

In some embodiments, the present disclosure provides a compound of Formula (VA):

(VA)

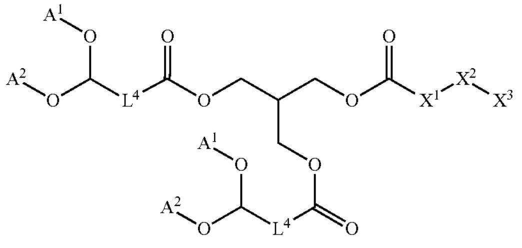

or a pharmaceutically acceptable salt thereof, wherein $L^4$, $A^1$, $A^2$, $X^1$, $X^2$, and $X^3$ are as defined above for Formula I and described in classes and subclasses herein, both singly and in combination.

In some embodiments, the present disclosure provides a compound of Formula (VI):

(VI)

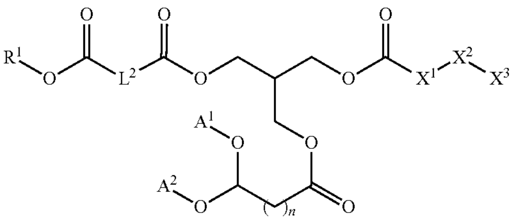

or a pharmaceutically acceptable salt thereof, wherein n is 1, 2, 3 or 4, and $L^2$, $R^1$, $A^1$, $A^2$, $X^1$, $X^2$, and $X^3$ are as defined above for Formula I and described in classes and subclasses herein, both singly and in combination.

In some embodiments, the present disclosure provides a compound of Formula (VIA):

(VIA)

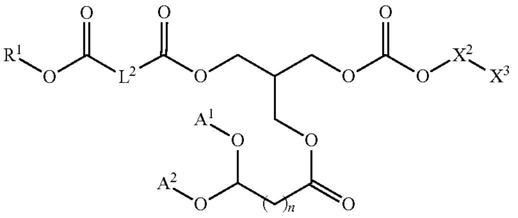

or a pharmaceutically acceptable salt thereof, wherein n is 1, 2, 3 or 4, and $L^2$, $R^1$, $A^1$, $A^2$, $X^2$, and $X^3$ are as defined above for Formula I and described in classes and subclasses herein, both singly and in combination.

In some embodiments, the present disclosure provides a compound of Formula (VII):

(VII)

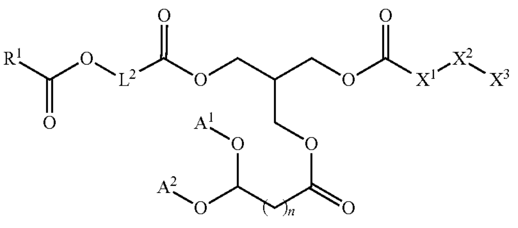

or a pharmaceutically acceptable salt thereof, wherein n is 1, 2, 3 or 4, and $L^2$, $R^1$, $A^1$, $A^2$, $X^2$, and $X^3$ are as defined above for Formula I and described in classes and subclasses herein, both singly and in combination.

In some embodiments, the present disclosure provides a compound of Formula (VITA):

(VIIA)

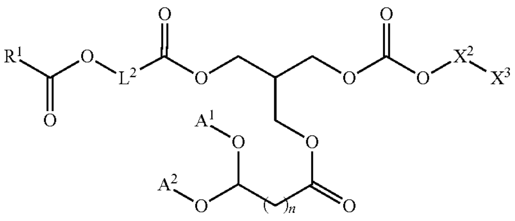

or a pharmaceutically acceptable salt thereof, wherein n is 1, 2, 3 or 4, and $L^2$, $R^1$, $A^1$, $A^2$, $X^1$, $X_2$, and $X^3$ are as defined above for Formula I and described in classes and subclasses herein, both singly and in combination.

In some embodiments of any of Formulae described herein, $L^1$ is a covalent bond, —C(O)—, or —OC(O)—. In some embodiments, $L^1$ is a covalent bond. In some embodiments, $L^1$ is —C(O)—. In some embodiments, $L^1$ is —OC (O)—.

In some embodiments of any Formulae described herein, $L^2$ is independently a covalent bond, an optionally substituted bivalent saturated or unsaturated, straight or branched $C_1$-$C_{12}$ hydrocarbon chain, or

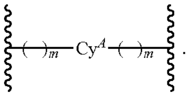

.

It will be appreciated that, throughout this disclosure,

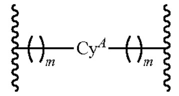

is intended to refer to the same moiety as $—(CH_2)_m—Cy^A—(CH_2)_m—$, and they may be used interchangeably.

In some embodiments, $L^2$ is a covalent bond. In some embodiments, $L^2$ is an optionally substituted bivalent saturated or unsaturated, straight or branched $C_1$-$C_{12}$ hydrocarbon chain. In some embodiments, $L^2$ is an optionally substituted bivalent saturated or unsaturated, straight or branched $C_1$-$C_9$ hydrocarbon chain. In some embodiments, $L^2$ is an optionally substituted bivalent saturated or unsaturated, straight or branched $C_1$-$C_6$ hydrocarbon chain. In some embodiments, $L^2$ is an optionally substituted bivalent saturated or unsaturated, straight or branched $C_1$-$C_3$ hydrocarbon chain. In some embodiments, $L^2$ is an optionally substituted bivalent saturated or unsaturated, straight or branched $C_4$-$C_8$ hydrocarbon chain. In some embodiments, $L^2$ is an optionally substituted bivalent saturated straight or branched $C_1$-$C_{12}$ hydrocarbon chain. In some embodiments, $L^2$ is an optionally substituted bivalent saturated straight or branched $C_1$-$C_9$ hydrocarbon chain. In some embodiments, $L^2$ is an optionally substituted bivalent saturated straight or branched $C_1$-$C_6$ hydrocarbon chain. In some embodiments, $L^2$ is an optionally substituted bivalent saturated straight or branched $C_1$-$C_3$ hydrocarbon chain. In some embodiments, $L^2$ is an optionally substituted bivalent saturated straight or branched $C_4$-$C_8$ hydrocarbon chain. In some embodiments, $L^2$ is an optionally substituted bivalent saturated straight or branched $C_6$ hydrocarbon chain. In some embodiments, $L^2$ is an optionally substituted bivalent saturated straight or branched $C_5$ hydrocarbon chain. In some embodiments, $L^2$ is an optionally substituted bivalent saturated straight or branched $C_4$ hydrocarbon chain. In some embodiments, $L^2$ is optionally substituted $—CH_2—$. In some embodiments, $L^2$ is optionally substituted $—CH_2CH_2—$. In some embodiments, $L^2$ is optionally substituted $—CH_2CH_2CH_2—$. In some embodiments, $L^2$ is optionally substituted $—CH_2CH_2CH_2CH_2—$. In some embodiments, $L^2$ is optionally substituted $—CH_2CH_2CH_2CH_2CH_2—$. In some embodiments, $L^2$ is optionally substituted $—CH_2CH_2CH_2CH_2CH_2CH_2—$. In some embodiments, $L^2$ is optionally substituted $—CH_2CH_2CH_2CH_2CH_2CH_2CH_2—$. In some embodiments, $L^2$ is

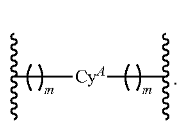

In some embodiments of any of Formulae described herein, $Cy^A$ is an optionally substituted ring selected from phenylene and 3- to 7-membered saturated or partially unsaturated carbocyclene. In some embodiments, $Cy^A$ is optionally substituted phenylene. In some embodiments, $Cy^A$ is

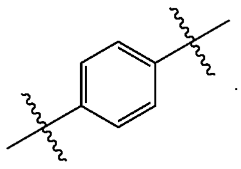 [SMILES: *c1ccc(*)cc1]

In some embodiments, $Cy^A$ is

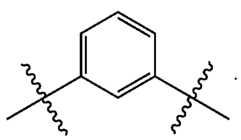 [SMILES: *c1cccc(*)c1]

In some embodiments, $Cy^A$ is

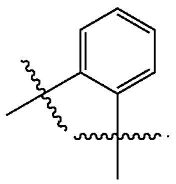 [SMILES: *c1ccccc1*]

In some embodiments, $Cy^A$ is optionally substituted 3- to 7-membered saturated or partially unsaturated carbocyclene. In some embodiments, $Cy^A$ is optionally substituted 5- to 6-membered saturated or partially unsaturated carbocyclene. In some embodiments, $Cy^A$ is optionally substituted 5- to 6-membered saturated carbocyclene. In some embodiments, $Cy^A$ is optionally substituted cyclohexylene. In some embodiments, $Cy^A$ is

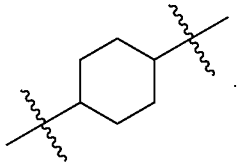 [SMILES: *C1CCC(*)CC1]

In some embodiments, $Cy^A$ is

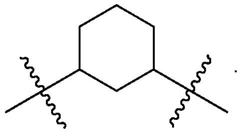 [SMILES: *C1CCCC(*)C1]

In some embodiments, $Cy^A$ is

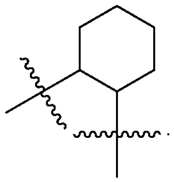 [SMILES: *C1CCCCC1*]

In some embodiments of any Formulae described herein, each m is independently 0, 1, or 2. In some embodiments, at least one m is 0. In some embodiments, at least one m is 1. In some embodiments, at least one m is 2. In some embodiments, both m's are 0. In some embodiments, both m's are 1. In some embodiments, both m's are 2.

In some embodiments of any of Formulae described herein, $L^3$ is a covalent bond, —C(O)—, —C(O)O—, —OC(O)—, —O—, or —OC(O)O—. In some embodiments, $L^3$ is a covalent bond. In some embodiments, $L^3$ is —C(O)—. In some embodiments, $L^3$ is —C(O)O—. In some embodiments, $L^3$ is —OC(O)—. In some embodiments, $L^3$ is —O—. In some embodiments, $L^3$ is —OC(O)O—.

In some embodiments of any of Formulae described herein, $R^1$ is

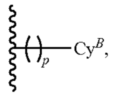

an optionally substituted saturated or unsaturated, straight or branched $C_1$-$C_{20}$ hydrocarbon chain wherein 1-3 methylene units are optionally and independently replaced with —O— or —NR—, or

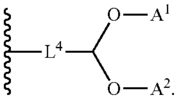

It will be appreciated that, throughout this disclosure,

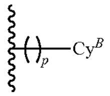

is intended to refer to the same moiety as —$(CH_2)_p$-$Cy^B$, and they may be used interchangeably.

In some embodiments, $R^1$ is

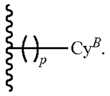

In some embodiments, $R^1$ is an optionally substituted saturated or unsaturated, straight or branched $C_1$-$C_{20}$ hydrocarbon chain wherein 1-3 methylene units are optionally and independently replaced with —O— or —NR—. In some embodiments, $R^1$ is an optionally substituted saturated or unsaturated, straight or branched $C_1$-$C_{15}$ hydrocarbon chain wherein 1-3 methylene units are optionally and independently replaced with —O— or —NR—. In some embodiments, $R^1$ is an optionally substituted saturated or unsaturated, straight or branched $C_1$-$C_{12}$ hydrocarbon chain wherein 1-3 methylene units are optionally and independently replaced with —O— or —NR—. In some embodiments, $R^1$ is an optionally substituted saturated or unsaturated, straight or branched $C_1$-$C_9$ hydrocarbon chain wherein 1-3 methylene units are optionally and independently replaced with —O— or —NR—. In some embodiments, $R^1$ is an optionally substituted saturated or unsaturated, straight or branched $C_1$-$C_6$ hydrocarbon chain wherein 1-2 methylene units are optionally and independently replaced with —O— or —NR—. In some embodiments, $R^1$ is an optionally substituted saturated or unsaturated, straight or branched $C_6$-$C_{20}$ hydrocarbon chain wherein 1-3 methylene units are optionally and independently replaced with —O— or —NR—. In some embodiments, $R^1$ is an optionally substituted saturated or unsaturated, straight or branched $C_9$-$C_{20}$ hydrocarbon chain wherein 1-3 methylene units are optionally and independently replaced with —O— or —NR—. In some embodiments, $R^1$ is an optionally substituted saturated or unsaturated, straight or branched $C_{12}$-$C_{20}$ hydrocarbon chain wherein 1-3 methylene units are optionally and independently replaced with —O— or —NR—. In some embodiments, $R^1$ is an optionally substituted saturated or unsaturated, straight or branched $C_{15}$-$C_{20}$ hydrocarbon chain wherein 1-3 methylene units are optionally and independently replaced with —O— or —NR—. In some embodiments, $R^1$ is an optionally substituted saturated or unsaturated, straight or branched $C_6$-$C_{15}$ hydrocarbon chain wherein 1-3 methylene units are optionally and independently replaced with —O— or —NR—.

In some embodiments, $R^1$ is an optionally substituted saturated or unsaturated, straight or branched $C_6$ hydrocarbon chain wherein 1-2 methylene units are optionally and independently replaced with —O— or —NR—. In some embodiments, $R^1$ is an optionally substituted saturated or unsaturated, straight or branched $C_7$ hydrocarbon chain wherein 1-2 methylene units are optionally and independently replaced with —O— or —NR—. In some embodiments, $R^1$ is an optionally substituted saturated or unsaturated, straight or branched $C_8$ hydrocarbon chain wherein 1-2 methylene units are optionally and independently replaced with —O— or —NR—. In some embodiments, $R^1$ is an optionally substituted saturated or unsaturated, straight or branched $C_9$ hydrocarbon chain wherein 1-3 methylene units are optionally and independently replaced with —O— or —NR—. In some embodiments, $R^1$ is an optionally substituted saturated or unsaturated, straight or branched $C_{10}$ hydrocarbon chain wherein 1-3 methylene units are optionally and independently replaced with —O— or —NR—. In some embodiments, $R^1$ is an optionally substituted saturated or unsaturated, straight or branched $C_{11}$ hydrocarbon chain wherein 1-3 methylene units are optionally and independently replaced with —O— or —NR—. In some embodiments, $R^1$ is an optionally substituted saturated or unsaturated, straight or branched $C_{12}$ hydrocarbon chain wherein 1-3 methylene units are optionally and independently replaced with —O— or —NR—. In some embodiments, $R^1$ is an optionally substituted saturated or unsaturated, straight or branched $C_{13}$ hydrocarbon chain wherein 1-3 methylene units are optionally and independently replaced with —O— or —NR—. In some embodiments, $R^1$ is an optionally substituted saturated or unsaturated, straight or branched $C_{14}$ hydrocarbon chain wherein 1-3 methylene units are optionally and independently replaced with —O— or —NR—. In some embodiments, $R^1$ is an optionally substituted saturated or unsaturated, straight or branched $C_{15}$ hydrocarbon chain wherein 1-3 methylene units are optionally and independently replaced with —O— or —NR—. In some embodiments, $R^1$ is an optionally substituted saturated or unsaturated, straight or branched $C_{16}$ hydrocarbon chain wherein 1-3 methylene units are optionally and independently replaced with —O— or —NR—. In some embodiments, $R^1$ is an optionally substituted saturated or unsaturated, straight or branched $C_{17}$ hydrocarbon chain wherein 1-3 methylene units are optionally and independently replaced with —O— or —NR—. In some embodiments, $R^1$ is an optionally substituted saturated or unsaturated, straight or branched $C_{18}$ hydrocarbon chain wherein 1-3 methylene units are optionally and independently replaced with —O— or —NR—. In some embodiments, $R^1$ is an optionally substituted saturated or unsaturated, straight or branched $C_{19}$ hydrocarbon chain wherein 1-3 methylene units are optionally and independently replaced with —O— or —NR—. In some embodiments, $R^1$ is an optionally substituted saturated or unsaturated, straight or branched $C_{20}$ hydrocarbon chain wherein 1-3 methylene units are optionally and independently replaced with —O— or —NR—. In some embodiments, $R^1$ is an optionally substituted saturated or unsaturated, straight or branched $C_1$-$C_{20}$ hydrocarbon chain. In some embodiments, $R^1$ is an optionally substituted saturated or unsaturated, straight or branched $C_1$-$C_{15}$ hydrocarbon chain. In some embodiments, $R^1$ is an optionally substituted saturated or unsaturated, straight or branched $C_1$-$C_{12}$ hydrocarbon chain. In some embodiments, $R^1$ is an optionally substituted saturated or unsaturated, straight or branched $C_1$-$C_9$ hydrocarbon chain. In some embodiments, $R^1$ is an optionally substituted saturated or unsaturated, straight or branched $C_1$-$C_6$ hydrocarbon chain. In some embodiments, $R^1$ is an optionally substituted saturated or unsaturated, straight or branched $C_6$-$C_{20}$ hydrocarbon chain. In some embodiments, $R^1$ is an optionally substituted saturated or unsaturated, straight or branched $C_9$-$C_{20}$ hydrocarbon chain. In some embodiments, $R^1$ is an optionally substituted saturated or unsaturated, straight or branched $C_{12}$-$C_{20}$ hydrocarbon chain. In some embodiments, $R^1$ is an optionally substituted saturated or unsaturated, straight or branched $C_{15}$-$C_{20}$ hydrocarbon chain. In some embodiments, $R^1$ is an optionally substituted saturated or unsaturated, straight or branched $C_6$-$C_{15}$ hydrocarbon chain.

In some embodiments, $R^1$ is an optionally substituted saturated or unsaturated, straight or branched $C_6$ hydrocarbon chain. In some embodiments, $R^1$ is an optionally substituted saturated or unsaturated, straight or branched $C_7$ hydrocarbon chain. In some embodiments, $R^1$ is an optionally substituted saturated or unsaturated, straight or branched $C_8$ hydrocarbon chain. In some embodiments, $R^1$ is an optionally substituted saturated or unsaturated, straight or branched $C_9$ hydrocarbon chain. In some embodiments, $R^1$ is an optionally substituted saturated or unsaturated, straight or branched $C_{10}$ hydrocarbon chain. In some embodiments, $R^1$ is an optionally substituted saturated or unsaturated, straight or branched $C_{11}$ hydrocarbon chain. In some embodiments, $R^1$ is an optionally substituted saturated or unsaturated, straight or branched $C_{12}$ hydrocarbon chain. In some embodiments, $R^1$ is an optionally substituted saturated or unsaturated, straight or branched $C_{13}$ hydrocarbon chain. In some embodiments, $R^1$ is an optionally substituted saturated or unsaturated, straight or branched $C_{14}$ hydrocarbon chain. In some embodiments, $R^1$ is an optionally substituted saturated or unsaturated, straight or branched $C_{15}$ hydrocarbon chain. In some embodiments, $R^1$ is an optionally substituted saturated or unsaturated, straight or branched $C_{16}$ hydrocarbon chain. In some embodiments, $R^1$ is an optionally substituted saturated or unsaturated, straight or branched $C_{17}$ hydrocarbon chain. In some embodiments, $R^1$ is an optionally substituted saturated or unsaturated, straight or branched $C_{18}$ hydrocarbon chain. In some embodiments, $R^1$ is an optionally substituted saturated or unsaturated, straight or branched $C_{19}$ hydrocarbon chain. In some embodiments, $R^1$ is an optionally substituted saturated or unsaturated, straight or branched $C_{20}$ hydrocarbon chain.

In some embodiments, $R^1$ is a saturated or unsaturated, straight or branched $C_1$-$C_{20}$ hydrocarbon chain. In some embodiments, $R^1$ is a saturated or unsaturated, straight or branched $C_1$-$C_{15}$ hydrocarbon chain. In some embodiments, $R^1$ is a saturated or unsaturated, straight or branched $C_1$-$C_{12}$ hydrocarbon chain. In some embodiments, $R^1$ is a saturated or unsaturated, straight or branched $C_1$-$C_9$ hydrocarbon chain. In some embodiments, $R^1$ is a saturated or unsaturated, straight or branched $C_1$-$C_6$ hydrocarbon chain. In some embodiments, $R^1$ is a saturated or unsaturated, straight or branched $C_6$-$C_{20}$ hydrocarbon chain. In some embodiments, $R^1$ is a saturated or unsaturated, straight or branched $C_9$-$C_{20}$ hydrocarbon chain. In some embodiments, $R^1$ is a saturated or unsaturated, straight or branched $C_{12}$-$C_{20}$ hydrocarbon chain. In some embodiments, $R^1$ is a saturated or unsaturated, straight or branched $C_{15}$-$C_{20}$ hydrocarbon chain. In some embodiments, $R^1$ is a saturated or unsaturated, straight or branched $C_6$-$C_{15}$ hydrocarbon chain.

In some embodiments, $R^1$ is a saturated or unsaturated, straight or branched $C_6$ hydrocarbon chain. In some embodiments, $R^1$ is a saturated or unsaturated, straight or branched $C_7$ hydrocarbon chain. In some embodiments, $R^1$ is a saturated or unsaturated, straight or branched $C_8$ hydrocarbon chain. In some embodiments, $R^1$ is a saturated or unsaturated, straight or branched $C_9$ hydrocarbon chain. In some embodiments, $R^1$ is a saturated or unsaturated, straight or branched $C_{10}$ hydrocarbon chain. In some embodiments, $R^1$ is a saturated or unsaturated, straight or branched $C_{11}$ hydrocarbon chain. In some embodiments, $R^1$ is a saturated or unsaturated, straight or branched $C_{12}$ hydrocarbon chain. In some embodiments, $R^1$ is a saturated or unsaturated, straight or branched $C_{13}$ hydrocarbon chain. In some embodiments, $R^1$ is a saturated or unsaturated, straight or branched $C_{14}$ hydrocarbon chain. In some embodiments, $R^1$ is a saturated or unsaturated, straight or branched $C_{15}$ hydrocarbon chain. In some embodiments, $R^1$ is a saturated or unsaturated, straight or branched $C_{16}$ hydrocarbon chain. In some embodiments, $R^1$ is a saturated or unsaturated, straight or branched $C_{17}$ hydrocarbon chain. In some embodiments, $R^1$ is a saturated or unsaturated, straight or branched $C_{18}$ hydrocarbon chain. In some embodiments, $R^1$ is a saturated or unsaturated, straight or branched $C_{19}$ hydrocarbon chain. In some embodiments, $R^1$ is a saturated or unsaturated, straight or branched $C_{20}$ hydrocarbon chain.

In some embodiments, $R^1$ is a saturated, branched $C_3$-$C_{20}$ hydrocarbon chain. In some embodiments, $R^1$ is a saturated, branched $C_3$-$C_{15}$ hydrocarbon chain. In some embodiments, $R^1$ is a saturated, branched $C_3$-$C_{12}$ hydrocarbon chain. In some embodiments, $R^1$ is a saturated, branched $C_3$-$C_9$ hydrocarbon chain. In some embodiments, $R^1$ is a saturated, branched $C_3$-$C_6$ hydrocarbon chain. In some embodiments, $R^1$ is a saturated, branched $C_6$-$C_{20}$ hydrocarbon chain. In some embodiments, $R^1$ is a saturated, branched $C_9$-$C_{20}$ hydrocarbon chain. In some embodiments, $R^1$ is a saturated, branched $C_{12}$-$C_{20}$ hydrocarbon chain. In some embodiments, $R^1$ is a saturated, branched $C_{15}$-$C_{20}$ hydrocarbon chain. In some embodiments, $R^1$ is a saturated, branched $C_6$-$C_{15}$ hydrocarbon chain.

In some embodiments, $R^1$ is a saturated, branched $C_6$ hydrocarbon chain. In some embodiments, $R^1$ is a saturated, branched $C_7$ hydrocarbon chain. In some embodiments, $R^1$ is a saturated, branched $C_8$ hydrocarbon chain. In some embodiments, $R^1$ is a saturated, branched $C_9$ hydrocarbon chain. In some embodiments, $R^1$ is a saturated, branched $C_{10}$ hydrocarbon chain. In some embodiments, $R^1$ is a saturated, branched $C_{11}$ hydrocarbon chain. In some embodiments, $R^1$ is a saturated, branched $C_{12}$ hydrocarbon chain. In some embodiments, $R^1$ is a saturated, branched $C_{13}$ hydrocarbon chain. In some embodiments, $R^1$ is a saturated, branched $C_{14}$ hydrocarbon chain. In some embodiments, $R^1$ is a saturated, branched $C_{15}$ hydrocarbon chain. In some embodiments, $R^1$ is a saturated, branched $C_{16}$ hydrocarbon chain. In some embodiments, $R^1$ is a saturated, branched $C_{17}$ hydrocarbon chain. In some embodiments, $R^1$ is a saturated, branched Cis hydrocarbon chain. In some embodiments, $R^1$ is a saturated, branched $C_{19}$ hydrocarbon chain. In some embodiments, $R^1$ is a saturated, branched $C_{20}$ hydrocarbon chain.

In some embodiments, $R^1$ is a saturated or unsaturated, straight or branched $C_1$-$C_{20}$ hydrocarbon chain optionally substituted with 1-6 halogen atoms. In some embodiments, $R^1$ is a saturated or unsaturated, straight or branched $C_1$-$C_{15}$ hydrocarbon chain optionally substituted with 1-6 halogen atoms. In some embodiments, $R^1$ is a saturated or unsaturated, straight or branched $C_1$-$C_{12}$ hydrocarbon chain optionally substituted with 1-6 halogen atoms. In some embodiments, $R^1$ is a saturated or unsaturated, straight or branched $C_1$-$C_9$ hydrocarbon chain optionally substituted with 1-6 halogen atoms. In some embodiments, $R^1$ is a saturated or unsaturated, straight or branched $C_1$-$C_6$ hydrocarbon chain optionally substituted with 1-6 halogen atoms. In some embodiments, $R^1$ is a saturated or unsaturated, straight or branched $C_6$-$C_{20}$ hydrocarbon chain optionally substituted with 1-6 halogen atoms. In some embodiments, $R^1$ is a saturated or unsaturated, straight or branched $C_9$-$C_{20}$ hydrocarbon chain optionally substituted with 1-6 halogen atoms. In some embodiments, $R^1$ is a saturated or unsaturated, straight or branched $C_{12}$-$C_{20}$ hydrocarbon chain optionally substituted with 1-6 halogen atoms. In some embodiments, $R^1$ is a saturated or unsaturated, straight or branched $C_{15}$-$C_{20}$ hydrocarbon chain optionally substituted with 1-6 halogen atoms. In some embodiments, $R^1$ is a saturated or unsaturated, straight or branched $C_6$-$C_{15}$ hydrocarbon chain optionally substituted with 1-6 halogen atoms.

In some embodiments, $R^1$ is a saturated or unsaturated, straight or branched $C_6$ hydrocarbon chain optionally substituted with 1-6 halogen atoms. In some embodiments, $R^1$ is a saturated or unsaturated, straight or branched $C_7$ hydrocarbon chain optionally substituted with 1-6 halogen atoms. In some embodiments, $R^1$ is a saturated or unsaturated, straight or branched $C_8$ hydrocarbon chain optionally substituted with 1-6 halogen atoms. In some embodiments, $R^1$ is a saturated or unsaturated, straight or branched $C_9$ hydrocarbon chain optionally substituted with 1-6 halogen atoms. In some embodiments, $R^1$ is a saturated or unsaturated, straight or branched $C_{10}$ hydrocarbon chain optionally substituted with 1-6 halogen atoms. In some embodiments, $R^1$ is a saturated or unsaturated, straight or branched $C_{11}$ hydrocarbon chain optionally substituted with 1-6 halogen atoms. In some embodiments, $R^1$ is a saturated or unsaturated, straight or branched $C_{12}$ hydrocarbon chain optionally substituted with 1-6 halogen atoms. In some embodiments, $R^1$ is a saturated or unsaturated, straight or branched $C_{13}$ hydrocarbon chain optionally substituted with 1-6 halogen atoms. In some embodiments, $R^1$ is a saturated or unsaturated, straight or branched $C_{14}$ hydrocarbon chain optionally substituted with 1-6 halogen atoms. In some embodiments, $R^1$ is a saturated or unsaturated, straight or branched $C_{15}$ hydrocarbon chain optionally substituted with 1-6 halogen atoms. In some embodiments, $R^1$ is a saturated or unsaturated, straight or branched $C_{16}$ hydrocarbon chain optionally substituted with 1-6 halogen atoms. In some embodiments, $R^1$ is a saturated or unsaturated, straight or branched $C_{17}$ hydrocarbon chain optionally substituted with 1-6 halogen atoms. In some embodiments, $R^1$ is a saturated or unsaturated, straight or branched $C_{18}$ hydrocarbon chain optionally substituted with 1-6 halogen atoms. In some embodiments, $R^1$ is a saturated or unsaturated, straight or branched $C_{19}$ hydrocarbon chain optionally substituted with 1-6 halogen atoms. In some embodiments, $R^1$ is a saturated or unsaturated, straight or branched $C_{20}$ hydrocarbon chain optionally substituted with 1-6 halogen atoms.

In some embodiments, $R^1$ is a saturated or unsaturated, straight or branched $C_1$-$C_{20}$ hydrocarbon chain optionally substituted with 1-6 fluorine atoms. In some embodiments, $R^1$ is a saturated or unsaturated, straight or branched $C_1$-$C_{15}$ hydrocarbon chain optionally substituted with 1-6 fluorine atoms. In some embodiments, $R^1$ is a saturated or unsaturated, straight or branched $C_1$-$C_{12}$ hydrocarbon chain optionally substituted with 1-6 fluorine atoms. In some embodiments, $R^1$ is a saturated or unsaturated, straight or branched $C_{1-9}$ hydrocarbon chain optionally substituted with 1-6 fluorine atoms. In some embodiments, $R^1$ is a saturated or unsaturated, straight or branched $C_1$-$C_6$ hydrocarbon chain optionally substituted with 1-6 fluorine atoms. In some embodiments, $R^1$ is a saturated or unsaturated, straight or branched $C_6$-$C_{20}$ hydrocarbon chain optionally substituted with 1-6 fluorine atoms. In some embodiments, $R^1$ is a saturated or unsaturated, straight or branched $C_9$-$C_{20}$ hydrocarbon chain optionally substituted with 1-6 fluorine atoms. In some embodiments, $R^1$ is a saturated or unsaturated, straight or branched $C_{12}$-$C_{20}$ hydrocarbon chain optionally substituted with 1-6 fluorine atoms. In some embodiments, $R^1$ is a saturated or unsaturated, straight or branched $C_{15}$-$C_{20}$ hydrocarbon chain optionally substituted with 1-6 fluorine atoms. In some embodiments, $R^1$ is a saturated or unsaturated, straight or branched $C_6$-$C_{15}$ hydrocarbon chain optionally substituted with 1-6 fluorine atoms.

In some embodiments, $R^1$ is a saturated or unsaturated, straight or branched $C_6$ hydrocarbon chain optionally substituted with 1-6 fluorine atoms. In some embodiments, $R^1$ is a saturated or unsaturated, straight or branched $C_7$ hydrocarbon chain optionally substituted with 1-6 fluorine atoms. In some embodiments, $R^1$ is a saturated or unsaturated, straight or branched $C_8$ hydrocarbon chain optionally substituted with 1-6 fluorine atoms. In some embodiments, $R^1$ is a saturated or unsaturated, straight or branched $C_9$ hydrocarbon chain optionally substituted with 1-6 fluorine atoms. In some embodiments, $R^1$ is a saturated or unsaturated, straight or branched $C_{10}$ hydrocarbon chain optionally substituted with 1-6 fluorine atoms. In some embodiments, $R^1$ is a saturated or unsaturated, straight or branched $C_{11}$ hydrocarbon chain optionally substituted with 1-6 fluorine atoms. In some embodiments, $R^1$ is a saturated or unsaturated, straight or branched $C_{12}$ hydrocarbon chain optionally substituted with 1-6 fluorine atoms. In some embodiments, $R^1$ is a saturated or unsaturated, straight or branched $C_{13}$ hydrocarbon chain optionally substituted with 1-6 fluorine atoms. In some embodiments, $R^1$ is a saturated or unsaturated, straight or branched $C_{14}$ hydrocarbon chain optionally substituted with 1-6 fluorine atoms. In some embodiments, $R^1$ is a saturated or unsaturated, straight or branched $C_{15}$ hydrocarbon chain optionally substituted with 1-6 fluorine atoms. In some embodiments, $R^1$ is a saturated or unsaturated, straight or branched $C_{16}$ hydrocarbon chain optionally substituted with 1-6 fluorine atoms. In some embodiments, $R^1$ is a saturated or unsaturated, straight or branched $C_{17}$ hydrocarbon chain optionally substituted with 1-6 fluorine atoms. In some embodiments, $R^1$ is a saturated or unsaturated, straight or branched Cis hydrocarbon chain optionally substituted with 1-6 fluorine atoms. In some embodiments, $R^1$ is a saturated or unsaturated, straight or branched $C_{19}$ hydrocarbon chain optionally substituted with 1-6 fluorine atoms. In some embodiments, $R^1$ is a saturated or unsaturated, straight or branched $C_{20}$ hydrocarbon chain optionally substituted with 1-6 fluorine atoms.

In some embodiments, $R^1$ is a saturated or unsaturated, straight or branched $C_1$-$C_{20}$ hydrocarbon chain substituted with 1-6 fluorine atoms. In some embodiments, $R^1$ is a saturated or unsaturated, straight or branched $C_1$-$C_{15}$ hydrocarbon chain substituted with 1-6 fluorine atoms.

In some embodiments, $R^1$ is a saturated or unsaturated, straight or branched $C_1$-$C_{12}$ hydrocarbon chain substituted with 1-6 fluorine atoms. In some embodiments, $R^1$ is a saturated or unsaturated, straight or branched $C_1$-$C_9$ hydrocarbon chain substituted with 1-6 fluorine atoms. In some embodiments, $R^1$ is a saturated or unsaturated, straight or branched $C_1$-$C_6$ hydrocarbon chain substituted with 1-6 fluorine atoms. In some embodiments, $R^1$ is a saturated or unsaturated, straight or branched $C_6$-$C_{20}$ hydrocarbon chain substituted with 1-6 fluorine atoms. In some embodiments, $R^1$ is a saturated or unsaturated, straight or branched $C_9$-$C_{20}$ hydrocarbon chain substituted with 1-6 fluorine atoms. In some embodiments, $R^1$ is a saturated or unsaturated, straight or branched $C_{12}$-$C_{20}$ hydrocarbon chain substituted with 1-6 fluorine atoms. In some embodiments, $R^1$ is a saturated or unsaturated, straight or branched $C_{15}$-$C_{20}$ hydrocarbon chain substituted with 1-6 fluorine atoms. In some embodiments, $R^1$ is a saturated or unsaturated, straight or branched $C_6$-$C_{15}$ hydrocarbon chain substituted with 1-6 fluorine atoms.

In some embodiments, $R^1$ is a saturated or unsaturated, straight or branched $C_6$ hydrocarbon chain substituted with 1-6 fluorine atoms. In some embodiments, $R^1$ is a saturated or unsaturated, straight or branched $C_7$ hydrocarbon chain substituted with 1-6 fluorine atoms. In some embodiments, $R^1$ is a saturated or unsaturated, straight or branched $C_8$ hydrocarbon chain substituted with 1-6 fluorine atoms. In some embodiments, $R^1$ is a saturated or unsaturated, straight or branched $C_9$ hydrocarbon chain substituted with 1-6 fluorine atoms. In some embodiments, $R^1$ is a saturated or unsaturated, straight or branched $C_{10}$ hydrocarbon chain substituted with 1-6 fluorine atoms. In some embodiments, $R^1$ is a saturated or unsaturated, straight or branched $C_{11}$ hydrocarbon chain substituted with 1-6 fluorine atoms. In some embodiments, $R^1$ is a saturated or unsaturated, straight or branched $C_{12}$ hydrocarbon chain substituted with 1-6 fluorine atoms. In some embodiments, $R^1$ is a saturated or unsaturated, straight or branched $C_{13}$ hydrocarbon chain substituted with 1-6 fluorine atoms. In some embodiments, $R^1$ is a saturated or unsaturated, straight or branched $C_{14}$ hydrocarbon chain substituted with 1-6 fluorine atoms. In some embodiments, $R^1$ is a saturated or unsaturated, straight or branched $C_{15}$ hydrocarbon chain substituted with 1-6 fluorine atoms. In some embodiments, $R^1$ is a saturated or unsaturated, straight or branched $C_{16}$ hydrocarbon chain substituted with 1-6 fluorine atoms. In some embodiments, $R^1$ is a saturated or unsaturated, straight or branched $C_{17}$ hydrocarbon chain substituted with 1-6 fluorine atoms. In some embodiments, $R^1$ is a saturated or unsaturated, straight or branched $C_{18}$ hydrocarbon chain substituted with 1-6 fluorine atoms. In some embodiments, $R^1$ is a saturated or unsaturated, straight or branched $C_{19}$ hydrocarbon chain substituted with 1-6 fluorine atoms. In some embodiments, $R^1$ is a saturated or unsaturated, straight or branched $C_{20}$ hydrocarbon chain substituted with 1-6 fluorine atoms.

In some embodiments, $R^1$ is

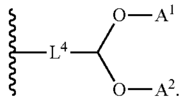

In some embodiments of any of Formulae described herein, $Cy^B$ is an optionally substituted ring selected from 3- to 12-membered saturated or partially unsaturated carbocyclyl, 1-adamantyl, 2-adamantyl,

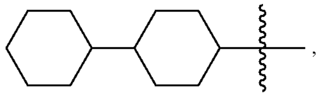 [SMILES: *C1CCC(C2CCCCC2)CC1]

sterolyl, and phenyl.

In some embodiments, $Cy^B$ is optionally substituted 3- to 12-membered saturated or partially unsaturated carbocyclyl. In some embodiments, $Cy^B$ is optionally substituted 3- to 7-membered saturated or partially unsaturated carbocyclyl. In some embodiments, $Cy^B$ is optionally substituted 5- to 6-membered saturated or partially unsaturated carbocyclyl. In some embodiments, $Cy^B$ is optionally substituted cyclopropyl. In some embodiments, $Cy^B$ is optionally substituted cyclobutyl. In some embodiments, $Cy^B$ is optionally substituted cyclopentyl. In some embodiments, $Cy^B$ is optionally substituted cyclohexyl. In some embodiments, $Cy^B$ is optionally substituted cycloheptyl. In some embodiments, $Cy^B$ is optionally substituted cyclododecanyl. In some embodiments, $R^1$ is cyclohexyl, optionally substituted with $C_1$-$C_6$ aliphatic.

In some embodiments, $Cy^B$ is optionally substituted 1-adamantyl. In some embodiments, $Cy^B$ is optionally substituted 2-adamantyl. In some embodiments, $Cy^B$ is optionally substituted

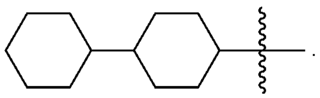 [SMILES: *C1CCC(C2CCCCC2)CC1]

In some embodiments, $Cy^B$ is optionally substituted sterolyl. In some embodiments, $Cy^B$ is optionally substituted cholesterolyl. In some embodiments, $Cy^B$ is optionally substituted phenyl.

In some embodiments of any of Formulae described herein, p is 0, 1, 2, or 3. In some embodiments, p is 0. In some embodiments, p is 1. In some embodiments, p is 2. In some embodiments, p is 3.

In some embodiments, $R^1$ is selected from:

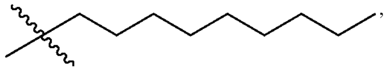

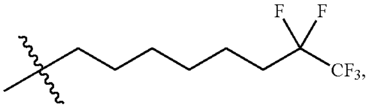

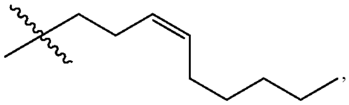

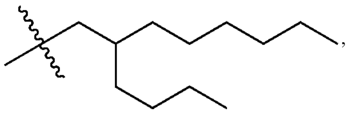

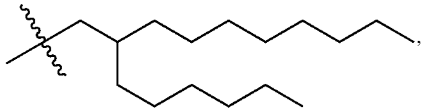

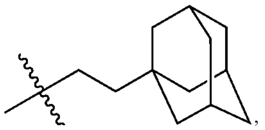

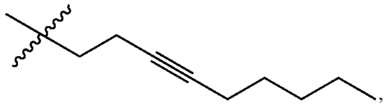

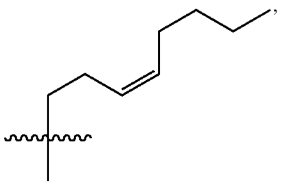

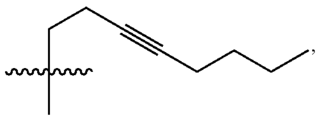

-continued

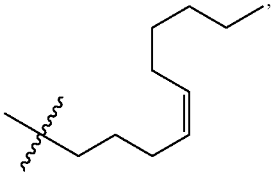,

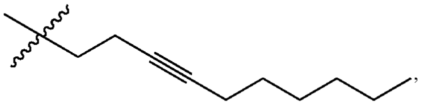,

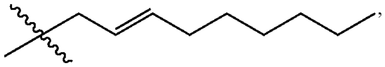,

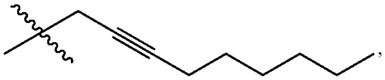,

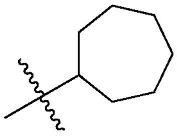, 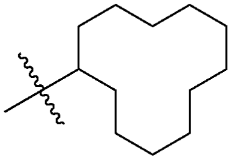,

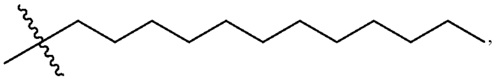,

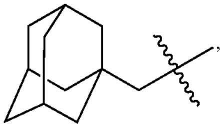, 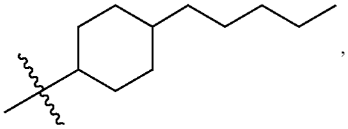,

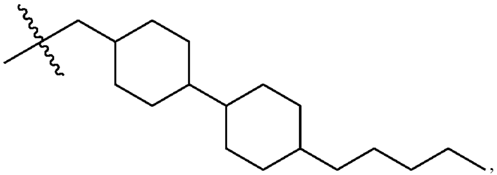,

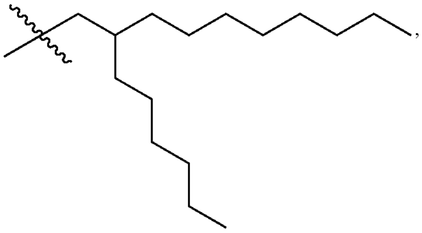,

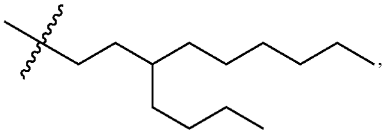,

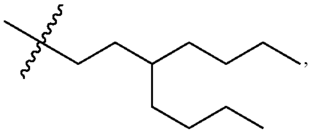,

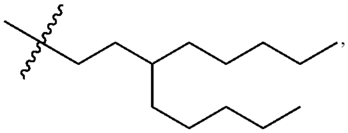,

-continued

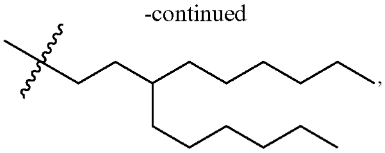,

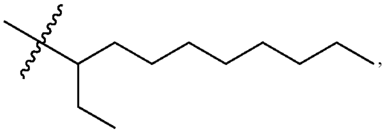,

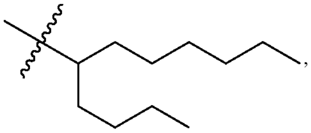,

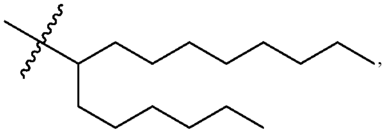,

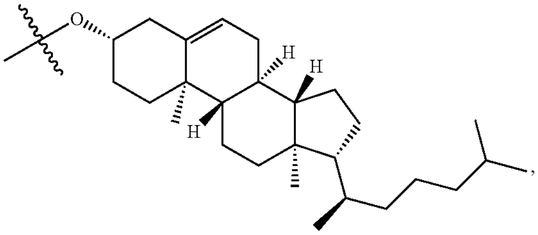, and

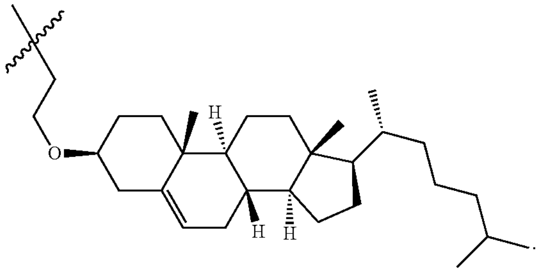.

In some embodiments of any Formulae described herein, each $L^4$ is independently a bivalent saturated or unsaturated, straight or branched $C_1$-$C_6$ hydrocarbon chain. In some embodiments, each $L^4$ is independently a bivalent saturated or unsaturated, straight or branched $C_1$-$C_5$ hydrocarbon chain. In some embodiments, each $L^4$ is independently a bivalent saturated or unsaturated, straight or branched $C_1$-$C_4$ hydrocarbon chain. In some embodiments, each $L^4$ is independently a bivalent saturated or unsaturated, straight or branched $C_1$-$C_3$ hydrocarbon chain. In some embodiments, each $L^4$ is independently $-CH_2-$, $-CH_2CH_2-$, or $-CH_2CH_2CH_2-$. In some embodiments, each $L^4$ is $-CH_2-$. In some embodiments, each $L^4$ is $-CH_2CH_2-$. In some embodiments, each $L^4$ is $-CH_2CH_2CH_2-$.

In some embodiments of any Formulae described herein, each $A^1$ and $A^2$ is independently an optionally substituted $C_1$-$C_{20}$ aliphatic or $-L^5-R^5$;

or $A^1$ and $A^2$, together with their intervening atoms, may form an optionally substituted ring:

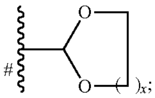;

wherein x and # are as described above and herein.

In some embodiments, $A^1$ and $A^2$ are the same. In some embodiments, $A^1$ and $A^2$ are different.

In some embodiments, $A^1$ is an optionally substituted $C_1$-$C_{20}$ aliphatic. In some embodiments, $A^1$ is an optionally substituted $C_1$-$C_{15}$ aliphatic. In some embodiments, $A^1$ an optionally substituted $C_1$-$C_{12}$ aliphatic. In some embodiments, $A^1$ an optionally substituted $C_1$-$C_9$ aliphatic. In some embodiments, $A^1$ is an optionally substituted $C_1$-$C_6$ aliphatic. In some embodiments, $A^1$ is an optionally substituted $C_6$-$C_{20}$ aliphatic. In some embodiments, $A^1$ is an optionally substituted $C_6$-$C_{12}$ aliphatic. In some embodiments, $A^1$ is an optionally substituted $C_{12}$-$C_{20}$ aliphatic. In some embodiments, $A^1$ is an optionally substituted $C_{15}$-$C_{20}$ aliphatic. In some embodiments, $A^1$ an optionally substituted $C_6$ aliphatic. In some embodiments, $A^1$ is an optionally substituted $C_7$ aliphatic. In some embodiments, $A^1$ an optionally substituted $C_8$ aliphatic. In some embodiments, $A^1$ an optionally substituted $C_9$ aliphatic. In some embodiments, $A^1$ is an optionally substituted $C_{10}$ aliphatic. In some embodiments, $A^1$ is an optionally substituted $C_{11}$ aliphatic. In some embodiments, $A^1$ is an optionally substituted $C_{12}$ aliphatic. In some embodiments, $A^1$ is an optionally substituted $C_{13}$ aliphatic. In some embodiments, $A^1$ is an optionally substituted $C_{14}$ aliphatic. In some embodiments, $A^1$ is an optionally substituted $C_{15}$ aliphatic. In some embodiments, $A^1$ an optionally substituted $C_{16}$ aliphatic.

In some embodiments, $A^1$ is a $C_1$-$C_{20}$ aliphatic. In some embodiments, $A^1$ is a $C_1$-$C_{15}$ aliphatic. In some embodiments, $A^1$ is a $C_1$-$C_{12}$ aliphatic. In some embodiments, $A^1$ is a $C_1$-$C_9$ aliphatic. In some embodiments, $A^1$ is a $C_1$-$C_6$ aliphatic. In some embodiments, $A^1$ is a $C_6$-$C_{20}$ aliphatic. In some embodiments, $A^1$ is a $C_6$-$C_{12}$ aliphatic. In some embodiments, $A^1$ is a $C_{12}$-$C_{20}$ aliphatic. In some embodiments, $A^1$ is a $C_{15}$-$C_{20}$ aliphatic. In some embodiments, $A^1$ is a $C_6$ aliphatic. In some embodiments, $A^1$ is a $C_7$ aliphatic. In some embodiments, $A^1$ is a $C_8$ aliphatic. In some embodiments, $A^1$ is a $C_9$ aliphatic. In some embodiments, $A^1$ is a $C_{10}$ aliphatic. In some embodiments, $A^1$ is a $C_{11}$ aliphatic. In some embodiments, $A^1$ is a $C_{12}$ aliphatic. In some embodiments, $A^1$ is a $C_{13}$ aliphatic. In some embodiments, $A^1$ is a $C_{14}$ aliphatic. In some embodiments, $A^1$ is a $C_{15}$ aliphatic. In some embodiments, $A^1$ is a $C_{16}$ aliphatic.

In some embodiments, $A^1$ is a $C_2$-$C_{20}$ alkenyl. In some embodiments, $A^1$ is a $C_2$-$C_{15}$ alkenyl. In some embodiments, $A^1$ is a $C_2$-$C_{12}$ alkenyl. In some embodiments, $A^1$ is a $C_2$-$C_9$ alkenyl. In some embodiments, $A^1$ is a $C_2$-$C_6$ alkenyl. In some embodiments, $A^1$ is a $C_6$-$C_{10}$ alkenyl. In some embodiments, $A^1$ is a $C_7$-$C_9$ alkenyl. In some embodiments, $A^1$ is a $C_6$-$C_{20}$ alkenyl. In some embodiments, $A^1$ is a $C_6$-$C_{12}$ alkenyl. In some embodiments, $A^1$ is a $C_{12}$-$C_{20}$ alkenyl. In some embodiments, $A^1$ is a $C_{15}$-$C_{20}$ alkenyl. In some embodiments, $A^1$ is a $C_6$ alkenyl. In some embodiments, $A^1$ is a $C_7$ alkenyl. In some embodiments, $A^1$ is a $C_8$ alkenyl. In some embodiments, $A^1$ is a $C_9$ alkenyl. In some embodiments, $A^1$ is a $C_{10}$ alkenyl. In some embodiments, $A^1$ is a $C_{11}$ alkenyl. In some embodiments, $A^1$ is a $C_{12}$ alkenyl. In some embodiments, $A^1$ is a $C_{13}$ alkenyl. In some embodiments, $A^1$ is a $C_{14}$ alkenyl. In some embodiments, $A^1$ is a $C_{15}$ alkenyl. In some embodiments, $A^1$ is a $C_{16}$ alkenyl.

In some embodiments, $A^1$ is a $C_1$-$C_{20}$ aliphatic, optionally substituted with 1-6 halogen atoms. In some embodiments, $A^1$ is a $C_1$-$C_{15}$ aliphatic, optionally substituted with 1-6 halogen atoms. In some embodiments, $A^1$ is a $C_1$-$C_{12}$ aliphatic, optionally substituted with 1-6 halogen atoms. In some embodiments, $A^1$ is a $C_1$-$C_9$ aliphatic, optionally substituted with 1-6 halogen atoms. In some embodiments, $A^1$ is a $C_1$-$C_6$ aliphatic, optionally substituted with 1-6 halogen atoms. In some embodiments, $A^1$ is a $C_6$-$C_{20}$ aliphatic, optionally substituted with 1-6 halogen atoms. In some embodiments, $A^1$ is a $C_6$-$C_{12}$ aliphatic, optionally substituted with 1-6 halogen atoms. In some embodiments, $A^1$ is a $C_{12}$-$C_{20}$ aliphatic, optionally substituted with 1-6 halogen atoms. In some embodiments, $A^1$ is a $C_{15}$-$C_{20}$ aliphatic, optionally substituted with 1-6 halogen atoms. In some embodiments, $A^1$ is a $C_6$ aliphatic, optionally substituted with 1-6 halogen atoms. In some embodiments, $A^1$ is a $C_7$ aliphatic, optionally substituted with 1-6 halogen atoms. In some embodiments, $A^1$ is a $C_8$ aliphatic, optionally substituted with 1-6 halogen atoms. In some embodiments, $A^1$ is a $C_9$ aliphatic, optionally substituted with 1-6 halogen atoms. In some embodiments, $A^1$ is a $C_{10}$ aliphatic, optionally substituted with 1-6 halogen atoms. In some embodiments, $A^1$ is a $C_{11}$ aliphatic, optionally substituted with 1-6 halogen atoms. In some embodiments, $A^1$ is a $C_{12}$ aliphatic, optionally substituted with 1-6 halogen atoms. In some embodiments, $A^1$ is a $C_{13}$ aliphatic, optionally substituted with 1-6 halogen atoms. In some embodiments, $A^1$ is a $C_{14}$ aliphatic, optionally substituted with 1-6 halogen atoms. In some embodiments, $A^1$ is a $C_{15}$ aliphatic, optionally substituted with 1-6 halogen atoms. In some embodiments, $A^1$ is a $C_{16}$ aliphatic, optionally substituted with 1-6 halogen atoms.

In some embodiments, $A^1$ is a $C_1$-$C_{20}$ aliphatic, optionally substituted with 1-6 fluorine atoms. In some embodiments, $A^1$ is a $C_1$-$C_{15}$ aliphatic, optionally substituted with 1-6 fluorine atoms. In some embodiments, $A^1$ is a $C_1$-$C_{12}$ aliphatic, optionally substituted with 1-6 fluorine atoms. In some embodiments, $A^1$ is a $C_1$-$C_9$ aliphatic, optionally substituted with 1-6 fluorine atoms. In some embodiments, $A^1$ is a $C_1$-$C_6$ aliphatic, optionally substituted with 1-6 fluorine atoms. In some embodiments, $A^1$ is a $C_6$-$C_{20}$ aliphatic, optionally substituted with 1-6 fluorine atoms. In some embodiments, $A^1$ is a $C_6$-$C_{12}$ aliphatic, optionally substituted with 1-6 fluorine atoms. In some embodiments, $A^1$ is a $C_{12}$-$C_{20}$ aliphatic, optionally substituted with 1-6 fluorine atoms. In some embodiments, $A^1$ is a $C_{15}$-$C_{20}$ aliphatic, optionally substituted with 1-6 fluorine atoms. In some embodiments, $A^1$ is a $C_6$ aliphatic, optionally substituted with 1-6 fluorine atoms. In some embodiments, $A^1$ is a $C_7$ aliphatic, optionally substituted with 1-6 fluorine atoms. In some embodiments, $A^1$ is a $C_1$ aliphatic, optionally substituted with 1-6 fluorine atoms. In some embodiments, $A^1$ is a $C_9$ aliphatic, optionally substituted with 1-6 fluorine atoms. In some embodiments, $A^1$ is a $C_{10}$ aliphatic, optionally substituted with 1-6 fluorine atoms. In some embodiments, $A^1$ is a $C_{11}$ aliphatic, optionally substituted with 1-6 fluorine atoms. In some embodiments, $A^1$ is a $C_{12}$ aliphatic, optionally substituted with 1-6 fluorine atoms. In some embodiments, $A^1$ is a $C_{13}$ aliphatic, optionally substituted with 1-6 fluorine atoms. In some embodiments, $A^1$ is a $C_{14}$ aliphatic, optionally substituted with 1-6 fluorine atoms. In some embodiments, $A^1$ is a $C_{15}$ aliphatic, optionally substituted with 1-6 fluorine atoms. In some embodiments, $A^1$ is a $C_{16}$ aliphatic, optionally substituted with 1-6 fluorine atoms.

In some embodiments, $A^1$ is a $C_1$-$C_{20}$ aliphatic, substituted with 1-6 fluorine atoms. In some embodiments, $A^1$ is a $C_1$-$C_{15}$ aliphatic, substituted with 1-6 fluorine atoms. In some embodiments, $A^1$ is a $C_1$-$C_{12}$ aliphatic, substituted with 1-6 fluorine atoms. In some embodiments, $A^1$ is a $C_1$-$C_9$ aliphatic, substituted with 1-6 fluorine atoms. In some embodiments, $A^1$ is a $C_1$-$C_6$ aliphatic, substituted with 1-6 fluorine atoms. In some embodiments, $A^1$ is a $C_6$-$C_{20}$ aliphatic, substituted with 1-6 fluorine atoms. In some embodiments, $A^1$ is a $C_6$-$C_{12}$ aliphatic, substituted with 1-6 fluorine atoms. In some embodiments, $A^1$ is a $C_{12}$-$C_{20}$ aliphatic, substituted with 1-6 fluorine atoms. In some embodiments, $A^1$ is a $C_{15}$-$C_{20}$ aliphatic, substituted with 1-6 fluorine atoms. In some embodiments, $A^1$ is a $C_6$ aliphatic, substituted with 1-6 fluorine atoms. In some embodiments, $A^1$ is a $C_7$ aliphatic, substituted with 1-6 fluorine atoms. In some embodiments, $A^1$ is a $C_8$ aliphatic, substituted with 1-6 fluorine atoms. In some embodiments, $A^1$ is a $C_9$ aliphatic, substituted with 1-6 fluorine atoms. In some embodiments, $A^1$ is a $C_{10}$ aliphatic, substituted with 1-6 fluorine atoms. In some embodiments, $A^1$ is a $C_{11}$ aliphatic, substituted with 1-6 fluorine atoms. In some embodiments, $A^1$ is a $C_{12}$ aliphatic, substituted with 1-6 fluorine atoms. In some embodiments, $A^1$ is a $C_{13}$ aliphatic, substituted with 1-6 fluorine atoms. In some embodiments, $A^1$ is a $C_{14}$ aliphatic, substituted with 1-6 fluorine atoms. In some embodiments, $A^1$ is a Cis aliphatic, substituted with 1-6 fluorine atoms. In some embodiments, $A^1$ is a $C_{16}$ aliphatic, substituted with 1-6 fluorine atoms.

In some embodiments, $A^1$ is:

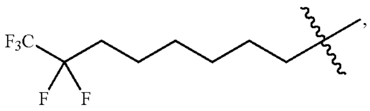,

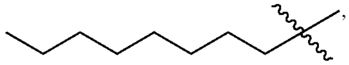,

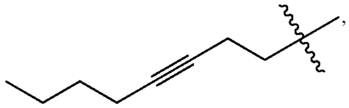,

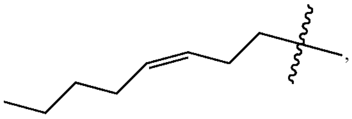,

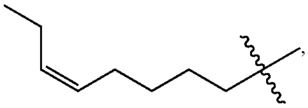,

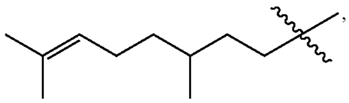,

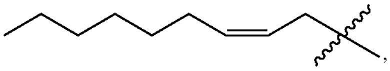,

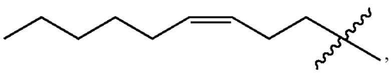,

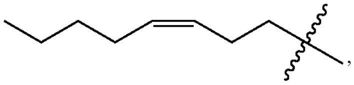,

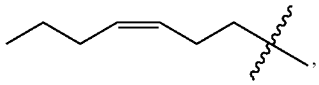,

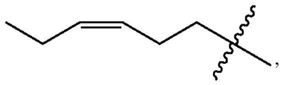,

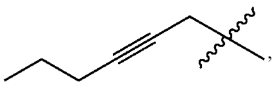,

-continued

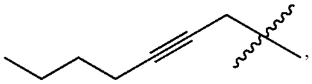,

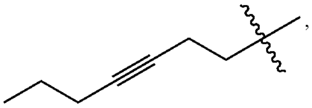,

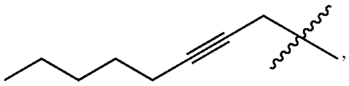,

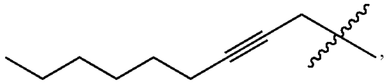,

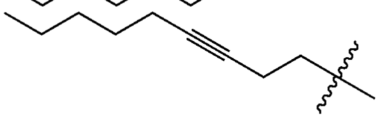,

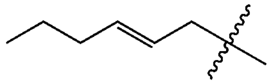,

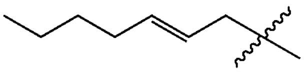,

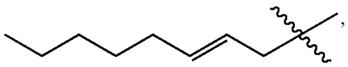,

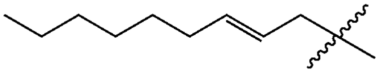, or

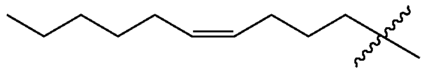.

In some embodiments, $A^1$ is

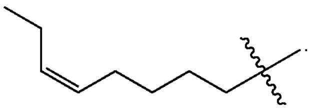 [SMILES: *CCCC/C=C\CC].

In some embodiments, $A^1$ is

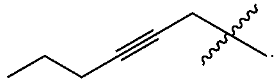 [SMILES: *CC#CCCC].

In some embodiments, $A^1$ is

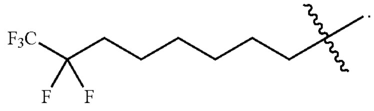 [SMILES: *CCCCCCC(F)(F)C(F)(F)F].

In some embodiments, $A^2$ is an optionally substituted $C_1$-$C_{20}$ aliphatic. In some embodiments, $A^2$ is an optionally substituted $C_1$-$C_{15}$ aliphatic. In some embodiments, $A^2$ is an optionally substituted $C_1$-$C_{12}$ aliphatic. In some embodiments, $A^2$ an optionally substituted $C_1$-$C_9$ aliphatic. In some embodiments, $A^2$ is an optionally substituted $C_1$-$C_6$ aliphatic. In some embodiments, $A^2$ is an optionally substituted $C_6$-$C_{20}$ aliphatic. In some embodiments, $A^2$ is an optionally substituted $C_6$-$C_{12}$ aliphatic. In some embodiments, $A^2$ is an optionally substituted $C_{12}$-$C_{20}$ aliphatic. In some embodiments, $A^2$ is an optionally substituted $C_{15}$-$C_{20}$ aliphatic. In some embodiments, $A^2$ an optionally substituted $C_6$ aliphatic. In some embodiments, $A^2$ is an optionally substituted $C_7$ aliphatic. In some embodiments, $A^2$ an optionally substituted $C_8$ aliphatic. In some embodiments, $A^2$ an optionally substituted $C_9$ aliphatic. In some embodiments, $A^2$ is an optionally substituted $C_{10}$ aliphatic. In some embodiments, $A^2$ is an optionally substituted $C_{11}$ aliphatic. In some embodiments, $A^2$ is an optionally substituted $C_{12}$ aliphatic. In some embodiments, $A^2$ is an optionally substituted $C_{13}$ aliphatic. In some embodiments, $A^2$ is an optionally substituted $C_{14}$ aliphatic. In some embodiments, $A^2$ is an optionally substituted $C_{15}$ aliphatic. In some embodiments, $A^2$ an optionally substituted $C_{16}$ aliphatic.

In some embodiments, $A^2$ is a $C_1$-$C_{20}$ aliphatic. In some embodiments, $A^2$ is a $C_1$-$C_{15}$ aliphatic. In some embodiments, $A^2$ is a $C_1$-$C_{12}$ aliphatic. In some embodiments, $A^2$ is a $C_1$-$C_9$ aliphatic. In some embodiments, $A^2$ is a $C_1$-$C_6$ aliphatic. In some embodiments, $A^2$ is a $C_6$-$C_{20}$ aliphatic. In some embodiments, $A^2$ is a $C_6$-$C_{12}$ aliphatic. In some embodiments, $A^2$ is a $C_{12}$-$C_{20}$ aliphatic. In some embodiments, $A^2$ is a $C_{15}$-$C_{20}$ aliphatic. In some embodiments, $A^2$ is a $C_6$ aliphatic. In some embodiments, $A^2$ is a $C_7$ aliphatic. In some embodiments, $A^2$ is a $C_8$ aliphatic. In some embodiments, $A^2$ is a $C_9$ aliphatic. In some embodiments, $A^2$ is a $C_{10}$ aliphatic. In some embodiments, $A^2$ is a $C_{11}$ aliphatic. In some embodiments, $A^2$ is a $C_{12}$ aliphatic. In some embodiments, $A^2$ is a $C_{13}$ aliphatic. In some embodiments, $A^2$ is a $C_{14}$ aliphatic. In some embodiments, $A^2$ is a $C_{15}$ aliphatic. In some embodiments, $A^2$ is a $C_{16}$ aliphatic.

In some embodiments, $A^2$ is a $C_2$-$C_{20}$ alkenyl. In some embodiments, $A^2$ is a $C_2$-$C_{15}$ alkenyl. In some embodiments, $A^2$ is a $C_2$-$C_{12}$ alkenyl. In some embodiments, $A^2$ is a $C_2$-$C_9$ alkenyl. In some embodiments, $A^2$ is a $C_2$-$C_6$ alkenyl. In some embodiments, $A^2$ is a $C_6$-$C_{10}$ alkenyl. In some embodiments, $A^2$ is a $C_7$-$C_9$ alkenyl. In some embodiments, $A^2$ is a $C_6$-$C_{20}$ alkenyl. In some embodiments, $A^2$ is a $C_6$-$C_{12}$ alkenyl. In some embodiments, $A^2$ is a $C_{12}$-$C_{20}$ alkenyl. In some embodiments, $A^2$ is a $C_{15}$-$C_{20}$ alkenyl. In some embodiments, $A^2$ is a $C_6$ alkenyl. In some embodiments, $A^2$ is a $C_7$ alkenyl. In some embodiments, $A^2$ is a $C_8$ alkenyl. In some embodiments, $A^2$ is a $C_9$ alkenyl. In some embodiments, $A^2$ is a $C_{10}$ alkenyl. In some embodiments, $A^2$ is a $C_{11}$ alkenyl. In some embodiments, $A^2$ is a $C_{12}$ alkenyl. In some embodiments, $A^2$ is a $C_{13}$ alkenyl. In some embodiments, $A^2$ is a $C_{14}$ alkenyl. In some embodiments, $A^2$ is a $C_{15}$ alkenyl. In some embodiments, $A^2$ is a $C_{16}$ alkenyl.

In some embodiments, $A^2$ is a $C_1$-$C_{20}$ aliphatic, optionally substituted with 1-6 halogen atoms. In some embodiments, $A^2$ is a $C_1$-$C_{15}$ aliphatic, optionally substituted with 1-6 halogen atoms. In some embodiments, $A^2$ is a $C_1$-$C_{12}$ aliphatic, optionally substituted with 1-6 halogen atoms. In some embodiments, $A^2$ is a $C_1$-$C_9$ aliphatic, optionally substituted with 1-6 halogen atoms. In some embodiments, $A^2$ is a $C_1$-$C_6$ aliphatic, optionally substituted with 1-6 halogen atoms. In some embodiments, $A^2$ is a $C_6$-$C_{20}$ aliphatic, optionally substituted with 1-6 halogen atoms. In some embodiments, $A^2$ is a $C_6$-$C_{12}$ aliphatic, optionally substituted with 1-6 halogen atoms. In some embodiments, $A^2$ is a $C_{12}$-$C_{20}$ aliphatic, optionally substituted with 1-6 halogen atoms. In some embodiments, $A^2$ is a $C_{15}$-$C_{20}$ aliphatic, optionally substituted with 1-6 halogen atoms. In some embodiments, $A^2$ is a $C_6$ aliphatic, optionally substituted with 1-6 halogen atoms. In some embodiments, $A^2$ is a $C_7$ aliphatic, optionally substituted with 1-6 halogen atoms. In some embodiments, $A^2$ is a $C_9$ aliphatic, optionally substituted with 1-6 halogen atoms. In some embodiments, $A^2$ is a $C_9$ aliphatic, optionally substituted with 1-6 halogen atoms. In some embodiments, $A^2$ is a $C_{10}$ aliphatic, optionally substituted with 1-6 halogen atoms. In some embodiments, $A^2$ is a $C_{11}$ aliphatic, optionally substituted with 1-6 halogen atoms. In some embodiments, $A^2$ is a $C_{12}$ aliphatic, optionally substituted with 1-6 halogen atoms. In some embodiments, $A^2$ is a $C_{13}$ aliphatic, optionally substituted with 1-6 halogen atoms. In some embodiments, $A^2$ is a $C_{14}$ aliphatic, optionally substituted with 1-6 halogen atoms. In some embodiments, $A^2$ is a $C_{15}$ aliphatic, optionally substituted with 1-6 halogen atoms. In some embodiments, $A^2$ is a $C_{16}$ aliphatic, optionally substituted with 1-6 halogen atoms.

In some embodiments, $A^2$ is a $C_1$-$C_{20}$ aliphatic, optionally substituted with 1-6 fluorine atoms. In some embodiments, $A^2$ is a $C_1$-$C_{12}$ aliphatic, optionally substituted with 1-6 fluorine atoms. In some embodiments, $A^2$ is a $C_1$-$C_{12}$ aliphatic, optionally substituted with 1-6 fluorine atoms. In some embodiments, $A^2$ is a $C_1$-$C_9$ aliphatic, optionally substituted with 1-6 fluorine atoms. In some embodiments, $A^2$ is a $C_1$-$C_6$ aliphatic, optionally substituted with 1-6 fluorine atoms. In some embodiments, $A^2$ is a $C_6$-$C_{20}$ aliphatic, optionally substituted with 1-6 fluorine atoms. In some embodiments, $A^2$ is a $C_6$-$C_{12}$ aliphatic, optionally substituted with 1-6 fluorine atoms. In some embodiments, $A^2$ is a $C_{12}$-$C_{20}$ aliphatic, optionally substituted with 1-6 fluorine atoms. In some embodiments, $A^2$ is a $C_{15}$-$C_{20}$ aliphatic, optionally substituted with 1-6 fluorine atoms. In some embodiments, $A^1$ is a $C_6$ aliphatic, optionally substituted with 1-6 fluorine atoms. In some embodiments, $A^2$ is a $C_7$ aliphatic, optionally substituted with 1-6 fluorine atoms. In some embodiments, $A^2$ is a $C_8$ aliphatic, optionally substituted with 1-6 fluorine atoms. In some embodiments, $A^2$ is a $C_9$ aliphatic, optionally substituted with 1-6 fluorine atoms. In some embodiments, $A^2$ is a $C_{10}$ aliphatic, optionally substituted with 1-6 fluorine atoms. In some embodiments, $A^2$ is a $C_{11}$ aliphatic, optionally substituted with 1-6 fluorine atoms. In some embodiments, $A^2$ is a $C_{12}$ aliphatic, optionally substituted with 1-6 fluorine atoms. In some embodiments, $A^2$ is a $C_{13}$ aliphatic, optionally substituted with 1-6 fluorine atoms. In some embodiments, $A^2$ is a $C_{14}$ aliphatic, optionally substituted with 1-6 fluorine atoms. In some embodiments, $A^2$ is a $C_{15}$ aliphatic, optionally substituted with 1-6 fluorine atoms. In some embodiments, $A^2$ is a $C_{16}$ aliphatic, optionally substituted with 1-6 fluorine atoms.

In some embodiments, $A^2$ is a $C_1$-$C_{20}$ aliphatic, substituted with 1-6 fluorine atoms. In some embodiments, $A^2$ is a $C_1$-$C_{15}$ aliphatic, substituted with 1-6 fluorine atoms. In some embodiments, $A^2$ is a $C_1$-$C_{12}$ aliphatic, substituted with 1-6 fluorine atoms. In some embodiments, $A^2$ is a $C_1$-$C_9$ aliphatic, substituted with 1-6 fluorine atoms. In some embodiments, $A^2$ is a $C_1$-$C_6$ aliphatic, substituted with 1-6 fluorine atoms. In some embodiments, $A^2$ is a $C_6$-$C_{20}$ aliphatic, substituted with 1-6 fluorine atoms. In some embodiments, $A^2$ is a $C_6$-$C_{12}$ aliphatic, substituted with 1-6 fluorine atoms. In some embodiments, $A^2$ is a $C_{12}$-$C_{20}$ aliphatic, substituted with 1-6 fluorine atoms. In some embodiments, $A^2$ is a $C_{15}$-$C_{20}$ aliphatic, substituted with 1-6 fluorine atoms. In some embodiments, $A^2$ is a $C_6$ aliphatic, substituted with 1-6 fluorine atoms. In some embodiments, $A^2$ is a $C_7$ aliphatic, substituted with 1-6 fluorine atoms. In some embodiments, $A^2$ is a $C_8$ aliphatic, substituted with 1-6 fluorine atoms. In some embodiments, $A^2$ is a $C_9$ aliphatic, substituted with 1-6 fluorine atoms. In some embodiments, $A^2$ is a $C_{10}$ aliphatic, substituted with 1-6 fluorine atoms. In some embodiments, $A^2$ is a $C^{11}$ aliphatic, substituted with 1-6 fluorine atoms. In some embodiments, $A^2$ is a $C_{12}$ aliphatic, substituted with 1-6 fluorine atoms. In some embodiments, $A^2$ is a $C_{13}$ aliphatic, substituted with 1-6 fluorine atoms. In some embodiments, $A^2$ is a $C_{14}$ aliphatic, substituted with 1-6 fluorine atoms. In some embodiments, $A^2$ is a $C_{15}$ aliphatic, substituted with 1-6 fluorine atoms. In some embodiments, $A^2$ is a $C_{16}$ aliphatic, substituted with 1-6 fluorine atoms.

In some embodiments, $A^2$ is:

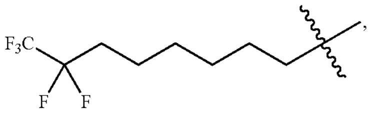
,
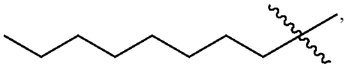
,
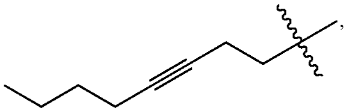
,
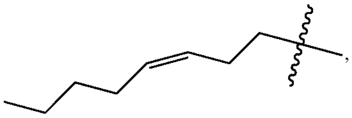
,
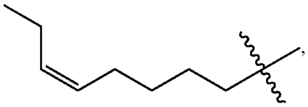
,
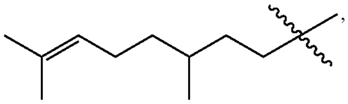
,
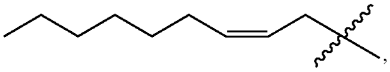
,
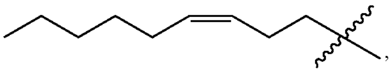
,
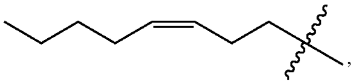
,
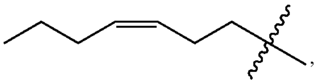
,
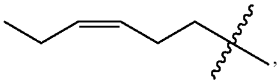
,
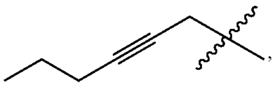
,
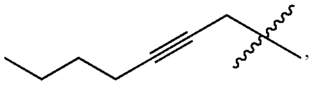
,
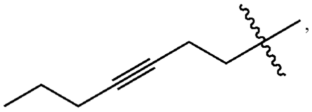
,
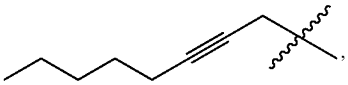
, -continued

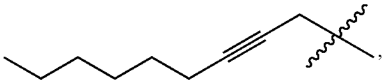
,
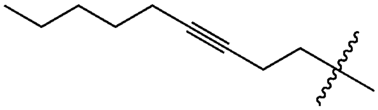
,
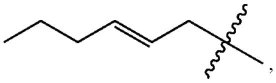
,
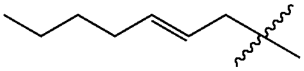
,
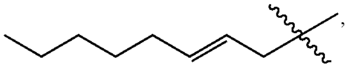
,
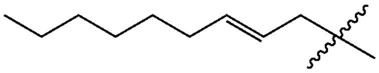
, or
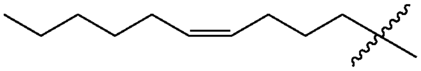
.

In some embodiments, $A^2$ is

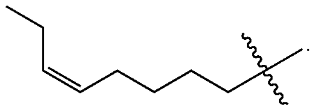 [SMILES: *CCCC/C=C\CC]
.

In some embodiments, $A^2$ is

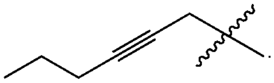 [SMILES: *CC#CCCC]
.

In some embodiments, $A^2$ is

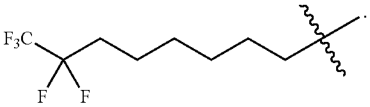 [SMILES: *CCCCCCC(F)(F)C(F)(F)F]
.

In some embodiments, $A^1$ is —$L^5$—$R^5$. In some embodiments, $A^2$ is —$L^5$—$R^5$.

In some embodiments, $A^1$ and $A^2$, together with their intervening atoms, may form an optionally substituted ring:

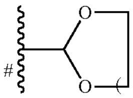
;

wherein x and # are as described above and herein.

In some embodiments, $A^1$ and $A^2$, together with their intervening atoms, may form an optionally substituted ring selected from the group consisting of:

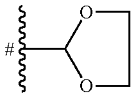 and 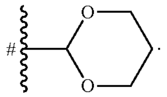

In some embodiments, $A^1$ and $A^2$, together with their intervening atoms, may form a ring selected from the group consisting of:

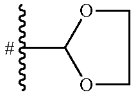 and 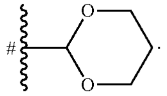

In some embodiments of any of Formulae described herein, each $L^5$ is independently a bivalent saturated or unsaturated, straight or branched $C_1$-$C_{20}$ hydrocarbon chain, wherein 1-3 methylene units are optionally and independently replaced with —O— or —NR—. In some embodiments, each $L^5$ is independently a bivalent saturated or unsaturated, straight or branched $C_1$-$C_{12}$ hydrocarbon chain, wherein 1-3 methylene units are optionally and independently replaced with —O— or —NR—. In some embodiments, each $L^5$ is independently a bivalent saturated or unsaturated, straight or branched $C_{12}$-$C_{20}$ hydrocarbon chain, wherein 1-3 methylene units are optionally and independently replaced with —O— or —NR—.

In some embodiments of any of Formulae described herein, each $L^5$ is independently a bivalent saturated or unsaturated, straight or branched $C_1$-$C_{20}$ hydrocarbon chain. In some embodiments, each $L^5$ is independently a bivalent saturated or unsaturated, straight or branched $C_1$-$C_{12}$ hydrocarbon chain. In some embodiments, each $L^5$ is independently a bivalent saturated or unsaturated, straight or branched $C_{12}$-$C_{20}$ hydrocarbon chain.

In some embodiments of any of Formulae described herein, each $R^5$ is independently an optionally substituted group selected from 6- to 10-membered aryl or saturated or partially unsaturated 3- to 8-membered carbocyclyl. In some embodiments, each $R^5$ is independently optionally substituted 6- to 10-membered aryl (e.g., phenyl). In some embodiments, each $R^5$ is independently optionally substituted saturated or partially unsaturated 3- to 8-membered carbocyclyl (e.g., cyclohexyl).

In some embodiments of any Formulae described herein, $X^1$ is a covalent bond, —O—, or —NR—. In some embodiments, $X^1$ is a covalent bond. In some embodiments, $X^1$ is —O—. In some embodiments, $X^1$ is —NR—. In some embodiments, $X^1$ is —NH—.

In some embodiments of any of Formulae described herein, $X^2$ is a covalent bond or an optionally substituted, bivalent saturated or unsaturated, straight or branched, $C_1$-$C_{12}$ hydrocarbon chain, wherein 1-3 methylene units are optionally and independently replaced with —O—, —NR—, or —$Cy^C$—.

In some embodiments, $X^2$ is a covalent bond.

In some embodiments, $X^2$ is an optionally substituted saturated or unsaturated, straight or branched $C_1$-$C_{12}$ hydrocarbon chain wherein 1-3 methylene units are optionally and independently replaced with —O—, —NR—, or —$Cy^C$—. In some embodiments, $X^2$ is an optionally substituted saturated or unsaturated, straight or branched $C_1$-$C_9$ hydrocarbon chain wherein 1-3 methylene units are optionally and independently replaced with —O—, —NR—, or —$Cy^C$—. In some embodiments, $X^2$ is an optionally substituted saturated or unsaturated, straight or branched $C_1$-$C_6$ hydrocarbon chain wherein 1-2 methylene units are optionally and independently replaced with —O—, —NR—, or —$Cy^C$—. In some embodiments, $X^2$ is an optionally substituted saturated or unsaturated, straight or branched $C_6$-$C_{12}$ hydrocarbon chain wherein 1-3 methylene units are optionally and independently replaced with —O—, —NR—, or —$Cy^C$—. In some embodiments, $X^2$ is an optionally substituted saturated or unsaturated, straight or branched $C_9$-$C_{12}$ hydrocarbon chain wherein 1-3 methylene units are optionally and independently replaced with —O—, —NR—, or —$Cy^C$—.

In some embodiments, $X^2$ is an optionally substituted bivalent saturated or unsaturated, straight or branched $C_1$-$C_{12}$ hydrocarbon chain, wherein 1-3 methylene units are optionally and independently replaced with —O— or —NR—. In some embodiments, $X^2$ is an optionally substituted bivalent saturated or unsaturated, straight or branched $C_1$-$C_6$ hydrocarbon chain, wherein 1-2 methylene units are optionally and independently replaced with —O— or —NR—. In some embodiments, $X^2$ is an optionally substituted bivalent saturated or unsaturated, straight or branched $C_1$-$C_{12}$ hydrocarbon chain, wherein 1-3 methylene units are optionally and independently replaced with —NR— (e.g., —N($C_{1-4}$ alkyl)-). In some embodiments, $X^2$ is an optionally substituted bivalent saturated or unsaturated, straight or branched $C_1$-$C_6$ hydrocarbon chain, wherein 1-2 methylene units are optionally and independently replaced with —NR— (e.g., —N($C_{1-4}$ alkyl)-). In some embodiments, $X^2$ is an optionally substituted bivalent saturated or unsaturated, straight or branched $C_1$-$C_{12}$ hydrocarbon chain, wherein 1-3 methylene units are optionally and independently replaced with —N($CH_3$)— or —N($CH_2CH_3$)—. In some embodiments, $X^2$ is an optionally substituted bivalent saturated or unsaturated, straight or branched $C_1$-$C_6$ hydrocarbon chain, wherein 1-2 methylene units are optionally and independently replaced with —N($CH_3$)— or —N($CH_2CH_3$)—.

In some embodiments, $X^2$ is an optionally substituted bivalent saturated or unsaturated, straight or branched $C_1$-$C_{12}$ hydrocarbon chain, wherein 1 methylene unit is optionally and independently replaced with —$Cy^C$— and 0-2 methylene units are optionally and independently replaced with —O— or —NR—. In some embodiments, $X^2$ is an optionally substituted bivalent saturated or unsaturated, straight or branched $C_1$-$C_{12}$ hydrocarbon chain, wherein 1 methylene unit is optionally and independently replaced with —$Cy^C$— (e.g.,

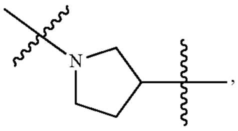, 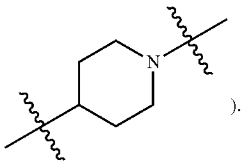).

In some embodiments, $X^2$ is an optionally substituted bivalent saturated or unsaturated, straight or branched $C_1$-$C_6$ hydrocarbon chain, wherein 1 methylene unit is optionally and independently replaced with —$Cy^C$— (e.g.,

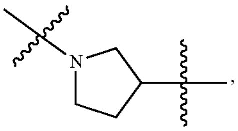,
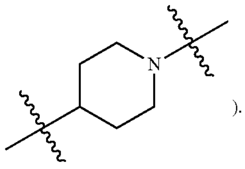
).

In some embodiments, $X^2$ is an optionally substituted bivalent saturated or unsaturated, straight or branched $C_1$-$C_{12}$ hydrocarbon chain. In some embodiments, $X^2$ is a bivalent saturated or unsaturated, straight or branched $C_1$-$C_{12}$ hydrocarbon chain. In some embodiments, $X^2$ is an optionally substituted bivalent saturated or unsaturated, straight or branched $C_1$-$C_6$ hydrocarbon chain. In some embodiments, $X^2$ is a bivalent saturated or unsaturated, straight or branched $C_1$-$C_6$ hydrocarbon chain. In some embodiments, $X^2$ is an optionally substituted bivalent saturated or unsaturated, straight or branched $C_1$-$C_4$ hydrocarbon chain. In some embodiments, $X^2$ is a bivalent saturated or unsaturated, straight or branched $C_1$-$C_4$ hydrocarbon chain. In some embodiments, $X^2$ is $—CH_2—$, $—CH_2CH_2—$, or $—CH_2CH_2CH_2—$.

In some embodiments of any Formulae described herein, $Cy^C$ is an optionally substituted ring selected from 3- to 7-membered saturated or partially unsaturated carbocyclene, phenylene, 3- to 7-membered saturated or partially unsaturated heterocyclene having 1-3 heteroatoms independently selected from nitrogen, oxygen, and sulfur, and 5- to 6-membered heteroarylene having 1-3 heteroatoms independently selected from nitrogen, oxygen, and sulfur.

In some embodiments, $Cy^C$ is optionally substituted 3- to 7-membered saturated or partially unsaturated carbocyclene. In some embodiments, $Cy^C$ is optionally substituted 5- to 6-membered saturated or partially unsaturated carbocyclene. In some embodiments, $Cy^C$ is optionally substituted 5- to 6-membered saturated carbocyclene. In some embodiments, $Cy^C$ is optionally substituted phenylene. In some embodiments, $Cy^C$ is optionally substituted 5- to 6-membered heteroarylene having 1-3 heteroatoms independently selected from nitrogen, oxygen, and sulfur.

In some embodiments, $Cy^C$ is optionally substituted 3- to 7-membered heterocyclene having 1-3 heteroatoms independently selected from nitrogen, oxygen, and sulfur. In some embodiments, $Cy^C$ is optionally substituted 5- to 6-membered heterocyclene having 1-2 heteroatoms independently selected from nitrogen, oxygen, and sulfur. In some embodiments, $Cy^C$ is optionally substituted 5-membered heterocyclene having 1-2 heteroatoms independently selected from nitrogen, oxygen, and sulfur. In some embodiments, $Cy^C$ is

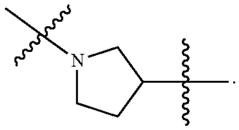 [SMILES: *C1CCN(*)C1]
.

In some embodiments, $Cy^C$ is optionally substituted 6-membered heterocyclene having 1-2 heteroatoms independently selected from nitrogen, oxygen, and sulfur. In some embodiments, $Cy^C$ is

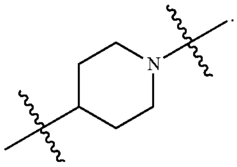 [SMILES: *C1CCN(*)CC1]
.

In some embodiments of any Formulae described herein, $X^3$ is hydrogen or an optionally substituted ring selected from 3- to 7-membered saturated or partially unsaturated carbocyclyl, phenyl, 3- to 7-membered saturated or partially unsaturated heterocyclyl having 1-3 heteroatoms independently selected from nitrogen, oxygen, and sulfur, or 5- to 6-membered heteroaryl having 1-3 heteroatoms independently selected from nitrogen, oxygen, and sulfur.

In some embodiments, $X^3$ is hydrogen. In some embodiments, $X^3$ is optionally substituted 3- to 7-membered saturated or partially unsaturated carbocyclyl. In some embodiments, $X^3$ is optionally substituted 5- to 6-membered saturated or partially unsaturated carbocyclyl. In some embodiments, $X^3$ is optionally substituted 5- to 6-membered saturated carbocyclyl. In some embodiments, $X^3$ is optionally substituted phenyl. In some embodiments, $X^3$ is optionally substituted 5- to 6-membered heteroaryl having 1-3 heteroatoms independently selected from nitrogen, oxygen, and sulfur.

In some embodiments, $X^3$ is optionally substituted 3- to 7-membered heterocyclyl having 1-3 heteroatoms independently selected from nitrogen, oxygen, and sulfur. In some embodiments, $X^3$ is optionally substituted 5- to 6-membered heterocyclyl having 1-2 heteroatoms independently selected from nitrogen, oxygen, and sulfur. In some embodiments, $X^3$ is optionally substituted 5-membered heterocyclyl having 1-2 heteroatoms independently selected from nitrogen, oxygen, and sulfur. In some embodiments, $X^3$ is optionally substituted 6-membered heterocyclyl having 1-2 heteroatoms independently selected from nitrogen, oxygen, and sulfur.

In some embodiments, $X^3$ is an optionally substituted ring selected from:

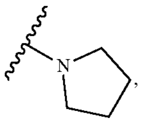,
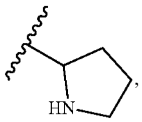,
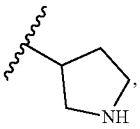,
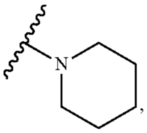,
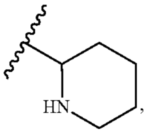,
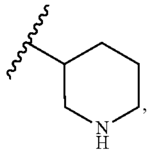,
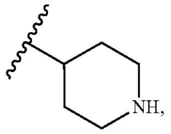,
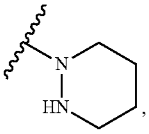,
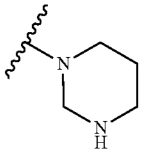, and
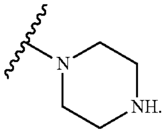.

In some embodiments, $X^3$ is ring selected from:
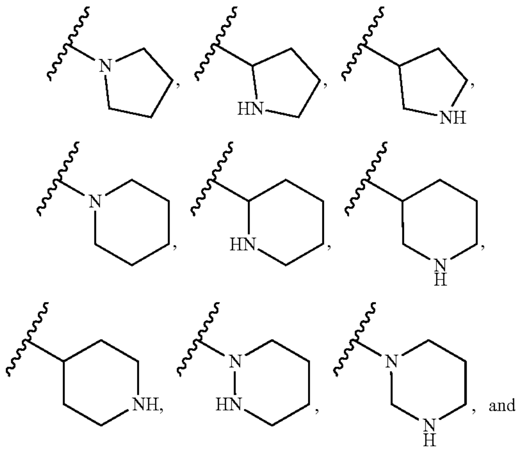
and
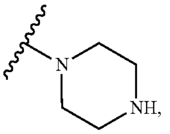
which is optionally substituted with $C_1$-$C_6$ aliphatic.
In some embodiments, $X^3$ is ring selected from:
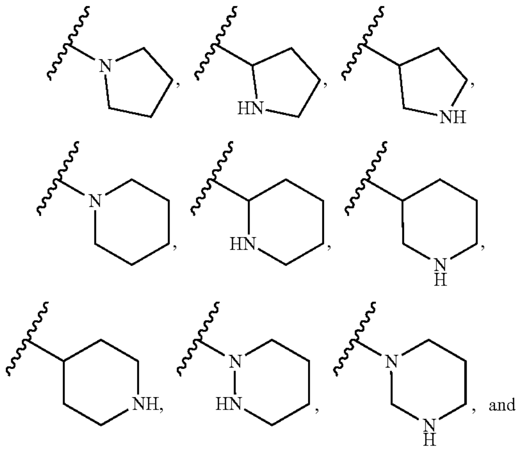
and
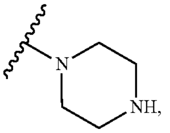
which is optionally substituted with methyl or ethyl.
In some embodiments, $X^3$ is selected from:
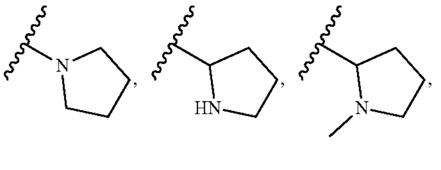
-continued
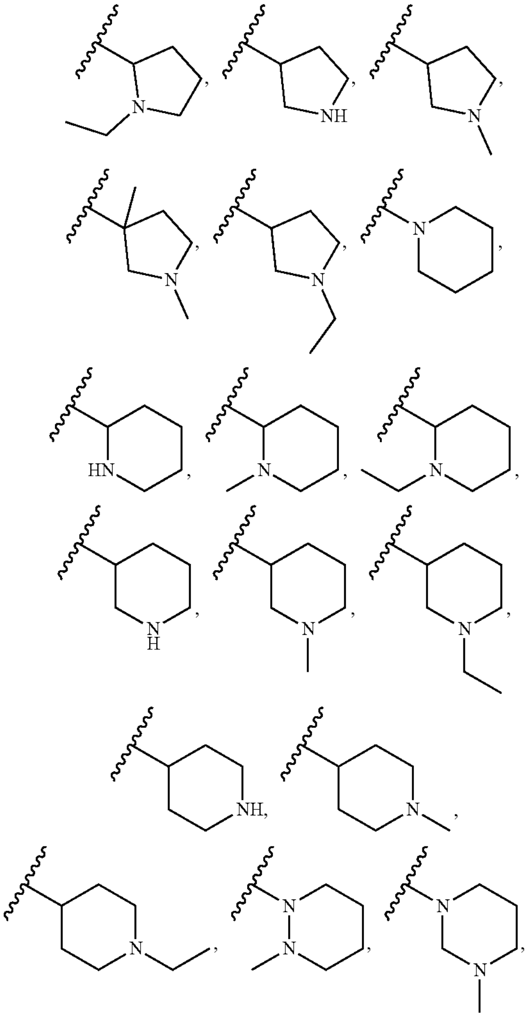
and
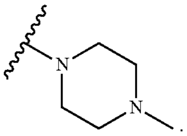
In some embodiments of any Formulae described herein, —$X^2$—$X^3$ is selected from:
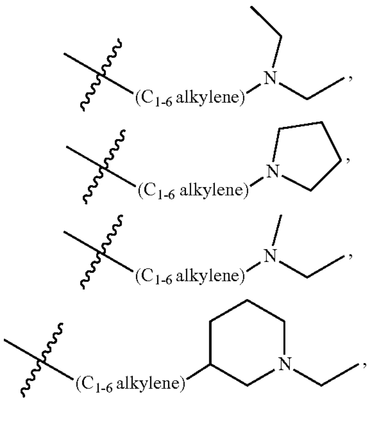
and -continued

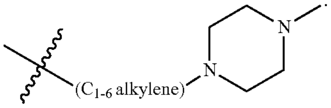

In some embodiments of any Formulae described herein, —$X^2$—$X^3$ is selected from:

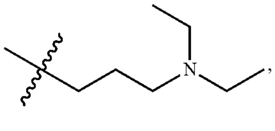
,
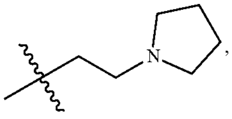
,
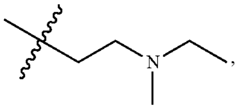
,
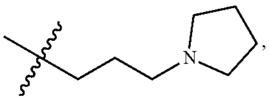
,
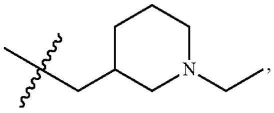
,
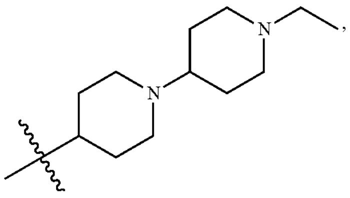
, and -continued

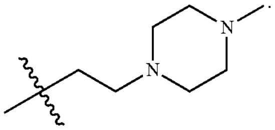

In some embodiments of any Formulae described herein, —$X^2$—$X^3$ is

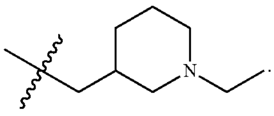 [SMILES: *CC1CCCN(CC)C1]

In some embodiments of any Formulae described herein, each R is independently hydrogen or an optionally substituted $C_1$-$C_6$ aliphatic group. In some embodiments, each R is hydrogen. In some embodiments, each R is independently an optionally substituted $C_1$-$C_6$ aliphatic group. In some embodiments, each R is independently an optionally substituted $C_1$-$C_6$ alkyl group. In some embodiments, each R is independently an optionally substituted $C_1$-$C_4$ alkyl group. In some embodiments, each R is independently an optionally substituted $C_1$-$C_2$ alkyl group. In some embodiments, each R is independently a $C_1$-$C_6$ alkyl group. In some embodiments, each R is independently a $C_1$-$C_4$ alkyl group. In some embodiments, each R is independently a $C_1$-$C_2$ alkyl group. In some embodiments, R is methyl. In some embodiments, R is ethyl.

In some embodiments of any Formulae described herein, n is 1, 2, 3 or 4. In some embodiments, n is 1. In some embodiments, n is 2. In some embodiments, n is 3. In some embodiments, n is 4.

In some embodiments, the present disclosure provides compounds selected from Table 1:

Example 4-1

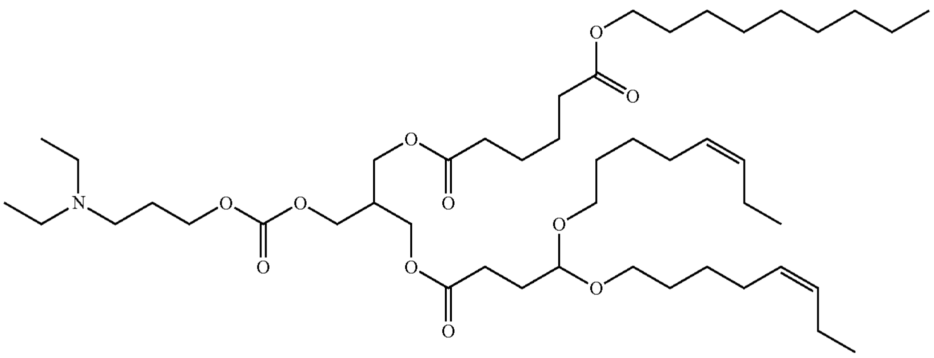

-continued
Example 4-2
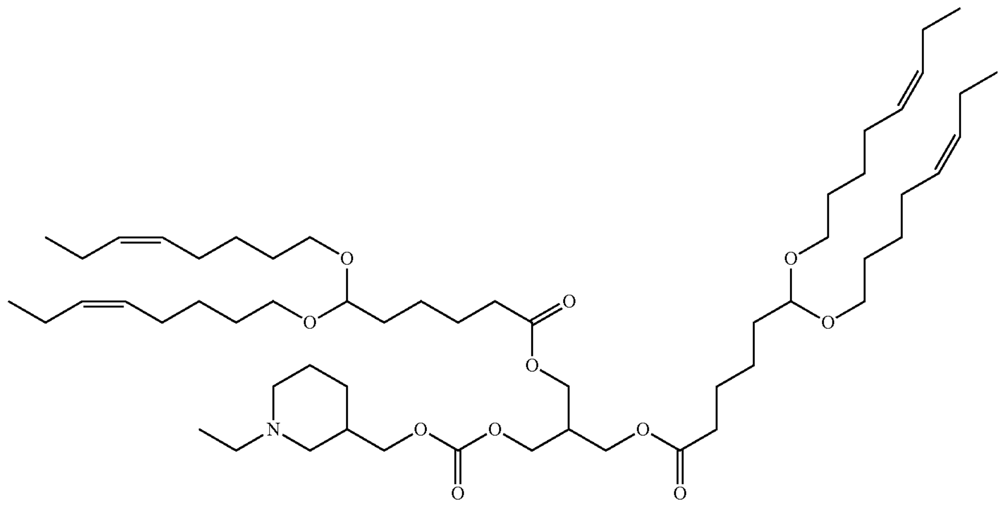
Example 4-3
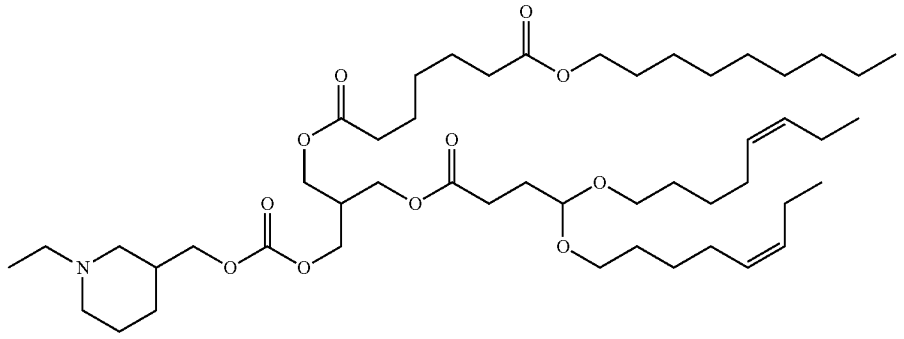
Example 4-4
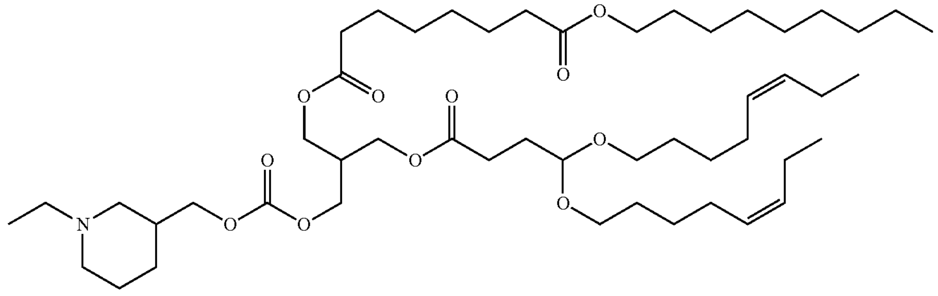
Example 4-5
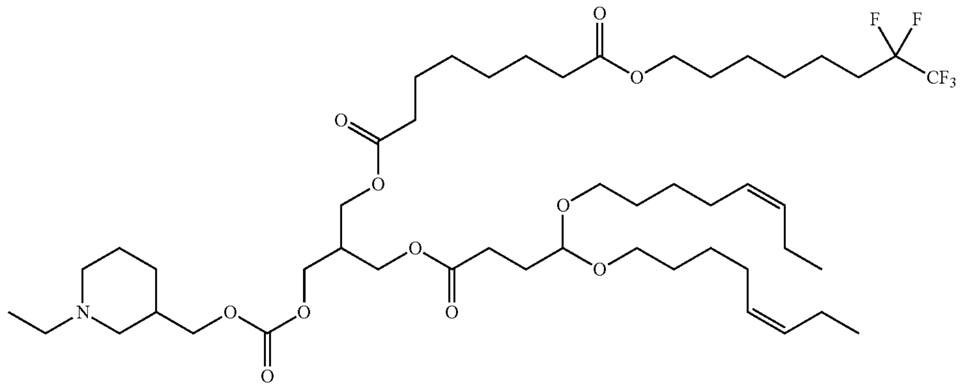

-continued
Example 4-6
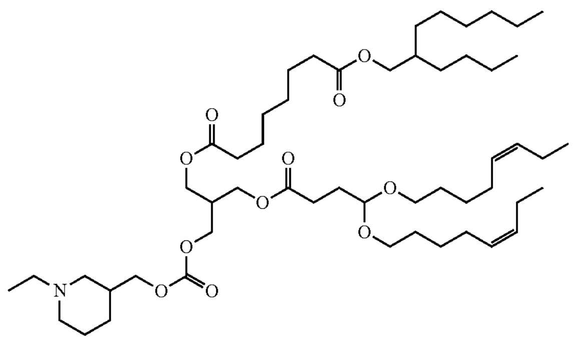
Example 4-7
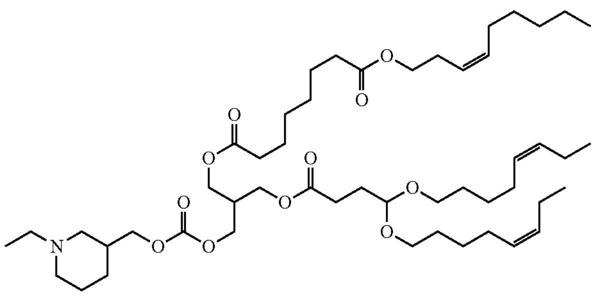
Example 4-8
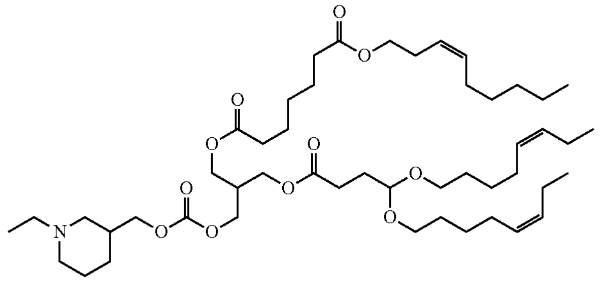
Example 4-9
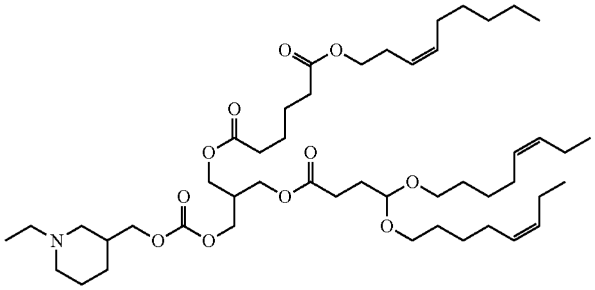
Example 4-10
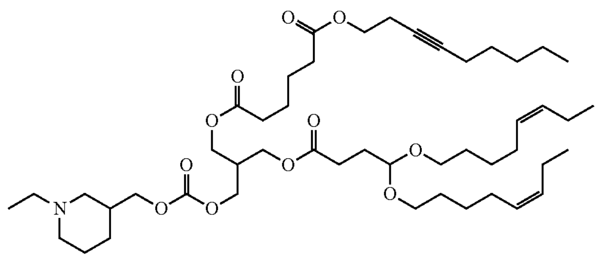
Example 4-11
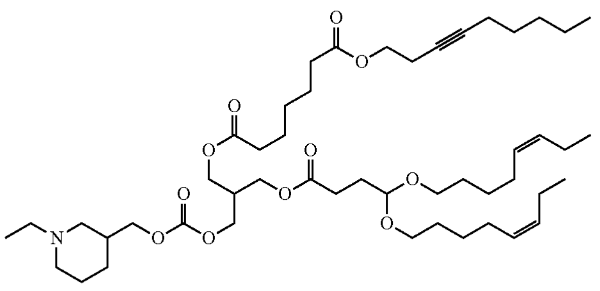
Example 4-12
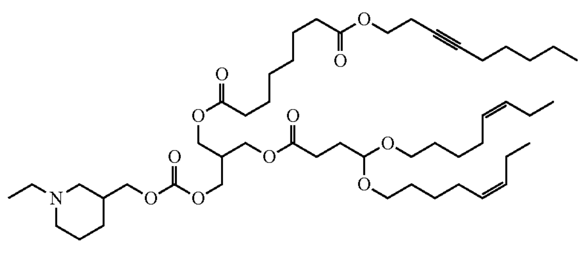
Example 4-13
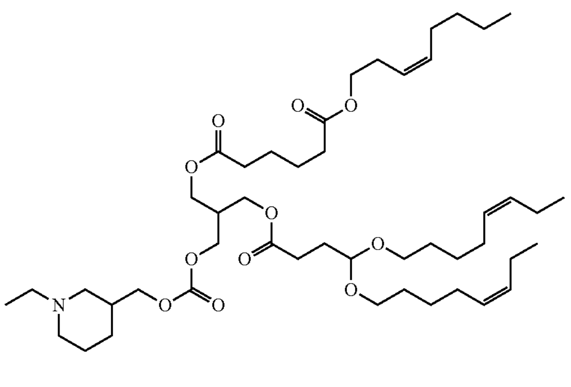

-continued
Example 4-14
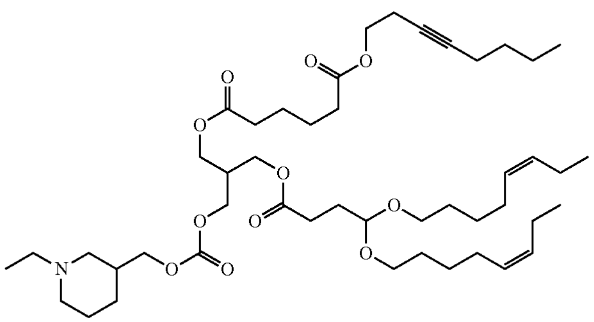
Example 4-15
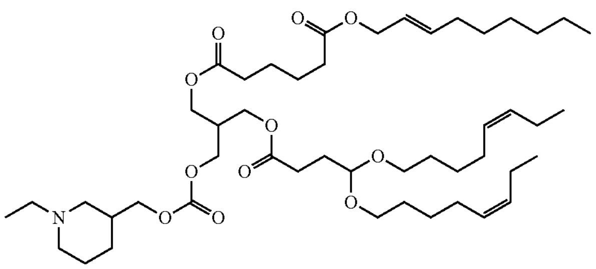
Example 4-16
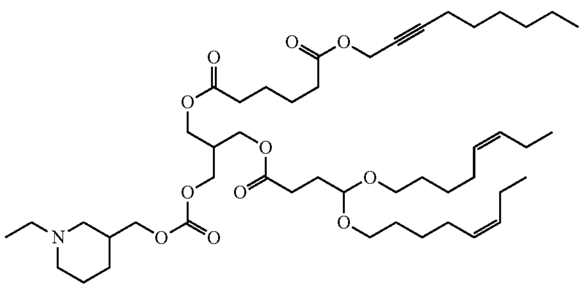
Example 4-17
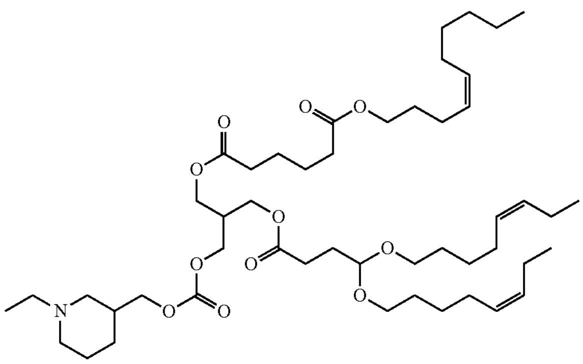
Example 4-18
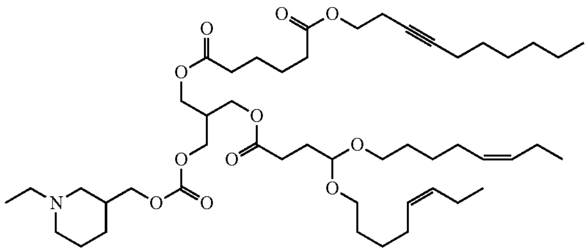
Example 4-19
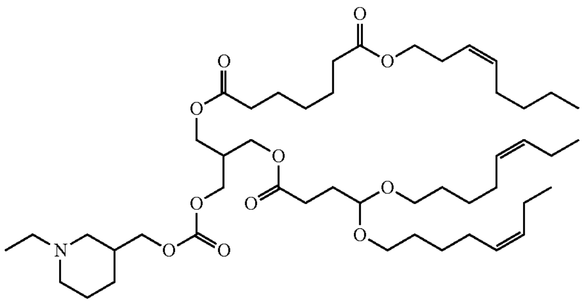
Example 4-20
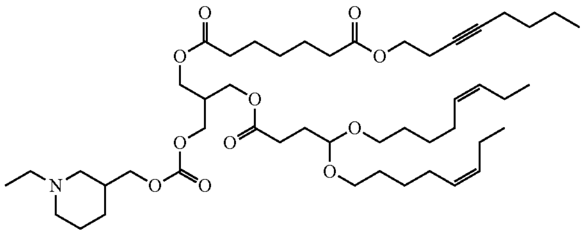
Example 4-21
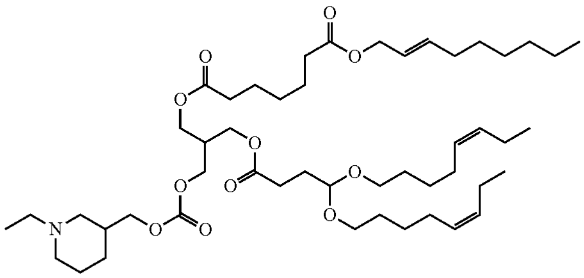

-continued
Example 4-22
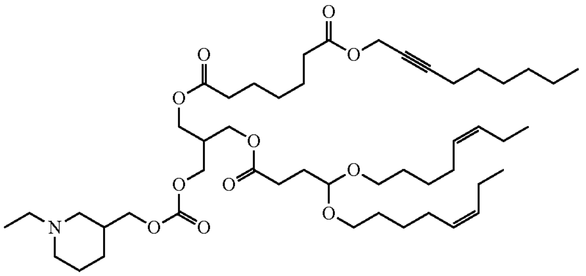
Example 4-23
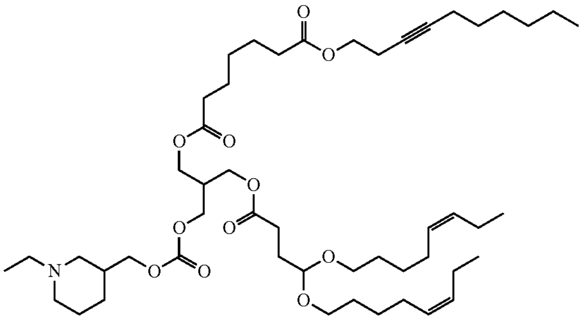
Example 4-24
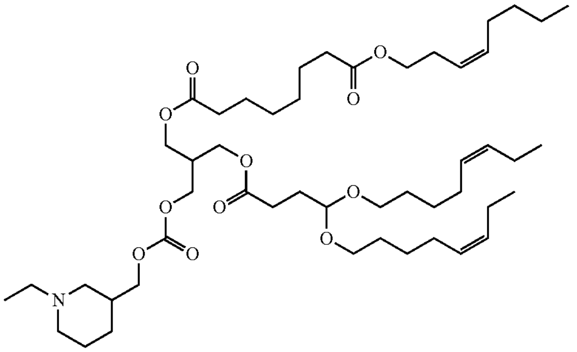
Example 4-25
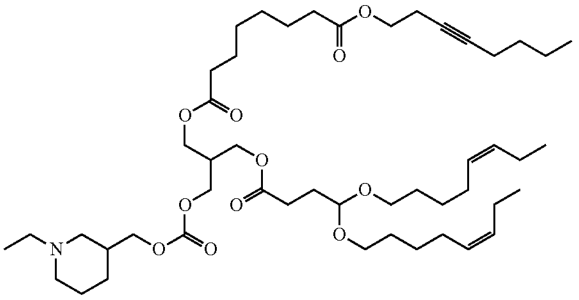
Example 4-26
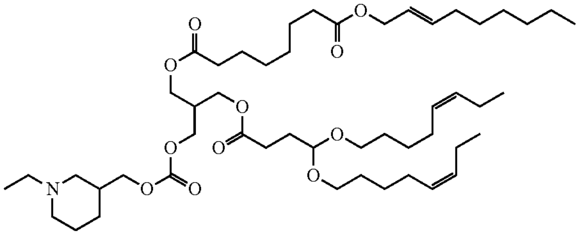
Example 4-27
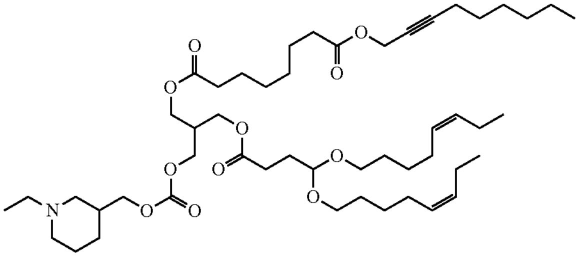
Example 4-28
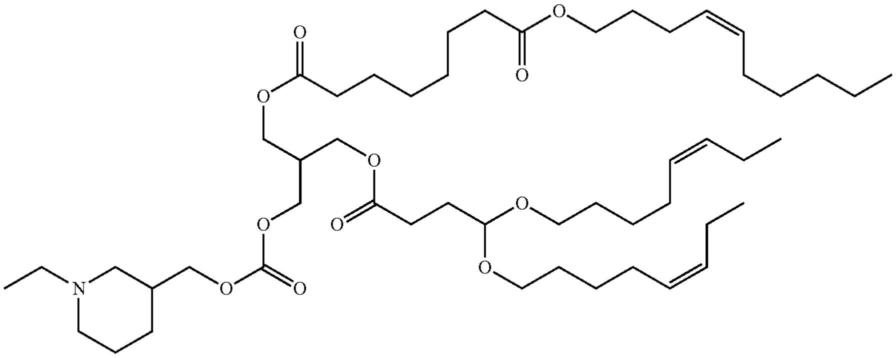

-continued
Example 4-29
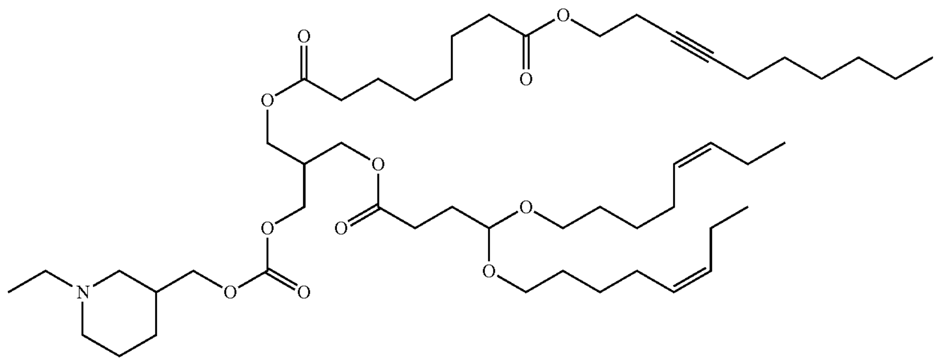
Example 4-30
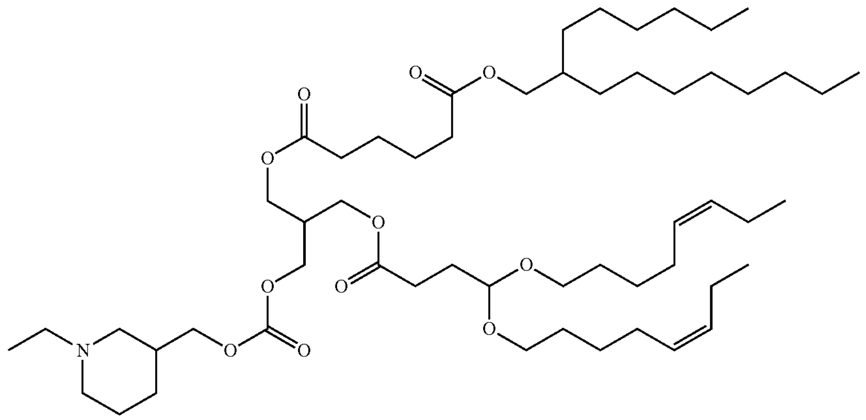
Example 4-31
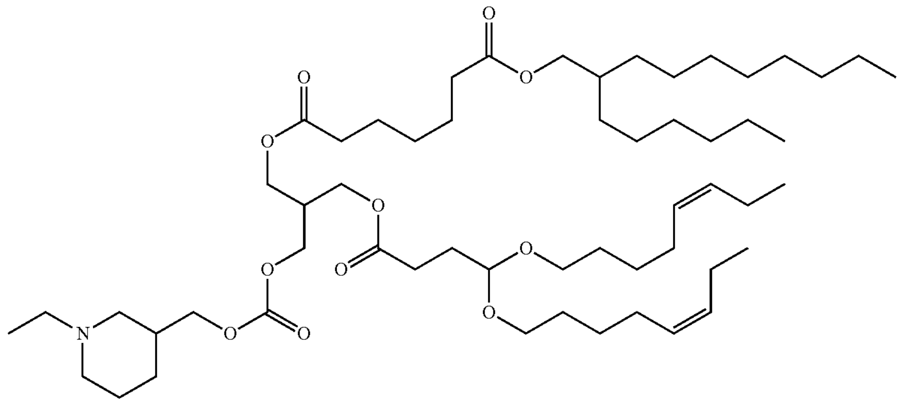
Example 4-32
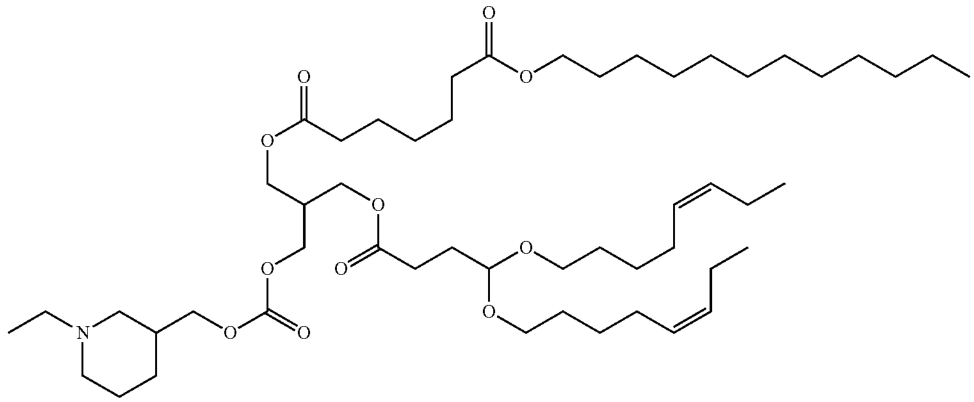

-continued
Example 4-33
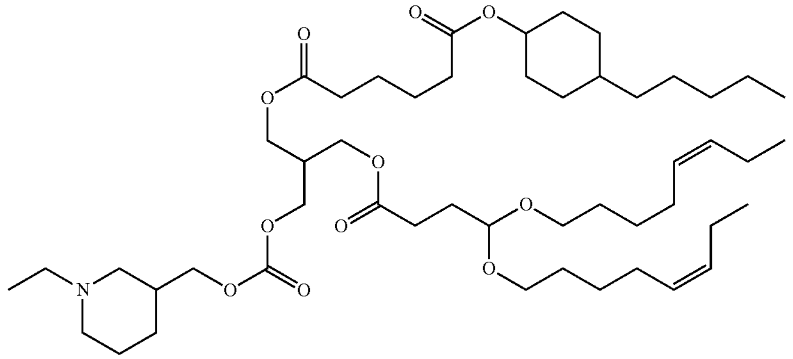
Example 4-34
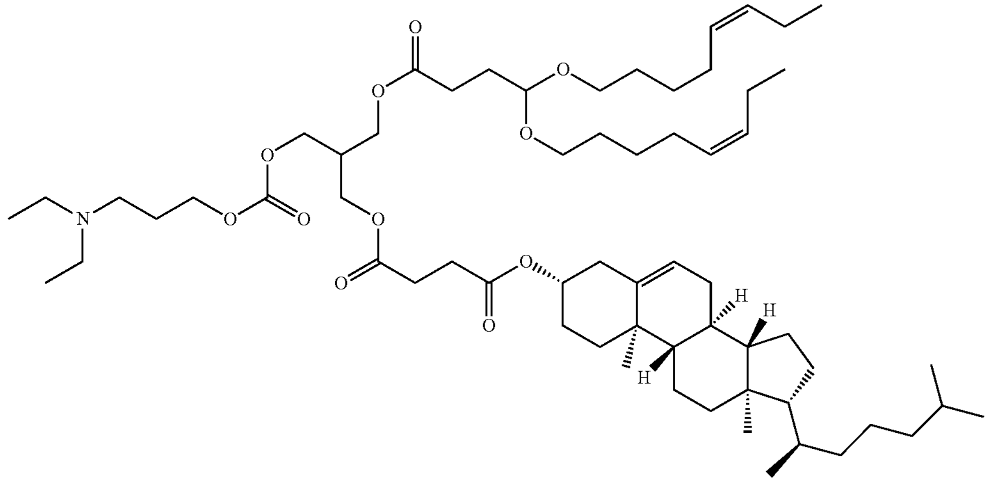
Example 4-35
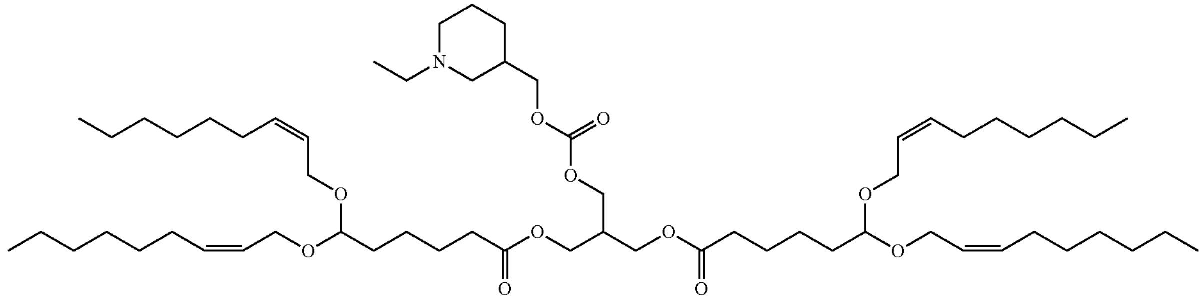
Example 4-36
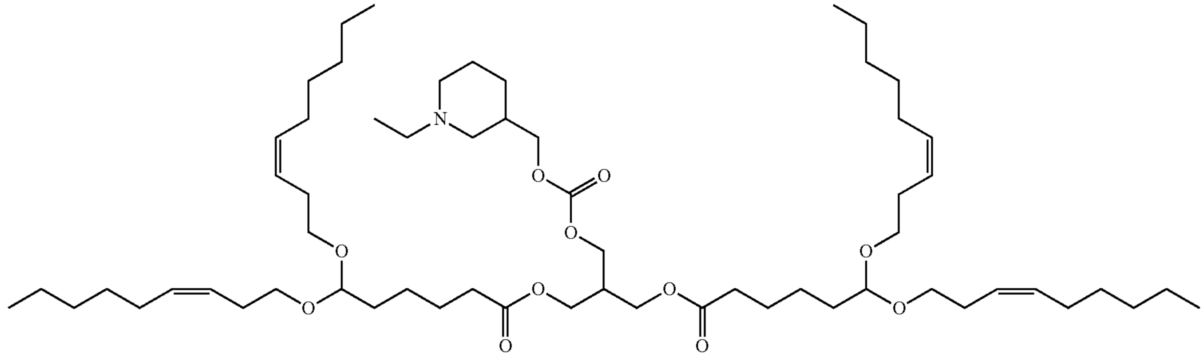

-continued
Example 4-37
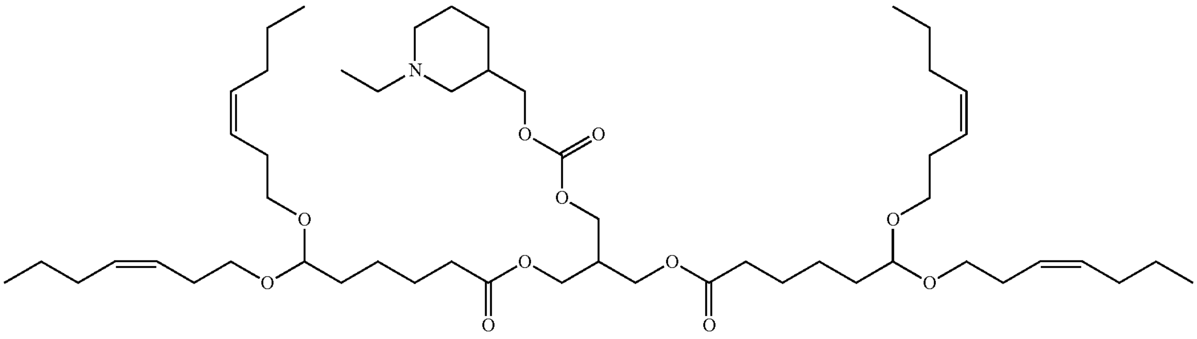
Example 4-38
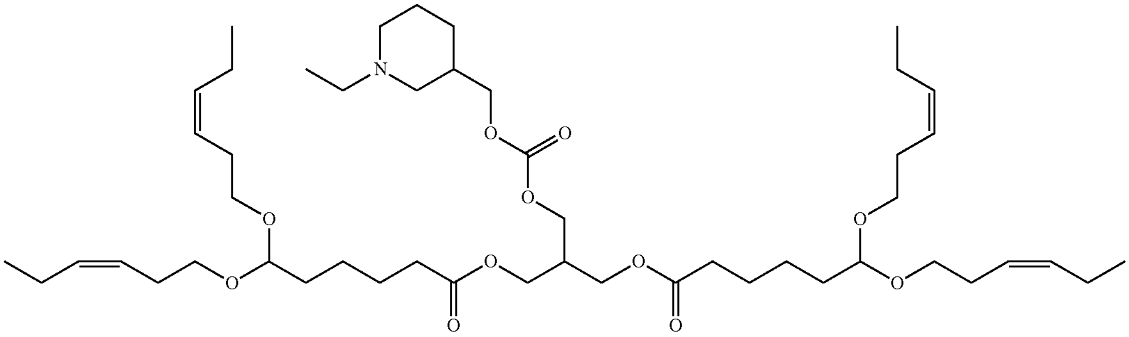
Example 4-39
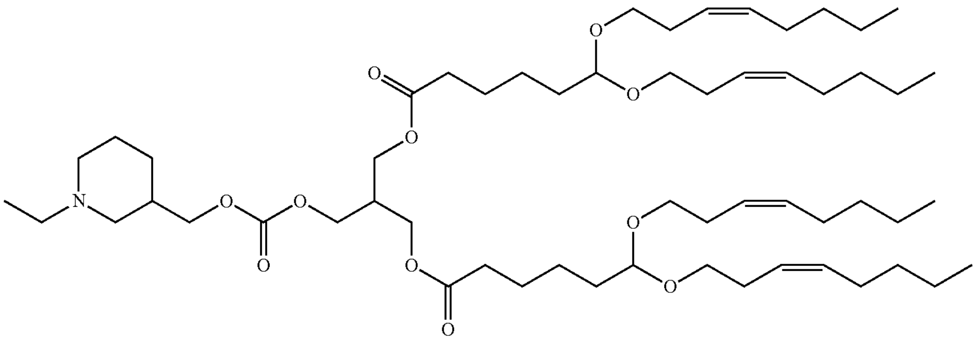
Example 4-40
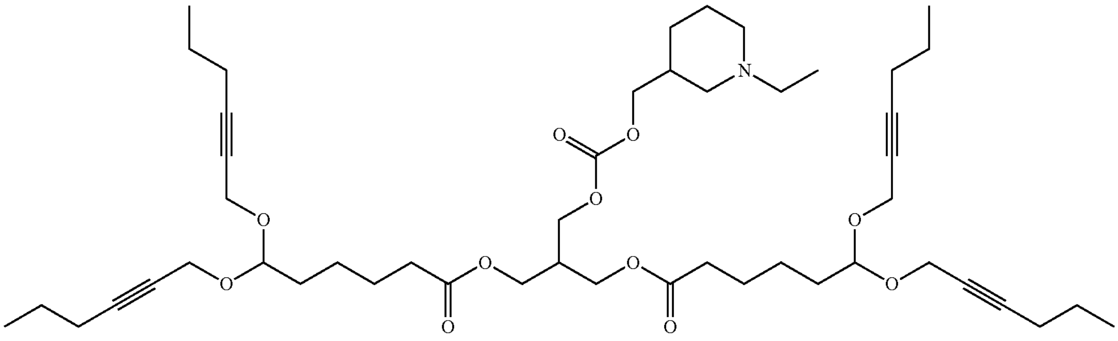

-continued
Example 4-41
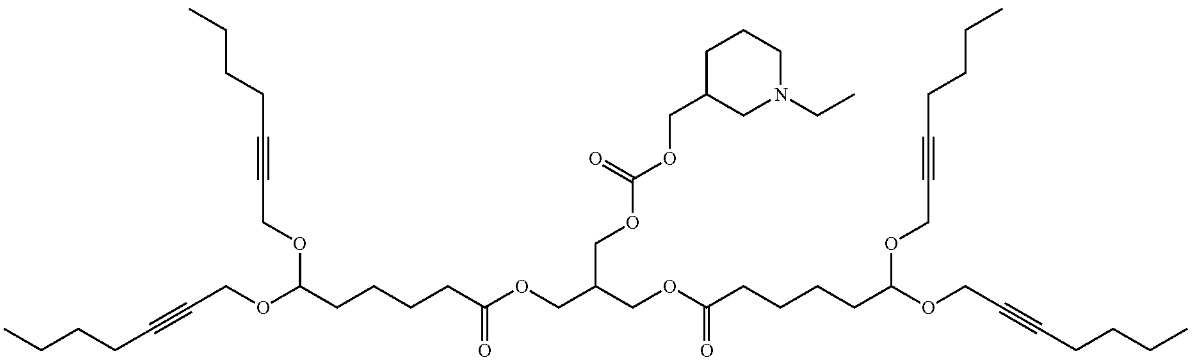
Example 4-42
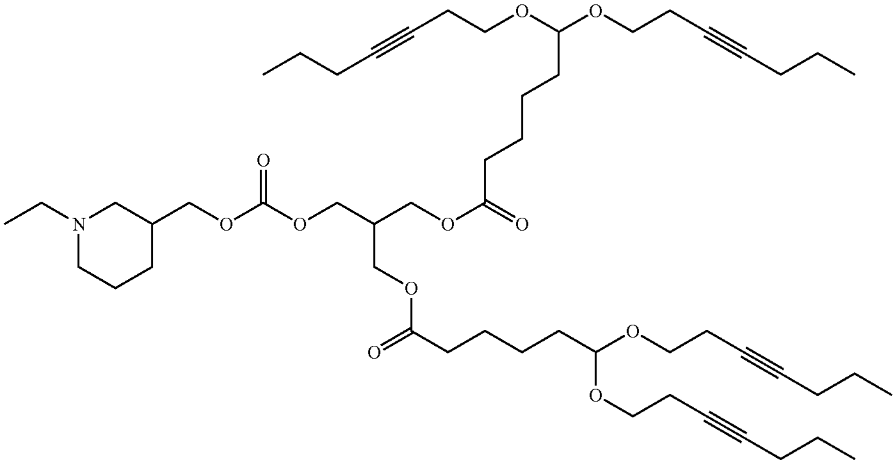
Example 4-43
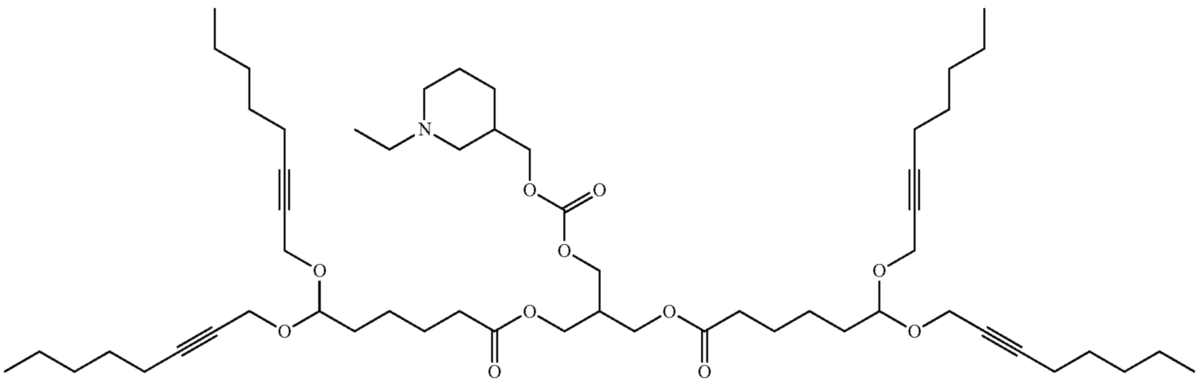
Example 4-44
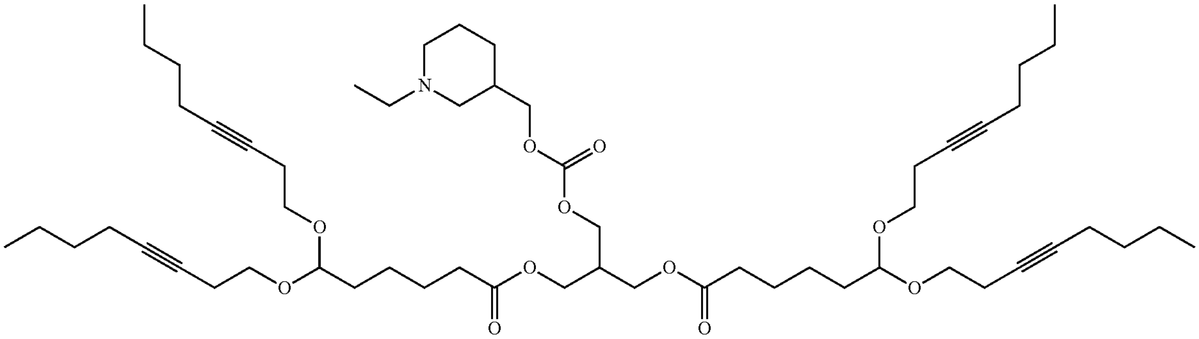

-continued
Example 4-45
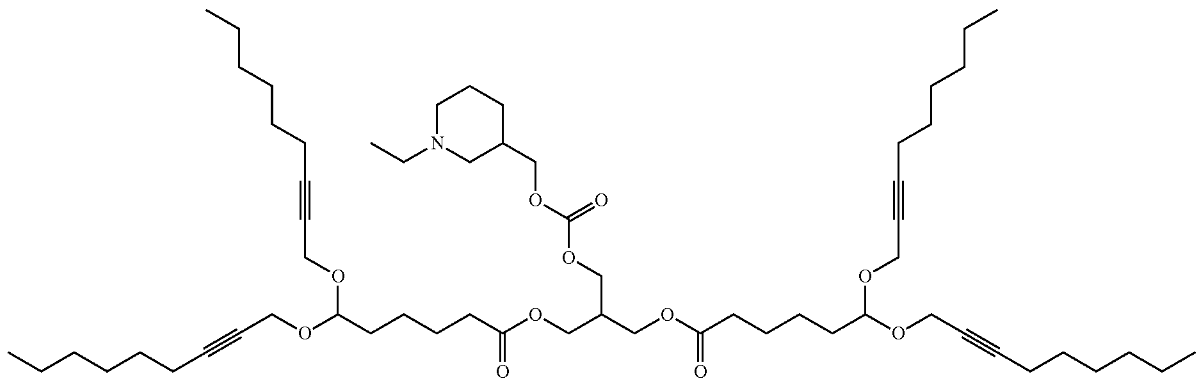
Example 4-46
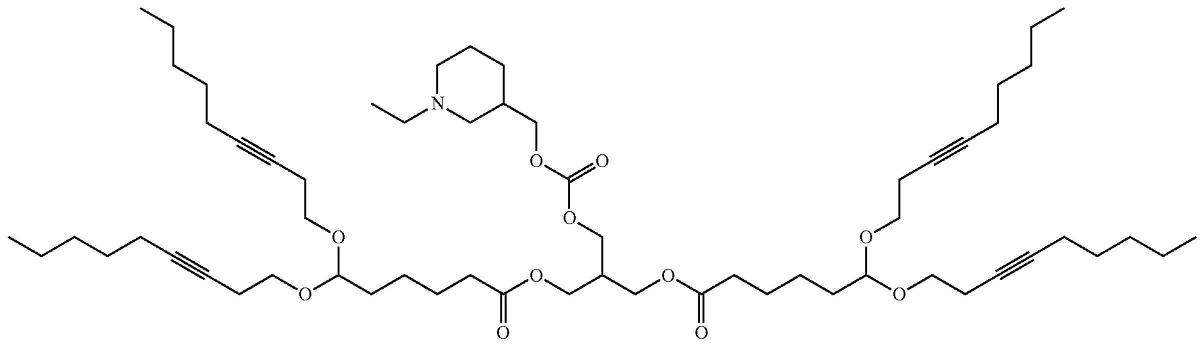
Example 4-47
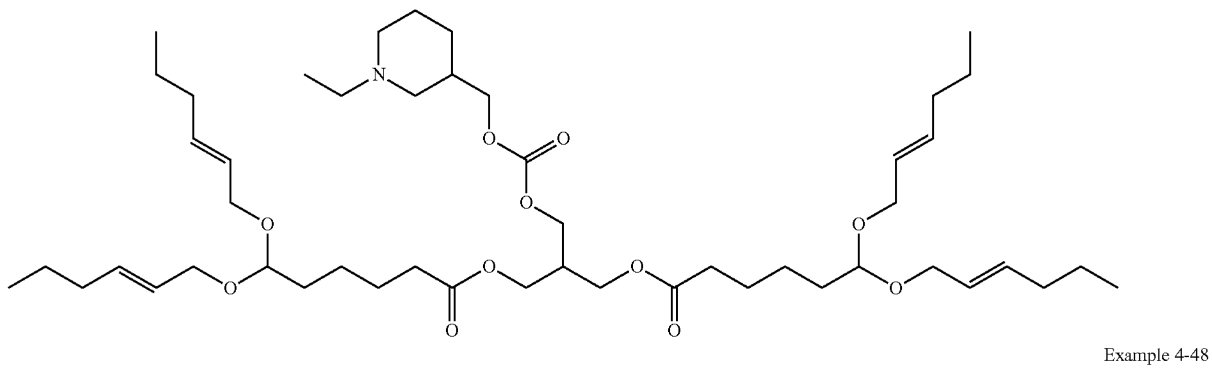
Example 4-48
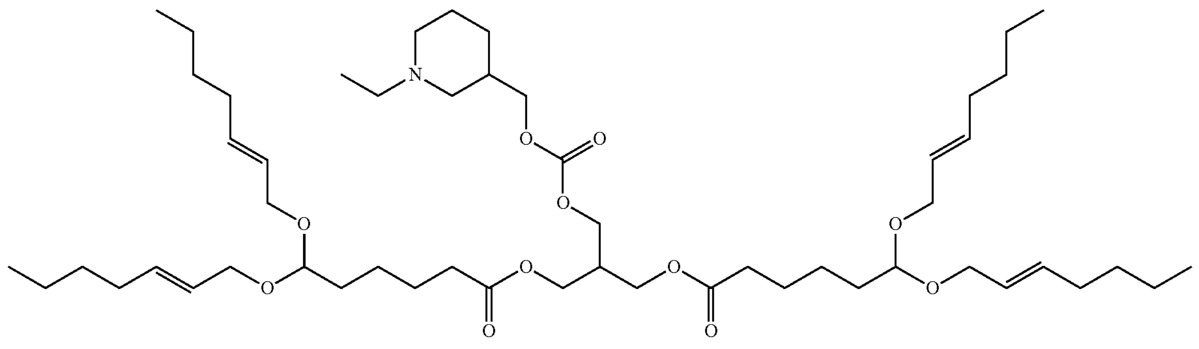

-continued
Example 4-49
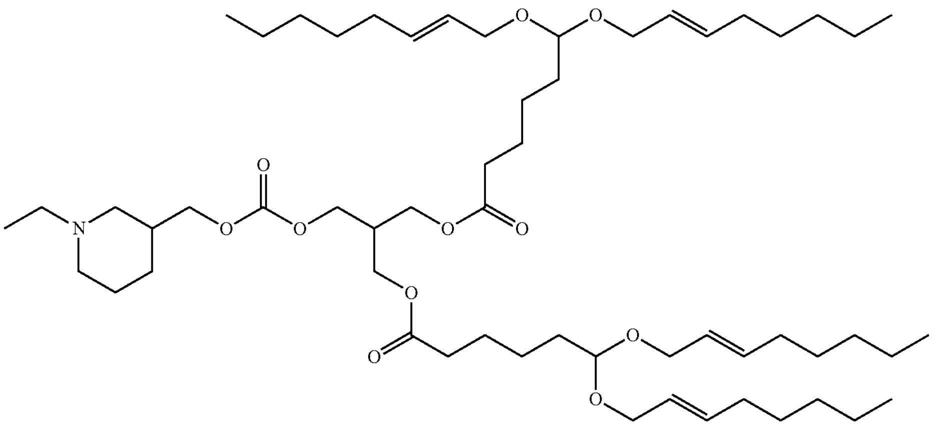
Example 4-50
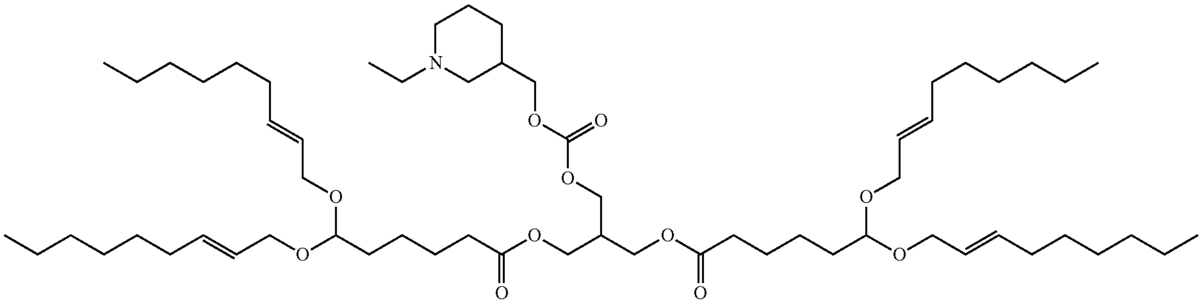
Example 4-51
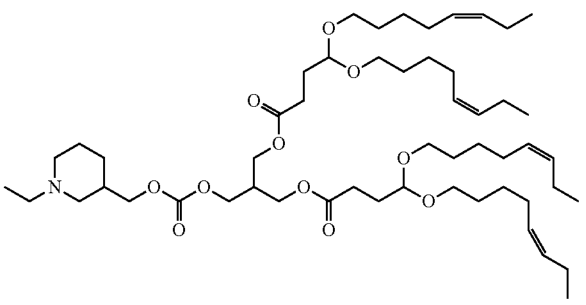
Example 4-52
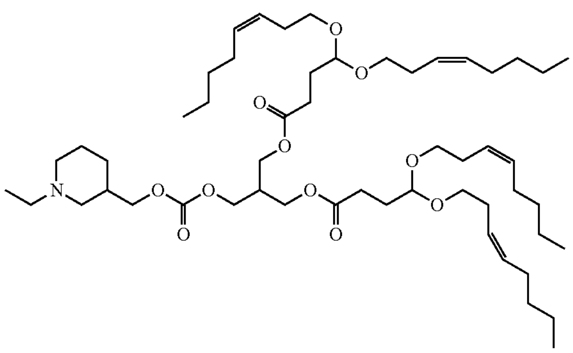
Example 4-53
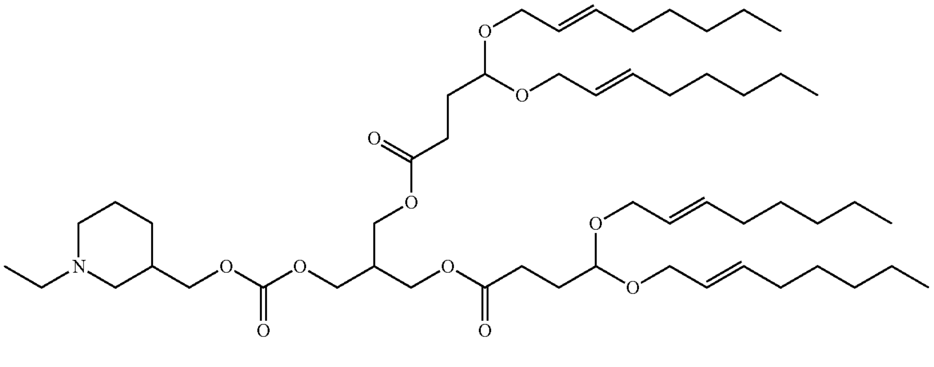

-continued
Example 4-54
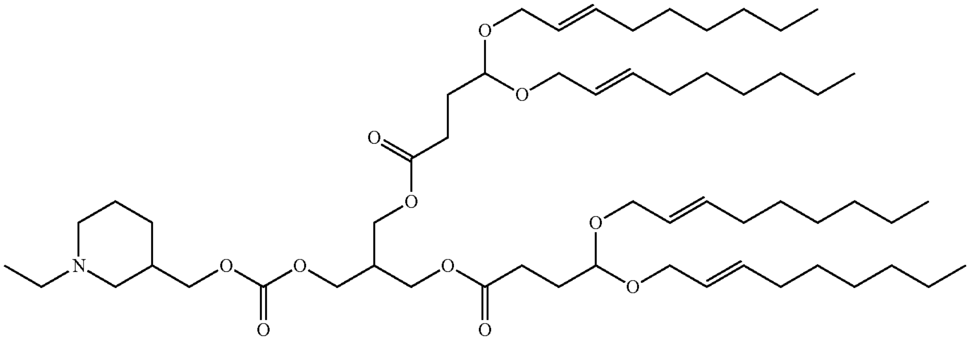
Example 4-55
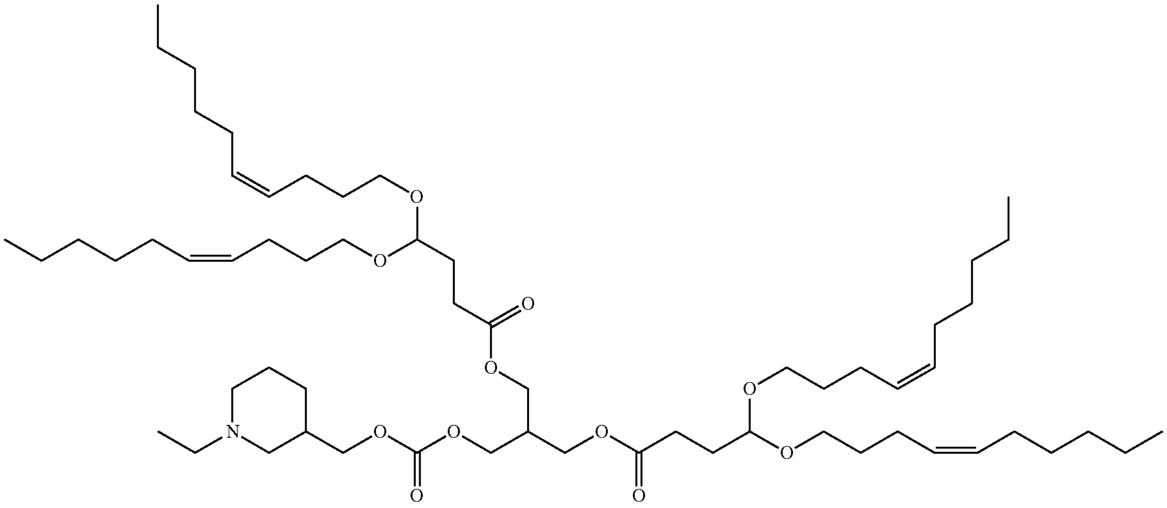
Example 4-56
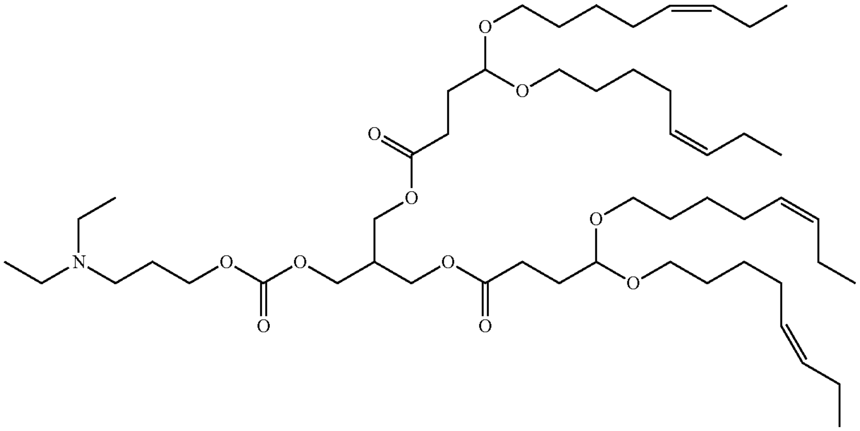
Example 4-57
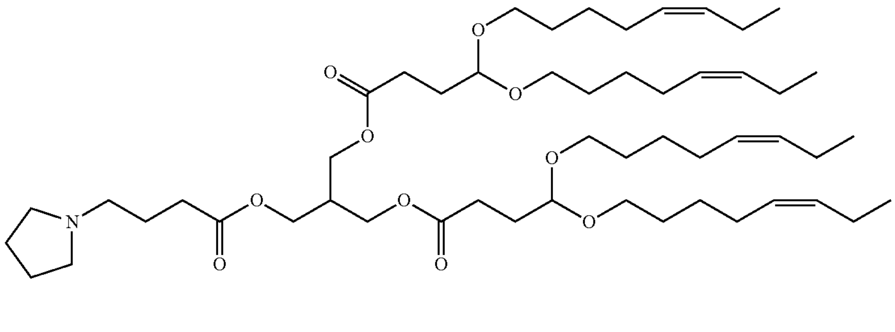

-continued
Example 4-58
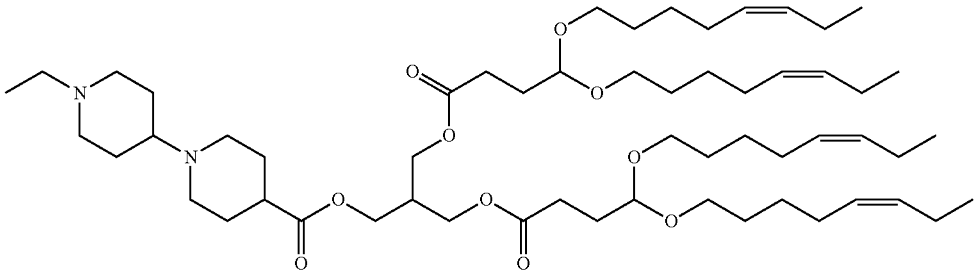
Example 4-59
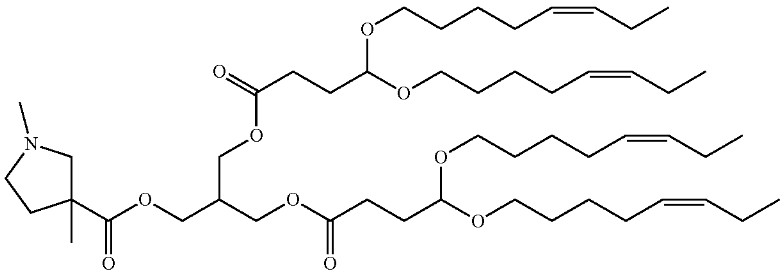
Example 4-60
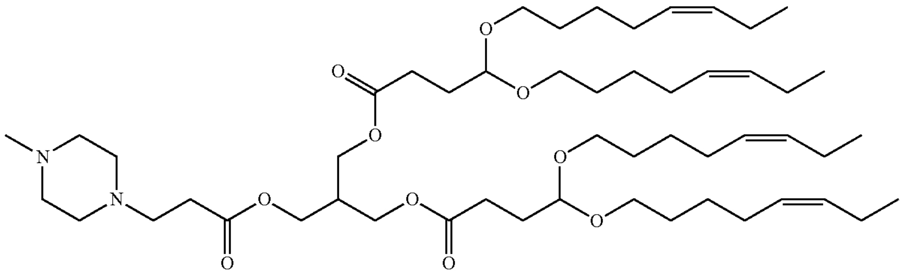
Example 4-61
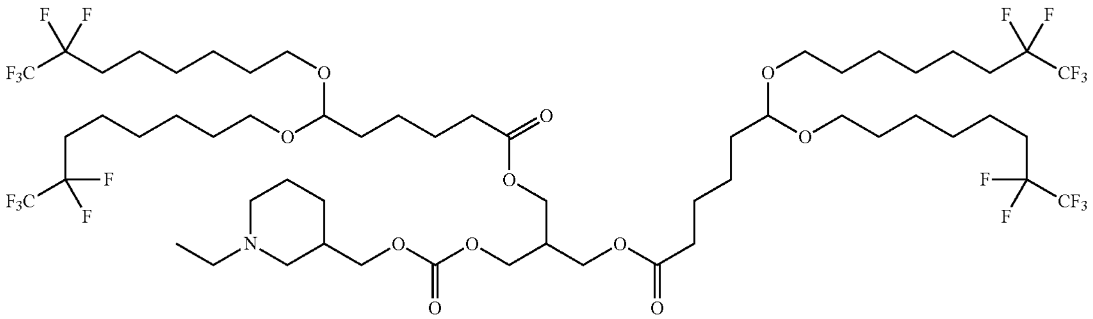
Example 4-62
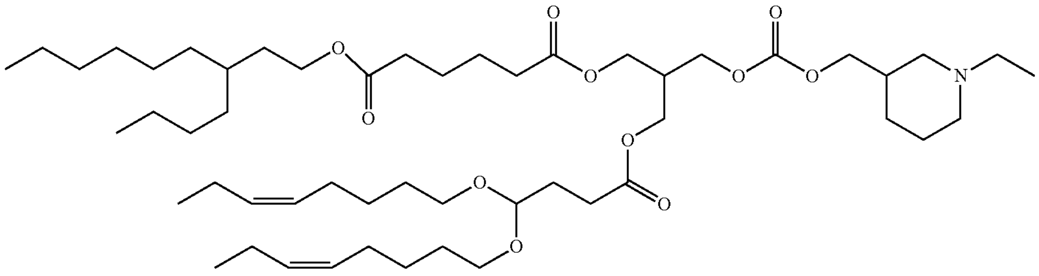

-continued
Example 4-63
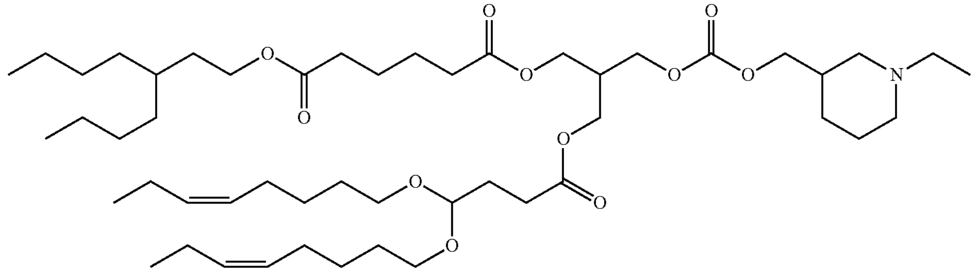
Example 4-64
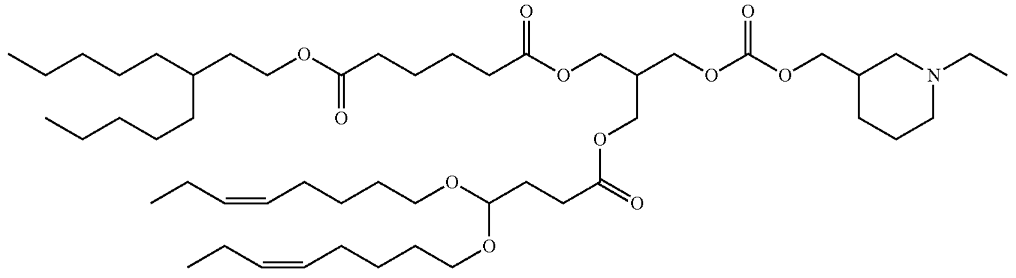
Example 4-65
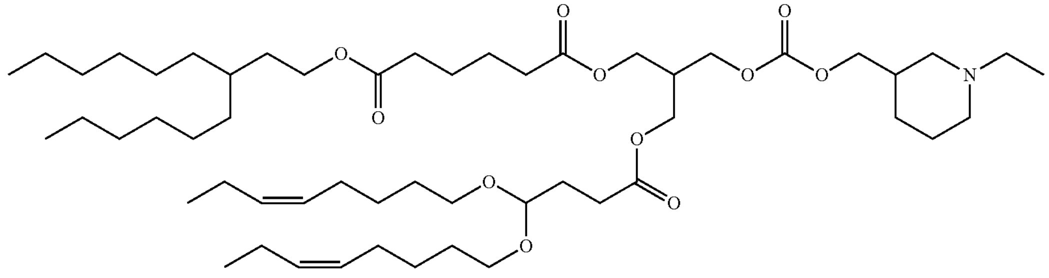
Example 4-66
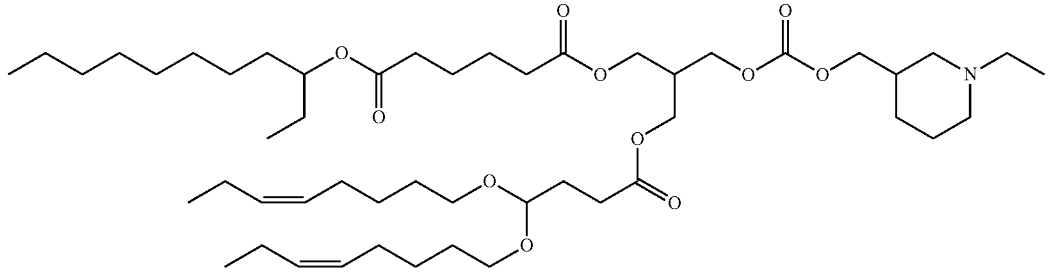
Example 4-67
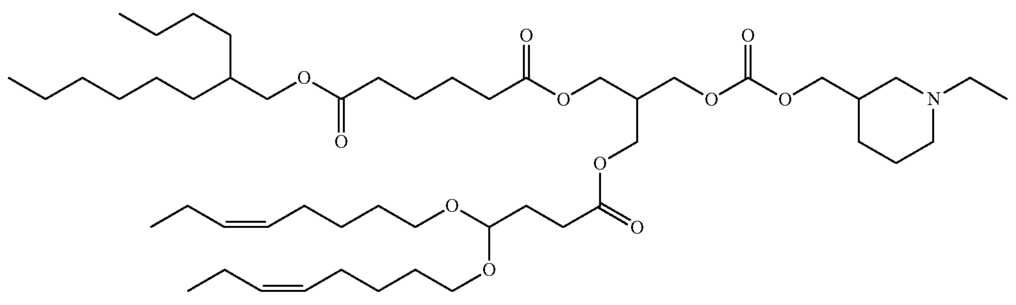

-continued
Example 4-68
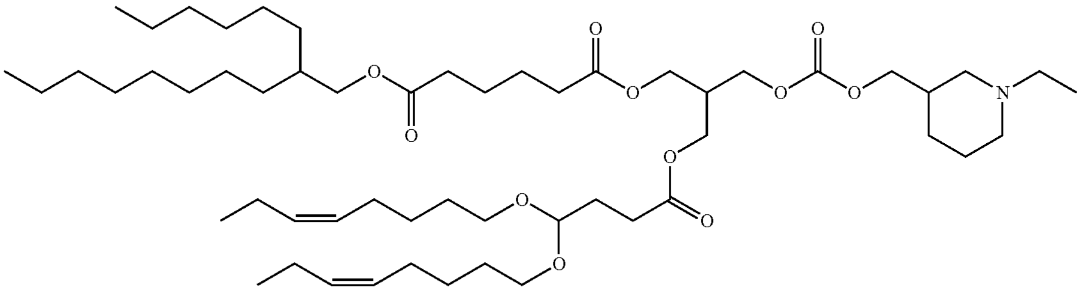
Example 4-69
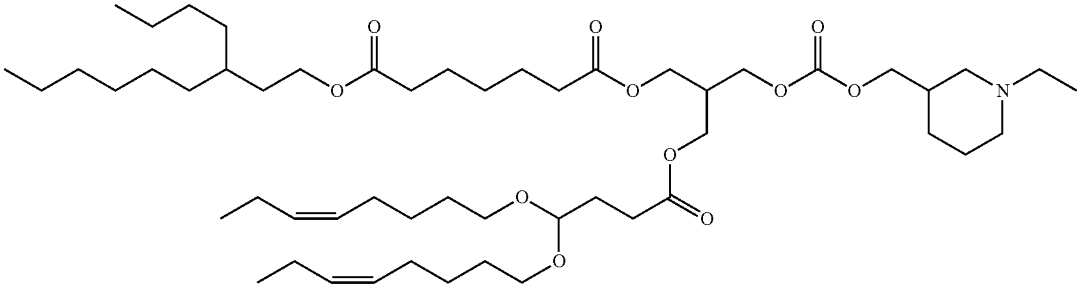
Example 4-70
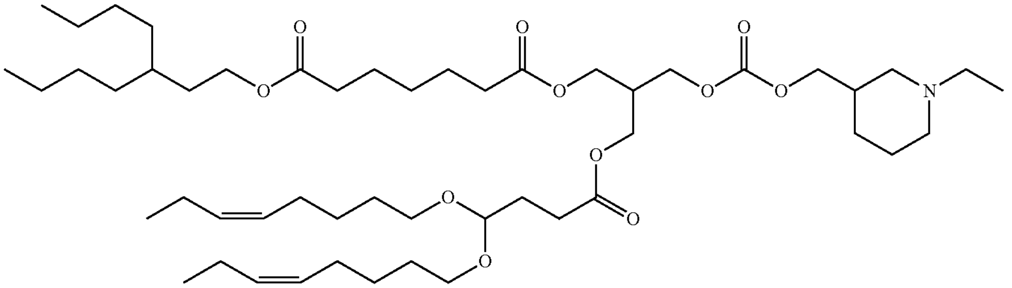
Example 4-71
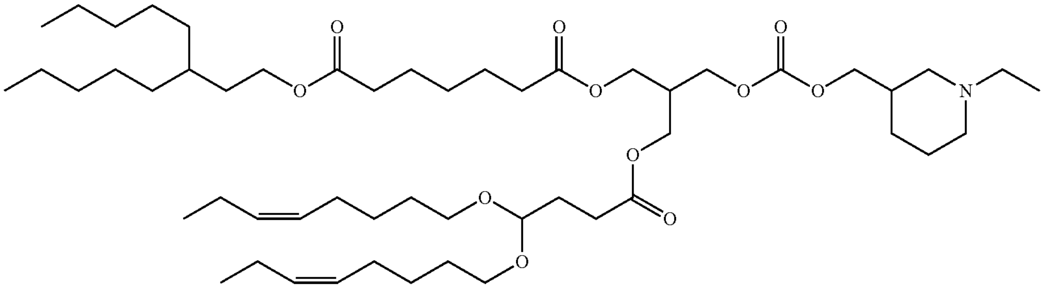
Example 4-72
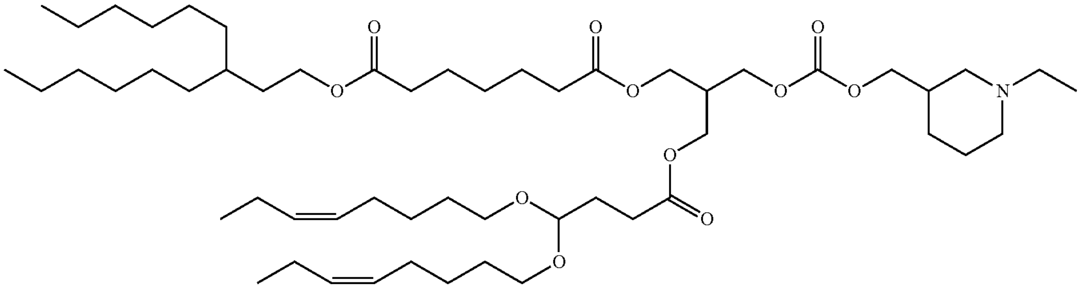

-continued
Example 4-73
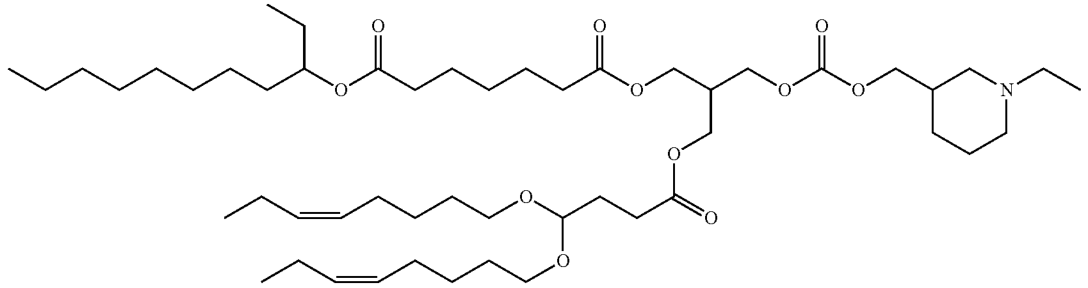
Example 4-74
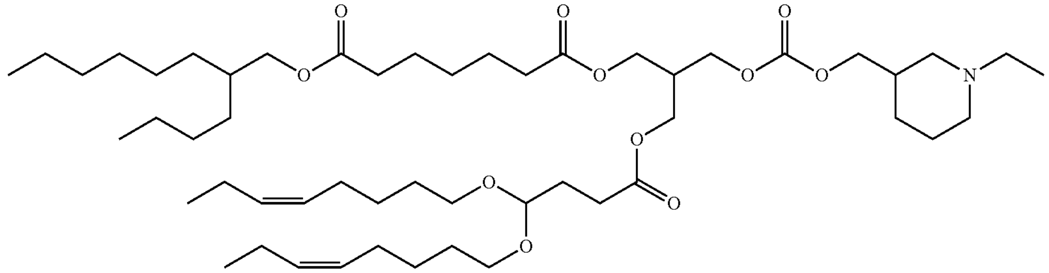
Example 4-75
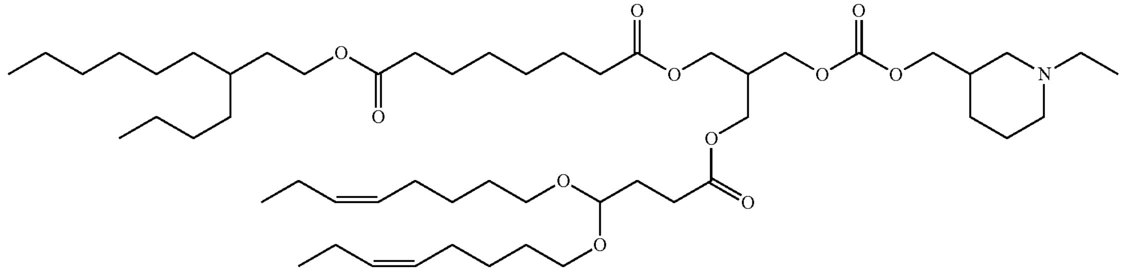
Example 4-76
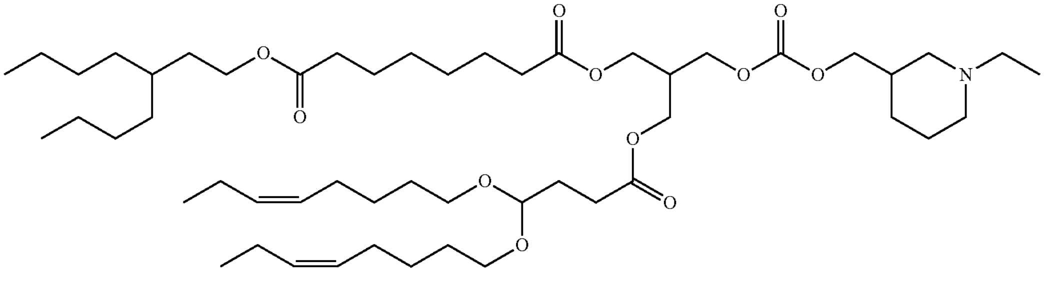
Example 4-77
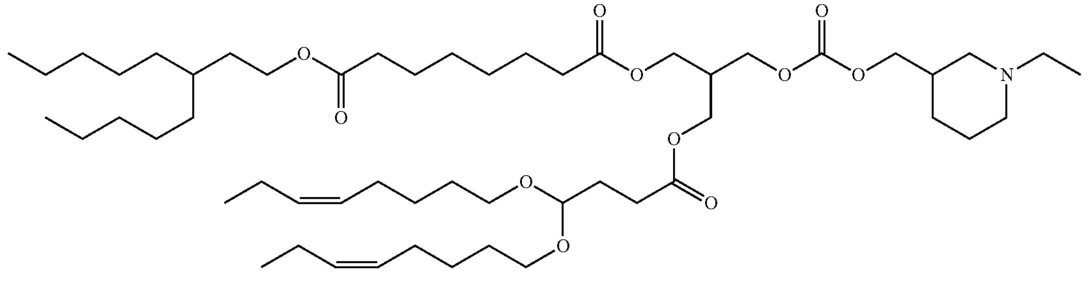

-continued
Example 4-78
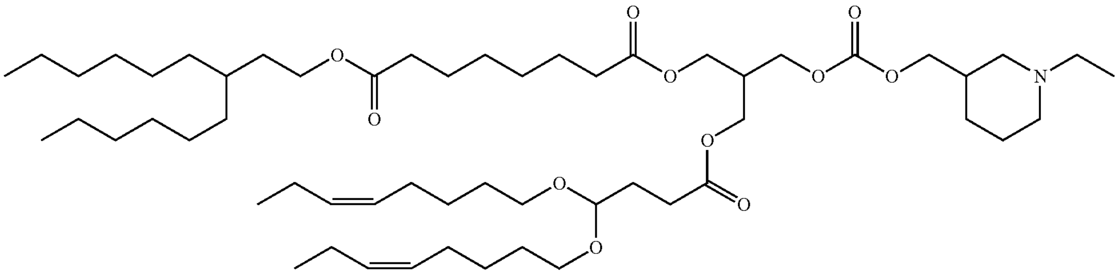
Example 4-79
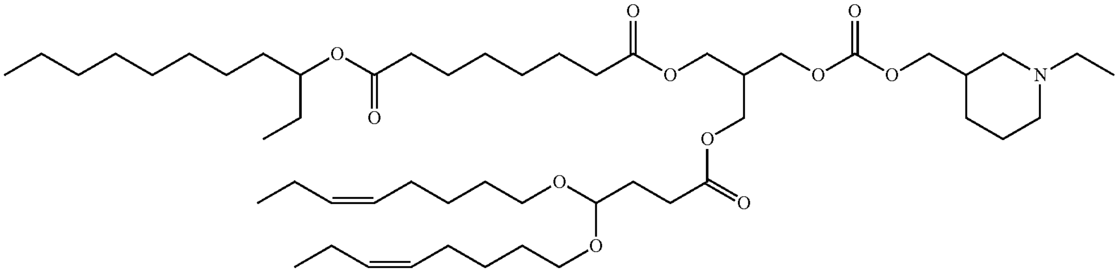
Example 4-80
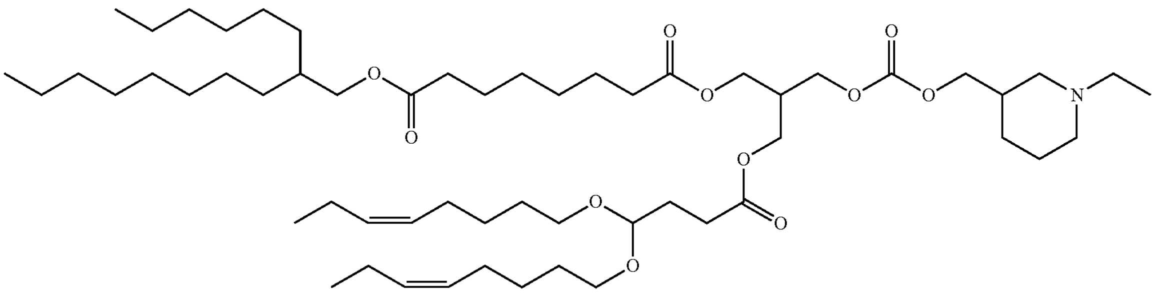
Example 4-81
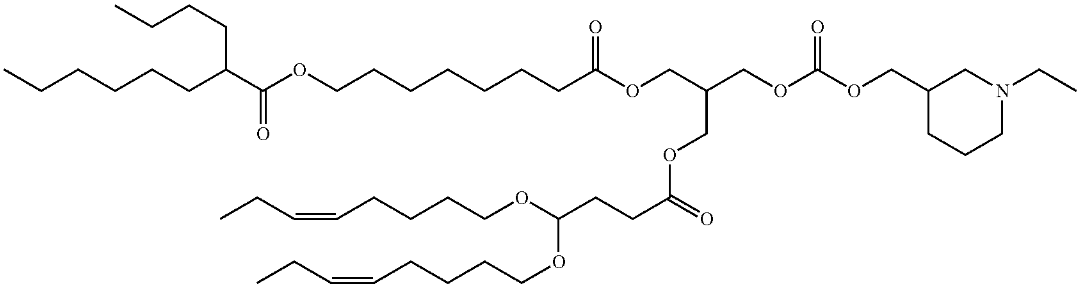
Example 4-82
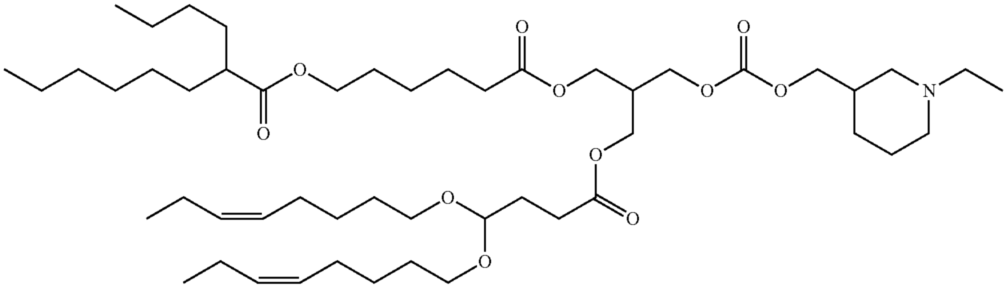

-continued

Example 4-83

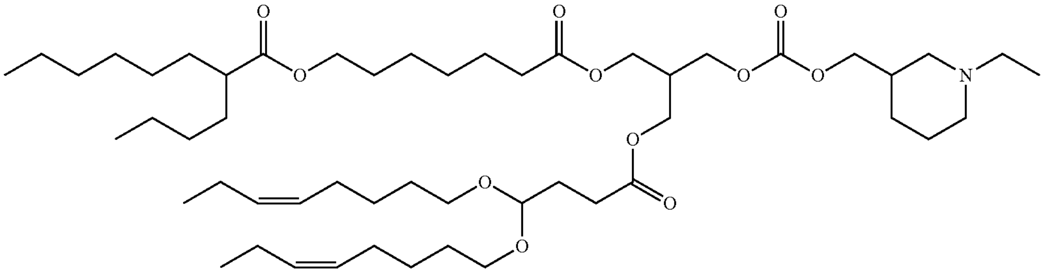

Example 4-84

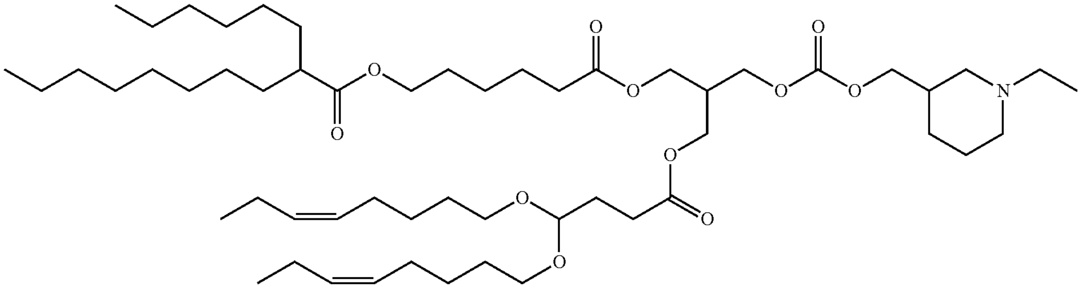

Example 4-85

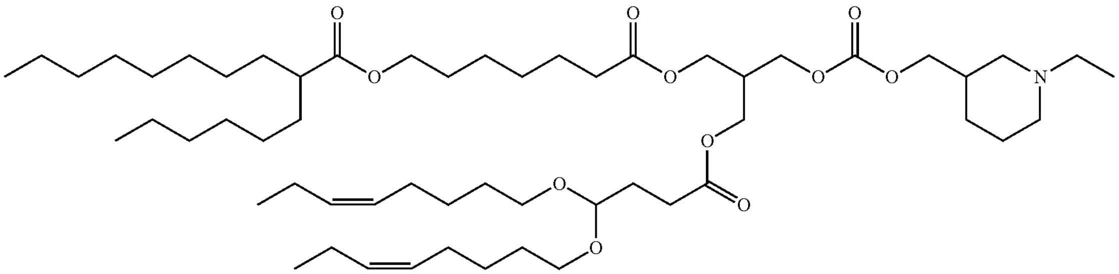

Example 4-86

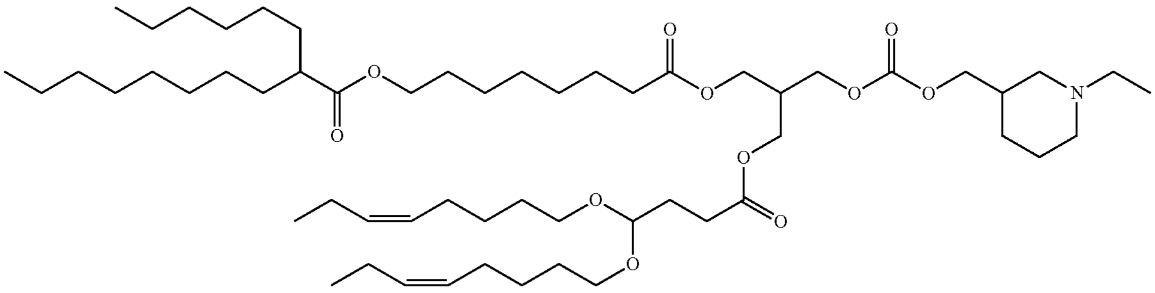

or a pharmaceutically acceptable salt thereof.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

It will be understood that, unless otherwise specified or prohibited by the foregoing definition of any of Formulae I, II, III, IIIA, IIIB, IIIC, IV, V, VA, VI, VIA, VII, and VIIA, embodiments of variables $L^1$, $L^2$, $Cy^A$, m, n, $L^3$, $R^1$, $Cy^B$, p, $L^4$, $A^1$, $A^2$, x, $L^5$, $R^5$, $X^1$, $X^2$, $Cy^C$, $X^3$, and R as defined above and described in classes and subclasses herein, apply to compounds of any of Formulae I, II, III, IIIA, IIIB, IIIC, IV, V, VA, VI, VIA, VII, and VIIA, both singly and in combination.

In some embodiments, provided compounds are provided and/or utilized in a salt form (e.g., a pharmaceutically acceptable salt form). Reference to a compound provided herein is understood to include reference to salts thereof, unless otherwise indicated.

It will be appreciated that throughout the present disclosure, unless otherwise indicated, reference to a compound of Formula I is intended to also include Formulae II, III, IIIA, IIIB, IIIC, IV, V, VA, VI, VIA, VII, and VIIA, and compound species of such formulae disclosed herein.

In some embodiments, the present disclosure encompasses the recognition that provided compounds display certain desirable characteristics, e.g., as compared to reference compounds or other known compounds. For example, in some embodiments, provided compounds exhibit more potent delivery to various cell types in one or more experiments described herein, and/or have one or more other characteristics that make them more suitable for delivery of cargos such as therapeutic or prophylactic agents than other known compounds. Without wishing to be bound by any particular theory, the present disclosure encompasses the recognition that provided compounds characterized as including at least one ester moiety in a tail structure display certain more desirable characteristics (e.g., more potent delivery to various cell types in one or more experiments described herein and/or accelerated degradation in vivo) than corresponding compounds lacking the same at least one ester moiety in a tail structure.

B. Ionizable Lipids

Among other things, the present disclosure describes compositions, preparations, nanoparticles, and/or nanomaterials that comprise one or more ionizable lipids as described herein.

Among other things, it was surprisingly found that different ratios of ionizable lipids influence one or more functional activities such as desired tropisms, stabilization, and drug delivery efficacy of compositions, preparations, nanoparticles, and/or nanomaterials described herein. For example, the present disclosure demonstrates a surprising finding that amounts of ionizable lipids different to those amounts described in the art (e.g., see U.S. Pat. No. 8,058,069 B2, or see, e.g., U.S. Pat. No. 9,364,435, the contents of both which are hereby incorporated by reference in their entireties herein) are important to and/or influence one or more functional activities of compositions, preparations, nanoparticles, and/or nanomaterials described herein. For example, in some embodiments, compositions, preparations, nanoparticles, and/or nanomaterials having an ionizable lipid that is at about 50 mol percent or less, based on total moles of components of the lipid nanoparticle, was found to be useful and/or critical to functional activity of lipid nanoparticles such as desired tropisms, stabilization, and drug delivery efficacy as described herein.

In some embodiments, an ionizable lipid may include an amine-containing group on the head group. In some embodiments, an ionizable lipid is or comprises a compound described herein (e.g., a compound of Formula I, II, III, IIIA, IIIB, IIIC, IV, V, VA, VI, VIA, VII, or VIIA). In some embodiments, an ionizable lipid is present in a lipid nanoparticle (LNP) preparation from about 30 mole percent to about 70 mole percent, based on total moles of components of the lipid nanoparticle. In some embodiments, an ionizable lipid is present from about 33 mol percent to about 60 mole percent, based on total moles of components of the lipid nanoparticle. In some embodiments, an ionizable lipid is present from about 34 mol percent to about 55 mole percent, based on total moles of components of the lipid nanoparticle. In some embodiments, an ionizable lipid is present from about 33 mol percent to about 51 mole percent, based on total moles of components of the lipid nanoparticle. In some embodiments, an ionizable lipid is present at about 34.7 mole percent, based on total moles of components of the lipid nanoparticle. In some embodiments, the ionizable lipid is present at about 47.5 mole percent, based on total moles of components of the lipid nanoparticle. In some embodiments, an ionizable lipid is present at about 50 mole percent, based on total moles of components of the lipid nanoparticle.

Among other things, in some embodiments, a lipid nanoparticle composition comprises an ionizable lipid. In some embodiments, a lipid nanoparticle preparation comprises an ionizable lipid; a phospholipid; a conjugate-linker lipid; and a cholesterol. In some embodiments, an ionizable lipid is or comprises a compound described herein (e.g., a compound of Formula I, II, III, IIIA, IIIB, IIIC, IV, V, VA, VI, VIA, VII, or VIIA). In some embodiments, an ionizable lipid is present in a LNP preparation from about 30 mole percent to about 70 mole percent, based on total moles of components of the lipid nanoparticle.

C. Sterols

Among other things, the present disclosure describes compositions, preparations, nanoparticles, and/or nanomaterials that comprise one or more sterols as described herein.

In some embodiments, a sterol is a cholesterol, or a variant or derivative thereof. In some embodiments, a cholesterol is modified. In some embodiments, a cholesterol is an oxidized cholesterol. In some embodiments, a cholesterol is esterified cholesterol. Unmodified cholesterol can be acted upon by enzymes to form variants that are side-chain or ring oxidized. In some embodiments, a cholesterol can be oxidized on the beta-ring structure or on the hydrocarbon tail structure. In some embodiments, a sterol is a phytosterol. Exemplary sterols that are considered for use in the disclosed lipid nanoparticles include but are not limited to 25-hydroxycholesterol (25-OH), 20α-hydroxycholesterol (20α-OH), 27-hydroxycholesterol, 6-keto-5α-hydroxycholesterol, 7-ketocholesterol, 7β-hydroxycholesterol, 7α-hydroxycholesterol, 7β-25-dihydroxycholesterol, beta-sitosterol, stigmasterol, brassicasterol, campesterol, or combinations thereof. In some embodiments, a side-chain oxidized cholesterol can enhance cargo delivery relative to other cholesterol variants. In some embodiments, a cholesterol is an unmodified cholesterol.

In some embodiments, a LNP composition comprises from about 20 mol percent to about 50 mol percent sterol. In some embodiments, a LNP composition comprises about 38 mol percent sterol. In some embodiments, a LNP composition comprises about 38.5 mol percent sterol. In some embodiments, a LNP composition comprises about 33.8 mol percent cholesterol. In some embodiments, a LNP composition comprises about 40% mol percent cholesterol.

D. Conjugate-Linker Lipids

Among other things, the present disclosure describes compositions, preparations, nanoparticles, and/or nanomaterials that comprise one or more conjugate-linker lipids as described herein.

In some embodiments, a conjugate-linker lipid is or comprises a polyethylene glycol (PEG)-lipid or PEG-modified lipid. In some embodiments, PEG or PEG-modified lipids may be alternately referred to as PEGylated lipids or PEG-lipids. Inclusion of a PEGylating lipid can be used to enhance lipid nanoparticle colloidal stability in vitro and circulation time in vivo. In some embodiments, the PEGylation is reversible in that the PEG moiety is gradually released in blood circulation. Exemplary PEG-lipids include but are not limited to PEG conjugated to saturated or unsaturated alkyl chains having a length of $C_6$-$C_{20}$. PEG-modified phosphatidylethanolamines, PEG-modified phosphatidic acids, PEG-modified ceramides (PEG-CER), PEG-modified dialkylamines, PEG-modified diacylglycerols (PEG-DAG), PEG-modified dialkylglycerols, and mixtures thereof. For example, in some embodiments, a PEG lipid may be PEG-c-DOMG, PEG-DMG, PEG-DLPE, PEG-DMPE, PEG-DPPE, PEG-DSG or a PEG-DSPE lipid.

In some embodiments, a conjugate-linker lipid comprises a polyethylene glycol lipid. In some embodiments, a conjugate-linker lipid comprises DiMystyrlGlycerol (DMG), 1,2-Dipalmitoyl-rac-glycerol, methoxypolyethylene Glycol (DPG-PEG), or 1,2-Distearoyl-rac-glycero-3-methylpolyoxyethylene (DSG-PEG). In some embodiments, a conjugate-linker lipid has an average molecular mass from about 500 Da to about 5000 Da. In some embodiments, a conjugate-linker lipid has an average molecular mass of about 2000 Da. In some embodiments, a LNP composition comprises from about 0 mol percent to about 5 mol percent conjugate-linker lipid. In some embodiments, a LNP composition comprises about 1.5 mol percent conjugate-linker lipid. In some embodiments, a LNP composition comprises about 2.5 mol percent conjugate-linker lipid. In some embodiments, a LNP composition comprises about 3 mol percent conjugate-linker lipid.

E. Phospholipids

Among other things, the present disclosure describes compositions, preparations, nanoparticles, and/or nanomaterials that comprise one or more phospholipids as described herein. In some embodiments, the present disclosure describes compositions, preparations, nanoparticles, and/or nanomaterials that comprise one or more (poly)unsaturated lipids.

In some embodiments, one or more phospholipids may assemble into one or more lipid bilayers. In some embodiments, one or more phospholipids may include a phospholipid moiety. In some embodiments, one or more phospholipids may include one or more fatty acid moieties. In some embodiments, one or more phospholipids may include a phospholipid moiety and one or more fatty acid moieties. In some embodiments, a phospholipid moiety includes but is not limited to phosphatidyl choline, phosphatidyl ethanolamine, phosphatidyl glycerol, phosphatidyl serine, phosphatidic acid, 2-lysophosphatidyl choline, and sphingomyelin. In some embodiments, a fatty acid moiety includes but is not limited to lauric acid, myristic acid, myristoleic acid, palmitic acid, palmitoleic acid, stearic acid, oleic acid, linoleic acid, alphalinolenic acid, erucic acid, phytanic acid, arachidic acid, arachidonic acid, eicosapentaenoic acid, behenic acid, docosapentaenoic acid, and docosahexaenoic acid. Non-natural species including natural species with modifications and substitutions including branching, oxidation, cyclization, and alkynes are also contemplated. For example, a phospholipid may be functionalized with or cross-linked to one or more alkynes (e.g., an alkenyl group in which one or more double bonds is replaced with a triple bond). Under appropriate reaction conditions, an alkyne group may undergo a copper-catalyzed cycloaddition upon exposure to an azide. Such reactions may be useful in functionalizing a lipid bilayer of a nanoparticle composition to facilitate membrane permeation or cellular recognition or in conjugating a nanoparticle composition to a useful component such as a targeting or imaging moiety (e.g., a dye).

Exemplary phospholipids include but are not limited to 1,2-distearoyl-snglycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-glycerophosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycerophosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl snglycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoylphosphatidylglycerol (DPPG), palmitoyloleoylphosphatidylethanolamine (POPE), distearoyl-phosphatidyl-ethanolamine (DSPE), dipalmitoyl phosphatidyl ethanolamine (DPPE), dimyristoylphosphoethanolamine (DMPE), 1-stearoyl-2-oleoyl-phosphatidy ethanolamine (SOPE), 1-stearoyl-2 oleoylphosphatidylcholine (SOPC), sphingomyelin, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine (LPE), or combinations thereof. In some embodiments, a phospholipid is DSPC. In some embodiments, a phospholipid is DMPC.

In some embodiments, the phospholipid comprises 1,2-dioleoyl-sn-glycero-3-phosphoethanolamine-N-(succinyl) (succinyl PE), 1,2-distearoyl-sn-glycero-3-phosphocholine (DSPC), cholesterol, 1,2-distearoyl-sn-glycero-3-phosphoethanolamine (DSPE), 1,2-dipalmitoyl-sn-glycero-3-phosphoethanolamine-N-(succinyl) (succinyl-DPPE), 1,2-dioleoyl-sn-glycero-3-phosphoethanolamine (DOPE), 1,2-dimyristoyl-sn-glycero-3-phosphocholine (DMPC), 1,2-dipalmitoyl-sn-glycero-3-phosphocholine (DPPC), or a combination thereof.

In some embodiments, the LNP composition comprises from about 0 mol percent to about 15 mol percent phospholipid. In some embodiments, the LNP composition comprises about 9 mol percent phospholipid. In some embodiments, the LNP composition comprises about 10 mol percent phospholipid.

F. Diameter

Among other things, the present disclosure describes compositions, preparations, nanoparticles, and/or nanomaterials that have an average hydrodynamic diameter from about 30 to about 220 nm. In some embodiments, compositions, preparations, nanoparticles, and/or nanomaterials described herein have an average hydrodynamic diameter that is about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, or any range having endpoints defined by any two of the aforementioned values. For example, in some embodiments, compositions, preparations, nanoparticles, and/or nanomaterials described herein have an average hydrodynamic diameter from between 50 nm to 200 nm.

In some embodiments, lipid nanoparticles described herein have an average hydrodynamic diameter from about 30 to about 220 nm. In some embodiments, lipid nanoparticles described herein have an average hydrodynamic diameter that is about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, or any range having endpoints defined by any two of the aforementioned values. For example, in some embodiments, lipid nanoparticles described herein have an average hydrodynamic diameter from between 50 nm to 200 nm.

G. Polydispersity

Among other things, the present disclosure describes compositions, preparations, nanoparticles, and/or nanomaterials that have a polydispersity index (PDI) of about 0.01 to about 0.3. In some embodiments, compositions, preparations, nanoparticles, and/or nanomaterials described herein have a PDI that is about 0.01, 0.02, 0.03, 0.04, 0.05, 0.06, 0.07, 0.08, 0.09, 0.1, 0.15, 0.2, 0.25, 0.3, or any range having endpoints defined by any two of the aforementioned values. For example, in some embodiments, compositions, preparations, nanoparticles, and/or nanomaterials described herein have a PDI from about 0.05 to about 0.2, about 0.06 to about 0.1, or about 0.07 to about 0.09.

In some embodiments, lipid nanoparticles described herein have a PDI from about 0.01 to about 0.3. In some embodiments, lipid nanoparticles described herein have a PDI that is about 0.01, 0.02, 0.03, 0.04, 0.05, 0.06, 0.07, 0.08, 0.09, 0.1, 0.15, 0.2, 0.25, 0.3, or any range having endpoints defined by any two of the aforementioned values. For example, in some embodiments, lipid nanoparticles described herein have a PDI from about 0.05 to about 0.2, about 0.06 to about 0.1, or about 0.07 to about 0.09.

H. Encapsulation Efficiency

Among other things, the present disclosure describes compositions, preparations, nanoparticles, and/or nanomaterials, wherein encapsulation effiency of provided compositions, preparations, nanoparticles, and/or nanomaterials is from about 80% to about 100%. In some embodiments, encapsulation effiency of compositions, preparations, nanoparticles, and/or nanomaterials described herein is about 80%, 85%, 90%, 91%, 92%, 93%, 94%, 95%, 95.5%, 96%, 96.5%, 97%, 97.5%, 98%, 98.5%, 99%, 99.5%, 100%, or any range having endpoints defined by any two of the aforementioned values. For example, in some embodiments, encapsulation effiency of compositions, preparations, nanoparticles, and/or nanomaterials described herein is from about 90% to about 100%, about 95% to about 100%, about 95% to about 98%, or about 95.5% to about 97.5%. In some embodiments, encapsulation effiency of compositions, preparations, nanoparticles, and/or nanomaterials described herein is at least about 90%, 91%, 92%, 93%, 94%, 95%, 96%, 97%, 98%, or 99%.

In some embodiments, encapsulation effiency of lipid nanoparticles described herein is from about 80% to about 100%. In some embodiments, encapsulation effiency of lipid nanoparticles described herein is about 80%, 85%, 90%, 91%, 92%, 93%, 94%, 95%, 95.5%, 96%, 96.5%, 97%, 97.5%, 98%, 98.5%, 99%, 99.5%, 100%, or any range having endpoints defined by any two of the aforementioned values. For example, in some embodiments, encapsulation effiency of lipid nanoparticles described herein is from about 90% to about 100%, about 95% to about 100%, about 95% to about 98%, or about 95.5% to about 97.5%. In some embodiments, encapsulation effiency of lipid nanoparticles described herein is at least about 90%, 91%, 92%, 93%, 94%, 95%, 96%, 97%, 98%, or 99%.

I. pKa

Among other things, the present disclosure describes compositions, preparations, nanoparticles, and/or nanomaterials that have a pKa from about 5 to about 9. In some embodiments, compositions, preparations, nanoparticles, and/or nanomaterials described herein have a pKa that is about 5.0, 5.5, 6.0, 6.5, 7.0, 7.5, 8.0, 8.5, or any range having endpoints defined by any two of the aforementioned values. In some embodiments, compositions, preparations, nanoparticles, and/or nanomaterials described herein have a pKa that is about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, or any range having endpoints defined by any two of the aforementioned values.

In some embodiments, lipid nanoparticles described herein have a pKa from about 5 to about 9. In some embodiments, lipid nanoparticles described herein have a pKa that is about 5.0, 5.5, 6.0, 6.5, 7.0, 7.5, 8.0, 8.5, or any range having endpoints defined by any two of the aforementioned values. In some embodiments, lipid nanoparticles described herein have a pKa that is about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, or any range having endpoints defined by any two of the aforementioned values.

II. Exemplary LNP Preparations

The present invention provides for compositions, preparations, nanoparticles, and/or nanomaterials that comprise lipid nanoparticles. In some embodiments, the lipid nanoparticle preparation comprises about 30 mole percent to about 70 mole percent ionizable lipid, about 5 mole percent to about 25 mole percent phospholipid, about 25 mole percent to about 45 mole percent cholesterol, and about 0 mole percent to about 5 mole percent conjugate-linker lipid.

In some embodiments, a lipid nanoparticle preparation comprises about 45 mole percent ionizable lipid, about 9 mole percent phospholipid, about 44 mole percent cholesterol, and about 2 mole percent conjugate-linker lipid. In some embodiments, a lipid nanoparticle preparation comprises about 50 mole percent ionizable lipid, about 9 mole percent phospholipid, about 38 mole percent cholesterol, and about 3 mole percent conjugate-linker lipid.

In some embodiments, a lipid nanoparticle preparation comprises about 47.5 mole percent ionizable lipid, about 10 mole percent phospholipid, about 40 mole percent cholesterol, and about 2.5 mole percent conjugate-linker lipid.

In some embodiments, a lipid nanoparticle preparation comprises about 40 mole percent to about 60 mole percent ionizable lipid of any one of Formulae I, II, III, IIIA, IIIB, IIIC, IV, V, VA, VI, VIA, VII, and VIIA, about 5 mole percent to about 15 mole percent 1-2-distearoyl-sn-glycero-3-phosphocholine, about 1 mole percent to about 5 mole percent C14PEG2000, and about 30 mole percent to about 47 mole percent cholesterol, based on the total moles of these four ingredients.

In some embodiments, a lipid nanoparticle (LNP) preparation comprises a mass ratio of (ionizable lipid, cholesterol, lipid-PEG, and phospholipid):mRNA from about 2:1 and 50:1. In some embodiments, a LNP preparation comprises a mass ratio of (ionizable lipid, cholesterol, lipid-PEG, and phospholipid):mRNA of about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1. In some embodiments, a lipid nanoparticle (LNP) preparation comprises a mass ratio of (ionizable lipid, cholesterol, lipid-PEG, and phospholipid):mRNA of about 11.7:1 and 19:1.

In some embodiments, a lipid nanoparticle preparation comprises a mass ratio of (ionizable lipid, cholesterol, lipid-PEG, and phospholipid):siRNA from about 2:1 and 50:1. In some embodiments, a LNP preparation comprises a mass ratio of (ionizable lipid, cholesterol, lipid-PEG, and phospholipid): siRNA of about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1. In some embodiments, a lipid nanoparticle (LNP) preparation comprises a mass ratio of (ionizable lipid, cholesterol, lipid-PEG, and phospholipid):siRNA of about 11.7:1 and 19:1.

In some embodiments, a lipid nanoparticle preparation comprises a mass ratio of (ionizable lipid, cholesterol, lipid-PEG, and phospholipid):NA from about 2:1 and 50:1. In some embodiments, a LNP preparation comprises a mass ratio of (ionizable lipid, cholesterol, lipid-PEG, and phospholipid):NA of about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1, about 30:1, about 31:1, about 32:1, about 33:1, about 34:1, about 35:1, about 36:1, about 37:1, about 38:1, about 39:1, about 40:1, about 41:1, about 42:1, about 43:1, about 44:1, about 45:1, about 46:1, about 47:1, about 48:1, about 49:1, about 50:1. In some embodiments, a lipid nanoparticle (LNP) preparation comprises a mass ratio of (ionizable lipid, cholesterol, lipid-PEG, and phospholipid):NA of about 11.7:1 and 40:1.

In some embodiments, NA comprises a base editor and sgRNA as described herein. In some embodiments, a mass ratio of base editor:gRNA is 1:1. In some embodiments, a mass ratio of base editor:gRNA is 2:1. In some embodiments, a mass ratio of base editor:gRNA is 3:1. In some embodiments, a mass ratio of base editor:gRNA is 4:1. In some embodiments, a mass ratio of base editor:gRNA is 5:1. In some embodiments, a mass ratio of base editor:gRNA is 6:1. In some embodiments, a mass ratio of base editor: gRNA is 7:1. In some embodiments, a mass ratio of base editor:gRNA is 8:1. In some embodiments, a mass ratio of base editor:gRNA is 9:1. In some embodiments, a mass ratio of base editor:gRNA is 10:1. In some embodiments, a mass ratio of base editor:gRNA is 1:2. In some embodiments, a mass ratio of base editor:gRNA is 1:3. In some embodiments, a mass ratio of base editor:gRNA is 1:4. In some embodiments, a mass ratio of base editor:gRNA is 1:5. In some embodiments, a mass ratio of base editor:gRNA is 1:6. In some embodiments, a mass ratio of base editor:gRNA is 1:7. In some embodiments, a mass ratio of base editor: gRNA is 1:8. In some embodiments, a mass ratio of base editor:gRNA is 1:9. In some embodiments, a mass ratio of base editor:gRNA is 1:10.

III. Pharmaceutical compositions

The present invention provides for compositions, preparations, nanoparticles, and/or nanomaterials that comprise pharmaceutical compositions. Among other things, in some embodiments, pharmaceutical compositions comprise lipid nanoparticles and lipid nanoparticle preparations described herein. For example, in some embodiments, lipid nanoparticles and lipid nanoparticle preparations described herein can be formulated in whole or in part as pharmaceutical compositions.

In some embodiments, pharmaceutical compositions may include one or more nanoparticle compositions described herein. For example, a pharmaceutical composition may comprise one or more nanoparticle compositions including one or more different therapeutic and/or prophylactics including but not limited to one or more nucleic acids of different types or encode different agents. In some embodiments, a pharmaceutical composition comprises one or more pharmaceutically acceptable excipients or accessory ingredients including but not limited to a pharmaceutically acceptable carrier.

A pharmaceutical composition may be administered to a subject. In some embodiments, a pharmaceutical composition is administered as described herein. In some in vivo approaches, the nanoparticle compositions disclosed herein are administered to a subject in a therapeutically effective amount as described herein.

In some embodiments, the ordinary skilled worker, considering the therapeutic context, age, and general health of the recipient, will be able to devise an appropriate dosage level and dosing regimen using the pharmaceutical compositions described herein for treatment of various conditions in various patients. For example, in some embodiments, a selected dosage depends upon the desired therapeutic effect, on the route of administration, and on the duration of the treatment desired. In some embodiments, generally dosage levels of about 0.001 mg to about 5 mg of nucleic acid per kg of body weight are administered each dosage to mammals. More specifically, in some embodiments, a preferential dose for nucleic acids within the disclosed nanoparticles is about 0.1 mg/kg to about 1.0 mg/kg. For the disclosed nanoparticles, generally dosage levels of about 0.2 mg to about 100 mg of four components (ionizable lipid, cholesterol, conjugate-linker conjugate, and phospholipid)/kg of body weight are administered to mammals. More specifically, in some embodiments, a preferential dose of the disclosed nanoparticles is about 0.5 mg/kg to about 5 mg/kg of the four components/kg of body weight.

In some embodiments, a pharmaceutical composition described herein is administered locally, for example by injection directly into a site to be treated. Typically, the injection causes an increased localized concentration of the composition which is greater than that which can be achieved by systemic administration. In some embodiments, a pharmaceutical composition described herein can be combined with a matrix as described herein to assist in creating an increased localized concentration of the polypeptide compositions by reducing the passive diffusion of the polypeptides out of the site to be treated.

A. Preparations for Parenteral Administration

In some embodiments, the compositions, preparations, nanoparticles, and/or nanomaterials disclosed herein, including those containing lipid nanoparticles, are administered in an aqueous solution, by parenteral injection. In some embodiments, a preparation may also be in the form of a suspension or emulsion. In general, pharmaceutical compositions are provided including effective amounts of a lipid nanoparticle, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

B. Controlled Delivery Polymeric Matrices

In some embodiments, the compositions, preparations, nanoparticles, and/or nanomaterials disclosed herein can also be administered in controlled release formulations. In some embodiments, controlled release polymeric devices can be made for long term release systemically following implantation of a polymeric device (such as a rod, cylinder, film, disk) or injection (such as microparticles). In some embodiments, a matrix can be in the form of microparticles such as microspheres. In some embodiments, an agent is dispersed within a solid polymeric matrix or microcapsules. In some embodiments, a core is of a different material than a polymeric shell of any of the described compositions, preparations, nanoparticles, and/or nanomaterials. In some embodiments, a peptide is dispersed or suspended in a core, which may be liquid or solid in nature, of any of the described compositions, preparations, nanoparticles, and/or nanomaterials. Unless specifically defined herein, microparticles, microspheres, and microcapsules are used interchangeably. In some embodiments, a polymer may be cast as a thin slab or film, ranging from nanometers to four centimeters, a powder produced by grinding or other standard techniques, or even a gel such as a hydrogel.

In some embodiments, non-biodegradable matrices are used for delivery of the described compositions, preparations, nanoparticles, and/or nanomaterials. In some embodiments, biodegradable matrices are used for delivery of the described compositions, preparations, nanoparticles, and/or nanomaterials. In some embodiments, biodegradable matrices are preferred. In some embodiments, biodegradable matrices comprise natural or synthetic polymers. In some embodiments, synthetic polymers are preferred due to the better characterization of degradation and release profiles. In some embodiments, a polymer is selected based on the period over which release is desired. In some embodiments, linear release may be most useful, although in others a pulse release or "bulk release" may provide more effective results. In some embodiments, a polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl. Polymer Sci., 35:755-774 (1988), the disclosure of which is hereby incorporated by reference in its entirety herein.

In some embodiments, the described compositions, preparations, nanoparticles, and/or nanomaterials can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

C. Cargo

Among other things, the present invention provides for compositions, preparations, nanoparticles, and/or nanomaterials that comprise cargo as described herein. In some embodiments, the compositions, preparations, nanoparticles, and/or nanomaterials include a therapeutic or prophylactic agent for delivery to a subject. In some embodiments, a therapeutic or prophylactic agent is encapsulated by a lipid nanoparticle. In some embodiments, a lipid nanoparticle is loaded with one or more nucleic acids.

D. Therapeutic and/or Prophylactic Agents

Cargo delivered via a LNP composition may be a biologically active agent. In some embodiments, the cargo is or comprises one or more biologically active agents, such as mRNA, guide RNA (gRNA), nucleic acid, RNA-guided DNA-binding agent, expression vector, template nucleic acid, antibody (e.g., monoclonal, chimeric, humanized, nanobody, and fragments thereof etc.), cholesterol, hormone, peptide, protein, chemotherapeutic and other types of antineoplastic agent, low molecular weight drug, vitamin, co-factor, nucleoside, nucleotide, oligonucleotide, enzymatic nucleic acid, antisense nucleic acid, triplex forming oligonucleotide, antisense DNA or RNA composition, chimeric DNA:RNA composition, allozyme, aptamer, ribozyme, decoys and analogs thereof, plasmid and other types of vectors, and small nucleic acid molecule, RNAi agent, short interfering nucleic acid (siNA), short interfering RNA (siRNA), double-stranded RNA (dsRNA), micro-RNA (miRNA), short hairpin RNA (shRNA) and "self-replicating RNA" (encoding a replicase enzyme activity and capable of directing its own replication or amplification in vivo) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), and iRNA (asymmetrical interfering RNA). The above list of biologically active agents is exemplary only, and is not intended to be limiting. Such compounds may be purified or partially purified, and may be naturally occurring or synthetic, and may be chemically modified.

Cargo delivered via a LNP composition may be an RNA, such as an mRNA molecule encoding a protein of interest. For example, in some embodiments, an mRNA for expressing a protein such as green fluorescent protein (GFP), an RNA-guided DNA-binding agent, or a Cas nuclease is described herein. LNP compositions that include a Cas nuclease mRNA, for example a Class 2 Cas nuclease mRNA that allows for expression in a cell of a Class 2 Cas nuclease such as a Cas9 or Cpf1 protein are provided. Further, cargo may contain one or more guide RNAs or nucleic acids encoding guide RNAs. A template nucleic acid, e.g., for repair or recombination, may also be included in the composition or a template nucleic acid may be used in the methods described herein. In some embodiments, cargo comprises an mRNA that encodes a *Streptococcus pyogenes* Cas9, optionally and an *S. pyogenes* gRNA. In some embodiments, cargo comprises an mRNA that encodes a *Neisseria meningitidis* Cas9, optionally and an nme gRNA.

"mRNA" refers to a polynucleotide and comprises an open reading frame that can be translated into a polypeptide (i.e., can serve as a substrate for translation by a ribosome and amino-acylated tRNAs). mRNA can comprise a phosphate-sugar backbone including ribose residues or analogs thereof, e.g., 2'-methoxy ribose residues. In some embodiments, the sugars of an mRNA phosphate-sugar backbone consist essentially of ribose residues, 2'-methoxy ribose residues, or a combination thereof. In general, mRNAs do not contain a substantial quantity of thymidine residues (e.g., 0 residues or fewer than 30, 20, 10, 5, 4, 3, or 2 thymidine residues; or less than 10%, 9%, 8%, 7%, 6%, 5%, 4%, 4%, 3%, 2%, 1%, 0.5%, 0.2%, or 0.1% thymidine content). An mRNA can contain modified uridines at some or all of its uridine positions.

E. CRISPR/Cas Cargo

In some embodiments, the disclosed compositions, preparations, nanoparticles, and/or nanomaterials comprise an mRNA encoding an RNA-guided DNA-binding agent, such as a Cas nuclease. In particular embodiments, the disclosed compositions, preparations, nanoparticles, and/or nanomaterials comprise an mRNA encoding a Class 2 Cas nuclease, such as *S. pyogenes* Cas9.

As used herein, an "RNA-guided DNA binding agent" means a polypeptide or complex of polypeptides having RNA and DNA binding activity, or a DNA-binding subunit of such a complex, wherein the DNA binding activity is sequence-specific and depends on the sequence of the RNA. Exemplary RNA-guided DNA binding agents include Cas cleavases/nickases and inactivated forms thereof ("dCas DNA binding agents"). "Cas nuclease", as used herein, encompasses Cas cleavases, Cas nickases, and dCas DNA binding agents. Cas cleavases/nickases and dCas DNA binding agents include a Csm or Cmr complex of a type III CRISPR system, the Cas10, Csm1, or Cmr2 subunit thereof, a Cascade complex of a type I CRISPR system, the Cas3 subunit thereof, and Class 2 Cas nucleases. As used herein, a "Class 2 Cas nuclease" is a single chain polypeptide with RNA-guided DNA binding activity. Class 2 Cas nucleases include Class 2 Cas cleavases/nickases (e.g., H840A, D10A, or N863 A variants), which further have RNA-guided DNA cleavases or nickase activity, and Class 2 dCas DNA binding agents, in which cleavase/nickase activity is inactivated. Class 2 Cas nucleases include, for example, Cas9, Cpf1, C2c1, C2c2, C2c3, HF Cas9 (e.g., N497A, R661A, Q695A, Q926A variants), HypaCas9 (e.g., N692A, M694A, Q695A, H698A variants), eSPCas9(1.0) (e.g., K810A, K1003A, R1060A variants), and eSPCas9(1.1) (e.g., K848A, K1003A, R1060A variants) proteins and modifications thereof. Cpf1 protein, Zetsche et al., Cell, 163: 1-13 (2015), is homologous to Cas9, and contains a RuvC-like nuclease domain. Cpf1 sequences of Zetsche are incorporated by reference in their entirety herein. See, e.g., Zetsche, Tables S1 and S3. See, e.g., Makarova et al., Nat Rev Microbiol, 13(11): 722-36 (2015); Shmakov et al., Molecular Cell, 60:385-397 (2015), the contents of which are hereby incorporated in its entirety herein.

As used herein, "ribonucleoprotein" (RNP) or "RNP complex" refers to a guide RNA together with an RNA-guided DNA binding agent, such as a Cas nuclease, e.g., a Cas cleavase, Cas nickase, or dCas DNA binding agent (e.g., Cas9). In some embodiments, the guide RNA guides the RNA-guided DNA binding agent such as Cas9 to a target sequence, and the guide RNA hybridizes with and the agent binds to the target sequence; in cases where the agent is a cleavase or nickase, binding can be followed by cleaving or nicking.

In some embodiments, cargo for a LNP composition includes at least one guide RNA comprising guide sequences that direct an RNA-guided DNA binding agent, which can be a nuclease (e.g., a Cas nuclease such as Cas9), to a target DNA. gRNA may guide the Cas nuclease or Class 2 Cas nuclease to a target sequence on a target nucleic acid molecule. In some embodiments, a gRNA binds with and provides specificity of cleavage by a Class 2 Cas nuclease. In some embodiments, a gRNA and the Cas nuclease may form a ribonucleoprotein (RNP), e.g., a CRISPR/Cas complex such as a CRISPR/Cas9 complex. In some embodiments, a CRISPR/Cas complex may be a Type-II CRISPR/Cas9 complex. In some embodiments, a CRISPR/Cas complex may be a Type-V CRISPR/Cas complex, such as a Cpf1/guide RNA complex. Cas nucleases and cognate gRNAs may be paired. gRNA scaffold structures that pair with each Class 2 Cas nuclease vary with the specific CRISPR/Cas system.

"Guide RNA", "gRNA", and simply "guide" are used herein interchangeably to refer to either a crRNA (also known as CRISPR RNA), or the combination of a crRNA and a trRNA (also known as tracrRNA). Guide RNAs can include modified RNAs as described herein. The crRNA and trRNA may be associated as a single RNA molecule (single guide RNA, sgRNA) or in two separate RNA molecules (dual guide RNA, dgRNA). "Guide RNA" or "gRNA" refers to each type. trRNA may be a naturally-occurring sequence, or a trRNA sequence with modifications or variations compared to naturally-occurring sequences.

As used herein, a "guide sequence" refers to a sequence within a guide RNA that is complementary to a target sequence and functions to direct a guide RNA to a target sequence for binding or modification (e.g., cleavage) by an RNA-guided DNA binding agent. A "guide sequence" may also be referred to as a "targeting sequence," or a "spacer sequence." A guide sequence can be 20 base pairs in length, e.g., in the case of *Streptococcus pyogenes* (i.e., Spy Cas9) and related Cas9 homologs/orthologs. Shorter or longer sequences can also be used as guides, e.g., 15-, 16-, 17-, 18-, 19-, 21-, 22-, 23-, 24-, or 25-nucleotides in length. In some embodiments, a target sequence is in a gene or on a chromosome, for example, and is complementary to a guide sequence. In some embodiments, a degree of complementarity or identity between a guide sequence and its corresponding target sequence may be about or at least 75%, 80%, 85%, 90%, 95%, 96%, 97%, 98%, 99%, or 100%. In some embodiments, a guide sequence and the target region may be 100% complementary or identical over a region of at least 15, 16, 17, 18, 19, or 20 contiguous nucleotides. In other embodiments, a guide sequence and a target region may contain at least one mismatch. For example, a guide sequence and a target sequence may contain 1, 2, 3, or 4 mismatches, where the total length of the target sequence is at least 17, 18, 19, 20 or more base pairs. In some embodiments, a guide sequence and a target region may contain 1-4 mismatches where a guide sequence comprises at least 17, 18, 19, 20 or more nucleotides. In some embodiments, a guide sequence and the target region may contain 1, 2, 3, or 4 mismatches where the guide sequence comprises 20 nucleotides.

Target sequences for RNA-guided DNA binding proteins such as Cas proteins include both the positive and negative strands of genomic DNA (i.e., the sequence given and the sequence's reverse compliment), as a nucleic acid substrate for a Cas protein is a double stranded nucleic acid. Accordingly, where a guide sequence is said to be "complementary to a target sequence", it is to be understood that the guide sequence may direct a guide RNA to bind to the reverse complement of a target sequence. Thus, in some embodiments, where the guide sequence binds the reverse complement of a target sequence, the guide sequence is identical to certain nucleotides of the target sequence (e.g., the target sequence not including the PAM) except for the substitution of U for T in the guide sequence.

The length of the targeting sequence may depend on the CRISPR/Cas system and components used. For example, different Class 2 Cas nucleases from different bacterial species have varying optimal targeting sequence lengths. Accordingly, the targeting sequence may comprise 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more than 50 nucleotides in length. In some embodiments, the targeting sequence length is 0, 1, 2, 3, 4, or 5 nucleotides longer or shorter than the guide sequence of a naturally-occurring nucleotide sequence.

CRISPR/Cas system. In certain embodiments, a Cas nuclease and gRNA scaffold will be derived from the same CRISPR/Cas system. In some embodiments, a targeting sequence may comprise or consist of 18-24 nucleotides. In some embodiments, a targeting sequence may comprise or consist of 19-21 nucleotides. In some embodiments, the targeting sequence may comprise or consist of 20 nucleotides.

In some embodiments, a sgRNA is a "Cas9 sgRNA" capable of mediating RNA-guided DNA cleavage by a Cas9 protein. In some embodiments, a sgRNA is a "Cpf1 sgRNA" capable of mediating RNA-guided DNA cleavage by a Cpf1 protein. In some embodiments, a gRNA comprises a crRNA and tracr RNA sufficient for forming an active complex with a Cas9 protein and mediating RNA-guided DNA cleavage. In some embodiments, a gRNA comprises a crRNA sufficient for forming an active complex with a Cpf1 protein and mediating RNA-guided DNA cleavage. See Zetsche 2015.

Certain embodiments of the invention also provide nucleic acids, e.g., expression cassettes, encoding the gRNA described herein. A "guide RNA nucleic acid" is used herein to refer to a guide RNA (e.g. an sgRNA or a dgRNA) and a guide RNA expression cassette, which is a nucleic acid that encodes one or more guide RNAs.

Certain embodiments of the present disclosure also provide delivery of adenine base editors ("ABEs") using the LNPs compositions, preparations, nanoparticles, and/or nanomaterials described herein. ABEs and methods of their use are described, e.g. in U.S. Pat. No. 10,113,163 and U.S. Patent Publication No. 2021/0130805, the contents of each of which are hereby incorporated by reference in their entireties.

Certain embodiments of the present disclosure also provide delivery of cytosine base editors ("CBEs") using the LNPs compositions, preparations, nanoparticles, and/or nanomaterials described herein. ABEs and methods of their use are described, e.g. in U.S. Pat. Nos. 10,167,457 and 9,840,699, the contents of each of which are hereby incorporated by reference in their entireties.

The term "base editor (BE)," or "nucleobase editor (NBE)" refers to an agent comprising a polypeptide that is capable of making a modification to a base (e.g., A, T, C, G, or U) within a nucleic acid sequence (e.g., DNA or RNA). In some embodiments, the base editor is capable of deaminating a base within a nucleic acid. In some embodiments, the base editor is capable of deaminating a base within a DNA molecule. In some embodiments, the base editor is capable of deaminating an adenine (A) in DNA. In some embodiments, the deaminase is a cytosine deaminase or a cytidine deaminase. In some embodiments, the base editor is a fusion protein comprising a nucleic acid programmable DNA binding protein (napDNAbp) fused to an adenosine deaminase. In some embodiments, the base editor is a Cas9 protein fused to an adenosine deaminase. In some embodiments, the base editor is a Cas9 nickase (nCas9) fused to an adenosine deaminase. In some embodiments, the base editor is a nuclease-inactive Cas9 (dCas9) fused to an adenosine deaminase. In some embodiments, the base editor is fused to an inhibitor of base excision repair, for example, a UGI domain, or a dISN domain. In some embodiments, the fusion protein comprises a Cas9 nickase fused to a deaminase and an inhibitor of base excision repair, such as a UGI or dISN domain. The term "nucleic acid programmable DNA binding protein" or "napDNAbp" refers to a protein that associates with a nucleic acid (e.g., DNA or RNA), such as a guide nucleic acid, that guides the napDNAbp to a specific nucleic acid sequence. For example, a Cas9 protein can associate with a guide RNA that guides the Cas9 protein to a specific DNA sequence that has complementary to the guide RNA. In some embodiments, the napDNAbp is a class 2 microbial CRISPR-Cas effector. In some embodiments, the napDNAbp is a Cas9 domain, for example a nuclease active Cas9, a Cas9 nickase (nCas9), or a nuclease inactive Cas9 (dCas9). Examples of nucleic acid programmable DNA binding proteins include, without limitation, Cas9 (e.g., dCas9 and nCas9), CasX, CasY, Cpf1, C2c1, C2c2, C2C3, and Argonaute. It should be appreciated, however, that nucleic acid programmable DNA binding proteins also include nucleic acid programmable proteins that bind RNA. For example, the napDNAbp may be associated with a nucleic acid that guides the napDNAbp to an RNA. Other nucleic acid programmable DNA binding proteins are also within the scope of this disclosure, though they may not be specifically listed in this disclosure.

F. Modified RNAs

In certain embodiments, the disclosed compositions, preparations, nanoparticles, and/or nanomaterials comprise modified nucleic acids, including modified RNAs.

Modified nucleosides or nucleotides can be present in an RNA, for example a gRNA or mRNA. A gRNA or mRNA comprising one or more modified nucleosides or nucleotides, for example, is called a "modified" RNA to describe the presence of one or more non-naturally and/or naturally occurring components or configurations that are used instead of or in addition to the canonical A, G, C, and U residues. In some embodiments, a modified RNA is synthesized with a non-canonical nucleoside or nucleotide, here called "modified."

Modified nucleosides and nucleotides can include one or more of: (i) alteration, e.g., replacement, of one or both of the non-linking phosphate oxygens and/or of one or more of the linking phosphate oxygens in the phosphodiester backbone linkage (an exemplary backbone modification); (ii) alteration, e.g., replacement, of a constituent of the ribose sugar, e.g., of the 2' hydroxyl on the ribose sugar (an exemplary sugar modification); (iii) wholesale replacement of the phosphate moiety with "dephospho" linkers (an exemplary backbone modification); (iv) modification or replacement of a naturally occurring nucleobase, including with a non-canonical nucleobase (an exemplary base modification); (v) replacement or modification of the ribose-phosphate backbone (an exemplary backbone modification); (vi) modification of the 3' end or 5' end of the oligonucleotide, e.g., removal, modification or replacement of a terminal phosphate group or conjugation of a moiety, cap or linker (such 3' or 5' cap modifications may comprise a sugar and/or backbone modification); and (vii) modification or replacement of the sugar (an exemplary sugar modification). Certain embodiments comprise a 5' end modification to an mRNA, gRNA, or nucleic acid. Certain embodiments comprise a 3' end modification to an mRNA, gRNA, or nucleic acid. A modified RNA can contain 5' end and 3' end modifications. A modified RNA can contain one or more modified residues at non-terminal locations. In certain embodiments, a gRNA includes at least one modified residue. In certain embodiments, an mRNA includes at least one modified residue.

Unmodified nucleic acids can be prone to degradation by, e.g., intracellular nucleases or those found in serum. For example, nucleases can hydrolyze nucleic acid phosphodiester bonds. Accordingly, in one aspect the RNAs (e.g. mRNAs, gRNAs) described herein can contain one or more modified nucleosides or nucleotides, e.g., to introduce stability toward intracellular or serum-based nucleases. In some embodiments, the modified gRNA molecules described herein can exhibit a reduced innate immune response when introduced into a population of cells, both in vivo and ex vivo. The term "innate immune response" includes a cellular response to exogenous nucleic acids, including single stranded nucleic acids, which involves the induction of cytokine expression and release, particularly the interferons, and cell death.

Accordingly, in some embodiments, RNA or nucleic acids in the disclosed the disclosed compositions, preparations, nanoparticles, and/or nanomaterials comprise at least one modification which confers increased or enhanced stability to the nucleic acid, including, for example, improved resistance to nuclease digestion in vivo. As used herein, the terms "modification" and "modified" as such terms relate to the nucleic acids provided herein, include at least one alteration which preferably enhances stability and renders the RNA or nucleic acid more stable (e.g., resistant to nuclease digestion) than the wild-type or naturally occurring version of the RNA or nucleic acid. As used herein, the terms "stable" and "stability" as such terms relate to the nucleic acids of the present invention, and particularly with respect to the RNA, refer to increased or enhanced resistance to degradation by, for example nucleases (i.e., endonucleases or exonucleases) which are normally capable of degrading such RNA. Increased stability can include, for example, less sensitivity to hydrolysis or other destruction by endogenous enzymes (e.g., endonucleases or exonucleases) or conditions within the target cell or tissue, thereby increasing or enhancing the residence of such RNA in the target cell, tissue, subject and/or cytoplasm. The stabilized RNA molecules provided herein demonstrate longer half-lives relative to their naturally occurring, unmodified counterparts (e.g. the wild-type version of the mRNA). Also contemplated by the terms "modification" and "modified" as such terms related to the mRNA of the LNP compositions disclosed herein are alterations which improve or enhance translation of mRNA nucleic acids, including for example, the inclusion of sequences which function in the initiation of protein translation (e.g., the Kozac consensus sequence). (Kozak, M., Nucleic Acids Res 15 (20): 8125-48 (1987), the contents of which are hereby incorporated by reference herein in its entirety).

In some embodiments, an RNA or nucleic acid of the disclosed compositions, preparations, nanoparticles, and/or nanomaterials disclosed herein have undergone a chemical or biological modification to render it more stable. Exemplary modifications to an RNA include the depletion of a base (e.g., by deletion or by the substitution of one nucleotide for another) or modification of a base, for example, the chemical modification of a base. The phrase "chemical modifications" as used herein, includes modifications which introduce chemistries which differ from those seen in naturally occurring RNA, for example, covalent modifications such as the introduction of modified nucleotides, (e.g., nucleotide analogs, or the inclusion of pendant groups which are not naturally found in such RNA molecules).

In some embodiments of a backbone modification, the phosphate group of a modified residue can be modified by replacing one or more of the oxygens with a different substituent. Further, the modified residue, e.g., modified residue present in a modified nucleic acid, can include the wholesale replacement of an unmodified phosphate moiety with a modified phosphate group as described herein. In some embodiments, the backbone modification of the phosphate backbone can include alterations that result in either an uncharged linker or a charged linker with unsymmetrical charge distribution. Examples of modified phosphate groups include, phosphorothioate, phosphoroselenates, borano phosphates, borano phosphate esters, hydrogen phosphonates, phosphoroamidates, alkyl or aryl phosphonates and phosphotriesters. The phosphorous atom in an unmodified phosphate group is achiral. However, replacement of one of the non-bridging oxygens with one of the above atoms or groups of atoms can render the phosphorous atom chiral. The stereogenic phosphorous atom can possess either the "R" configuration (herein Rp) or the "S" configuration (herein Sp). The backbone can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens. The phosphate group can be replaced by non-phosphorus containing connectors in certain backbone modifications. In some embodiments, the charged phosphate group can be replaced by a neutral moiety. Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

G. mRNA

In some embodiments, the disclosed compositions, preparations, nanoparticles, and/or nanomaterials comprise an mRNA comprising an open reading frame (ORF) encoding an RNA-guided DNA binding agent, such as a Cas nuclease, or Class 2 Cas nuclease as described herein. In some embodiments, an mRNA comprising an ORF encoding an RNA-guided DNA binding agent, such as a Cas nuclease or Class 2 Cas nuclease, is provided, used, or administered. An mRNA may comprise one or more of a 5' cap, a 5' untranslated region (UTR), a 3' UTRs, and a polyadenine tail. The mRNA may comprise a modified open reading frame, for example to encode a nuclear localization sequence or to use alternate codons to encode the protein.

mRNA in the disclosed compositions, preparations, nanoparticles, and/or nanomaterials may encode, for example, a secreted hormone, enzyme, receptor, polypeptide, peptide or other protein of interest that is normally secreted. In one embodiment of the invention, the mRNA may optionally have chemical or biological modifications which, for example, improve the stability and/or half-life of such mRNA or which improve or otherwise facilitate protein production.

In addition, suitable modifications include alterations in one or more nucleotides of a codon such that the codon encodes the same amino acid but is more stable than the codon found in the wild-type version of the mRNA. For example, an inverse relationship between the stability of RNA and a higher number cytidines (C's) and/or uridines (U's) residues has been demonstrated, and RNA devoid of C and U residues have been found to be stable to most RNases (Heidenreich, et al. J Biol Chem 269, 2131-8 (1994), the disclosure of which is hereby incorporated by reference herein in its entirety). In some embodiments, the number of C and/or U residues in an mRNA sequence is reduced. In another embodiment, the number of C and/or U residues is reduced by substitution of one codon encoding a particular amino acid for another codon encoding the same or a related amino acid. Contemplated modifications to the mRNA nucleic acids of the present invention also include the incorporation of pseudouridines. The incorporation of pseudouridines into the mRNA nucleic acids of the present invention may enhance stability and translational capacity, as well as diminishing immunogenicity in vivo. See, e.g., Kariko, K., et al., Molecular Therapy 16 (11): 1833-1840 (2008), the contents of which is hereby incorporated by reference herein in its entirety. Substitutions and modifications to the mRNA of the present invention may be performed by methods readily known to one or ordinary skill in the art.

The constraints on reducing the number of C and U residues in a sequence will likely be greater within the coding region of an mRNA, compared to an untranslated region, (i.e., it will likely not be possible to eliminate all of the C and U residues present in the message while still retaining the ability of the message to encode the desired amino acid sequence). The degeneracy of the genetic code, however presents an opportunity to allow the number of C and/or U residues that are present in the sequence to be reduced, while maintaining the same coding capacity (i.e., depending on which amino acid is encoded by a codon, several different possibilities for modification of RNA sequences may be possible).

The term modification also includes, for example, the incorporation of non-nucleotide linkages or modified nucleotides into the mRNA sequences of the present invention (e.g., modifications to one or both the 3' and 5' ends of an mRNA molecule encoding a functional secreted protein or enzyme). Such modifications include the addition of bases to an mRNA sequence (e.g., the inclusion of a poly A tail or a longer poly A tail), the alteration of the 3' UTR or the 5' UTR, complexing the mRNA with an agent (e.g., a protein or a complementary nucleic acid molecule), and inclusion of elements which change the structure of an mRNA molecule (e.g., which form secondary structures).

The poly A tail is thought to stabilize natural messengers. Therefore, in one embodiment a long poly A tail can be added to an mRNA molecule thus rendering the mRNA more stable. Poly A tails can be added using a variety of art-recognized techniques. For example, long poly A tails can be added to synthetic or in vitro transcribed mRNA using poly A polymerase (Yokoe, et al. Nature Biotechnology. 1996; 14: 1252-1256, the contents of which is hereby incorporated by reference herein in its entirety). A transcription vector can also encode long poly A tails. In addition, poly A tails can be added by transcription directly from PCR products. In one embodiment, the length of the poly A tail is at least about 90, 200, 300, 400 at least 500 nucleotides. In one embodiment, the length of the poly A tail is adjusted to control the stability of a modified mRNA molecule of the invention and, thus, the transcription of protein. For example, since the length of the poly A tail can influence the half-life of an mRNA molecule, the length of the poly A tail can be adjusted to modify the level of resistance of the mRNA to nucleases and thereby control the time course of protein expression in a cell. In one embodiment, the stabilized mRNA molecules are sufficiently resistant to in vivo degradation (e.g., by nucleases), such that they may be delivered to the target cell without a transfer vehicle.

In some embodiment embodiments, an mRNA can be modified by the incorporation 3' and/or 5' untranslated (UTR) sequences which are not naturally found in the wild-type mRNA. In one embodiment, 3' and/or 5' flanking sequence which naturally flanks an mRNA and encodes a second, unrelated protein can be incorporated into the nucleotide sequence of an mRNA molecule encoding a therapeutic or functional protein in order to modify it. For example, 3' or 5' sequences from mRNA molecules which are stable (e.g., globin, actin, GAPDH, tubulin, histone, or citric acid cycle enzymes) can be incorporated into the 3' and/or 5' region of a sense mRNA nucleic acid molecule to increase the stability of the sense mRNA molecule. See, e.g., US2003/0083272, the contents of which is hereby incorporated by reference herein in its entirety. More detailed descriptions of the mRNA modifications can be found in US2017/0210698A1, at pages 57-68, which content is incorporated herein by reference in its entirety.

H. Template Nucleic Acid

The compositions, preparations, nanoparticles, and/or nanomaterials and methods disclosed herein may include a template nucleic acid. A template may be used to alter or insert a nucleic acid sequence at or near a target site for an RNA-guided DNA binding protein such as a Cas nuclease, e.g., a Class 2 Cas nuclease. In some embodiments, the methods comprise introducing a template to the cell. In some embodiments, a single template may be provided. In some embodiments, two or more templates may be provided such that editing may occur at two or more target sites. For example, different templates may be provided to edit a single gene in a cell, or two different genes in a cell.

In some embodiments, a template may be used in homologous recombination. In some embodiments, the homologous recombination may result in the integration of the template sequence or a portion of the template sequence into the target nucleic acid molecule. In some embodiments, a template may be used in homology-directed repair, which involves DNA strand invasion at the site of the cleavage in the nucleic acid. In some embodiments, homology-directed repair may result in including the template sequence in the edited target nucleic acid molecule. In some embodiments, a template may be used in gene editing mediated by non-homologous end joining. In some embodiments, a template sequence has no similarity to the nucleic acid sequence near the cleavage site. In some embodiments, a template or a portion of the template sequence is incorporated. In some embodiments, a template includes flanking inverted terminal repeat (ITR) sequences.

In some embodiments, a template sequence may correspond to, comprise, or consist of an endogenous sequence of a target cell. It may also or alternatively correspond to, comprise, or consist of an exogenous sequence of a target cell. As used herein, the term "endogenous sequence" refers to a sequence that is native to the cell. The term "exogenous sequence" refers to a sequence that is not native to a cell, or a sequence whose native location in the genome of the cell is in a different location. In some embodiments, the endogenous sequence may be a genomic sequence of the cell.

In some embodiments, the endogenous sequence may be a chromosomal or extrachromosomal sequence. In some embodiments, an endogenous sequence may be a plasmid sequence of the cell.

In some embodiments, a template contains ssDNA or dsDNA containing flanking invert-terminal repeat (ITR) sequences. In some embodiments, a template is provided as a vector, plasmid, minicircle, nanocircle, or PCR product.

In some embodiments, a nucleic acid is purified. In some embodiments, a nucleic acid is purified using a precipitation method (e.g., LiCl precipitation, alcohol precipitation, or an equivalent method, e.g., as described herein). In some embodiments, a nucleic acid is purified using a chromatography-based method, such as an HPLC-based method or an equivalent method (e.g., as described herein). In some embodiments, a nucleic acid is purified using both a precipitation method (e.g., LiCl precipitation) and an HPLC-based method. In some embodiments, the nucleic acid is purified by tangential flow filtration (TFF).

IV. Methods of Manufacturing LNPs

Methods of manufacturing lipid nanoparticles are known in the art. In some embodiments, the described compositions, preparations, nanoparticles, and/or nanomaterials are manufactured using microfluidics. For instance, exemplary methods of using microfluidics to form lipid nanoparticles are described by Leung, A. K. K, et al., *J Phys Chem,* 116:18440-18450 (2012), Chen, D., et al., *J Am Chem Soc,* 134:6947-6951 (2012), and Belliveau, N. M., et al., *Molecular Therapy-Nucleic Acids,* 1: e37 (2012), the disclosures of which are hereby incorporated by reference in their entireties.

Briefly, a cargo, such as a cargo described herein, is prepared in a first buffer solution. The other lipid nanoparticle components (such as ionizable lipid, conjugate-linker lipids, cholesterol, and phospholid) are prepared in a second buffer solution. In some embodiments, a syringe pump introduces the two solutions into a microfluidic device. The two solutions come into contact within the microfluidic device to form lipid nanoparticles encapsulating the cargo.

Figure 2:
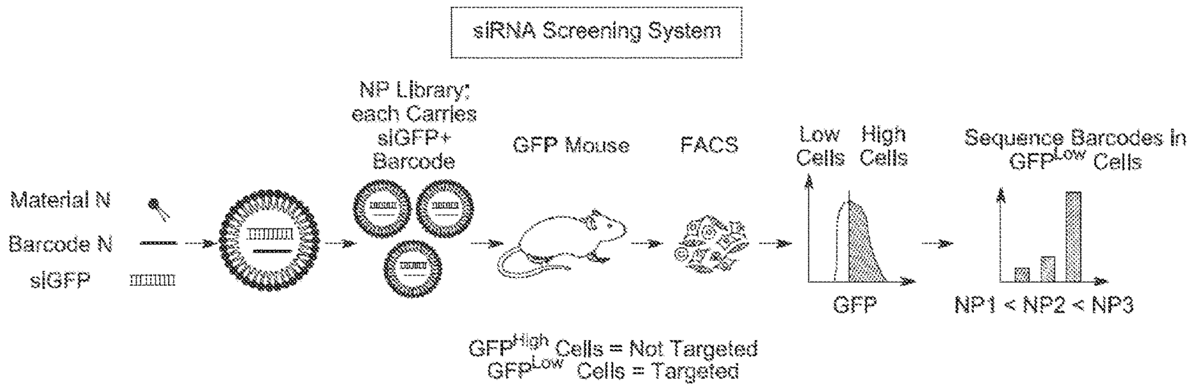
FIG. 2 depicts an exemplary siRNA screening system of LNP preparations, in accordance with an embodiment of the present disclosure.

Methods of screening the disclosed lipid nanoparticles are described in International Patent Application No. PCT/US2018/058171, which is incorporated by reference in its entirety herein. FIG. 1 depicts an exemplary mRNA screening system of LNP preparations, in accordance with an embodiment of the present disclosure. FIG. 2 depicts an exemplary siRNA screening system of LNP preparations, in accordance with an embodiment of the present disclosure. In some embodiments, the screening methods characterize vehicle delivery preparations to identify preparations with a desired tropism and that deliver functional cargo to the cytoplasm of specific cells. In some embodiments, the screening method uses a reporter that has a functionality that can be detected when delivered to the cell. For example, detecting a functional reporter in a cell indicates that the LNP preparation delivers functional cargo to the cell. Among other things, in some embodiments, a chemical composition identifier is included in each different delivery vehicle formulation to keep track of the chemical composition specific for each different delivery vehicle formulation. In some embodiments, a chemical composition identifier is a nucleic acid barcode. In some embodiments, a sequence of the nucleic acid barcode is paired to which chemical components were used to formulate the LNP preparation in which it is loaded so that when the nucleic acid barcode is sequenced, the chemical composition of the delivery vehicle that delivered the barcode is identified. Representative barcodes include, but are not limited to, barcodes described by Sago, 2018 PNAS, Sago, JACS 2018, the disclosure of which is hereby incorporated by reference in its entirety. Representative reporters include, but are not limited to siRNA, mRNA, nuclease protein, nuclease mRNA, small molecules, epigenetic modifiers, and phenotypic modifiers. DNA (genomic and DNA barcodes) can be isolated using QuickExtract (Lucigen) and sequenced using Illumina MiniSeq as described by Sago et al. PNAS 2018, Sago et al. JACs 2018, Sago, Lokugamage et al. Nano Letters 2018, the disclosures of which are hereby incorporated by reference in their entireties).

V. Methods of Use

Among other things, the present disclosure describes methods of using compositions, preparations, nanoparticles, and/or nanomaterials described herein. For example, in some embodiments, the present disclosure describes methods of using compositions, preparations, nanoparticles, and/or nanomaterials to deliver cargo to specific cells, tissues, or organs, as described herein. As another example, in some embodiments, the present disclosure describes methods of treatment and/or delaying and/or arresting progression of a disease or disorder using compositions, preparations, nanoparticles, and/or nanomaterials as described herein. In some embodiments, compositions, preparations, nanoparticles, and/or nanomaterials described herein are for use in medicine.

In some embodiments, compositions, preparations, nanoparticles, and/or nanomaterials described herein deliver therapeutic or prophylactic agents to specific cells or organs in a subject in need thereof. In some embodiments, the compositions, preparations, nanoparticles, and/or nanomaterials deliver therapeutic or prophylactic agents to specific cells or organs in a subject in need thereof in the absence of a targeting ligand. In some embodiments, the compositions, preparations, nanoparticles, and/or nanomaterials are useful to treat or prevent diseases in a subject in need thereof.

A. Methods of Delivering Cargo to Cells, Tissue, or Organs

Among other things, in some embodiments, compositions, preparations, nanoparticles, and/or nanomaterials disclosed herein target a particular type or class of cells (e.g., cells of a particular organ or system thereof), tissues, and/organs. In some embodiments, the present disclosure provides methods of delivering one or more cargos described herein to a subject in need thereof. In some embodiments, such methods comprise in vivo and/or in vitro delivery. In some embodiments, such methods comprise in vivo delivery. In some embodiments, such methods comprise in vitro delivery. In some embodiments, the present disclosure provides for methods of delivering one or more therapeutic and/or prophylactic nucleic acids to a subject in need thereof are described herein.

In some embodiments, a composition, preparation, nanoparticle, and/or nanomaterial comprises a therapeutic and/or prophylactic of interest that may be specifically delivered to liver cells in the subject. Exemplary liver cells include but are not limited to hepatocytes.

In some embodiments, a composition, preparation, nanoparticle, and/or nanomaterial comprises a therapeutic and/or prophylactic of interest that may be specifically delivered to spleen cells in the subject. Exemplary spleen cells include but are not limited to splenic monocytes, splenic T cells, splenic memory B cells, or splenic B cells.

In some embodiments, a composition, preparation, nanoparticle, and/or nanomaterial comprises a therapeutic and/or prophylactic of interest that may be specifically delivered to bone marrow cells in the subject. Exemplary bone marrow cells include but are not limited to bone marrow monocytes, bone marrow B cells, bone marrow memory B cells, or bone marrow T cells.

In some embodiments, a composition, preparation, nanoparticle, and/or nanomaterial comprises a therapeutic and/or prophylactic of interest that may be specifically delivered to immune cells in the subject. Exemplary immune cells include but are not limited to CD8+, CD4+, or CD8+CD4+ cells.

In some embodiments, a composition, preparation, nanoparticle, and/or nanomaterial comprises a therapeutic and/or prophylactic of interest that may be specifically delivered to hematopoietic stem cells in the subject. Unless otherwise specified, it is understood that the terms "hematopoietic stem cells (HSCs)" and "hematopoietic stem and progenitor cells (HSPCs)" are used interchangeably in the present disclosure.

In some embodiments, composition, preparation, nanoparticle, and/or nanomaterial comprises a therapeutic and/or prophylactic of interest that may be specifically delivered to heart cells (e.g., cardiomyocytes).

In some embodiments, composition, preparation, nanoparticle, and/or nanomaterial comprises a therapeutic and/or prophylactic of interest that may be specifically delivered to muscle cells (e.g., myocytes).

In some embodiments, the lipid nanoparticles can be formulated to be delivered in the absence of a targeting ligand to a mammalian liver hepatocytes, liver immune cells, spleen T cells, or lung endothelial cells. Specific delivery to a particular class or type of cells indicates that a higher proportion of lipid nanoparticles are delivered to target type or class of cells. In some embodiments, specific delivery may result in a greater than 2 fold, 5 fold, 10 fold, 15 fold, or 20 fold compared to delivery using a conventional nanoparticle system (e.g., MC3-containing LNPs).

B. Methods of Producing a Polypeptide

Among other things, in some embodiments, methods of using compositions, preparations, nanoparticles, and/or nanomaterials disclosed herein are used for methods of producing a polypeptide. Among other things, in some embodiments, lipid nanoparticles described herein can be used for producing a polypeptide in a target cell in a subject in need thereof. For example, in some embodiments, lipid nanoparticles described herein can be used for producing a polypeptide in a target cell in a subject in need thereof. In some embodiments, compositions, preparations, nanoparticles, and/or nanomaterials disclosed herein comprise one or more nucleic sequences to be delivered to a cell.

In some embodiments, one or more nucleic acids are expressed in a cell. In some embodiments, expression of a nucleic acid sequence involves one or more of the following: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

C. Methods of Gene Regulation

Among other things, in some embodiments, methods of using compositions, preparations, nanoparticles, and/or nanomaterials disclosed herein are used for gene regulation. Among other things, in some embodiments, lipid nanoparticles described herein can be used for reducing and/or increasing gene expression in a target cell in a subject in need thereof. For example, in some embodiments, lipid nanoparticles described herein can deliver one or more nucleic acids to a target cell in the subject without a targeting ligand. In some embodiments, a nucleic acid is an inhibitor nucleic acid. In some embodiments, an inhibitory nucleic acid is an siRNA. In some embodiments, a nucleic acid is a nucleic acid described herein. As another example, in some embodiments, lipid nanoparticles described herein can deliver cargo to a target cell in the subject without a targeting ligand. In some embodiments, cargo is any cargo described herein.

Among other things, in some embodiments, methods of using compositions, preparations, nanoparticles, and/or nanomaterials disclosed herein for editing of a gene in a cell in a subject in need thereof.

In some embodiments, a cell that is targeted for gene regulation is an immune cell. The immune cell can be a T cell, such as CD8+ T cell, CD4+ T cell, or T regulatory cell. Other exemplary immune cells for gene editing include but are not limited to macrophages, dendritic cells, B cells or natural killer cells. In some embodiments, the cell that is targeted for gene regulation in a hepatocyte.

Exemplary genes that can be targeted include but are not limited to T cell receptors, B cell receptors, CTLA4, PD1, FOXO1, FOXO3, AKTs, CCR5, CXCR4, LAG3, TIM3, Killer immunoglobulin-like receptors, GITR, BTLA, LFA-4, T4, LFA-1, Bp35, CD27L receptor, TNFRSF8, TNFRSF5, CD47, CD52, ICAM-1, LFA-3, L-selectin, Ki-24, MB1, B7, B70, M-CSFR, TNFR-II, IL-7R, OX-40, CD137, CD137L, CD3OL, CD40L, FasL, TRAIL, CD257, LIGHT, TRAIL-R1, TRAILR2, TRAIL-R4, TWEAK-R, TNFR, BCMA, B7DC, BTLA, B7-H1, B7-H2, B7-H3, ICOS, VEGFR2, NKG2D, JAG1, GITR, CD4, CCR2, GATA-3, MTORC1, MTORC2, RAPTOR, GATOR, FOXP3, NFAT, IL2R, and IL7. Other exemplary genes that can be targeted include but are not limited to OCT, G6Pase, Mut, PCCA, PCCB, and PAH. Exemplary tumor-associated antigens that can be recognized by T cells and are contemplated for targeting, include but are not limited to MAGE1, MAGE3, MAGE6, BAGE, GAGE, NYESO-1, MART1/Melan A, MC1R, GP100, tyrosinase, TRP-1, TRP-2, PSA, CEA, Cyp-B, Her2/Neu, hTERT, MUC1, PRAME, WT1, RAS, CDK-4, MUM-1, KRAS, MSLN and β-catenin.

D. Subjects to be Treated

In some embodiments, subjects who are treated are mammals experiencing cancer, autoimmune disease, infections disease, organ transplant, organ failure, protein deficiency, or a combination thereof. In some embodiments, a subject is a human. In some embodiments, methods described herein may cause hepatocytes to translate certain proteins. In some embodiments, methods described herein may be used to deliver one or more DNA, mRNA, sgRNA, or siRNA to a hepatocyte. In some embodiments, methods described herein may be used to deliver one or more DNA, mRNA, sgRNA, or siRNA to a splenic T cell. In some embodiments, methods described herein may be used to deliver one or more DNA, mRNA, sgRNA, or siRNA to a splenic B cell. In some embodiments, methods described herein may be used to deliver one or more DNA, mRNA, sgRNA, or siRNA to a splenic monocyte. In some embodiments, methods described herein may be used to deliver one or more DNA, mRNA, sgRNA, or siRNA to a bone marrow cell.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

EXEMPLARY EMBODIMENTS

1. A compound of Formula I:

(I)

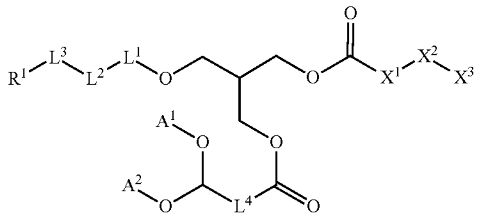

or a pharmaceutically acceptable salt thereof, wherein:

$L^1$ is a covalent bond, —C(O)—, or —OC(O)—;

$L^2$ is a covalent bond, an optionally substituted bivalent saturated or unsaturated, straight or branched $C_1$-$C_{12}$ hydrocarbon chain, or

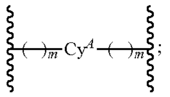

$Cy^A$ is an optionally substituted ring selected from phenylene and 3- to 7-membered saturated or partially unsaturated carbocyclene;

each m is independently 0, 1, or 2;

$L^3$ is a covalent bond, —C(O)—, —C(O)O—, —OC(O)—, —O—, or —OC(O)O—;

$R^1$ is

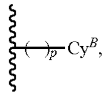

an optionally substituted saturated or unsaturated, straight or branched $C_1$-$C_{20}$ hydrocarbon chain wherein 1-3 methylene units are optionally and independently replaced with —O— or —NR—, or

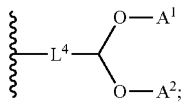

$Cy^B$ is an optionally substituted ring selected from 3- to 12-membered saturated or partially unsaturated carbocyclyl, 1-adamantyl, 2-adamantyl,

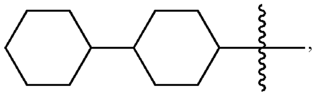 [SMILES: *C1CCC(C2CCCCC2)CC1]

sterolyl, and phenyl;

p is 0, 1, 2, or 3;

each $L^4$ is independently a bivalent saturated or unsaturated, straight or branched $C_1$-$C_6$ hydrocarbon chain;

each $A^1$ and $A^2$ is independently an optionally substituted $C_1$-$C_{20}$ aliphatic or —$L^5$—$R^5$;

or $A^1$ and $A^2$, together with their intervening atoms, may form an optionally substituted ring:

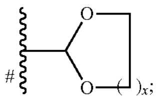

where x is selected from 1 or 2; and # represents the point of attachment to $L^4$;

each $L^5$ is independently a bivalent saturated or unsaturated, straight or branched $C_1$-$C_{20}$ hydrocarbon chain, wherein 1-3 methylene units are optionally and independently replaced with —O— or —NR—;

each $R^5$ is independently an optionally substituted group selected from a 5- to 10-membered aryl ring or a 3- to 8-membered carbocyclic ring;

$X^1$ is a covalent bond, —O—, or —NR—;

$X^2$ is a covalent bond or an optionally substituted, bivalent saturated or unsaturated, straight or branched, $C_1$-$C_{12}$ hydrocarbon chain, wherein 1-3 methylene units are optionally and independently replaced with —O—, —NR—, or —$Cy^C$—;

$Cy^C$ is an optionally substituted ring selected from 3- to 7-membered saturated or partially unsaturated carbocyclene, phenylene, 3- to 7-membered saturated or partially unsaturated heterocyclene having 1-3 heteroatoms independently selected from nitrogen, oxygen, and sulfur, and 5- to 6-membered heteroarylene having 1-3 heteroatoms independently selected from nitrogen, oxygen, and sulfur;

$X^3$ is hydrogen or an optionally substituted ring selected from 3- to 7-membered saturated or partially unsaturated carbocyclyl, phenyl, 3- to 7-membered saturated or partially unsaturated heterocyclyl having 1-3 heteroatoms independently selected from nitrogen, oxygen, and sulfur, or 5- to 6-membered heteroaryl having 1-3 heteroatoms independently selected from nitrogen, oxygen, and sulfur; and each R is independently hydrogen or an optionally substituted $C_1$-$C_6$ aliphatic group;

provided that when $L^3$ is a covalent bond, then $R^1$ must be

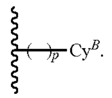

2. The compound of embodiment 1, wherein the compound is of Formula (II):

(II)

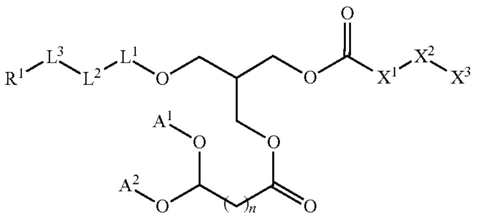

or a pharmaceutically acceptable salt thereof, wherein n is 1, 2, 3 or 4.

3. The compound of embodiment 1, wherein the compound is of Formula (III):

(III)

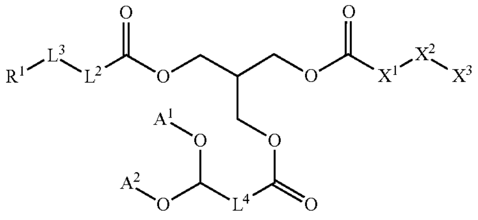

or a pharmaceutically acceptable salt thereof.

4. The compound of embodiment 1 or 3, wherein the compound is of Formula (IIIA):

(IIIA)

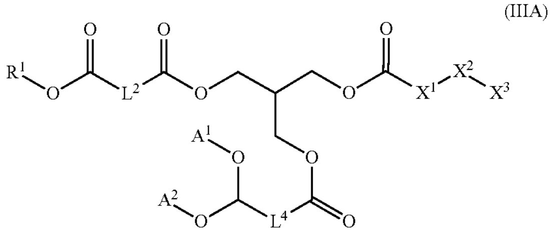

or a pharmaceutically acceptable salt thereof.

5. The compound of embodiment 1, 3, or 4, wherein the compound is of Formula (IIIB):

(IIIB)

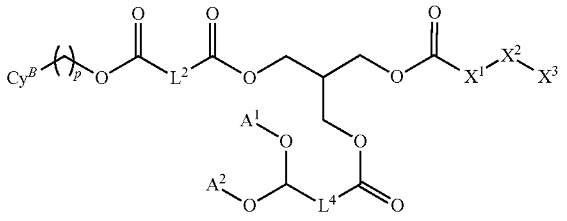

or a pharmaceutically acceptable salt thereof.

6. The compound of embodiment 1 or 3, wherein the compound is of Formula (IIIC):

(IIIC)

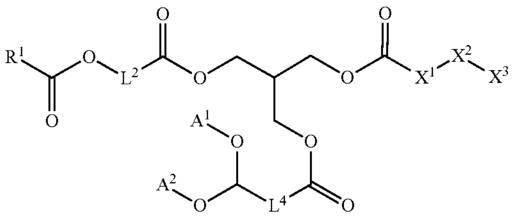

or a pharmaceutically acceptable salt thereof.

7. The compound of embodiment 1, wherein the compound is of Formula (IV):

(IV)

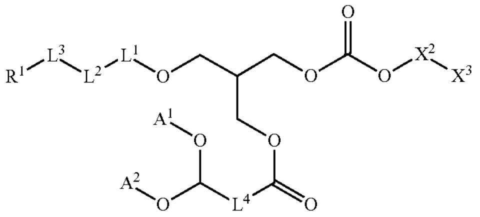

or a pharmaceutically acceptable salt thereof.

8. The compound of embodiment 1, wherein the compound is of Formula (V):

(V)

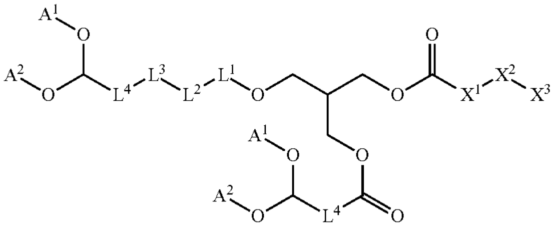

or a pharmaceutically acceptable salt thereof.

9. The compound of embodiment 1 or 8, wherein the compound is of Formula (VA):

(VA)

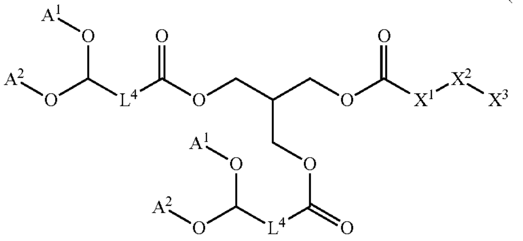

or a pharmaceutically acceptable salt thereof.

10. The compound of embodiment 1 or 2, wherein the compound is of Formula (VI):

(VI)

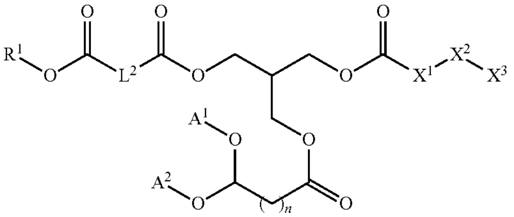

or a pharmaceutically acceptable salt thereof, wherein n is 1, 2, 3 or 4.

11. The compound of embodiment 1, 2, or 10, wherein the compound is of Formula (VIA):

(VIA)

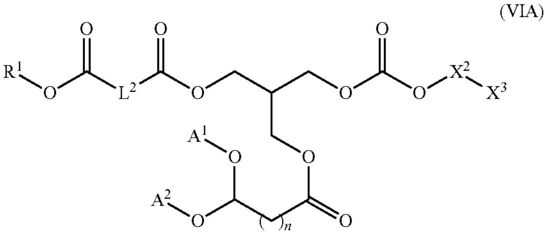

or a pharmaceutically acceptable salt thereof, wherein n is 1, 2, 3 or 4.

12. The compound of embodiment 1 or 2, wherein the compound is of Formula (VII):

(VII)

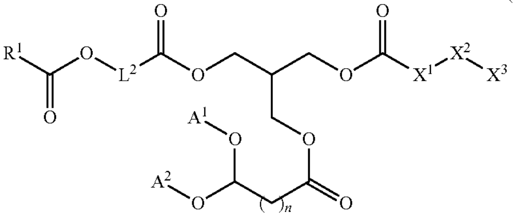

or a pharmaceutically acceptable salt thereof, wherein n is 1, 2, 3 or 4.

13. The compound of embodiment 1, 2, or 12, wherein the compound is of Formula (VIIA):

(VIIA)

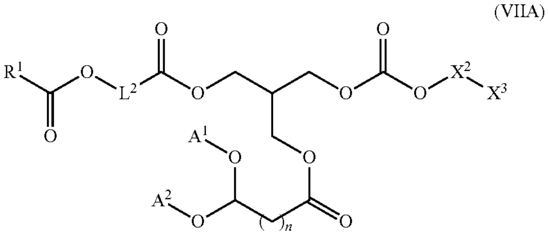

or a pharmaceutically acceptable salt thereof, wherein n is 1, 2, 3 or 4.

14. The compound of any one of embodiments 1-11, wherein $L^1$ is a covalent bond.

15. The compound of any one of embodiments 1-11, wherein $L^1$ is —C(O)—.

16. The compound of any one of embodiments 1-11, wherein $L^1$ is —OC(O)—.

17. The compound of any one of embodiments 1-16, wherein $L^2$ is a covalent bond.

18. The compound of any one of embodiments 1-16, wherein $L^2$ is an optionally substituted bivalent saturated or unsaturated, straight or branched $C_1$-$C_{12}$ hydrocarbon chain.

19. The compound of embodiment 18, wherein $L^2$ is an optionally substituted bivalent saturated or unsaturated, straight or branched $C_4$-$C_8$ hydrocarbon chain.

20. The compound of embodiment 18, wherein $L^2$ is optionally substituted —$CH_2CH_2$—.

21. The compound of embodiment 18, wherein $L^2$ is optionally substituted —$CH_2CH_2CH_2CH_2$—.

22. The compound of embodiment 18, wherein $L^2$ is optionally substituted —$CH_2CH_2CH_2CH_2CH_2$—.

23. The compound of embodiment 18, wherein $L^2$ is optionally substituted —$CH_2CH_2CH_2CH_2CH_2CH_2$—.

24. The compound of embodiment 18, wherein $L^2$ is optionally substituted —$CH_2CH_2CH_2CH_2CH_2CH_2CH_2$—.

25. The compound of any one of embodiments 1-16, wherein $L^2$ is

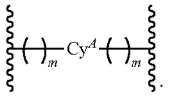

26. The compound of embodiment 25, wherein $Cy^A$ is optionally substituted phenylene.

27. The compound of embodiment 25, wherein $Cy^A$ is optionally substituted 3- to 7-membered saturated or partially unsaturated carbocyclene.

28. The compound of any one of embodiments 1-27, wherein $L^3$ is a covalent bond.

29. The compound of any one of embodiments 1-27, wherein $L^3$ is —C(O)—.

30. The compound of any one of embodiments 1-27, wherein $L^3$ is —C(O)O—.

31. The compound of any one of embodiments 1-27, wherein $L^3$ is —OC(O)—.

32. The compound of any one of embodiments 1-27, wherein $L^3$ is —OC(O)O—.

33. The compound of any one of embodiments 1-32, wherein $R^1$ is

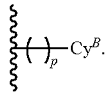

34. The compound of embodiment 33, wherein $Cy^B$ is optionally substituted 3- to 12-membered saturated or partially unsaturated carbocyclyl.

35. The compound of embodiment 34, wherein $Cy^B$ is optionally substituted cyclohexyl.

36. The compound of embodiment 33, wherein $Cy^B$ is optionally substituted 1-adamantyl.

37. The compound of embodiment 33, wherein $Cy^B$ is optionally substituted

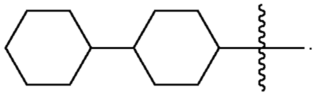

38. The compound of embodiment 33, wherein $Cy^B$ is optionally substituted sterolyl.

39. The compound of embodiment 33, where in p is 0, 1, or 2.

40. The compound of any one of embodiments 1-32, wherein $R^1$ is an optionally substituted saturated or unsaturated, straight or branched $C_1$-$C_{20}$ hydrocarbon chain wherein 1-3 methylene units are optionally and independently replaced with —O— or —NR—.

41. The compound of embodiment 40, wherein $R^1$ is an optionally substituted saturated or unsaturated, straight or branched $C_6$-$C_{20}$ hydrocarbon chain wherein 1-3 methylene units are optionally and independently replaced with —O— or —NR—.

42. The compound of embodiment 41, wherein $R^1$ is a saturated or unsaturated, straight or branched $C_6$-$C_{20}$ hydrocarbon chain.

43. The compound of embodiment 42, wherein $R^1$ is a saturated, branched $C_6$-$C_{20}$ hydrocarbon chain.

44. The compound of embodiment 42, wherein $R^1$ is a saturated, branched C9-$C_{20}$ hydrocarbon chain.

45. The compound of embodiment 41, wherein $R^1$ is a saturated or unsaturated, straight or branched $C_6$-$C_{20}$ hydrocarbon chain optionally substituted with 1-6 fluorine atoms.

46. The compound of any one of embodiments 1-32, wherein $R^1$ is selected from:

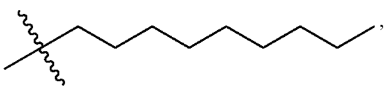

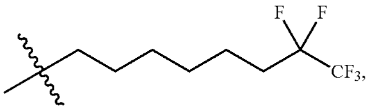

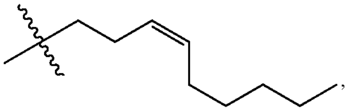

-continued

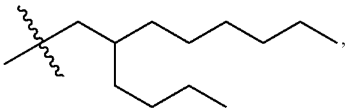

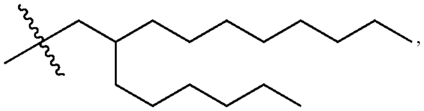

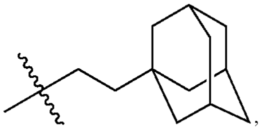

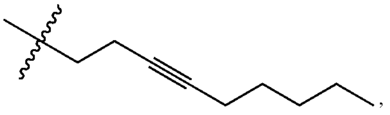

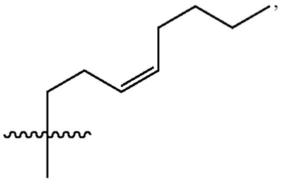

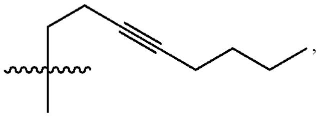

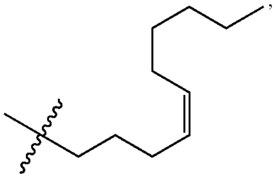

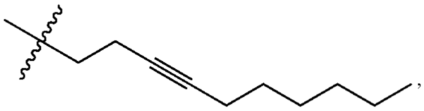

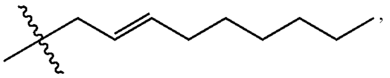

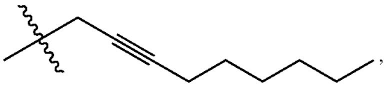

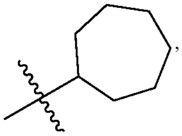

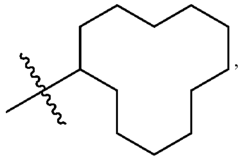

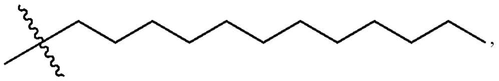

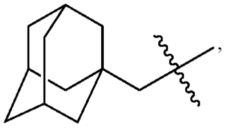

-continued

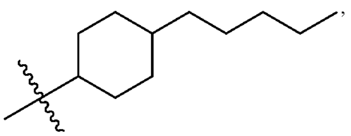

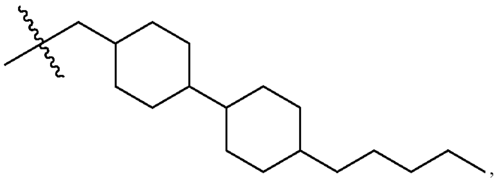

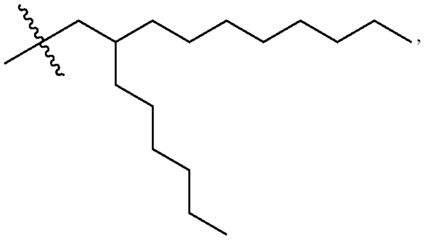

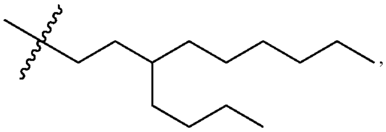

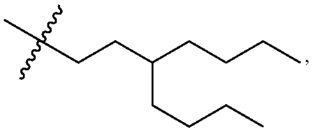

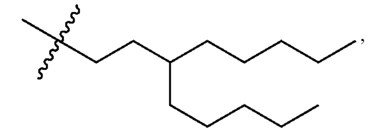

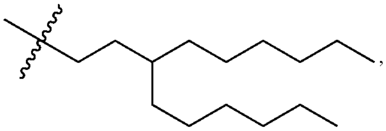

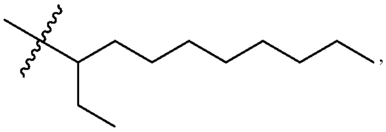

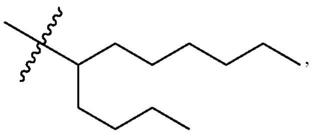

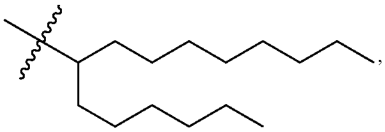

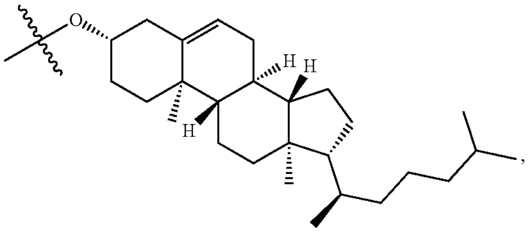

and

-continued

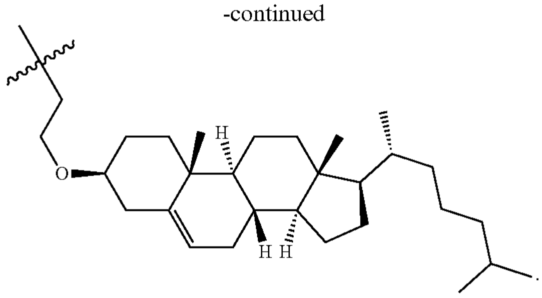

47. The compound of any one of embodiments 1-45, wherein $R^1$ does not comprise a 1,4-diene.

48. The compound of any one of embodiments 1-32, wherein $R^1$ is

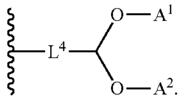

49. The compound of embodiment 48, wherein $L^4$ is a bivalent saturated or unsaturated, straight or branched $C_1$-$C_6$ hydrocarbon chain.

50. The compound of any one of embodiments 1-49, wherein each $A^1$ is independently an optionally substituted $C_1$-$C_{20}$ aliphatic.

51. The compound of embodiment 50, wherein each $A^1$ is independently an optionally substituted $C_6$-$C_{12}$ aliphatic.

52. The compound of embodiment 51, wherein $A^1$ is a $C_6$-$C_{10}$ alkenyl.

53. The compound of embodiment 51, wherein $A^1$ is a $C_7$-$C_9$ alkenyl.

54. The compound of embodiment 51, wherein $A^1$ is a $C_8$ alkenyl.

55. The compound of any one of embodiments 1-54, wherein each $A^2$ is independently an optionally substituted $C_1$-$C_{20}$ aliphatic.

56. The compound of embodiment 55, wherein each $A^2$ is independently an optionally substituted $C_6$-$C_{12}$ aliphatic.

57. The compound of embodiment 56, wherein $A^1$ is a $C_6$-$C_{10}$ alkenyl.

58. The compound of embodiment 56, wherein $A^1$ is a $C_7$-$C_9$ alkenyl.

59. The compound of embodiment 56, wherein $A^1$ is a $C_8$ alkenyl.

60. The compound of any one of embodiments 1-56, wherein each of $A^1$ and $A^2$ is independently selected from:

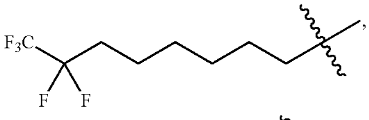

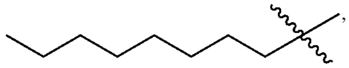

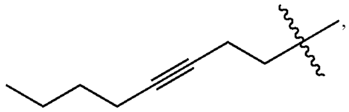

-continued

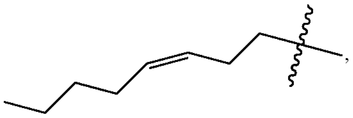

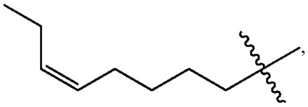

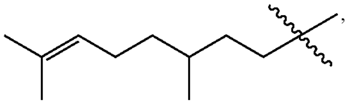

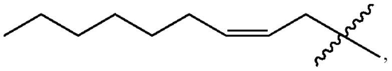

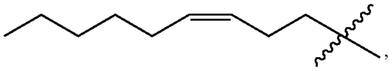

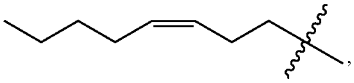

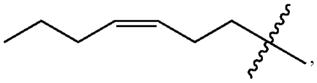

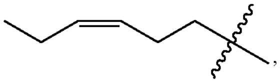

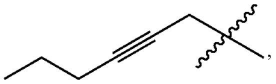

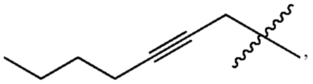

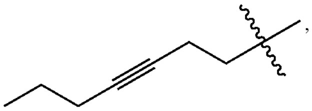

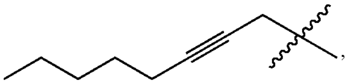

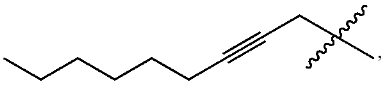

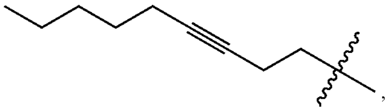

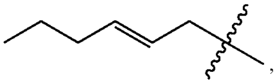

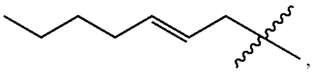

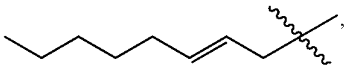

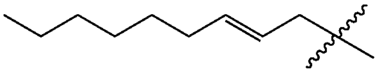

and

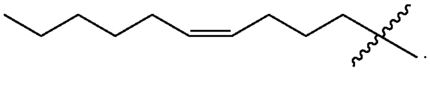

61. The compound of embodiment 60, wherein each of $A^1$ and $A^2$ is independently selected from: is

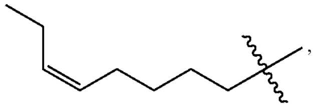

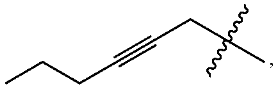

and

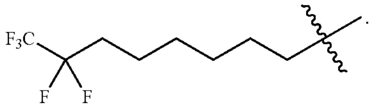

62. The compound of any one of embodiments 1-59, wherein $A^1$ and $A^2$ do not comprise a 1,4-diene.

63. The compound of any one of embodiments 1-62, wherein $X^1$ is a covalent bond.

64. The compound of any one of embodiments 1-62, wherein $X^1$ is —O—.

65. The compound of any one of embodiments 1-62, wherein $X^1$ is —NR—.

66. The compound of any one of embodiments 1-65, wherein $X^2$ is a covalent bond.

67. The compound of any one of embodiments 1-65, wherein $X^2$ is an optionally substituted, bivalent saturated or unsaturated, straight or branched, $C_1$-$C_{12}$ hydrocarbon chain, wherein 1-3 methylene units are optionally and independently replaced with —O—, —NR—, or —$Cy^C$—.

68. The compound of embodiment 67, wherein $X^2$ is an optionally substituted saturated or unsaturated, straight or branched $C_1$-$C_6$ hydrocarbon chain wherein 1-2 methylene units are optionally and independently replaced with —O—, —NR—, or —$Cy^C$—.

69. The compound of embodiment 67 or 68, wherein $Cy^C$ is optionally substituted 3- to 7-membered saturated or partially unsaturated carbocyclene.

70. The compound of embodiment 67 or 68, wherein $Cy^C$ is an optionally substituted 3- to 7-membered saturated or partially unsaturated heterocyclene having 1-3 heteroatoms independently selected from nitrogen, oxygen, and sulfur.

71. The compound of any one of embodiments 1-70, wherein $X^3$ is hydrogen.

72. The compound of any one of embodiments 1-70, wherein $X^3$ is optionally substituted 3- to 7-membered saturated or partially unsaturated heterocyclyl having 1-3 heteroatoms independently selected from nitrogen, oxygen, and sulfur.

73. The compound of any one of embodiments 1-65, wherein —$X^2$—$X^3$ is selected from:

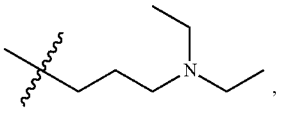

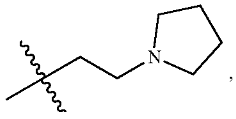

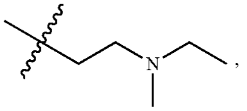

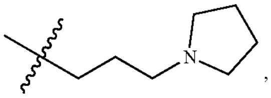

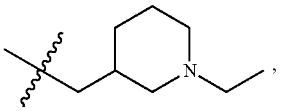

-continued

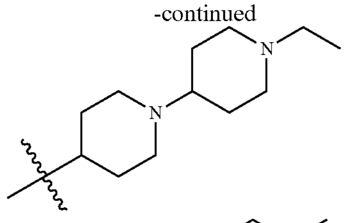

, and

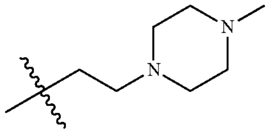

.

74. The compound of any one of embodiments 1-65, wherein —$X^2$—$X^3$ is

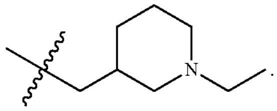 [SMILES: *CC1CCCN(CC)C1]

.

75. The compound of any one of embodiments 1-74, wherein R is hydrogen.

76. The compound of any one of embodiments 1-74, wherein R is an optionally substituted $C_1$-$C_6$ aliphatic group.

77. The compound of any one of embodiments 1-76 wherein $L^2$ does not comprise a 1,4-diene.

78. The compound of embodiment 1, wherein the compound is selected from Table 1, or a pharmaceutically acceptable salt thereof.

79. A lipid nanoparticle (LNP) preparation comprising an ionizable lipid according to any one of embodiments 1-78.

80. A lipid nanoparticle (LNP) preparation comprising:
 an ionizable lipid according to any one of embodiments 1-78;
 a phospholipid;
 a cholesterol; and
 a conjugate-linker lipid (e.g., polyethylene glycol lipid).

81. The LNP preparation of embodiment 80, further comprising one or more contaminants and/or degradants.

82. The LNP preparation of embodiment 80, excluding one or more contaminants and/or degradants.

83. The LNP preparation of embodiment 79 or 80, further comprising a therapeutic and/or prophylactic agent.

84. The LNP preparation of embodiment 83, wherein the therapeutic and/or prophylactic agent is or comprises one or more nucleic acids.

85. The LNP preparation of embodiment 84, wherein the one or more nucleic acids comprises a base editor, gRNA, or a combination thereof.

86. The LNP preparation of embodiment 85, wherein a mass ratio of base editor to gRNA is 1:1.

87. The LNP preparation of embodiment 84, wherein the one or more nucleic acids is or comprises RNA.

88. The LNP preparation of embodiment 87, wherein the RNA is or comprises mRNA, antisense RNA, siRNA, shRNA, miRNA, gRNA, or a combination thereof.

89. The LNP preparation of embodiment 85, wherein the one or more nucleic acids is or comprises DNA.

90. The LNP preparation of any one of embodiments 84-89, wherein the one or more nucleic acids comprises both RNA and DNA.

91. The LNP preparation of any one of embodiments 83-90, wherein the LNP preparation is formulated to deliver the therapeutic and/or prophylactic agent to target cells.

92. The LNP preparation of embodiment 91, wherein the target cells are or comprise spleen cells (e.g., splenic B cells, splenic T cells, splenic monocytes), liver cells (e.g., hepatocytes), bone marrow cells (e.g., bone marrow monocytes), immune cells, muscle cells (e.g., myocytes), heart cells (e.g., cardiomyocytes), kidney cells, or cells in the central nervous system.

93. The LNP preparation of embodiment 91, wherein the target cells are or comprise hematopoietic stem cells.

94. The LNP preparation of any one of embodiments 79-93, wherein the ionizable lipid comprises a compound according to any one of embodiments 1-58, or a combination thereof.

95. The LNP preparation of any one of embodiments 79-94, wherein the LNP preparation comprises less than about 70 mol percent or less of the ionizable lipid.

96. The LNP preparation of any one of embodiments 79-95, wherein the LNP preparation comprises from about 30 mol percent to about 70 mol percent ionizable lipid.

97. The LNP preparation of any one of embodiments 79-96, wherein the LNP preparation comprises about 50 mol percent ionizable lipid.

98. The LNP preparation of any one of embodiments 79-96, wherein the LNP preparation comprises about 35 mol percent ionizable lipid.

99. The LNP preparation of any one of embodiments 79-96, wherein the LNP preparation comprises about 47.5 mol percent ionizable lipid.

100. The LNP preparation of any one of embodiments 80-99, wherein the phospholipid comprises 1,2-dioleoyl-sn-glycero-3-phosphoethanolamine-N-(succinyl) (succinyl PE), 1,2-distearoyl-sn-glycero-3-phosphocholine (DSPC), cholesterol, 1,2-distearoyl-sn-glycero-3-phosphoethanolamine (DSPE), 1,2-dipalmitoyl-sn-glycero-3-phosphoethanolamine-N-(succinyl) (succinyl-DPPE), 1,2-dioleoyl-sn-glycero-3-phosphoethanolamine (DOPE), 1,2-dimyristoyl-sn-glycero-3-phosphocholine (DMPC), 1,2-dipalmitoyl-sn-glycero-3-phosphocholine (DPPC), or a combination thereof.

101. The LNP preparation of any one of embodiments 80-100, wherein the phospholipid is or comprises DSPC.

102. The LNP preparation of any one of embodiments 80-101, wherein the LNP preparation comprises from about 10 mol percent to about 65 mol percent phospholipid.

103. The LNP preparation of any one of embodiments 80-102, wherein the LNP preparation comprises about 9 mol percent phospholipid.

104. The LNP preparation of any one of embodiments 80-102, wherein the LNP preparation comprises about 10 mol percent phospholipid.

105. The LNP preparation of any one of embodiments 80-102, wherein the LNP preparation comprises about 16 mol percent phospholipid.

106. The LNP preparation of any one of embodiments 80-105, wherein the conjugate-linker lipid comprises a polyethylene glycol lipid.

107. The LNP preparation of any one of embodiments 80-106, wherein the conjugate-linker lipid comprises DiMystyrlGlycerol (DMG), 1,2-Dipalmitoyl-rac-glycerol, 1,2-Dipalmitoyl-rac-glycerol, methoxypolyethylene Glycol (DPG-PEG), 1,2-Distearoyl-rac-glycero-3-methylpolyoxyethylene (DSG-PEG), or any combination thereof.

108. The LNP preparation of any one of embodiments 80-107, wherein the conjugate-linker lipid has an average molecular mass from about 500 Da to about 5000 Da.

109. The LNP preparation of any one of embodiments 80-108, wherein the conjugate-linker lipid has an average molecular mass of about 2000 Da.
110. The LNP preparation of any one of embodiments 80-109, wherein the LNP preparation comprises from about 0 mol percent to about 5 mol percent conjugate-linker lipid.
111. The LNP preparation of any one of embodiments 80-110, wherein the LNP preparation comprises about 1.5 mol percent conjugate-linker lipid.
112. The LNP preparation of any one of embodiments 80-110, wherein the LNP preparation comprises about 2.5 mol percent conjugate-linker lipid.
113. The LNP preparation of any one of embodiments 80-110, wherein the LNP preparation comprises about 3 mol percent conjugate-linker lipid.
114. The LNP preparation of any one of embodiments 80-113, wherein the LNP preparation comprises from about 20 mol percent to about 50 mol percent sterol.
115. The LNP preparation of any one of embodiments 80-114, wherein the LNP preparation comprises about 46.5 mol percent sterol.
116. The LNP preparation of any one of embodiments 80-114, wherein the LNP preparation comprises about 38 mol percent sterol.
117. The LNP preparation of any one of embodiments 80-114, wherein the LNP preparation comprises about 38.5 mol percent sterol.
118. The LNP preparation of any one of embodiments 80-114, wherein the LNP preparation comprises about 40 mol percent sterol.
119. The LNP preparation of any one of embodiments 80-118, wherein the sterol is a cholesterol, or a variant or derivative thereof.
120. The LNP preparation of any one of embodiments 80-119, wherein the cholesterol is an oxidized cholesterol.
121. The LNP preparation of any one of embodiments 80-119, wherein the cholesterol is an esterified cholesterol.
122. The LNP preparation of any one of embodiments 80-118, wherein the sterol is a phytosterol.
123. A pharmaceutical composition comprising a LNP preparation of any one of embodiments 79-122 and a pharmaceutically acceptable excipient.
124. A method for administering a therapeutic and/or prophylactic agent to a subject in need thereof, the method comprising administering the LNP preparation of any one of 79-122 or the pharmaceutical composition of embodiment 123 to the subject.
125. A method for treating a disease or a disorder in a subject in need thereof, the method comprising administering the LNP preparation of any one of embodiments 79-122, or the pharmaceutical composition of embodiment 123, to the subject, wherein the therapeutic and/or prophylactic agent is effective to treat the disease.
126. A method for delaying and/or arresting progression a disease or a disorder in a subject in need thereof, the method comprising administering the LNP preparation of any one of embodiments 79-122, or the pharmaceutical composition of embodiment 123, to the subject, wherein the therapeutic and/or prophylactic agent is effective to treat the disease.
127. A method of delivering a therapeutic and/or prophylactic agent to a mammalian cell derived from a subject, the method comprising contacting the cell of the subject having been administered the LNP preparation of any one of embodiments 79-122 or the pharmaceutical composition of embodiment 123.
128. The method of embodiment 103, comprising administering to the subject the LNP preparation of any one embodiments 79-122 or the pharmaceutical composition of embodiment 123.
129. A method of producing a polypeptide of interest in a mammalian cell, the method comprising contacting the cell with the LNP preparation of any one of embodiments 79-122 or the pharmaceutical composition of embodiment 123, wherein the therapeutic and/or prophylactic agent is or comprises an mRNA, and wherein the mRNA encodes the polypeptide of interest, whereby the mRNA is capable of being translated in the cell to produce the polypeptide of interest.
130. A method of inhibiting production of a polypeptide of interest in a mammalian cell, the method comprising contacting the cell with the LNP preparation of any one of embodiments 79-122 or the pharmaceutical composition of embodiment 123, wherein the therapeutic and/or prophylactic agent is or comprises an RNA, whereby the RNA is capable of inhibiting production of the polypeptide of interest.
131. The method of embodiment 130, wherein the RNA comprises an antisense RNA, a miRNA, a shRNA, a siRNA, or a gRNA.
132. A method of specifically delivering a therapeutic and/or prophylactic agent to a mammalian organ, the method comprising contacting a mammalian organ with the LNP nanoparticle composition of any one of embodiments 79-122 or the pharmaceutical composition of embodiment 123, whereby the therapeutic and/or prophylactic agent is delivered to the organ.
133. The method of embodiment 132, comprising administering to a subject the LNP preparation of any one of embodiments 79-122 or the pharmaceutical composition of embodiment 123 to the subject.
134. A method of preparing a LNP preparation of any one of embodiments 79-122.
135. A method of manufacturing a LNP preparation of any one of embodiments 79-122. 136. A method of manufacturing an intermediate (e.g., any intermediate that may be stored or shipped) of any one of embodiments 79-122.
137. A method of characterizing a compound according to embodiments 1-78.
138. A method of characterizing a LNP preparation of any one of embodiments 79-122.
139. A method of providing a LNP preparation of any one of embodiments 79-122, comprising assessing one or more characteristics of the LNP preparation and establishing one or more characteristics of the LNP preparation (e.g., compared to a reference sample).
140. A method of vaccinating by administering the LNP preparation of any one of embodiments 79-122, or the pharmaceutical composition of embodiment 123.
141. A method of inducing an adaptive immune response in a subject, comprising administering to the subject an effective amount of a composition comprising at least one RNA; wherein the composition comprises a LNP preparation comprising a compound of any one of embodiments 1-78, or a pharmaceutically acceptable salt thereof.

Exemplification

The present disclosure exemplifies compositions, preparations, formulations, nanoparticles, and/or nanomaterials described herein. The present disclosure also exemplifies methods of preparing, characterizing, and validating compositions, preparations, formulations, nanoparticles, and/or nanomaterials described herein.

Example 1: Materials and Methods

The present Example provides exemplary materials and methods of preparing, characterizing, and validating compositions, preparations, nanoparticles, and/or nanomaterials described herein.

LNP Preparations

Among other things, the present Example provides for exemplary LNP preparations.

Lipid nanoparticle components were dissolved in 100% ethanol at specified lipid component molar ratios. Nucleic acid (NA) cargo was dissolved in 10 mM citrate, 100 mM NaCl, pH 4.0, resulting in a concentration of NA cargo of approximately 0.22 mg/mL. In some embodiments, NA cargos include both a functional NA and a reporter DNA barcode mixed at mass ratios of 1:10 to 10:1 functional NA to barcode. As described herein, a NA can be a siRNA, an anti-sense, an expressing DNA, or mRNA.

Figure 3:
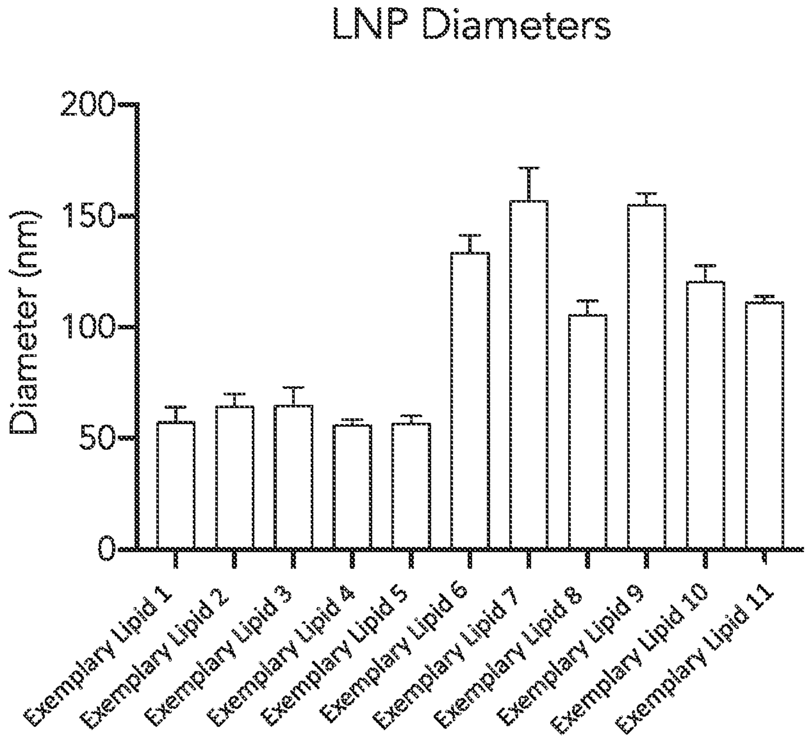
FIG. 3 depicts a bar graph that shows average diameters (nm) of exemplary LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11).
Figure 4:
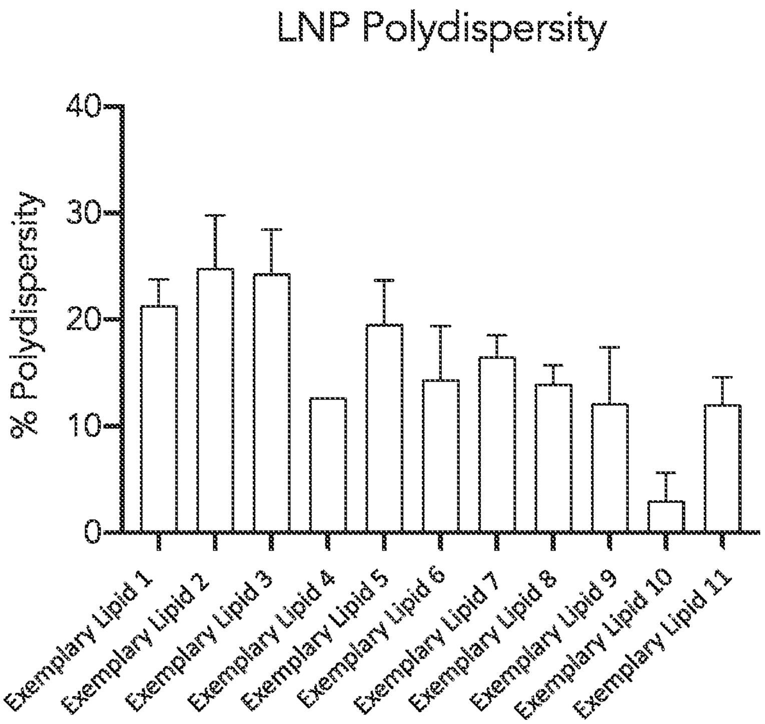
FIG. 4 depicts a bar graph that shows average polydispersity (%) of exemplary LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11).

LNPs were prepared with molar ratios of molar ratios of either 35% Ionizable Lipid: 46.5% Cholesterol: 2.5% PEG2000-DMG: 16% DSPC; 50% Ionizable Lipid: 38.5% Cholesterol: 1.5% PEG2000-DMG: 10% DSPC; or 50% Ionizable Lipid: 38% Cholesterol: 3% PEG2000-DMG: 9% DSPC and a total lipid to NA mass ratio of 11.7 to 25. LNPs were formed by microfluidic mixing of the lipid and NA solutions using a Precision Nanosystems NanoAssemblr Spark or Benchtop series Instruments, according to the manufacturers protocol. A ratio of aqueous to organic solvent of approximately 2:1 or 3:1 was maintained during mixing using differential flow rates. After mixing, LNPs were collected, diluted in PBS (approximately 1:1 v/v). Further buffer exchange was conducted using dialysis in PBS at 4° C. for 4 to 24 hours against a 20 kDa filter. After this initial dialysis, each individual LNP preparation was characterized via dynamic light scattering (DLS) to measure the size (e.g., diameter) and polydispersity (see FIGS. 3 and 4). In addition, pKa of a subpopulation of LNPs was measured via a 2-(p-toluidino)-6-napthalene sulfonic acid (TNS) assay. LNPs falling within specific diameter and polydispersity ranges were pooled, and further dialyzed against phosphate buffer saline (PBS) at 4° C. for 1 to 4 hours against a 100 kDa dialysis cassette. After the second dialysis, LNPs were sterile filtered using 0.22 μM filter and stored at 4° C. for further use.

LNP Characterization

DLS—LNP hydrodynamic diameter and polydispersity index (PDI) were measured using high throughput dynamic light scattering (DLS) (DynaPro plate reader II, Wyatt). LNPs were diluted 1× PBS to an appropriate concentration and analyzed.

Concentration & Encapsulation Efficiency

Concentration of NA was determined by Qubit microRNA kit (for siRNA) or HS RNA kit (for mRNA) per manufacturer's instructions. Encapsulation efficiency was determined by measuring nucleic acid concentration in unlysed and lysed LNPs.

pKa

A stock solution of 10 mM HEPES (Sigma Aldrich), 10 mM MES (Sigma Aldrich), 10 mM sodium acetate (Sigma), and 140 nM sodium chloride (Sigma Aldrich) was prepared, and pH was adjusted using hydrogen chloride and sodium hydroxide to a range of about pH 4-10. Using four replicates for each pH value, 140 μL pH-adjusted buffer was added to a 96-well plate, followed by the addition 5 μL of 2-(p-toluidino)-6-napthalene sulfonic acid (60 μg/mL). 5 μL of LNP was added to each well. After 5 min of incubation under gentle shaking, fluorescence was measured using an excitation wavelength of 325 nm and emission wavelength of 435 nm (BioTek Synergy H4 Hybrid).

LNP Administration

Male and female mice aged approximately 8-12 weeks were used for the studies described by the present Example. Each mouse was temporarily restrained, and pooled LNP was administered intravenously (IV) via tail vein injection in up to five animals per experiment. Age-matched mice were also used to administer vehicle (1× PBS) via tail vein injection in up to three animals per experiment. Additional routes of administration can also be conducted including intracerebral ventricular (ICV), intracisterna manga (ICM), intrathecal (IT), intramuscular (IM), nebulization, intranasal (IN), subcutaneous (SC), intraarticular, and intradermal (ID). At 72 hours post-dose, tissues including liver, spleen, bone marrow, kidney, lung, muscle (e.g. skeletal and cardiac), and blood were collected for analysis.

Barcoding Sequencing

DNA (genomic and DNA barcodes) were isolated using QuickExtract (Lucigen) and sequenced using Illumina MiniSeq as described herein, normalizing frequency DNA barcode counts in FACS isolated samples to frequency in injected input. These data were plotted as 'Fold Above Input' (see FIGS. 5-6).

Confirmation

Structural and functional features of the provided LNPs were confirmed based on protocols described herein.

LNP Preparation

Lipid nanoparticle components were dissolved in 100% ethanol at specified lipid component molar ratios. Nucleic acid (NA) cargo was dissolved in 10 mM citrate, 100 mM NaCl, pH 4.0, resulting in a concentration of NA cargo of approximately 0.22 mg/mL. In some embodiments, NA cargos include a functional NA (e.g., siRNA, anti-sense, expressing DNA, mRNA). LNPs were formulated with molar ratios of either 35% Ionizable Lipid: 46.5% Cholesterol: 2.5% PEG2000-DMG: 16% DSPC; 50% Ionizable Lipid: 38.5% Cholesterol: 1.5% PEG2000-DMG: 10% DSPC; or 50% Ionizable Lipid: 38% Cholesterol: 3% PEG2000-DMG: 9% DSPC and a total lipid to NA mass ratio of 11.7 to 25. LNPs were formulated with a total lipid to NA mass ratio of 11.7 to 25. LNPs were formed by microfluidic mixing of the lipid and NA solutions using a Precision Nanosystems NanoAssemblr Spark or Benchtop series Instruments, according to the manufacturers protocol. A 2:1 or 3:1 ratio of aqueous to organic solvent was maintained during mixing using differential flow rates. After mixing, LNPs were collected, diluted in PBS (approximately 1:1 v/v), and further buffer exchange was conducted using dialysis in PBS at 4° C. for 8 to 24 hours against a 20 kDa filter. After this initial dialysis, each individual LNP formulation was characterized via DLS to measure the size and polydispersity, and the pKa of a subpopulation of LNPs was measured via TNS assay. After dialysis, LNPs are sterile filtered using 0.22 micron sterile filter and stored at 4° C. for further use.

LNP Characterization

DLS

LNP hydrodynamic diameter and polydispersity index (PDI) were measured using high throughput dynamic light scattering (DLS) (DynaPro plate reader II, Wyatt). LNPs were diluted 1× PBS to an appropriate concentration and analyzed.

Concentration & Encapsulation Efficiency

Concentration of NA was determined by Qubit microRNA kit (for siRNA) or HS RNA kit (for mRNA) per manufacturer's instructions. Encapsulation efficiency was determined by measuring unlysed and lysed LNPs.

pKa

A stock solution of 10 mM HEPES (Sigma Aldrich), 10 mM MES (Sigma Aldrich), 10 mM sodium acetate (Sigma), and 140 nM sodium chloride (Sigma Aldrich) was prepared and pH adjusted using hydrogen chloride and sodium hydroxide to a range of about pH 4-10. Using four replicates for each pH, 140 μL pH-adjusted buffer was added to a 96-well plate, followed by the addition 5 μL of 2-(p-toluidino)-6-napthalene sulfonic acid (60 μg/mL). 5 μL of LNP was added to each well. After 5 min of incubation under gentle shaking, fluorescence was measured using an excitation wavelength of 325 nm and emission wavelength of 435 nm (BioTek Synergy H4 Hybrid).

LNP Administration

Male and female mice aged approximately 8-12 weeks were used for studies described by the present Example. Each mouse was temporarily restrained, and pooled LNP was administered IV via tail vein injection in up to five animals per experiment. Age-matched mice was also used to administer vehicle (1× PBS) via tail vein injection in up to three animals per experiment. At 72 hours post-dose, tissues including liver and kidney were collected for analysis.

hEPO Expression

For human EPO (hEPO) protein expression, mice were temporarily restrained and bled at 6 hours post-administration (via tail vein). Blood was collected in heparin tubes, processed to plasma, and stored at −80° C. until ready to use. Appropriate dilutions of plasma were used to measure hEPO protein using R&D systems ELISA kit (DuoSet; DY286-05) according to manufacturer's instructions.

NHP 1L-6

The quantification of 1L-6 in plasma from NHPs was conducted from plasma stored at −80° C. until use. Appropriate dilutions of plasma were used to measure IL-6 protein using MSD U-Plex assay using manufacturer's instructions.

Example 2: Exemplary LNP Characterizations

The present Example provides exemplary compositions, preparations, nanoparticles, and/or nanomaterials, and materials and methods for characterizing such compositions, preparations, nanoparticles, and/or nanomaterials described herein.

Eleven LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11), which are exemplary compounds of Formula I and exemplary compounds of compounds 4-1 to 4-86, were selected for further characterization and experimentation. Average diameters (nm) of eleven exemplary LNP preparations were measured as described herein (see FIG. 3). Average LNP polydispersity (%) of eleven exemplary LNP preparations were also measured as described herein (see FIG. 4).

Example 3: Exemplary LNP Preparations are Delivered to Various Cell Types

The present Example provides exemplary LNP compositions, preparations, nanoparticles, and/or nanomaterials with potent delivery to various cell types as described herein.

Figure 5:
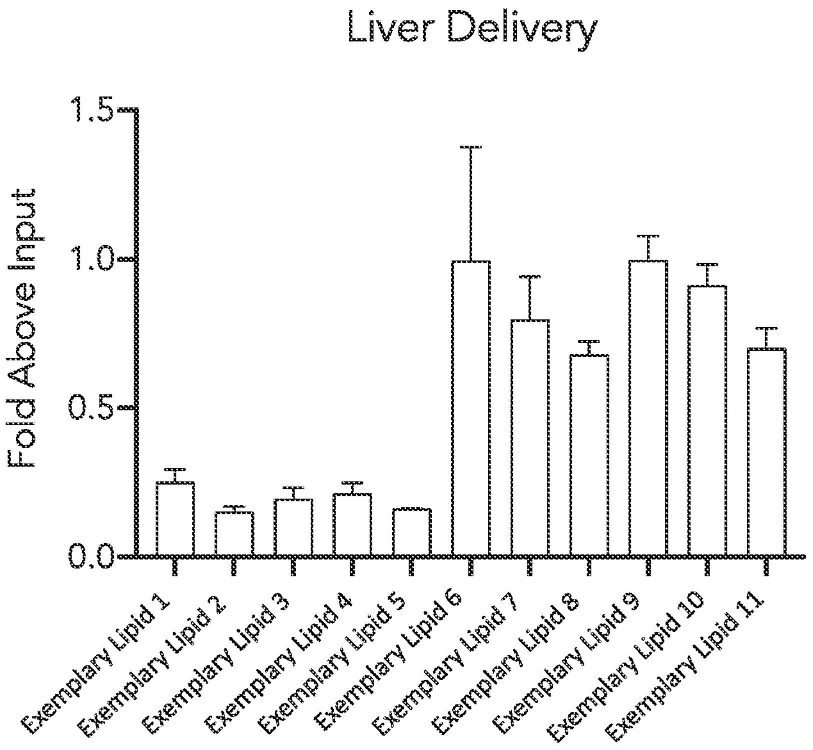
FIG. 5 depicts a bar graph that shows potent delivery of exemplary LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11) to the liver.
Figure 6:
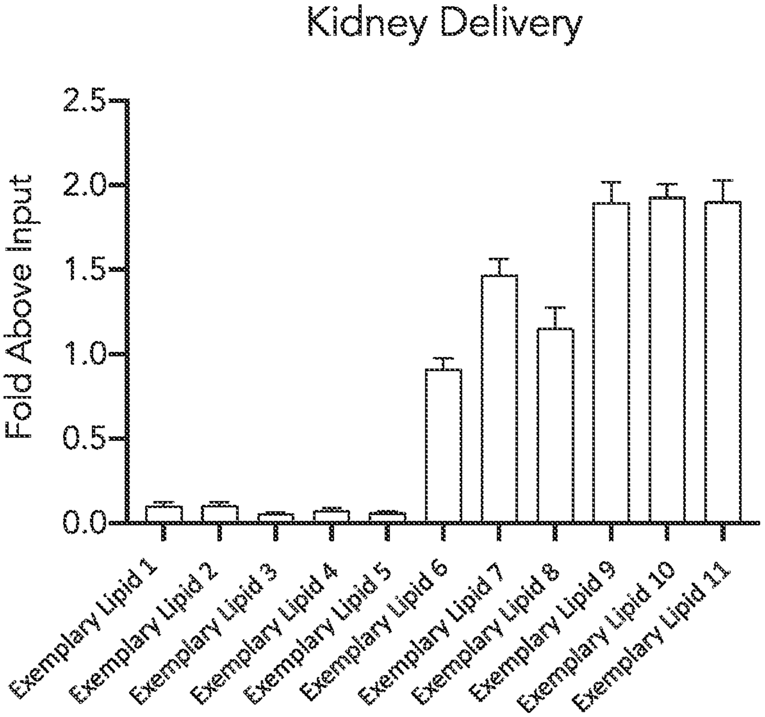
FIG. 6 depicts a bar graph that shows potent delivery of exemplary LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11) to the kidney.

Eleven LNP preparations (Exemplary Lipid 1, Exemplary Lipid 2, Exemplary Lipid 3, Exemplary Lipid 4, Exemplary Lipid 5, Exemplary Lipid 6, Exemplary Lipid 7, Exemplary Lipid 8, Exemplary Lipid 9, Exemplary Lipid 10, Exemplary Lipid 11, which are exemplary compounds of Formula I and exemplary compounds of compounds 4-1 to 4-86) were selected to assess delivery across a variety of tissues (see FIGS. 5-6). Using the methods described in Example 1, DNA (genomic and DNA barcodes) were isolated using QuickExtract (Lucigen) and sequenced using Illumina MiniSeq as described herein, normalizing frequency DNA barcode counts in FACS isolated samples to frequency in injected input. These data were plotted as 'Fold Above Input' (see FIGS. 5-8).

Unexpectedly, representative data in FIGS. 5-6 shows that screening platforms described herein can identify several highly potent LNP preparations to determine what type of LNP preparation would be most potent for a particular cell type. Accordingly, in some embodiments, the present example demonstrates that lipids characterized by having a degradable tail feature show potent delivery across various cell types, including liver cells and kidney cells.

Example 4: Synthesis of Ionizable Lipids

The present Example provides exemplary materials and methods of preparing, characterizing, and validating ionizable lipids as described herein.

General

All reactions were run using anhydrous grade solvents under an atmosphere of nitrogen in flasks or vials with magnetic stirring, unless otherwise noted. Anhydrous solvents were purchased from Sigma-Aldrich and used as received. Flash column chromatography was performed using a Biotage® Selekt or Teledyne-Isco Combiflash® Nextgen300+ with prepacked silica gel cartridges. Thin layer chromatography was performed using Merck silica gel 60 plates, and compounds were visualized using iodine. Nuclear magnetic resonance (NMR) spectroscopy was performed either using a Varian INOVA 500 MHz or a Bruker AVANCE 400 MHz spectrometer; chemical shifts are reported in δ parts per million (ppm) referenced to tetramethylsilane at δ=0.00 ppm for $CDCl_3$ samples, and residual solvent peak (δ=2.50 ppm) for DMSO samples. Ultra-performance liquid chromatography-mass spectrometry (UPLC-MS) was performed using a Waters Acquity UPLC H-class Plus with QDa detector ($ESI^+$) using one of the following general methods.

Method A (5 min run): Column-XTERRA RP 18 (4.6×50 mm), 5 μm, mobile phase: initially 50% [0.1% HCOOH in water] and 50% [0.1% HCOOH in (70:30) ACN: THF]; then to 2% [0.1% HCOOH in water] and 98% [0.1% HCOOH in (70:30) ACN: THF] in 2.65 min, held this mobile phase composition up to 3.75 min, and finally back to initial condition, i.e; 50% [0.1% HCOOH in water] and 50% [0.1% HCOOH in (70:30) ACN: THF] in 4.90 min, held this mobile phase composition up to 5.10 min. Flow=1.2 mL/min.

Method B (12 min run): Column-XTERRA RP 18 (4.6×50 mm), 5 μm, (mobile phase: initially 80% [0.1% HCOOH in water] and 20% [0.1% HCOOH in (70:30) ACN: THF]; held this initial condition for 0.75 min; then to 65% [0.1% HCOOH in water] and 35% [0.1% HCOOH in (70:30) ACN: THF] in 3.0 min, then to 2% [0.1% HCOOH in water] and 98% [0.1% HCOOH in (70:30) ACN: THF] in 6.0 min, held this mobile phase composition up to 9.0 min, and finally back to initial condition, i.e.; 80% [0.1% HCOOH in water]

and 20% [0.1% HCOOH in (70:30) ACN: THF] in 11.00 min, held this mobile phase composition up to 12.10 min. Flow=1.2 ml/min.

Method C (6 min run): Column-BEH C18 (2.1×50 mm), 1.7 μM, mobile phase: initially 90% [0.1% HCOOH in water] and 10% ACN; then to 5% [0.1% HCOOH in water] and 95% ACN over 3 min, held this mobile phase composition for 2 min, and finally back to initial condition over 1 min, i.e; 90% [0.1% HCOOH in water] and 10% ACN. Flow=0.5 mL/min.

List of Abbreviations

Ac: acetyl
ACN: acetonitrile
d: doublet
DCM: dichloromethane
DIPEA: N,N-diisopropylethylamine
DMAP: 4-(dimethylamino)pyridine
DMF: N,N-dimethylformamide
DMSO: dimethyl sulfoxide
EDC: N-(3-Dimethylaminopropyl)-N'-ethylcarbodiimide hydrochloride
Eq or eqv: equivalents
Et: ethyl
i-Pr: isopropyl
m: multiplet
Me: methyl
p: pentet
PPTS: pyridinium p-toluenesulfonate
q: quartet
Rt: retention time
s: singlet
t: triplet
TEA: triethylamine
THF: tetrahydrofuran General Synthesis Certain exemplary lipids were prepared according to the below general synthetic scheme, which uses Example 4-1 for illustration.

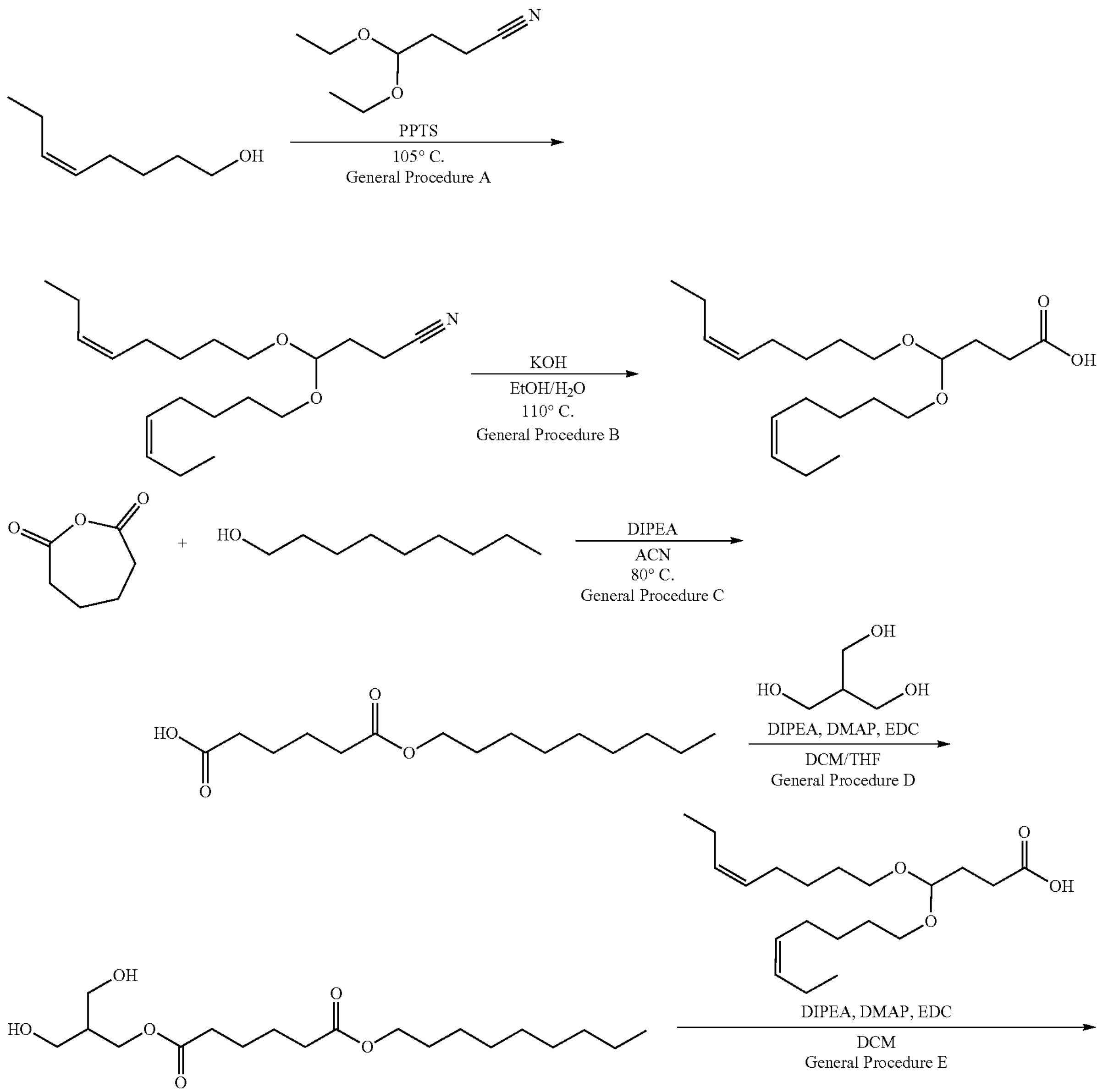

-continued
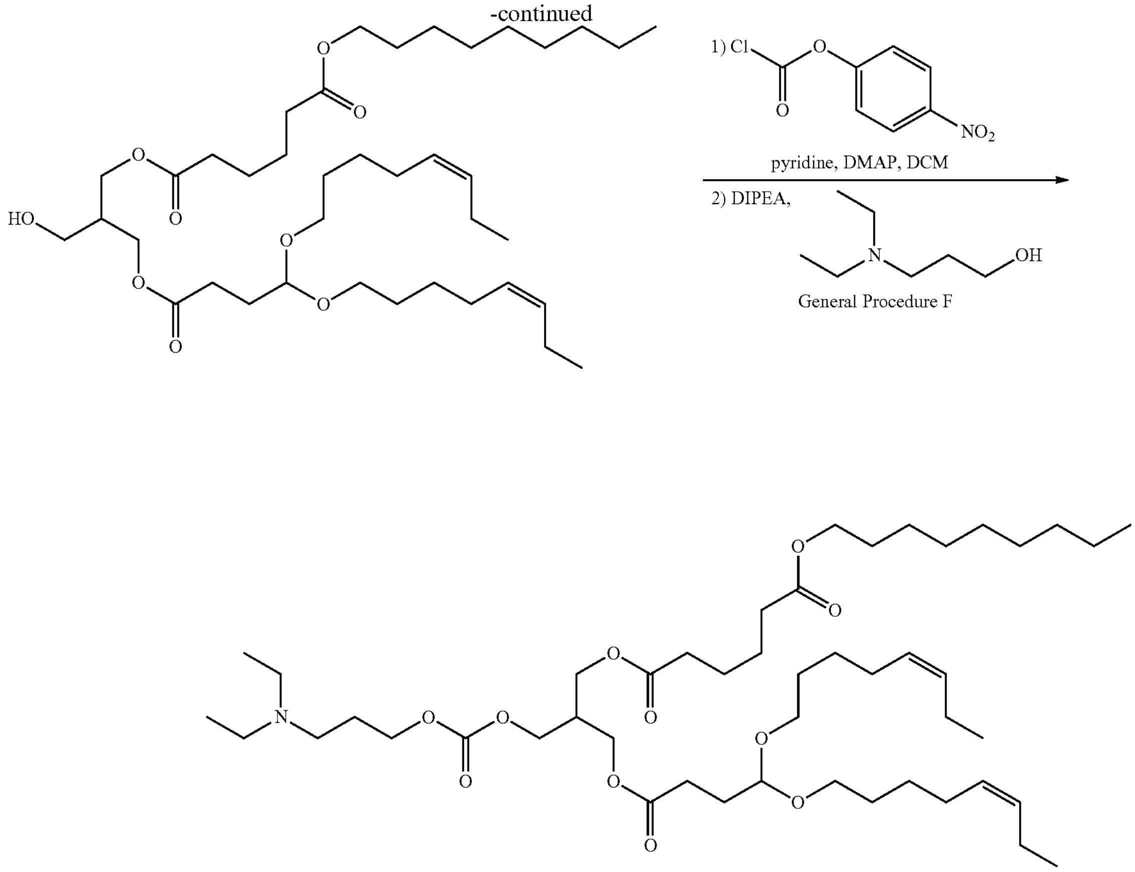
Example 4-1
Example 4-1: 3-((4,4-bis(((Z)-oct-5-en-1-yl)oxy) butanoyl)oxy)-2-((((3-(diethylamino)propoxy)carbonyl)oxy)methyl)propyl nonyl adipate
Example 4-1
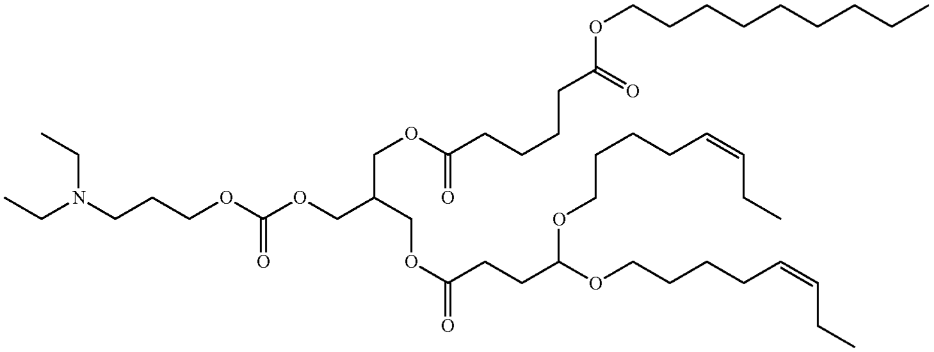

Step 1: 4,4-bis(((Z)-oct-5-en-1-yl)oxy)butanenitrile

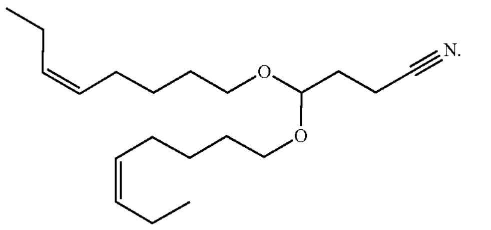 [SMILES: CC/C=C\CCCCOC(CCC#N)OCCCC/C=C\CC]

General Procedure A: to a vial containing pyridinium p-toluene sulfonate (0.12 g, 0.48 mmol, 0.05 Eq) was added 4,4-diethyoxybutanenitrile (1.5 g, 9.5 mmol, 1 Eq) and cis-5-octen-1-ol (3.7 g, 29 mmol, 3 Eq). The vial was tightly capped, and the resulting mixture was heated at 105° C. for 72 h. After this time, the mixture was allowed to cool to room temperature. The crude material was purified by silica gel column chromatography using a gradient of 0 to 100% dichloromethane in hexanes to afford 4,4-bis(((Z)-oct-5-en-1-yl)oxy)butanenitrile (1.14 g, 37%) as a colorless oil. $^{1}$H NMR (500 MHz, Chloroform-d) δ 5.43-5.27 (m, 4H), 4.56 (t, J=5.3 Hz, 1H), 3.61 (dt, J=9.3, 6.6 Hz, 2H), 3.44 (dt, J=9.3, 6.6 Hz, 2H), 2.42 (t, J=7.4 Hz, 2H), 2.12-1.91 (m, 9H), 1.66-1.54 (m, 5H), 1.49-1.36 (m, 4H), 0.96 (t, J=7.6 Hz, 6H).

Step 2: 4,4-bis(((Z)-oct-5-en-1-yl)oxy)butanoic acid

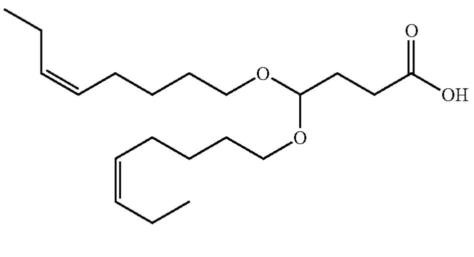 [SMILES: CC/C=C\CCCCOC(CCC(=O)O)OCCCC/C=C\CC]

General Procedure B: to a vial containing 4,4-bis(((Z)-oct-5-en-1-yl)oxy)butanenitrile (1.14 g, 3.54 mmol, 1 Eq) was added potassium hydroxide (0.60 g, 10.6 mmol, 3 Eq) followed by ethanol (3.5 mL) and water (3.5 mL). The vial was tightly capped, and the reaction mixture was heated to 110° C. for 18 h. After this time, the mixture was allowed to cool to room temperature. The mixture was diluted with ethyl acetate (20 mL), and the pH was adjusted to ~5 by the addition of 1M HCl. The resulting biphasic mixture was separated, and the aqueous phase was extracted two more times with ethyl acetate (2×20 mL). The organic extracts were combined, dried over sodium sulfate, filtered and concentrated to afford 4,4-bis(((Z)-oct-5-en-1-yl)oxy)butanoic acid (1.16 g, 96% yield) as a sticky white solid. $^{1}$H NMR (400 MHz, Chloroform-d) δ 5.41-5.24 (m, 4H), 4.45 (t, J=5.6 Hz, 1H), 3.51 (dt, J=9.0, 6.7 Hz, 2H), 3.39 (dt, J=9.0, 6.7 Hz, 2H), 2.17 (t, J=7.6 Hz, 2H), 2.08-1.98 (m, 8H), 1.81 (q, J=7.3 Hz, 2H), 1.59-1.52 (m, 4H), 1.44-1.32 (m, 4H), 0.94 (t, J=7.5 Hz, 6H).

Step 3: 6-(nonyloxy)-6-oxohexanoic acid

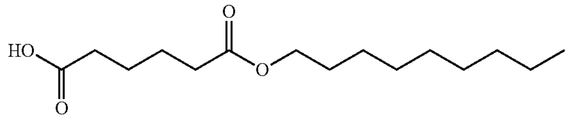 [SMILES: CCCCCCCCCOC(=O)CCCCC(=O)O]

General Procedure C: to a solution of nonan-1-ol (2.5 g, 17 mmol, 1 Eq) in ACN (70 mL) was added DIPEA (6.7 g, 52 mmol, 3 Eq) and oxepane-2,7-dione (6.7 g, 52 mmol, 3 Eq). The resulting mixture was heated at 80° C. for 16. After this time, the mixture was cooled to room temperature and concentrated. The crude material thus obtained was purified by silica gel column chromatography using a gradient of 0 to 100% ethyl acetate in hexanes. The resulting orange suspension was triturated with hexanes and filtered to afford 6-(nonyloxy)-6-oxohexanoic acid as a white solid (374 mg, 8% yield). $^{1}$H NMR (500 MHz, Chloroform-d) δ 4.06 (t, J=6.8 Hz, 2H), 2.41-2.37 (m, 2H), 2.35-2.32 (m, 2H), 1.73-1.58 (m, 6H), 1.33-1.27 (m, 12H), 0.88 (t, J=7.2 Hz, 3H).

Step 4: 3-hydroxy-2-(hydroxymethyl)propyl nonyl adipate

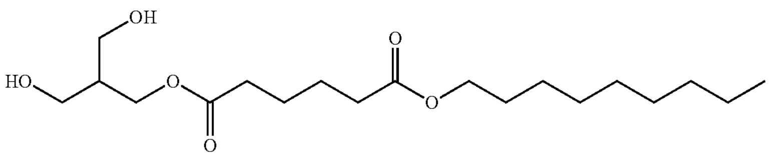 [SMILES: CCCCCCCCCOC(=O)CCCCC(=O)OCC(CO)CO]

General Procedure D: to a solution of 2-(hydroxymethyl) propane-1,3-diol (1.0 g, 9.4 mmol, 1 Eq) in DCM (25 mL) and THF (25 mL) were added 6-(nonyloxy)-6-oxohexanoic acid (2.6 g, 9.4 mmol), DIPEA (1.8 g, 14 mmol, 1.5 Eq), DMAP (0.12 g, 0.94 mmol, 0.1 Eq), and EDC (2.0 g, 10 mmol, 1.1 Eq). The resulting mixture was stirred at 23° C. for 16 h. After this time, the reaction mixture was concentrated, redissolved in ethyl acetate (25 mL), and washed with a solution of 5% aqueous citric acid (25 mL). The aqueous layer was extracted two more times with ethyl acetate (2×25 mL). The organic layers were combined, dried over sodium sulfate, filtered, and concentrated. The crude material thus obtained was purified by silica gel column chromatography using a gradient of 0 to 90% ethyl acetate in hexanes to afford 3-hydroxy-2-(hydroxymethyl)propyl nonyl adipate as a colorless oil (0.773 g, 23% yield). $^1$H NMR (500 MHz, Chloroform-d) δ 4.27 (d, J=6.3 Hz, 2H), 4.06 (t, J=6.8 Hz, 2H), 3.82-3.73 (m, 4H), 2.38-2.31 (m, 6H), 2.07-2.00 (m, 1H), 1.68-1.58 (m, 4H), 1.64-1.56 (m, 2H), 1.31-1.26 (m, 12H), 0.88 (t, J=7.1 Hz, 3H).

Step 5: 3-((4,4-bis(((Z)-oct-5-en-1-yl)oxy)butanoyl) oxy)-2-(hydroxymethyl)propyl nonyl adipate

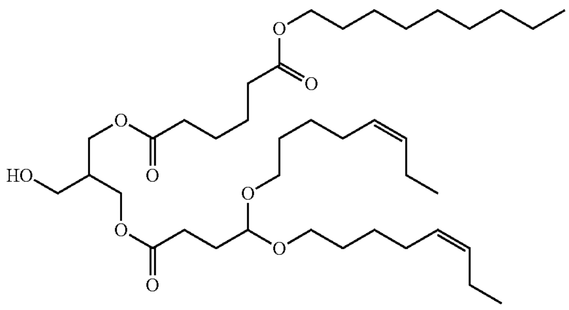 [SMILES: CC/C=C\CCCCOC(CCC(=O)OCC(CO)COC(=O)CCCCC(=O)OCCCCCCCCC)OCCCC/C=C\CC]

General Procedure E: to a solution of 3-hydroxy-2-(hydroxymethyl)propyl nonyl adipate (137 mg, 0.381 mmol, 1.1 Eq) in DCM (2.1 mL) were added 4,4-bis(((Z)-oct-5-en-1-yl)oxy)butanoic acid (118 mg, 0.347 mmol, 1 Eq), DIPEA (90 mg, 0.69 mmol, 2 Eq), DMAP (9 mg, 0.07 mmol, 0.2 Eq), and EDC (100 mg, 0.52 mmol, 1.5 Eq). The resulting mixture was stirred at 23° C. for 16 h. After this time, the reaction mixture was concentrated, redissolved in ethyl acetate (5 mL), and washed with water (5 mL). The aqueous layer was extracted two more times with ethyl acetate (2×5 mL). The organic layers were combined, dried over sodium sulfate, filtered, and concentrated. The crude material thus obtained was purified by silica gel column chromatography using a gradient of 0 to 40% ethyl acetate in hexanes to afford 3-((4,4-bis(((Z)-oct-5-en-1-yl)oxy)butanoyl)oxy)-2-(hydroxymethyl)propyl nonyl adipate as a colorless oil (113 mg, 48% yield). $^1$H NMR (500 MHz, Chloroform-d) δ 5.40-5.28 (m, 4H), 4.49 (t, J=5.5 Hz, 1H), 4.21-4.15 (m, 4H), 4.05 (t, J=6.8 Hz, 2H), 3.62 (dd, J=6.4, 5.5 Hz, 2H), 3.57 (dt, J=9.4, 6.6 Hz, 2H), 3.40 (dt, J=9.3, 6.6 Hz, 2H), 2.41 (t, J=7.5 Hz, 2H), 2.38-2.30 (m, 4H), 2.26 (t, J=6.3 Hz, 1H), 2.22-2.17 (m, 1H), 2.07-2.00 (m, 8H), 1.93 (ddd, J=7.9, 7.2, 5.5 Hz, 2H), 1.67-1.65 (m, 4H), 1.62-1.54 (m, 6H), 1.43-1.37 (m, 4H), 1.31-1.25 (m, 12H), 0.95 (t, J=7.6 Hz, 6H), 0.88 (t, J=7.1 Hz, 3H).

Step 6: 3-((4,4-bis(((Z)-oct-5-en-1-yl)oxy)butanoyl) oxy)-2-((((3-(diethylamino)propoxy)carbonyl)oxy) methyl)propyl nonyl adipate (Example 4-1)

General Procedure F: To a solution of 3-((4,4-bis(((Z)-oct-5-en-1-yl)oxy)butanoyl)oxy)-2-(hydroxymethyl)propyl nonyl adipate (114 mg, 0.167 mmol, 1 Eq) in DCM (3 mL) were added pyridine (26 mg, 0.33 mmol, 2 Eq), DMAP (6 mg, 0.05 mmol, 0.3 Eq), and 4-nitrophenyl carbonochloridate (50 mg, 0.025 mmol, 1.5 Eq). The resulting mixture was stirred at 23° C. for 1 h. After this time, DIPEA (86 mg, 0.67 mmol, 4 Eq) and 3-(diethylamino)propan-1-ol (87 mg, 0.67 mmol, 4 Eq) were added to the mixture, and it was stirred at 23° C. for 16 h. After completion of the reaction, the mixture was diluted with DCM (5 mL) and washed with 0.6 M sodium carbonate (4×5 mL), water (5 mL), and brine (5 mL). The organic layer was dried over sodium sulfate, filtered, and concentrated. The crude material thus obtained was purified by silica gel column chromatography using a gradient of 0 to 25% methanol in DCM to afford 3-((4,4-bis(((Z)-oct-5-en-1-yl)oxy)butanoyl)oxy)-2-((((3-(diethylamino)propoxy)carbonyl)oxy)methyl)propyl nonyl adipate as a pale yellow oil (120 mg, 86%). $^1$H NMR (500 MHz, Chloroform-d) δ 5.40-5.28 (m, 4H), 4.48 (t, J=5.6 Hz, 1H), 4.20-4.12 (m, 8H), 4.05 (t, J=6.8 Hz, 2H), 3.57 (dt, J=9.3, 6.6 Hz, 2H), 3.40 (dt, J=9.3, 6.6 Hz, 2H), 2.51 (q, J=7.1 Hz, 6H), 2.44-2.28 (m, 8H), 2.07-2.00 (m, 8H), 1.94-1.90 (m, 2H), 1.81 (dt, J=13.8, 6.8 Hz, 2H), 1.67-1.53 (m, 9H), 1.41 (tdd, J=10.2, 7.1, 5.5 Hz, 4H), 1.31-1.27 (m, 12H), 1.01 (t, J=7.1 Hz, 6H), 0.95 (t, J=7.6 Hz, 6H), 0.88 (t, J=7.1 Hz, 3H). UPLC-MS (Method C): Rt 3.46 min, m/z calculated [M+H]: 840.61, found: 840.70.

Certain other exemplary lipids were prepared according to the below general synthetic scheme, using Example 4-2 for illustration.

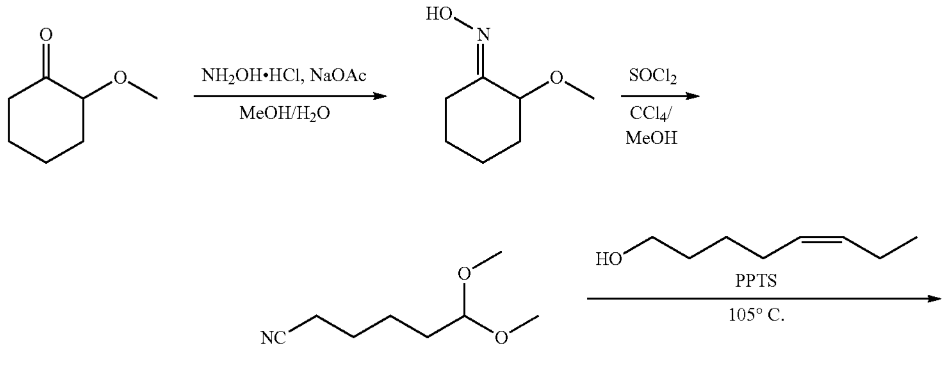

-continued
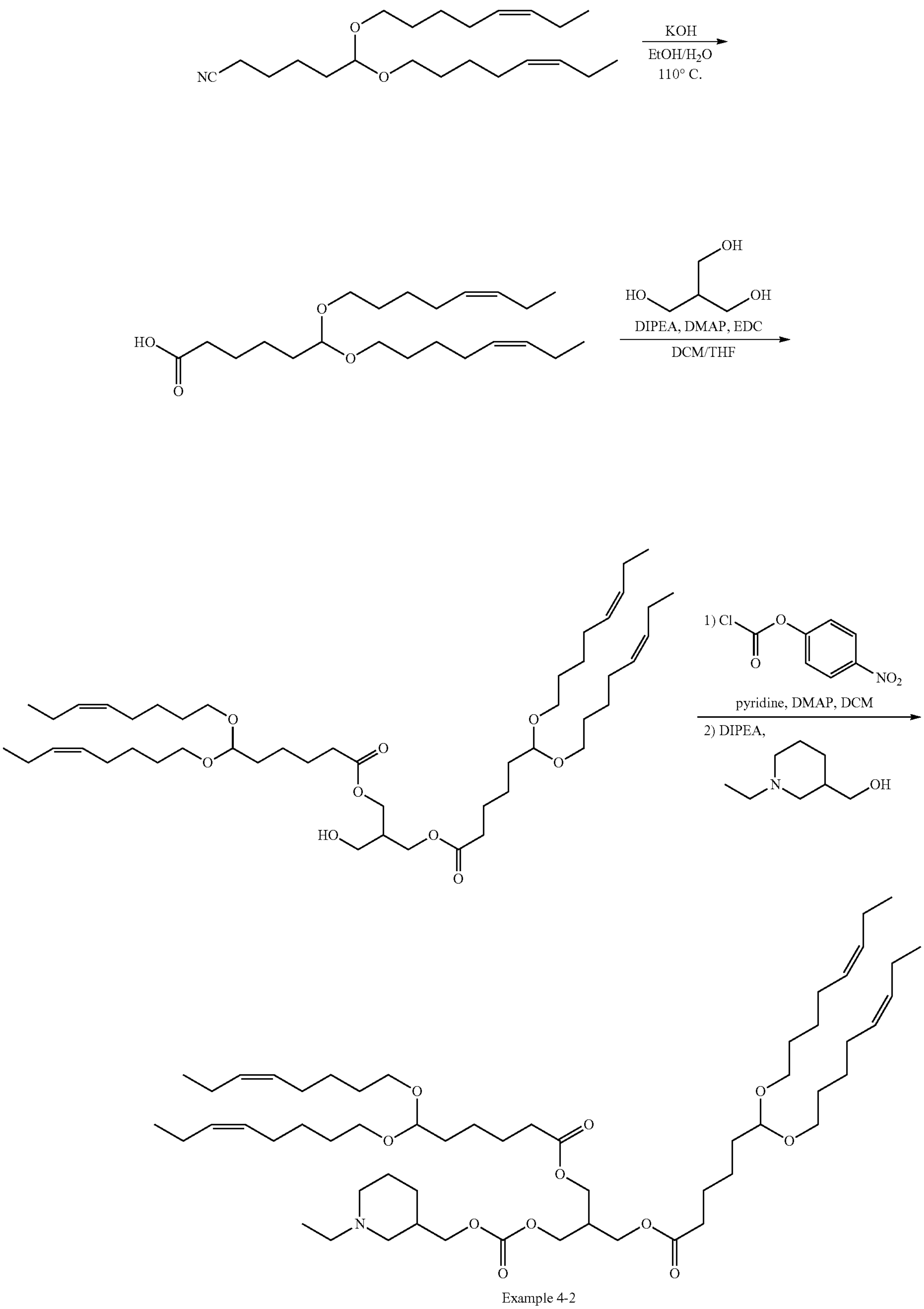
Example 4-2

Example 4-2: 2-(((((1-ethylpiperidin-3-yl)methoxy)carbonyl)oxy)methyl)propane-1,3-diyl bis(6,6-bis(((Z)-oct-5-en-1-yl)oxy)hexanoate)

Example 4-2

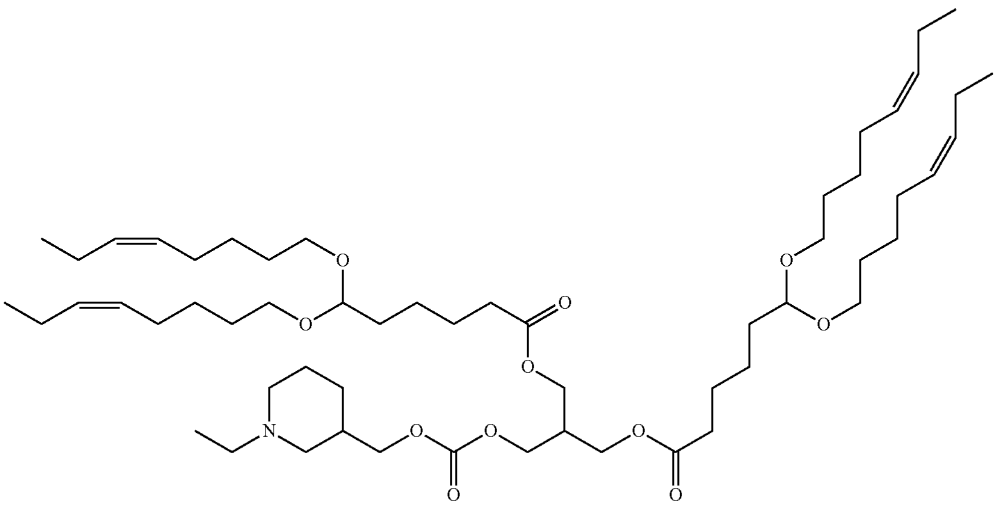

Step 1: 2-methoxycyclohexan-1-one oxime

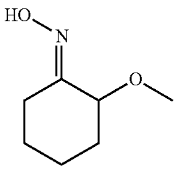

To a stirred solution of 2-methoxycyclohexan-1-one (5 g, 39.0 mmol) in MeOH—$H_2O$ (150 ml, 1:2) was added sodium acetate (6.41 g, 78.1 mmol) followed by the addition of hydroxylamine hydrochloride (5.43 g, 78.1 mmol). The resulting mixture was heated at 70° C. in a sealed tube for 16 h. After that time, MeOH was evaporated and the mixture was diluted with water, extracted with ethyl acetate (3×50 mL), washed with brine and dried over sodium sulfate and concentrated under reduced pressure. The crude thus obtained was purified by flash column chromatography eluting with 3% ethyl acetate in hexane to afford 2-methoxycyclohexan-1-one oxime (4.1 g, 88%) as colorless oil. $^1$H NMR (400 MHz, DMSO-$d_6$) δ 1.17-1.32 (m, 1H), 1.40-1.56 (m, 2H), 1.59-1.82 (m, 3H), 1.92-1.99 (m, 1H), 2.93-3.01 (m, 1H), 3.11 (s, 3H), 3.63 (s, 1H), 10.61 (s, 1H).

Step 2: 6,6-dimethoxyhexanenitrile

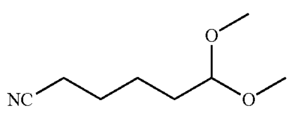

To a stirred solution of 2-methoxycyclohexan-1-one oxime (2.0 g, 14.0 mmol) in $CCl_4$ (20 ml) was added thionyl chloride (1.2 ml, 16.8 mmol) dropwise at 0° C. and stirred for 10 min. After that time, dry MeOH (20 ml) was added to the reaction mixture at 5-10° C. After addition was complete, the reaction mixture was allowed to reach room temperature and was left for 2 h. The mixture was then diluted with ethyl acetate and washed with brine, dried over sodium sulfate and concentrated to afford 6,6-dimethoxyhexanenitrile (1.6 g, 81%) as light yellow oil. $^1$H NMR (400 MHz, Chloroform-d) δ 1.44-1.56 (m, 2H), 1.57-1.75 (m, 4H), 2.34 (t, J=7.0 Hz, 2H), 3.31 (s, 6H), 4.34 (t, J=5.5 Hz, 1H).

Step 3: 6,6-bis(((Z)-oct-5-en-1-yl)oxy)hexanenitrile

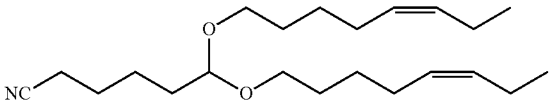 [SMILES: CC/C=C\CCCCOC(CCCCC#N)OCCCC/C=C\CC]

Prepared from 6,6-dimethoxyhexanenitrile and (Z)-oct-5-en-1-ol according to General Procedure A, yield 400 mg (30%). $^1$H NMR (400 MHz, Chloroform-d) δ 0.94 (t, J=7.5 Hz, 6H), 1.34-1.46 (m, 4H), 1.44-1.74 (m, 11H), 1.96-2.10 (m, 8H), 2.33 (t, J=7.1 Hz, 2H), 3.34-3.45 (m, 2H), 3.51-3.61 (m, 2H), 5.25-5.42 (m, 4H).

Step 4: 6,6-bis(((Z)-oct-5-en-1-yl)oxy)hexanoic acid

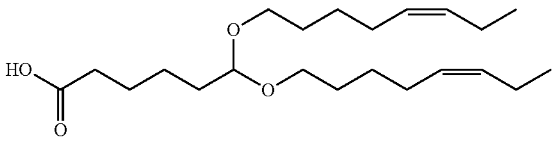 [SMILES: CC/C=C\CCCCOC(CCCCC(=O)O)OCCCC/C=C\CC]

Prepared from 6,6-bis(((Z)-oct-5-en-1-yl)oxy)hexanenitrile according to General Procedure B, yield 400 mg (95%).

$^1$H NMR (400 MHz, DMSO-$d_6$) δ 0.91 (t, J=7.5 Hz, 6H), 1.20-1.41 (m, 6H), 1.42-1.55 (m, 8H), 1.92-2.06 (m, 8H), 2.18 (t, J=7.3 Hz, 2H), 3.31-3.40 (m, 2H), 3.43-3.53 (m, 2H), 4.41 (t, J=5.6 Hz, 1H), 5.23-5.42 (m, 4H), 11.96 (s, 1H).

Step 5: 2-(hydroxymethyl)propane-1,3-diyl bis(6,6-bis(((Z)-oct-5-en-1-yl)oxy)hexanoate)

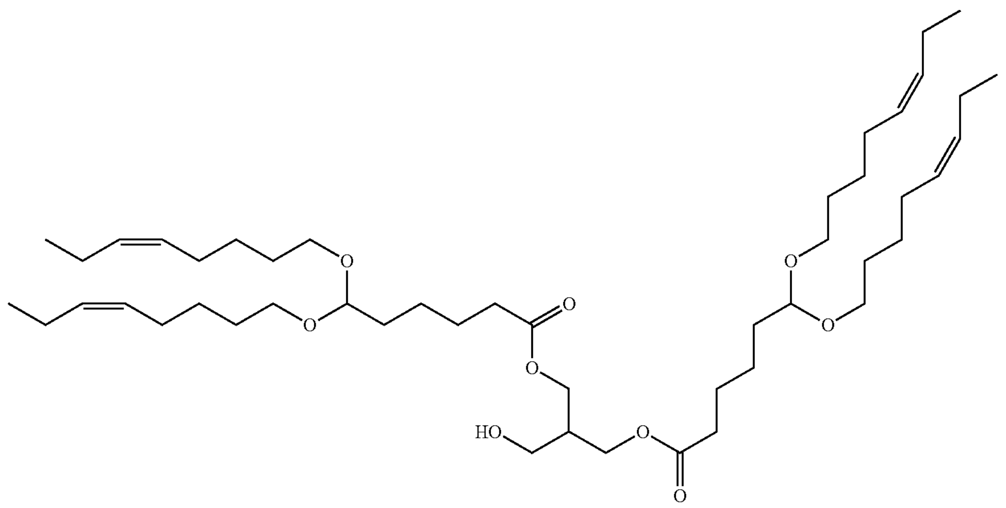 [SMILES: CC/C=C\CCCCOC(CCCCC(=O)OCC(CO)COC(=O)CCCCC(OCCCC/C=C\CC)OCCCC/C=C\CC)OCCCC/C=C\CC]

To a stirred solution of 2-(hydroxymethyl)propane-1,3-diol (30 mg, 0.28 mmol, 1 Eq) in DCM:THF (1:1) (4 mL) were added 6,6-bis(((Z)-oct-5-en-1-yl)oxy)hexanoic acid (260 mg, 0.70 mmol, 2.5 Eq), DIPEA (0.15 mL, 0.85 mmol, 3 Eq), DMAP (10.37 mg, 0.09 mmol, 0.3 Eq), and EDC (162.67 mg, 0.85 mmol, 3 Eq). The resulting mixture was stirred at 25° C. for 16 h. Upon completion, the reaction mixture was diluted with ethyl acetate (30 mL) and washed with 10% saturated $NaHCO_3$ solution (40 mL×2) and water (40 mL). The combined organic layers were dried over anhydrous $Na_2SO_4$, filtered and concentrated. The crude material was purified by silica gel column chromatography using a gradient of 0 to 30% ethyl acetate in hexanes to afford 2-(hydroxymethyl)propane-1,3-diyl bis(6,6-bis(((Z)-oct-5-en-1-yl)oxy)hexanoate) (55 mg, 24%) as a colorless oil. $^1$H NMR (400 MHz, Chloroform-d) δ 0.94 (t, J=7.5 Hz, 12H), 1.31-1.46 (m, 15H), 1.56-1.71 (m, 10H), 1.92-2.11 (m, 22H), 2.32 (t, J=7.6 Hz, 4H), 3.31-3.45 (m, 4H), 3.51-3.63 (m, 6H), 4.16 (t, J=6.9 Hz, 3H), 4.34-4.52 (m, 2H), 5.04-5.62 (m, 8H).

Step 6: 2-(((((1-ethylpiperidin-3-yl)methoxy)carbonyl)oxy)methyl)propane-1,3-diyl bis(6,6-bis(((Z)-oct-5-en-1-yl)oxy)hexanoate) (Example 4-2)

To a stirred solution of 2-(hydroxymethyl)propane-1,3-diyl bis(6,6-bis(((Z)-oct-5-en-1-yl)oxy)hexanoate) (55 mg, 0.068 mmol, 1 Eq) in DCM (2 mL) were added pyridine (0.014 mL, 0.17 mmol, 2.5 Eq), DMAP (2.5 mg, 0.02 mmol, 0.3 Eq) and 4-nitrophenyl carbonochloridate (34 mg, 0.17 mmol, 2.5 Eq). The reaction mixture was stirred at 25° C. for 1 h. Then (1-ethylpiperidin-3-yl)methanol (39 mg, 0.27 mmol, 4 Eq) and DIPEA (0.047 mL, 0.27 mmol, 4 Eq) were added. The reaction mixture was stirred at 25° C. for 16 h. Upon completion, the reaction mixture was diluted with dichloromethane (20 mL), washed with 1M aqueous $Na_2CO_3$ (10 mL×2), water (5 mL×2), and brine (10 mL×2), then finally dried over anhydrous $Na_2SO_4$, filtered and concentrated under reduced pressure. The crude material was purified by silica gel column chromatography using a gradient of 0 to 20% methanol in dichloromethane to afford 2-(((((1-ethylpiperidin-3-yl)methoxy)carbonyl)oxy)methyl)

propane-1,3-diyl bis(6,6-bis(((Z)-oct-5-en-1-yl)oxy)hexanoate) (29 mg, 45%) as a pale yellow oil. UPLC-MS (Method A): Rt 1.70 min, m/z calculated [M+H]: 976.74, found: 977.27.

The following Examples 4-3 to 4-34 were prepared using similar methods as those described for Example 4-1.

Example 4-3

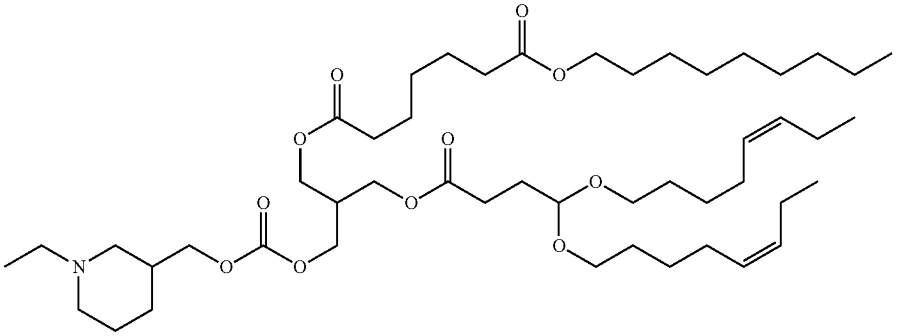

Example 4-3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-nonyl heptanedioate $^1$H NMR (400 MHz, Chloroform-d) δ 5.43-5.18 (m, 4H), 4.23-4.11 (m, 6H), 4.09-4.03 (m, 3H), 3.69-3.63 (m, 5H), 3.11-3.04 (m, 1H), 2.87-2.77 (m, 2H), 2.66-2.62 (m, 2H), 2.23-2.17 (m, 1H), 2.38-2.25 (m, 6H), 2.11-1.98 (m, 8H), 1.66-1.27 (m, 40H), 0.96 (t, J=7.5 Hz, 6H), 0.86 (t, J=10.0 Hz, 3H). UPLC-MS (Method C): Rt 3.49 min, m/z calculated [M+H]: 866.63, found: 866.79.

Example 4-4

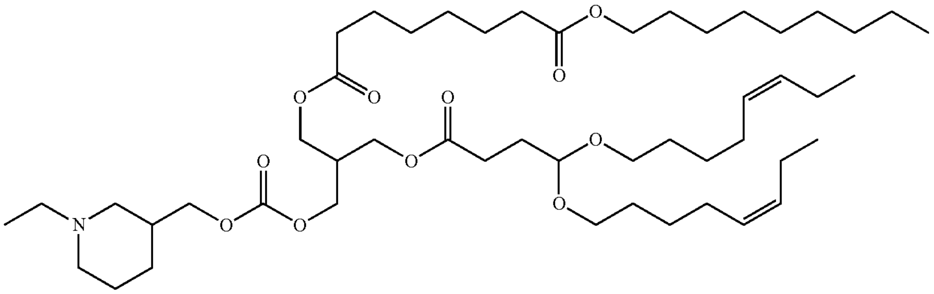

Example 4-4: 1-(3-((4,4-bis(((Z)-oct-5-en-1-yl)oxy) butanoyl)oxy)-2-(((((1-ethylpiperidin-3-yl)methoxy) carbonyl)oxy)methyl)propyl) 8-nonyl octanedioate $^1$H NMR (400 MHz, Chloroform-d) δ 5.44-5.24 (m, 4H), 4.24-4.12 (m, 6H), 4.09-4.03 (m, 3H), 3.69-3.62 (m, 5H), 3.11-3.04 (m, 1H), 2.82 (t, J=6.5 Hz, 2H), 2.64 (t, J=6.5 Hz, 2H), 2.35-2.25 (m, 6H), 2.23-2.17 (m, 1H), 2.12-1.98 (m, 8H), 1.72-1.23 (m, 42H), 0.96 (t, J=7.6 Hz, 6H), 0.87 (t, J=10.0 Hz, 3H). UPLC-MS (Method C): Rt 3.53 min, m/z calculated [M+H]: 880.64, found: 880.79.

Example 4-5

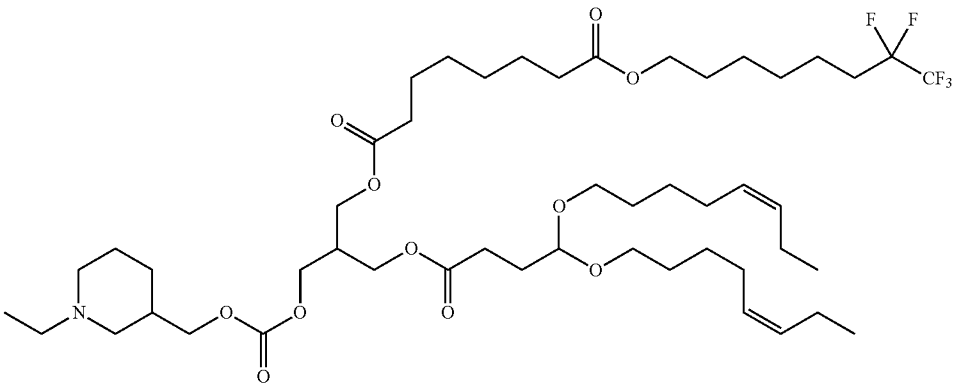

Example 4-5: 1-(3-((4,4-bis(((Z)-oct-5-en-1-yl)oxy) butanoyl)oxy)-2-(((((1-ethylpiperidin-3-yl)methoxy) carbonyl)oxy)methyl)propyl) 8-(7,7,8,8,8-pentafluorooctyl) octanedioate $^1$H NMR (400 MHz, Chloroform-d) δ 5.46-5.22 (m, 4H), 4.23-4.12 (m, 6H), 4.08-4.05 (m, 3H), 3.69-3.62 (m, 5H), 3.11-3.04 (m, 1H), 2.82 (dd, J=7.2, 5.8 Hz, 2H), 2.64 (dd, J=7.0, 6.0 Hz, 2H), 2.37-2.26 (m, 6H), 2.23-2.17 (m, 1H), 2.13-1.97 (m, 8H), 1.73-1.29 (m, 38H), 0.96 (t, J=7.5 Hz, 6H). UPLC-MS (Method C): Rt 3.34 min, m/z calculated [M+H]: 956.58, found: 956.78.

Example 4-6

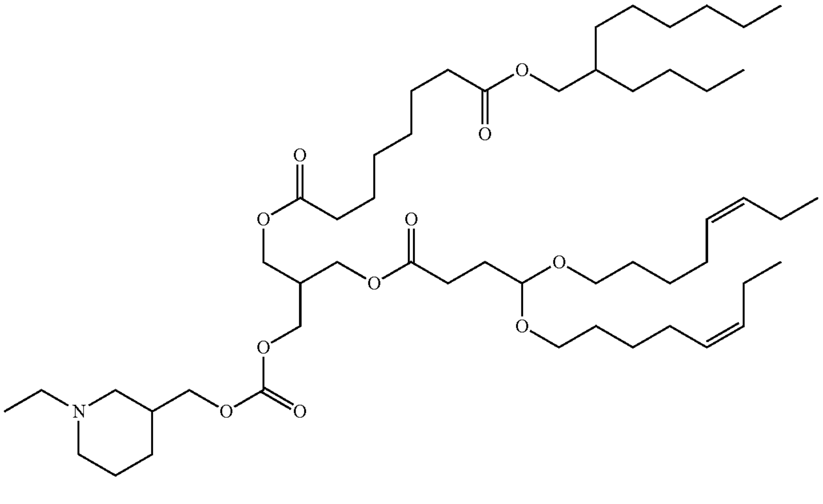

Example 4-6: 1-(3-((4,4-bis(((Z)-oct-5-en-1-yl)oxy) butanoyl)oxy)-2-(((((1-ethylpiperidin-3-yl)methoxy) carbonyl)oxy)methyl)propyl) 8-(2-butyloctyl) octanedioate $^1$H NMR (400 MHz, Chloroform-d) δ 5.44-5.26 (m, 4H), 4.24-4.11 (m, 6H), 3.97-3.95 (m, 3H), 3.69-3.62 (m, 5H), 3.11-3.04 (m, 1H), 2.82 (t, J=6.5 Hz, 2H), 2.64 (t, J=6.5 Hz, 2H), 2.36-2.27 (m, 6H), 2.23-2.17 (m, 1H), 2.11-1.99 (m, 8H), 1.68-1.20 (m, 45H), 0.95 (t, J=7.6 Hz, 6H), 0.88 (t, J=8.0 Hz, 6H). UPLC-MS (Method C): Rt 3.73 min, m/z calculated [M+H]: 922.69, found: 922.88.

Example 4-7

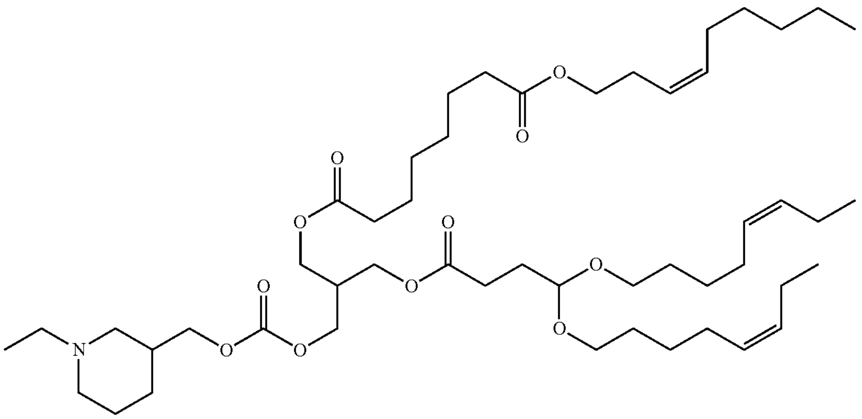

Example 4-7: 1-(3-((4,4-bis(((Z)-oct-5-en-1-yl)oxy) butanoyl)oxy)-2-(((((1-ethylpiperidin-3-yl)methoxy) carbonyl)oxy)methyl)propyl) 8-((Z)-non-3-en-1-yl) octanedioate $^1$H NMR (400 MHz, Chloroform-d) δ 5.55-5.26 (m, 6H), 4.22-4.13 (m, 6H), 4.06-4.04 (m, 3H), 3.69-3.62 (m, 5H), 3.11-3.04 (m, 1H), 2.84-2.81 (m, 2H), 2.64-2.62 (m, 2H), 2.40-2.27 (m, 6H), 2.23-2.17 (m, 1H), 2.09-2.00 (m, 10H), 1.64-1.25 (m, 36H), 0.96 (t, J=7.5 Hz, 6H), 0.88 (t, J=8.0 Hz, 3H). UPLC-MS (Method C): Rt 3.42 min, m/z calculated [M+H]: 878.63, found: 878.79.

Example 4-8

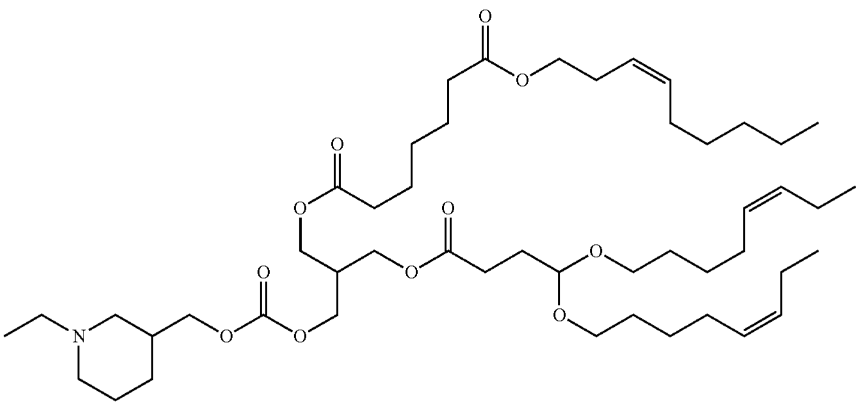

Example 4-8: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-((Z)-non-3-en-1-yl) heptanedioate

$^1$H NMR (400 MHz, Chloroform-d) δ 5.54-5.27 (m, 6H), 4.18-4.04 (m, 9H), 3.69-3.62 (m, 5H), 3.11-3.04 (m, 1H), 2.81-2.78 (m, 2H), 2.65-2.61 (m, 2H), 2.47-2.24 (m, 7H), 2.07-2.01 (m, 10H), 1.70-1.57 (m, 14H), 1.50-1.26 (m, 20H), 0.99-0.92 (m, 6H), 0.88 (t, J=6.8 Hz, 3H). UPLC-MS (Method C): Rt 3.38 min, m/z calculated [M+H]: 864.61, found: 864.69.

Example 4-9

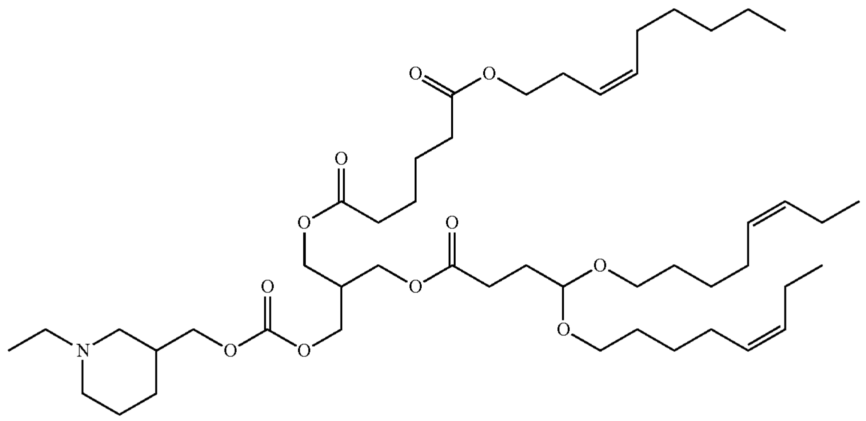

Example 4-9: 3-((4,4-bis(((Z)-oct-5-en-1-yl)oxy)butanoyl)oxy)-2-(((((1-ethylpiperidin-3-yl)methoxy)carbonyl)oxy)methyl)propyl ((Z)-non-3-en-1-yl) adipate

$^1$H NMR (400 MHz, Chloroform-d) δ 5.54-5.27 (m, 6H), 4.19-4.03 (m, 9H), 3.65 (t, J=6.5 Hz, 2H), 2.82-2.77 (m, 2H), 2.65-2.60 (m, 2H), 2.54-2.30 (m, 7H), 2.07-1.91 (m, 20H), 1.70-1.59 (m, 10H), 1.51-1.26 (m, 16H), 0.97-0.93 (m, 6H), 0.88 (t, J=6.8 Hz, 3H). UPLC-MS (Method C): Rt 3.33 min, m/z calculated [M+H]: 850.60, found: 850.79.

Example 4-10

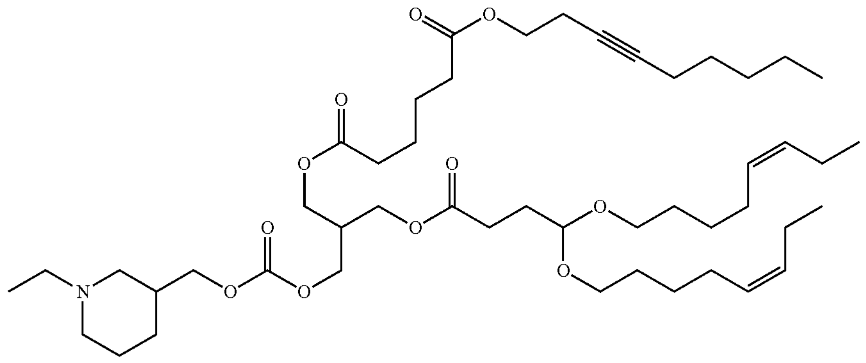

Example 4-10: 3-((4,4-bis(((Z)-oct-5-en-1-yl)oxy)butanoyl)oxy)-2-(((((1-ethylpiperidin-3-yl)methoxy)carbonyl)oxy)methyl)propyl non-3-yn-1-yl adipate

$^1$H NMR (400 MHz, Chloroform-d) δ 5.41-5.26 (m, 4H), 4.15-4.05 (m, 9H), 3.66 (dt, J=11.7, 6.4 Hz, 2H), 2.82-2.78 (m, 2H), 2.65-2.61 (m, 2H), 2.50-2.32 (m, 13H), 2.19-1.99 (m, 14H), 1.73-1.27 (m, 30H), 0.95 (t, J=7.5 Hz, 6H), 0.91-0.88 (m, 6H). UPLC-MS (Method C): Rt 3.25 min, m/z calculated [M+H]: 848.58, found: 848.79.

Example 4-11

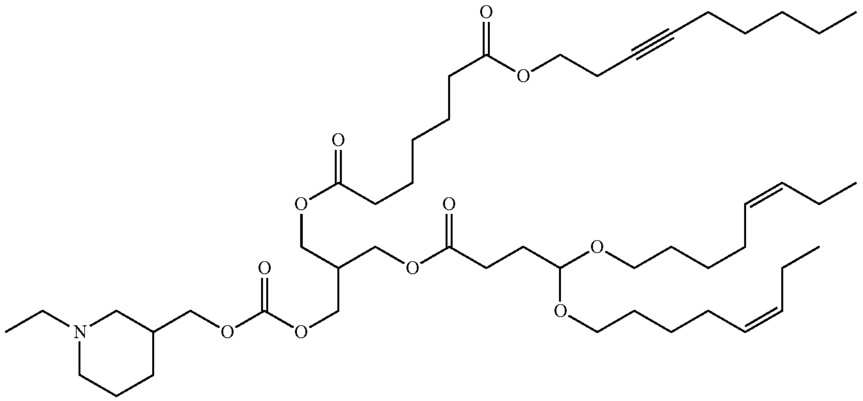

Example 4-11: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(non-3-yn-1-yl) heptanedioate

$^1$H NMR (400 MHz, Chloroform-d) δ 5.42-5.27 (m, 4H), 4.21-4.04 (m, 9H), 3.69-3.62 (m, 5H), 3.11-3.04 (m, 1H), 2.84-2.78 (m, 2H), 2.65-2.61 (m, 2H), 2.50-2.39 (m, 6H), 2.38-2.27 (m, 7H), 2.09-2.00 (m, 10H), 1.71-1.25 (m, 28H), 0.95 (t, J=7.5 Hz, 6H), 0.89 (t, J=7.1 Hz, 3H). UPLC-MS (Method C): Rt 3.29 min, m/z calculated [M+H]: 862.60, found: 862.79.

Example 4-12

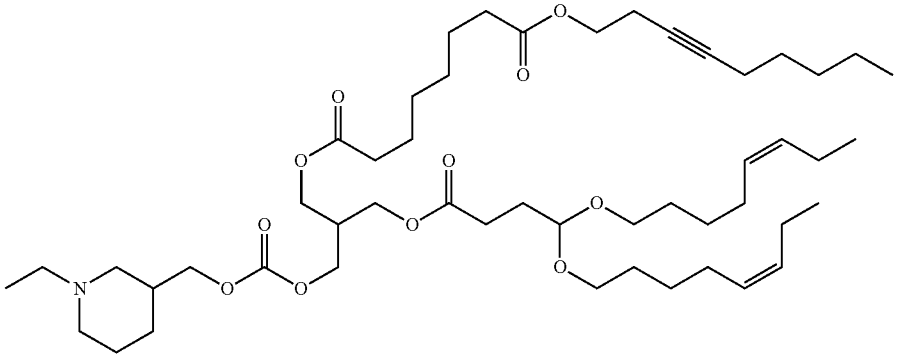

Example 4-12: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(non-3-yn-1-yl) octanedioate $^1$H NMR (400 MHz, Chloroform-d) δ 5.41-5.28 (m, 4H), 4.21-4.11 (m, 9H), 3.69-3.62 (m, 5H), 3.11-3.04 (m, 1H), 2.82 (t, J=6.4 Hz, 2H), 2.64 (t, J=6.5 Hz, 2H), 2.50-2.43 (m, 6H), 2.34-2.29 (m, 7H), 2.23-2.17 (m, 1H), 2.15-2.00 (m, 12H), 1.64-1.29 (m, 27H), 0.95 (t, J=7.5 Hz, 6H), 0.89 (t, J=7.0 Hz, 3H). UPLC-MS (Method C): Rt 3.36 min, m/z calculated [M+H]: 876.61, found: 876.79.

Example 4-13

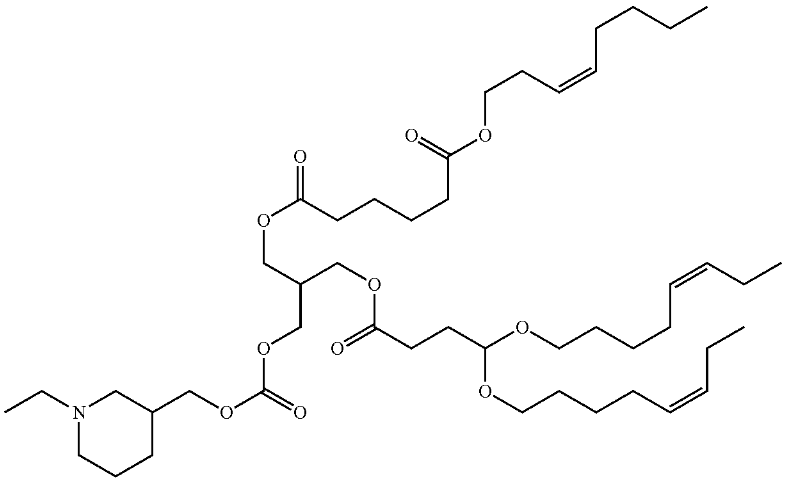

Example 4-13: 3-((4,4-bis(((Z)-oct-5-en-1-yl)oxy)butanoyl)oxy)-2-(((((1-ethylpiperidin-3-yl)methoxy)carbonyl)oxy)methyl)propyl ((Z)-oct-3-en-1-yl) adipate $^1$H NMR (400 MHz, Chloroform-d) δ 5.54-5.46 (m, 2H), 5.37-5.28 (m, 4H), 4.14 (dd, J=8.6, 6.0 Hz, 6H), 4.06 (t, J=6.9 Hz, 5H), 3.65 (t, J=6.6 Hz, 4H), 2.81 (t, J=6.5 Hz, 2H), 2.63 (t, J=6.5 Hz, 2H), 2.42-2.29 (m, 14H), 2.09-1.99 (m, 10H), 1.67-1.55 (m, 10H), 1.46-1.29 (m, 10H), 0.96 (t, J=7.5 Hz, 6H), 0.92-0.85 (m, 6H).

Example 4-14

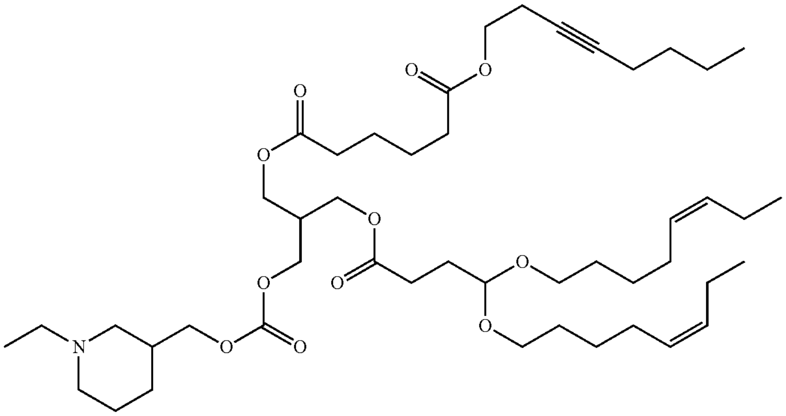

Example 4-14: 3-((4,4-bis(((Z)-oct-5-en-1-yl)oxy) butanoyl)oxy)-2-(((((1-ethylpiperidin-3-yl)methoxy) carbonyl)oxy)methyl)propyl oct-3-yn-1-yl adipate $^{1}$H NMR (400 MHz, Chloroform-d) δ 5.42-5.28 (m, 4H), 4.16-4.11 (m, 11H), 3.65 (t, J=6.6 Hz, 4H), 2.81 (t, J=6.5 Hz, 2H), 2.63 (t, J=6.5 Hz, 2H), 2.48 (tt, J=7.0, 2.4 Hz, 4H), 2.42-2.32 (m, 9H), 2.14 (tt, J=7.0, 2.4 Hz, 4H), 2.09-2.00 (m, 8H), 1.68-1.64 (m, 6H), 1.62-1.55 (m, 4H), 1.48-1.36 (m, 9H), 0.96 (t, J=7.5 Hz, 6H), 0.90 (t, J=7.1 Hz, 6H).

Example 4-15

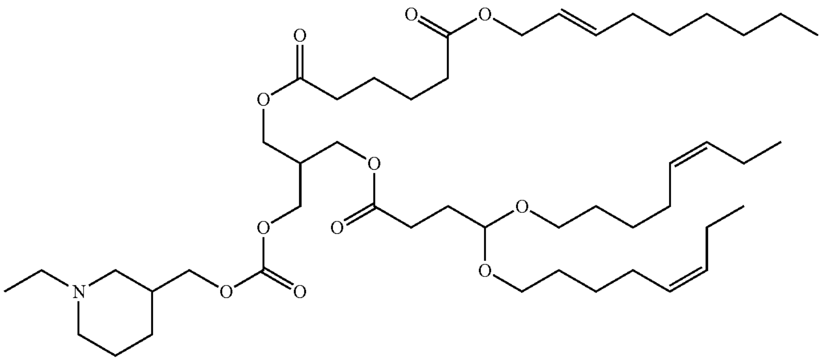

Example 4-15: 3-((4,4-bis(((Z)-oct-5-en-1-yl)oxy) butanoyl)oxy)-2-(((((1-ethylpiperidin-3-yl)methoxy) carbonyl)oxy)methyl)propyl ((E)-non-2-en-1-yl) adipate $^{1}$H NMR (400 MHz, Chloroform-d) δ 5.76 (dtt, J=14.7, 6.7, 1.2 Hz, 1H), 5.55 (dtt, J=14.7, 6.7, 1.2 Hz, 1H), 5.44-5.25 (m, 4H), 4.51 (dd, J=6.5, 1.1 Hz, 4H), 4.16-4.12 (m, 6H), 3.69-3.63 (m, 5H), 2.81 (t, J=6.5 Hz, 2H), 2.63 (t, J=6.5 Hz, 2H), 2.42-2.31 (m, 11H), 2.13-1.97 (m, 12H), 1.69-1.55 (m, 12H), 1.46-1.24 (m, 11H), 0.96 (t, J=7.5 Hz, 6H), 0.90-0.86 (m, 6H).

Example 4-16

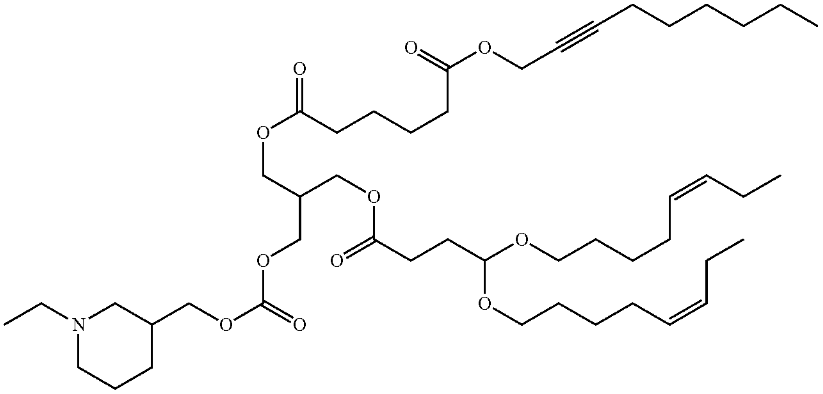

Example 4-16: 3-((4,4-bis(((Z)-oct-5-en-1-yl)oxy) butanoyl)oxy)-2-(((((1-ethylpiperidin-3-yl)methoxy) carbonyl)oxy)methyl)propyl non-2-yn-1-yl adipate

$^1$H NMR (400 MHz, Chloroform-d) δ 5.44-5.26 (m, 4H), 4.66 (t, J=2.2 Hz, 4H), 4.14 (dd, J=8.8, 6.0 Hz, 6H), 3.69-3.63 (m, 5H), 2.81 (t, J=6.5 Hz, 2H), 2.63 (t, J=6.5 Hz, 2H), 2.38-2.32 (m, 9H), 2.23 (tt, J=7.2, 2.2 Hz, 4H), 2.09-2.00 (m, 8H), 1.68-1.65 (m, 8H), 1.62-1.55 (m, 4H), 1.47-1.24 (m, 13H), 0.96 (t, J=7.5 Hz, 6H), 0.89 (t, J=6.9 Hz, 6H).

Example 4-17

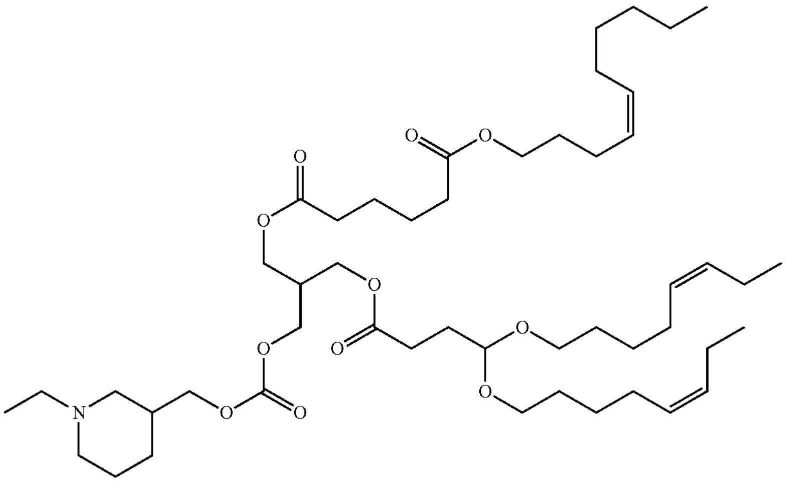

Example 4-17: 3-((4,4-bis(((Z)-oct-5-en-1-yl)oxy) butanoyl)oxy)-2-(((((1-ethylpiperidin-3-yl)methoxy) carbonyl)oxy)methyl)propyl ((Z)-dec-4-en-1-yl) adipate

$^1$H NMR (400 MHz, Chloroform-d) δ 5.44-5.28 (m, 6H), 4.14 (dd, J=8.5, 6.0 Hz, 6H), 4.06 (t, J=6.7 Hz, 4H), 3.69-3.63 (m, 5H), 2.81 (t, J=6.5 Hz, 2H), 2.63 (t, J=6.5 Hz, 2H), 2.44-2.30 (m, 9H), 2.12-1.96 (m, 14H), 1.67-1.55 (m, 12H), 1.46-1.24 (m, 13H), 0.96 (t, J=7.5 Hz, 6H), 0.88 (t, J=6.9 Hz, 6H).

Example 4-18

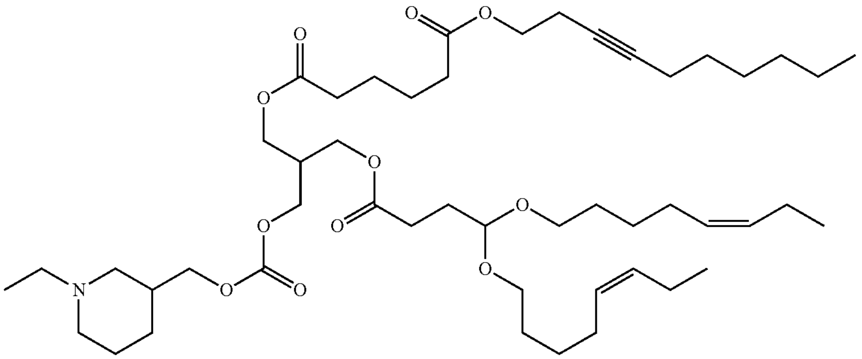

Example 4-18: 3-((4,4-bis(((Z)-oct-5-en-1-yl)oxy)butanoyl)oxy)-2-(((((1-ethylpiperidin-3-yl)methoxy)carbonyl)oxy)methyl)propyl dec-3-yn-1-yl adipate

$^1$H NMR (400 MHz, Chloroform-d) δ 5.46-5.23 (m, 4H), 4.16-4.11 (m, 11H), 3.65 (t, J=6.6 Hz, 4H), 2.81 (t, J=6.5 Hz, 2H), 2.63 (t, J=6.5 Hz, 2H), 2.48 (tt, J=7.1, 2.4 Hz, 4H), 2.42-2.32 (m, 9H), 2.15-2.00 (m, 12H), 1.69-1.57 (m, 10H), 1.48-1.25 (m, 13H), 0.96 (t, J=7.5 Hz, 6H), 0.89 (t, J=6.9 Hz, 6H).

Example 4-19

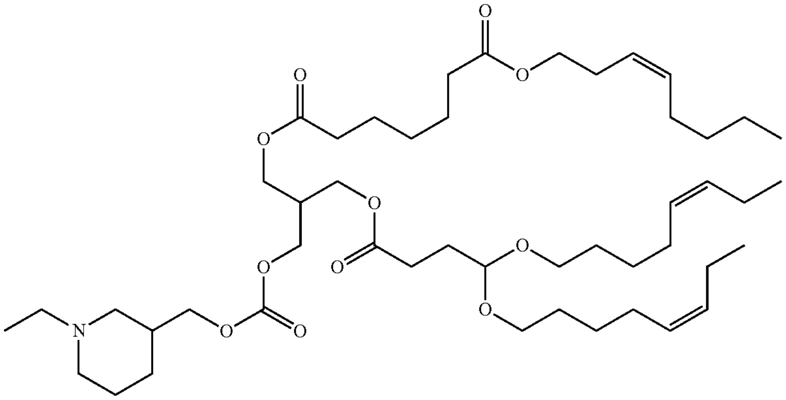

Example 4-19: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-((Z)-oct-3-en-1-yl) heptanedioate

$^1$H NMR (400 MHz, Chloroform-d) δ 5.53-5.46 (m, 2H), 5.42-5.26 (m, 4H), 4.22-4.11 (m, 7H), 4.06 (t, J=6.9 Hz, 3H), 3.69-3.63 (m, 5H), 2.82 (t, J=6.5 Hz, 2H), 2.64 (t, J=6.5 Hz, 2H), 2.36-2.28 (m, 6H), 2.23-2.17 (m, 1H), 2.09-2.00 (m, 8H), 1.68-1.55 (m, 20H), 1.51-1.29 (m, 14H), 0.96 (t, J=7.5 Hz, 6H), 0.93-0.86 (m, 3H). UPLC-MS (Method C): Rt 3.43 min, m/z calculated [M+H]: 850.60, found: 850.69.

Example 4-20

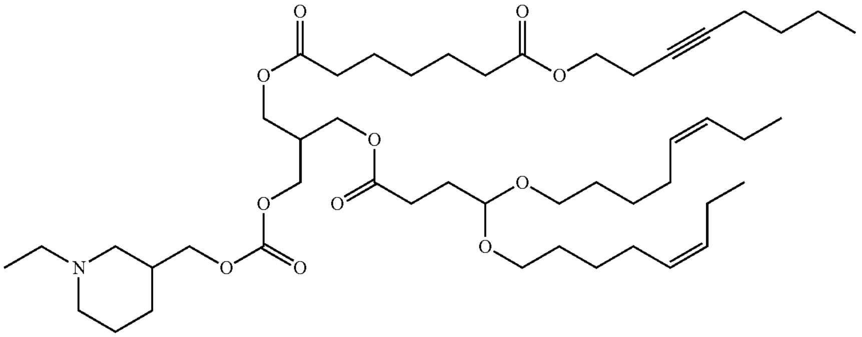

Example 4-20: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(oct-3-yn-1-yl) heptanedioate

$^1$H NMR (400 MHz, Chloroform-d) δ 5.42-5.28 (m, 4H), 4.21-4.11 (m, 10H), 3.69-3.63 (m, 5H), 2.82 (t, J=6.5 Hz, 2H), 2.64 (t, J=6.5 Hz, 2H), 2.47 (tt, J=7.0, 2.4 Hz, 2H), 2.33 (tdd, J=7.6, 3.7, 1.9 Hz, 4H), 2.23-2.17 (m, 1H), 2.14 (tt, J=7.0, 2.4 Hz, 4H), 2.09-2.00 (m, 8H), 1.68-1.34 (m, 30H), 0.95 (t, J=7.5 Hz, 6H), 0.90 (t, J=7.1 Hz, 3H). UPLC-MS (Method C): Rt 3.30 min, m/z calculated [M+H]: 848.58, found: 848.69.

Example 4-21

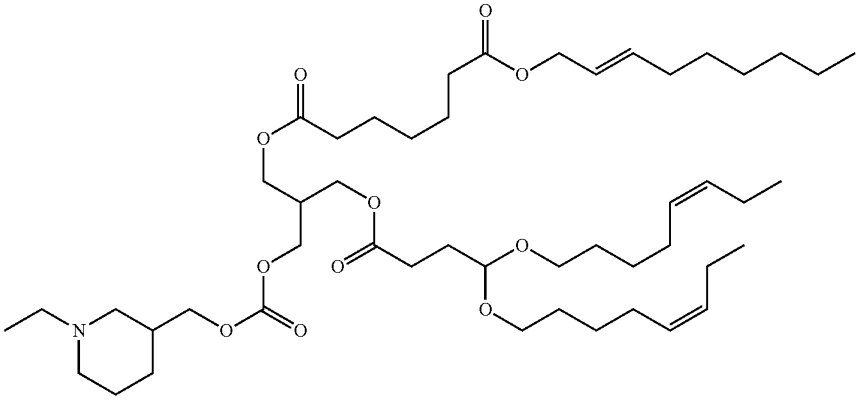

Example 4-21: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-((E)-non-2-en-1-yl) heptanedioate

$^1$H NMR (400 MHz, Chloroform-d) δ 5.42-5.28 (m, 4H), 4.51-4.49 (dd, J=6.5, 1.1 Hz, 2H), 4.21-4.11 (m, 8H), 3.69-3.63 (m, 5H), 3.11-3.02 (m, 1H), 2.82 (t, J=6.5 Hz, 2H), 2.64 (t, J=6.5 Hz, 2H), 2.47 (tt, J=7.0, 2.4 Hz, 2H), 2.33 (tdd, J=7.6, 3.7, 1.9 Hz, 4H), 2.23-2.17 (m, 1H), 2.14 (tt, J=7.0, 2.4 Hz, 2H), 2.09-2.00 (m, 10H), 1.68-1.34 (m, 33H), 0.95 (t, J=7.5 Hz, 6H), 0.90 (t, J=7.1 Hz, 3H). UPLC-MS (Method C): Rt 3.59 min, m/z calculated [M+H]: 864.61, found: 864.69.

Example 4-22

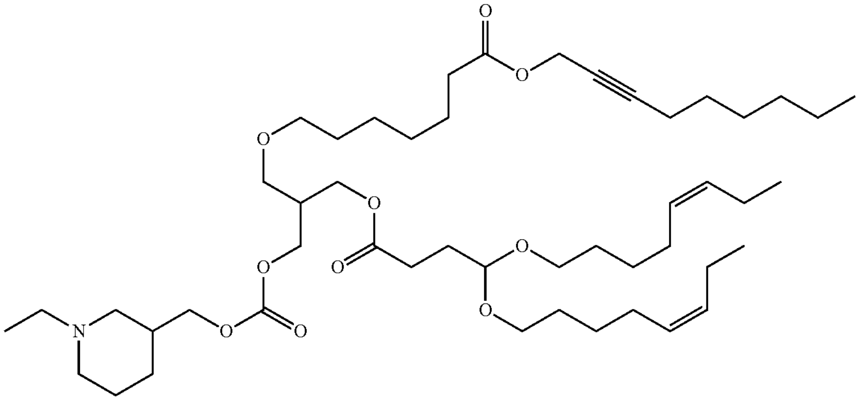

Example 4-22: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(non-2-yn-1-yl) heptanedioate $^1$H NMR (400 MHz, Chloroform-d) δ 5.42-5.26 (m, 4H), 4.66 (t, J=2.2 Hz, 2H), 4.22-4.12 (m, 8H), 3.69-3.63 (m, 5H), 2.82 (td, J=6.6, 4.7 Hz, 2H), 2.64 (td, J=6.6, 2.3 Hz, 2H), 2.37-2.30 (m, 6H), 2.23-2.19 (m, 3H), 2.09-2.00 (m, 8H), 1.70-1.25 (m, 36H), 0.96 (t, J=7.5 Hz, 6H), 0.88 (t, J=6.9 Hz, 3H). UPLC-MS (Method C): Rt 3.52 min, m/z calculated [M+H]: 862.60, found: 862.69.

Example 4-23

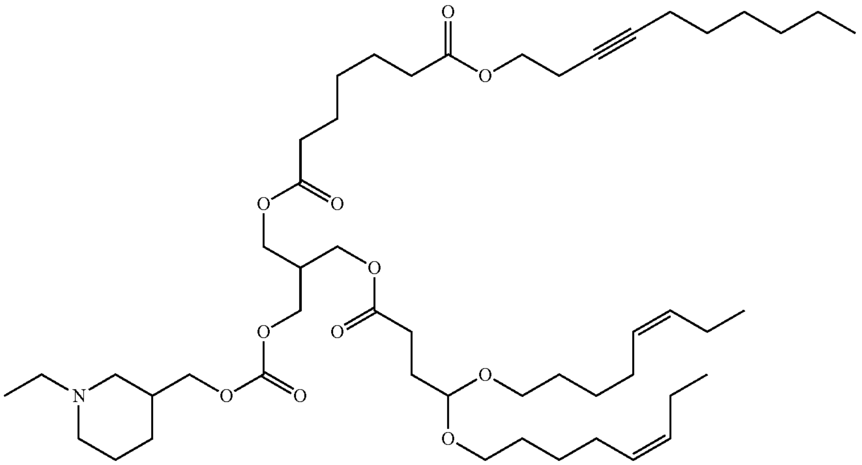

Example 4-23: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(dec-3-yn-1-yl) heptanedioate $^1$H NMR (400 MHz, Chloroform-d) δ 5.42-5.28 (m, 4H), 4.22-4.11 (m, 10H), 3.69-3.63 (m, 4H), 3.11-3.02 (m, 1H), 2.82 (td, J=6.5, 4.7 Hz, 2H), 2.64 (td, J=6.6, 2.1 Hz, 2H), 2.50-2.45 (m, 2H), 2.33 (tdd, J=7.7, 3.9, 2.0 Hz, 4H), 2.23-2.17 (m, 1H), 2.15-2.00 (m, 10H), 1.68-1.25 (m, 36H), 0.96 (t, J=7.5 Hz, 6H), 0.88 (t, J=6.9 Hz, 3H). UPLC-MS (Method C): Rt 3.53 min, m/z calculated [M+H]: 876.61, found: 876.79.

Example 4-24

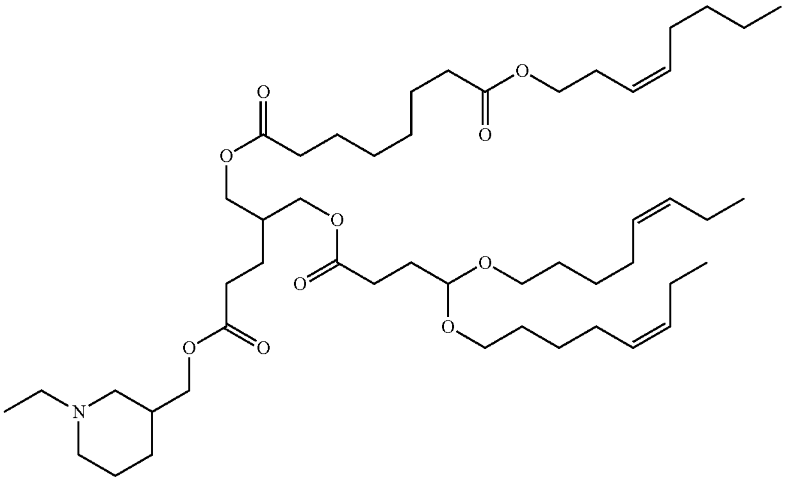

Example 4-24: 1-(3-((4,4-bis(((Z)-oct-5-en-1-yl) oxy)butanoyl)oxy)-2-(((((1-ethylpiperidin-3-yl) methoxy)carbonyl)oxy)methyl)propyl) 8-((Z)-oct-3-en-1-yl) octanedioate $^1$H NMR (400 MHz, Chloroform-d) δ 5.53-5.46 (m, 1H), 5.44-5.28 (m, 5H), 4.22-4.13 (m, 6H), 4.08-4.04 (m, 4H), 3.69-3.63 (m, 5H), 3.11-3.02 (m, 1H), 2.82 (t, J=6.5 Hz, 2H), 2.64 (t, J=6.5 Hz, 2H), 2.38-2.27 (m, 6H), 2.23-2.17 (m, 1H), 2.09-2.00 (m, 10H), 1.64-1.29 (m, 33H), 0.95 (t, J=7.5 Hz, 6H), 0.88 (t, J=7.0 Hz, 3H). UPLC-MS (Method C): Rt 3.38 min, m/z calculated [M+H]: 864.61, found: 864.79.

Example 4-25

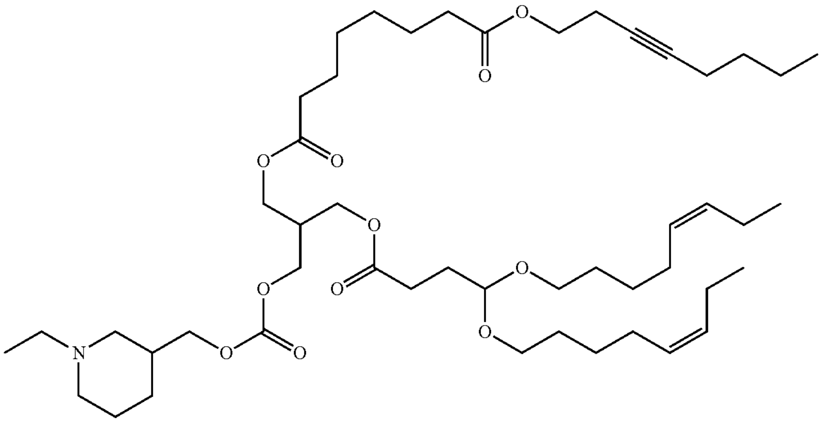

Example 4-25: 1-(3-((4,4-bis(((Z)-oct-5-en-1-yl) oxy)butanoyl)oxy)-2-(((((1-ethylpiperidin-3-yl) methoxy)carbonyl)oxy)methyl)propyl) 8-(oct-3-yn-1-yl) octanedioate $^1$H NMR (400 MHz, Chloroform-d) δ 5.42-5.28 (m, 4H), 4.22-4.11 (m, 10H), 3.69-3.63 (m, 5H), 2.82 (t, J=6.5 Hz, 2H), 2.64 (t, J=6.5 Hz, 2H), 2.47 (ddt, J=7.0, 4.7, 2.4 Hz, 4H), 2.32 (dtd, J=7.5, 4.6, 2.3 Hz, 4H), 2.23-2.17 (m, 1H), 2.16-2.01 (m, 10H), 1.64-1.32 (m, 32H), 0.96 (t, J=7.5 Hz, 6H), 0.90 (t, J=7.1 Hz, 3H). UPLC-MS (Method C): Rt 3.28 min, m/z calculated [M+H]: 862.60, found: 862.79.

Example 4-26

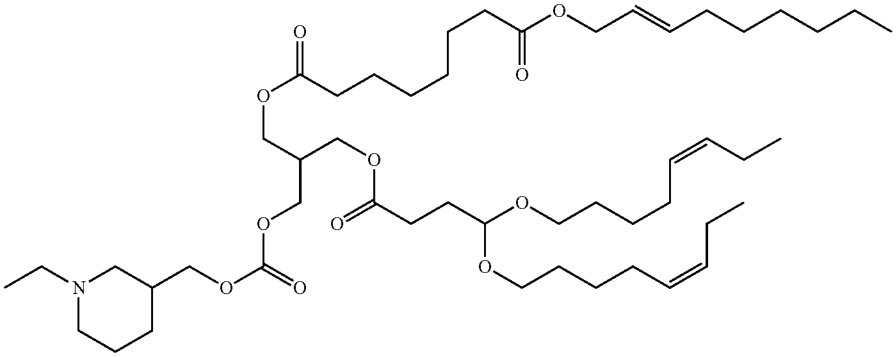

Example 4-26: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-((E)-non-2-en-1-yl) octanedioate

$^1$H NMR (400 MHz, Chloroform-d) δ 5.80-5.73 (m, 1H), 5.59-5.51 (m, 1H), 5.42-5.28 (m, 4H), 4.51-4.49 (m, 2H), 4.21-4.14 (m, 7H), 3.69-3.63 (m, 5H), 3.11-3.02 (m, 1H), 2.82 (t, J=6.5 Hz, 2H), 2.64 (t, J=6.5 Hz, 2H), 2.35-2.26 (m, 4H), 2.23-2.17 (m, 1H), 2.09-2.00 (m, 10H), 1.66-1.25 (m, 38H), 0.95 (t, J=7.5 Hz, 6H), 0.88 (t, J=7.0 Hz, 3H). UPLC-MS (Method C): Rt 3.49 min, m/z calculated [M+H]: 878.63, found: 878.79.

Example 4-27

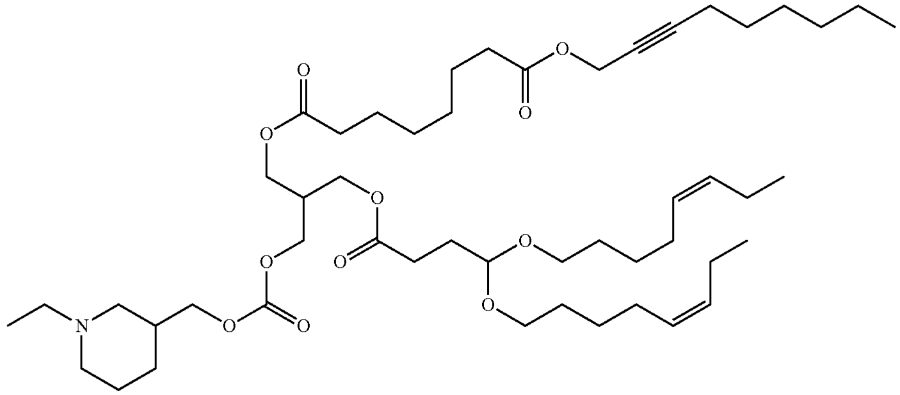

Example 4-27: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(non-2-yn-1-yl) octanedioate

$^1$H NMR (400 MHz, Chloroform-d) δ 5.42-5.28 (m, 4H), 4.66 (t, J=2.2 Hz, 2H), 4.22-4.12 (m, 8H), 3.69-3.63 (m, 5H), 2.82 (t, J=6.4 Hz, 2H), 2.64 (t, J=6.5 Hz, 2H), 2.35-2.29 (m, 5H), 2.23-2.19 (m, 3H), 2.09-2.00 (m, 8H), 1.64-1.25 (m, 37H), 0.96 (t, J=7.5 Hz, 6H), 0.88 (t, J=6.9 Hz, 3H). UPLC-MS (Method C): Rt 3.37 min, m/z calculated [M+H]: 876.61, found: 876.79.

Example 4-28

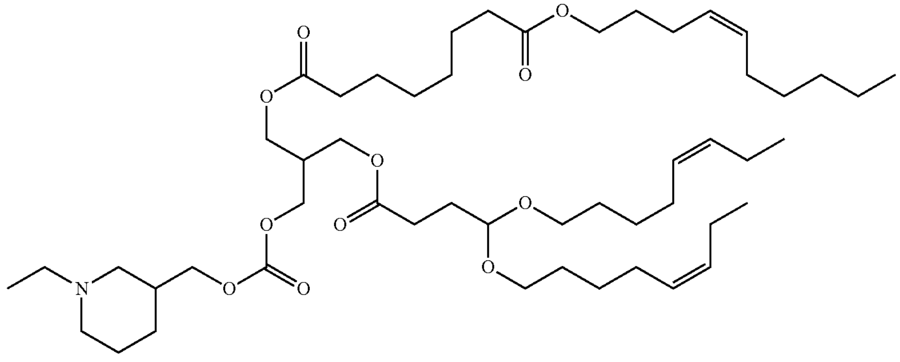

Example 4-28: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-((Z)-dec-4-en-1-yl) octanedioate

$^1$H NMR (400 MHz, Chloroform-d) δ 5.44-5.28 (m, 6H), 4.22-4.04 (m, 10H), 3.69-3.63 (m, 5H), 2.82 (t, J=6.4 Hz, 2H), 2.64 (t, J=6.5 Hz, 2H), 2.34-2.28 (m, 5H), 2.23-2.17 (m, 1H), 2.12-1.98 (m, 12H), 1.69-1.26 (m, 42H), 0.95 (t, J=7.5 Hz, 6H), 0.88 (t, J=6.8 Hz, 3H). UPLC-MS (Method C): Rt 3.48 min, m/z calculated [M+H]: 892.64, found: 892.79.

Example 4-29

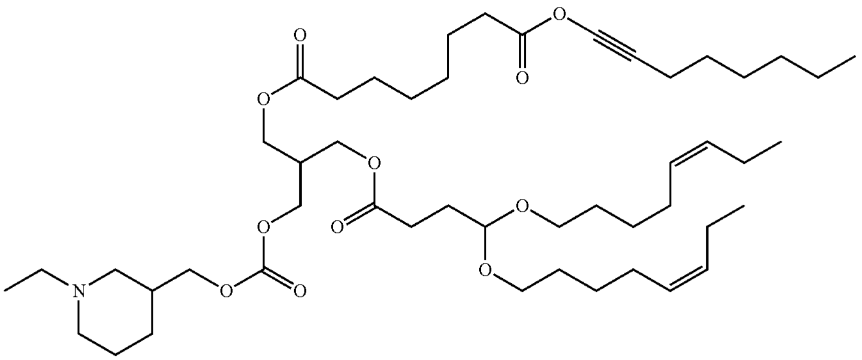

Example 4-29: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(dec-3-yn-1-yl) octanedioate

$^1$H NMR (400 MHz, Chloroform-d) δ 5.44-5.26 (m, 4H), 4.22-4.11 (m, 9H), 3.69-3.63 (m, 5H), 2.82 (t, J=6.4 Hz, 2H), 2.64 (t, J=6.5 Hz, 2H), 2.50-2.45 (tt, J=7.1, 2.4 Hz, 2H), 2.34-2.29 (m, 6H), 2.23-2.17 (m, 1H), 2.15-2.02 (m, 12H), 1.65-1.26 (m, 35H), 0.96 (t, J=7.6 Hz, 6H), 0.89 (t, J=6.9 Hz, 3H). UPLC-MS (Method C): Rt 3.42 min, m/z calculated [M+H]: 890.63, found: 890.69.

Example 4-30

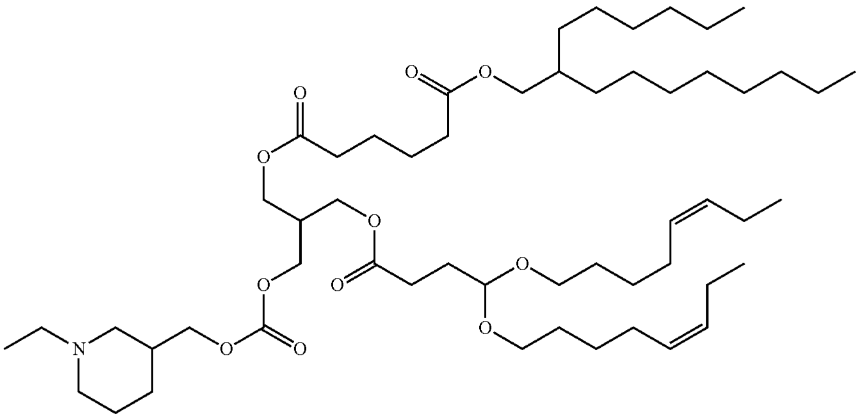

Example 4-30: 3-((4,4-bis(((Z)-oct-5-en-1-yl)oxy)butanoyl)oxy)-2-(((((1-ethylpiperidin-3-yl)methoxy)carbonyl)oxy)methyl)propyl (2-hexyldecyl) adipate

$^1$H NMR (400 MHz, Chloroform-d) δ 5.44-5.28 (m, 4H), 4.22-4.13 (m, 7H), 3.96 (dd, J=5.8, 1.3 Hz, 2H), 3.69-3.63 (m, 5H), 3.11-3.04 (m, 1H), 2.82 (t, J=6.5 Hz, 2H), 2.64 (t, J=6.5 Hz, 2H), 2.36-2.31 (m 4H), 2.23-2.17 (m, 1H), 2.09-2.00 (m, 8H), 1.68-1.38 (m, 26H), 1.32-1.26 (m, 25H), 0.96 (t, J=7.5 Hz, 6H), 0.88 (t, J=6.7 Hz, 6H). UPLC-MS (Method C): UPLC-MS (Method C): Rt 3.93 min, m/z calculated [M+H]: 950.72, found: 950.98.

Example 4-31

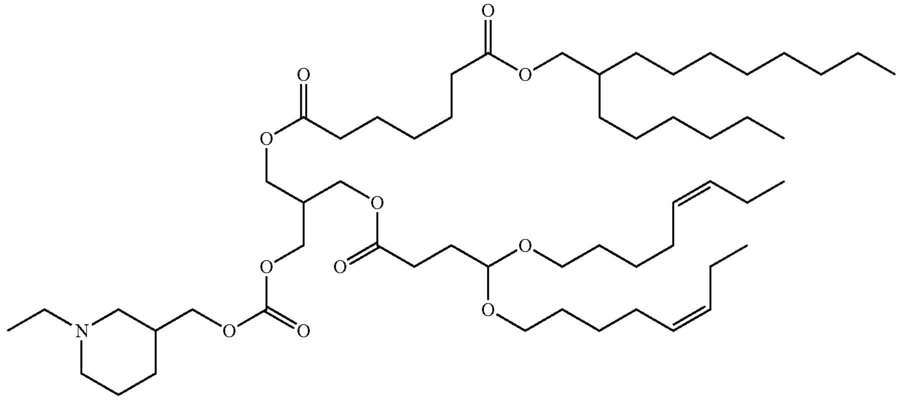

Example 4-31: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(2-hexyldecyl) heptanedioate

$^1$H NMR (400 MHz, Chloroform-d) δ 5.42-5.28 (m, 4H), 4.22-4.14 (m, 7H), 3.96 (d, J=5.8 Hz, 3H), 3.69-3.63 (m, 5H), 2.82 (t, J=6.5 Hz, 2H), 2.64 (t, J=6.5 Hz, 2H), 2.35-2.29 (m, 4H), 2.23-2.17 (m, 1H), 2.10-2.00 (m, 8H), 1.68-1.26 (m, 53H), 0.96 (t, J=7.6 Hz, 6H), 0.90-0.86 (m, 6H). UPLC-MS (Method C): Rt 3.99 min, m/z calculated [M+H]: 964.74, found: 964.98.

Example 4-32

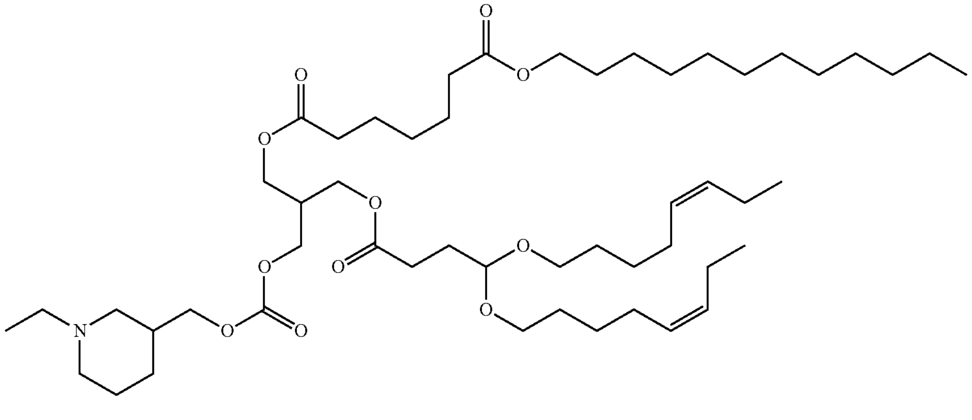

Example 4-32: 1-(3-((4,4-bis(((Z)-oct-5-en-1-yl) oxy)butanoyl)oxy)-2-(((((1-ethylpiperidin-3-yl) methoxy)carbonyl)oxy)methyl)propyl) 7-dodecyl heptanedioate $^1$H NMR (400 MHz, Chloroform-d) δ 5.42-5.28 (m, 4H), 4.21-4.13 (m, 6H), 4.09-4.03 (m, 3H), 3.69-3.63 (m, 5H), 3.11-3.04 (m, 1H), 2.82 (t, J=6.5 Hz, 2H), 2.64 (t, J=6.5 Hz, 2H), 2.35-2.28 (m, 4H), 2.23-2.17 (m, 1H), 2.09-2.00 (m, 8H), 1.67-1.26 (m, 48H), 0.95 (t, J=7.5 Hz, 6H), 0.90-0.84 (m, 3H). UPLC-MS (Method C): Rt 3.70 min, m/z calculated [M+H]: 908.67, found: 908.88.

Example 4-33

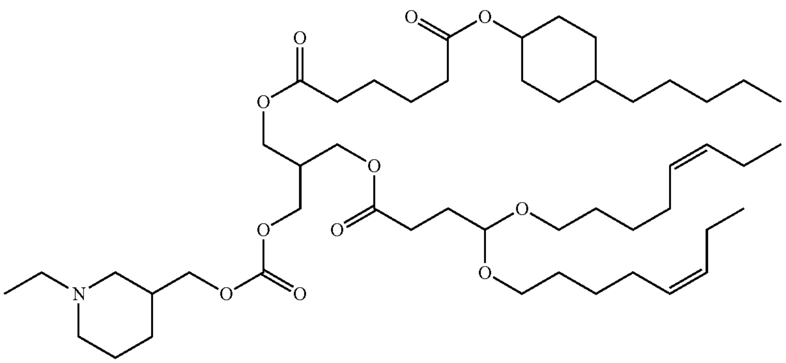

Example 4-33: 3-((4,4-bis(((Z)-oct-5-en-1-yl)oxy) butanoyl)oxy)-2-(((((1-ethylpiperidin-3-yl)methoxy) carbonyl)oxy)methyl)propyl (4-pentylcyclohexyl) adipate $^1$H NMR (400 MHz, Chloroform-d) δ 5.42-5.28 (m, 4H), 4.68-4.62 (m, 1H), 4.21-4.13 (m, 7H), 3.69-3.63 (m, 5H), 3.11-3.04 (m, 1H), 2.82 (t, J=6.5 Hz, 2H), 2.64 (t, J=6.5 Hz, 2H), 2.38-2.27 (m, 4H), 2.23-2.17 (m, 1H), 2.09-1.92 (m, 8H), 1.99-1.76 (m, 6H), 1.68-1.38 (m, 23H), 1.33-1.15 (m, 14H), 0.96 (t, J=7.5 Hz, 6H), 0.88 (td, J=7.0, 2.7 Hz, 3H). UPLC-MS (Method C): Rt 3.49 min, m/z calculated [M+H]: 878.63, found: 878.89.

Example 4-34

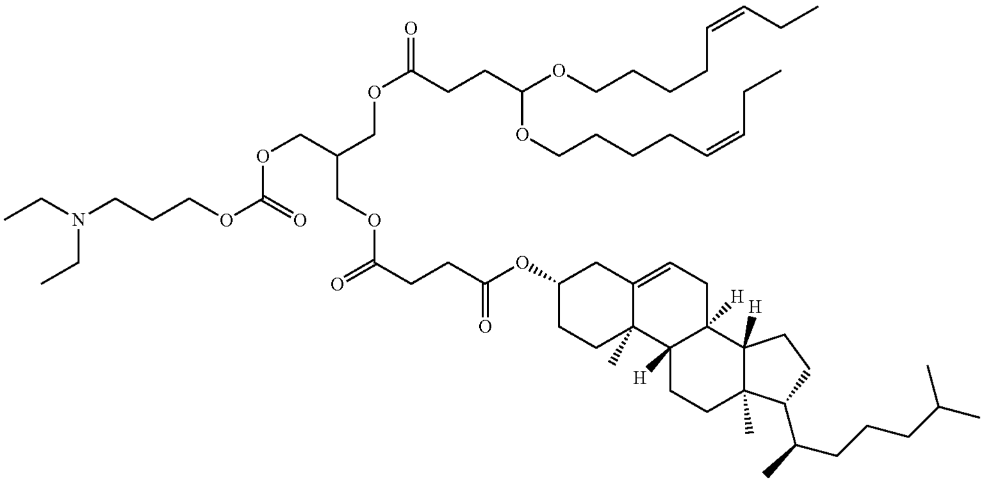

Example 4-34: 3-((4,4-bis(((Z)-oct-5-en-1-yl)oxy)butanoyl)oxy)-2-((((3-(diethylamino)propoxy)carbonyl)oxy)methyl)propyl ((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl) succinate UPLC-MS (Method A): Rt 1.99 min, m/z calculated [M+H]: 1054.78, found: 1055.13.

The following Examples 4-35 to 4-61 were prepared using similar methods as those described for Example 4-2.

Example 4-35

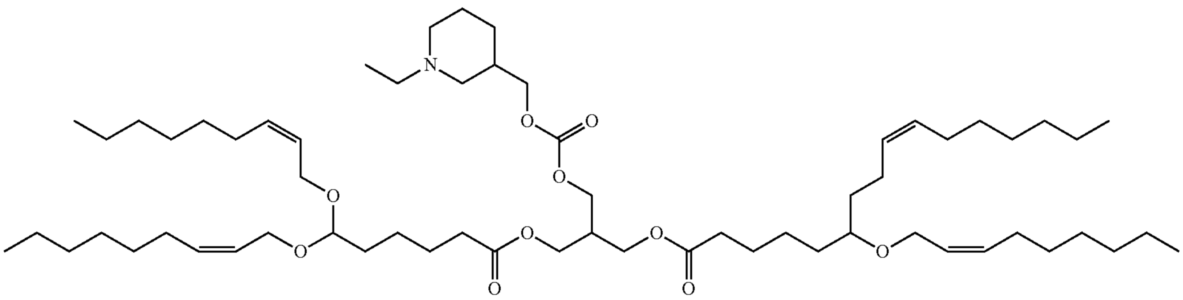

Example 4-35: 2-(((((1-ethylpiperidin-3-yl)methoxy)carbonyl)oxy)methyl)propane-1,3-diyl bis(6,6-bis(((Z)-non-2-en-1-yl)oxy)hexanoate)

UPLC-MS (Method A): Rt 2.52 min, m/z calculated [M+H]: 1032.80, found: 1033.2.

Example 4-36

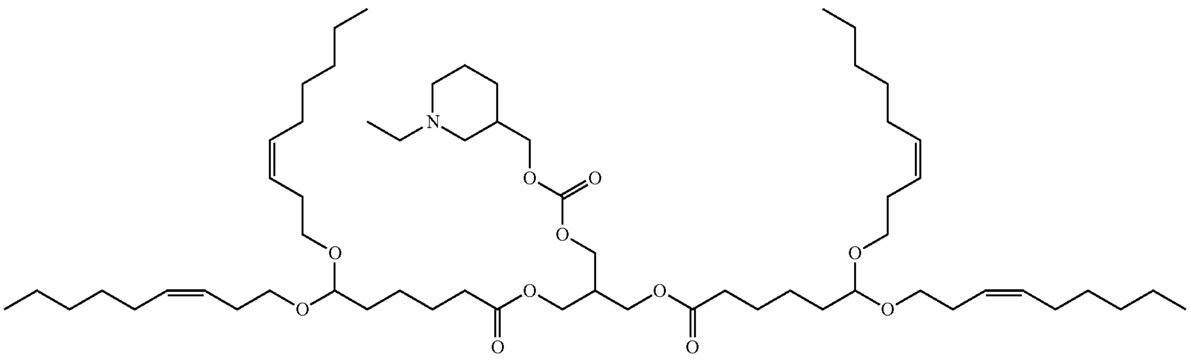

Example 4-36: 2-(((((1-ethylpiperidin-3-yl)methoxy)carbonyl)oxy)methyl)propane-1,3-diyl bis(6,6-bis(((Z)-non-3-en-1-yl)oxy)hexanoate)
UPLC-MS (Method A): Rt 2.51 min, m/z calculated [M+H]: 1032.80, found: 1033.2.
Example 4-37
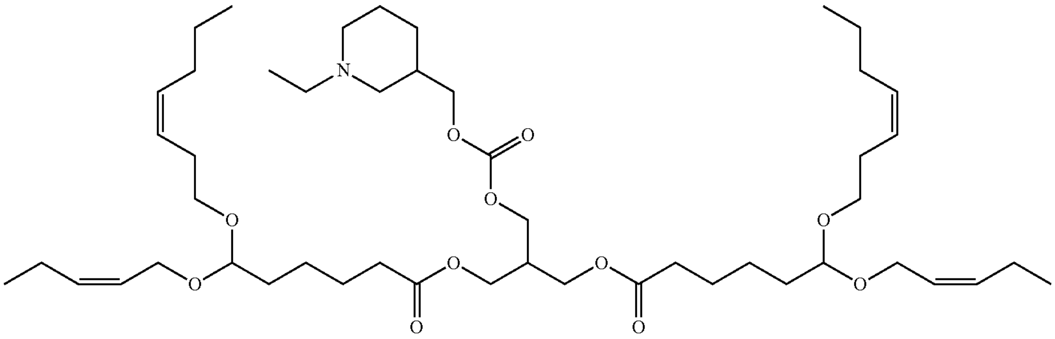
Example 4-37: 2-(((((1-ethylpiperidin-3-yl)methoxy)carbonyl)oxy)methyl)propane-1,3-diyl bis(6,6-bis(((Z)-hept-3-en-1-yl)oxy)hexanoate)
UPLC-MS (Method A): Rt 2.51 min, m/z calculated [M+H]: 920.67, found: 920.2.
Example 4-38
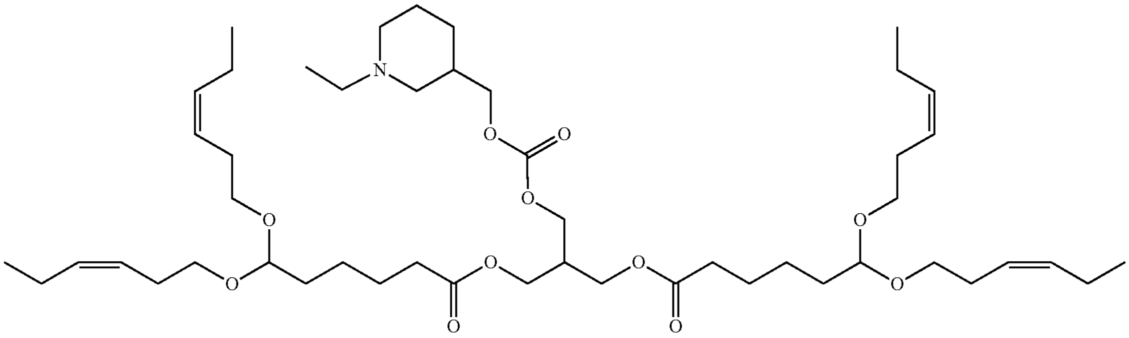

Example 4-38: 2-(((((1-ethylpiperidin-3-yl) methoxy)carbonyl)oxy)methyl)propane-1,3-diyl bis (6,6-bis(((Z)-hex-3-en-1-yl)oxy)hexanoate)
UPLC-MS (Method A): Rt 2.07 min, m/z calculated [M+H]: 864.61, found: 864.9.
Example 4-39
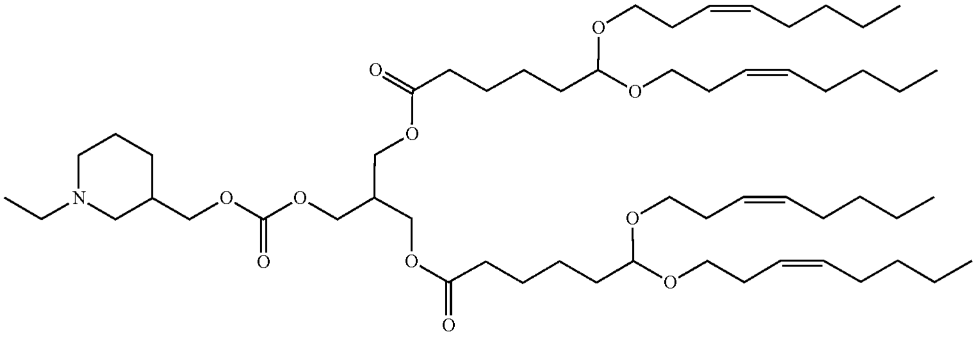
Example 4-39: 2-(((((1-ethylpiperidin-3-yl) methoxy)carbonyl)oxy)methyl)propane-1,3-diyl bis (6,6-bis(((Z)-oct-3-en-1-yl)oxy)hexanoate)
UPLC-MS (Method A): Rt 2.20 min, m/z calculated [M+H]: 976.74, found: 977.4.
Example 4-40
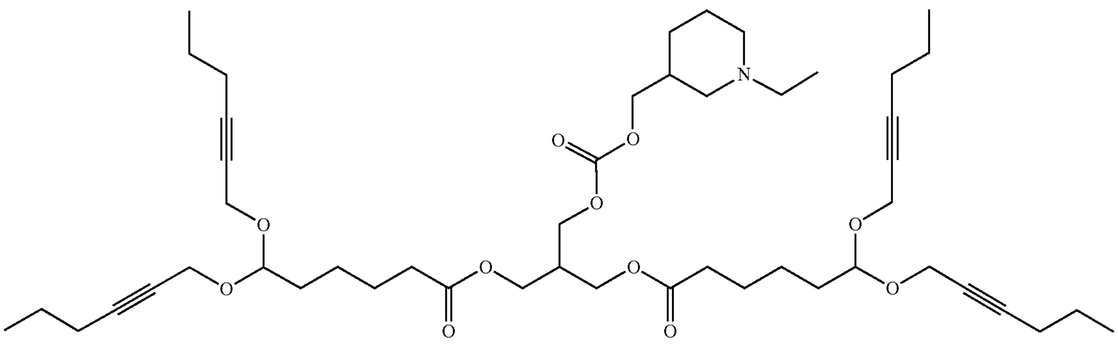

Example 4-40: 2-(((((1-ethylpiperidin-3-yl) methoxy)carbonyl)oxy)methyl)propane-1,3-diyl bis (6,6-bis(hex-2-yn-1-yloxy)hexanoate)
UPLC-MS (Method A): Rt 1.91 min, m/z calculated [M+H]: 856.55, found: 856.1.
Example 4-41
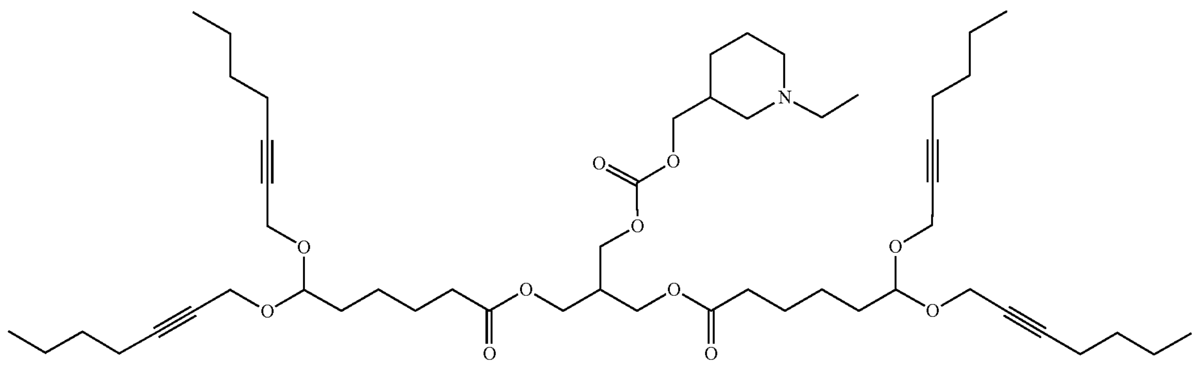
Example 4-41: 2-(((((1-ethylpiperidin-3-yl) methoxy)carbonyl)oxy)methyl)propane-1,3-diyl bis (6,6-bis(hept-2-yn-1-yloxy)hexanoate)
UPLC-MS (Method A): Rt 1.88 min, m/z calculated [M+H]: 912.61, found: 913.1.
Example 4-42
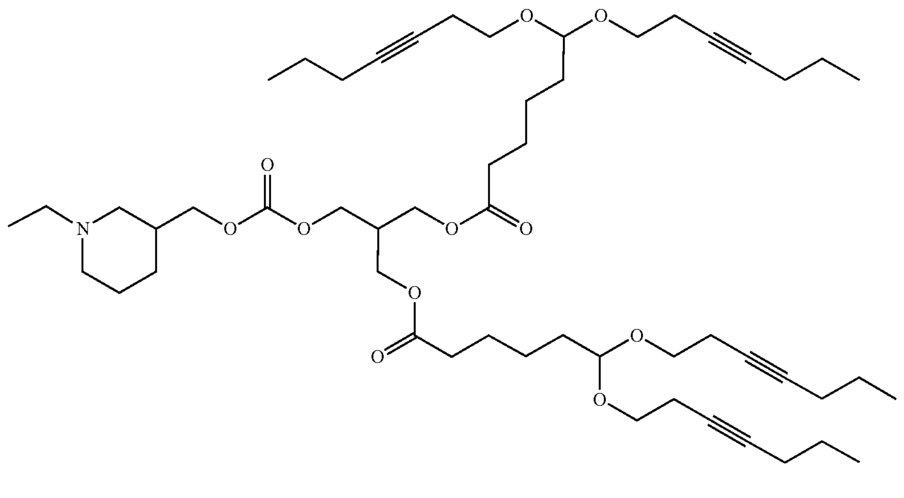

Example 4-42: 2-(((((1-ethylpiperidin-3-yl) methoxy)carbonyl)oxy)methyl)propane-1,3-diyl bis (6,6-bis(hept-3-yn-1-yloxy)hexanoate)
UPLC-MS (Method A): Rt 1.83 min, m/z calculated [M+H]: 912.61, found: 913.1.
Example 4-43
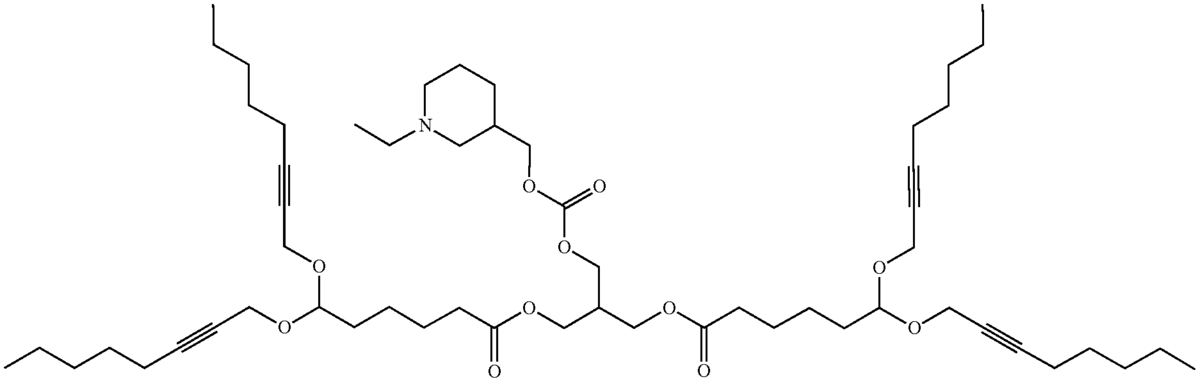
Example 4-43: 2-(((((1-ethylpiperidin-3-yl) methoxy)carbonyl)oxy)methyl)propane-1,3-diyl bis (6,6-bis(oct-2-yn-1-yloxy)hexanoate)
UPLC-MS (Method A): Rt 2.17 min, m/z calculated [M+H]: 968.67, found: 968.1.
Example 4-44
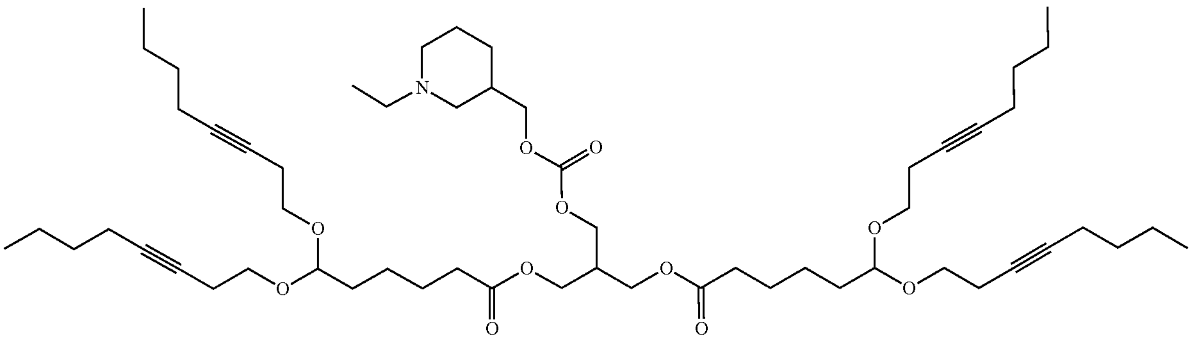

Example 4-44: 2-(((((1-ethylpiperidin-3-yl)methoxy)carbonyl)oxy)methyl)propane-1,3-diyl bis(6,6-bis(oct-3-yn-1-yloxy)hexanoate)
UPLC-MS (Method A): Rt 2.13 min, m/z calculated [M+H]: 968.67, found: 968.1.
Example 4-45
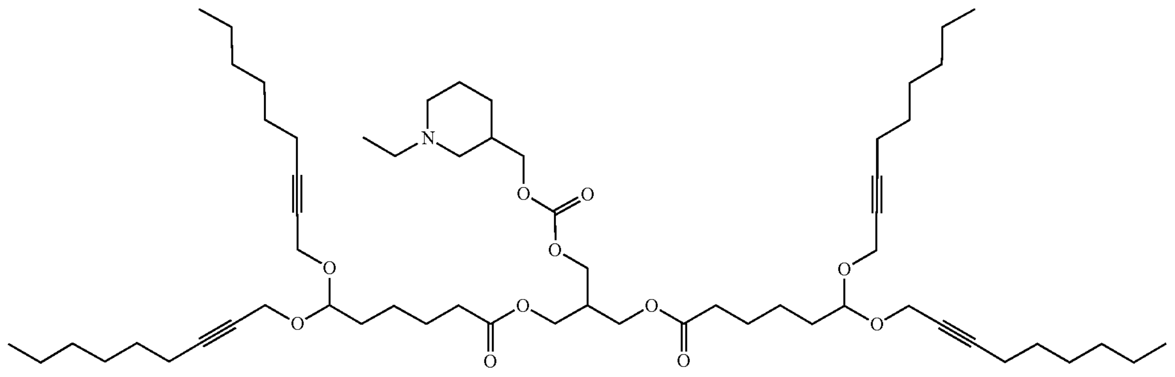
Example 4-45: 2-(((((1-ethylpiperidin-3-yl)methoxy)carbonyl)oxy)methyl)propane-1,3-diyl bis(6,6-bis(non-2-yn-1-yloxy)hexanoate)
UPLC-MS (Method A): Rt 2.29 min, m/z calculated [M+H]: 1024.74, found: 1025.2.
Example 4-46
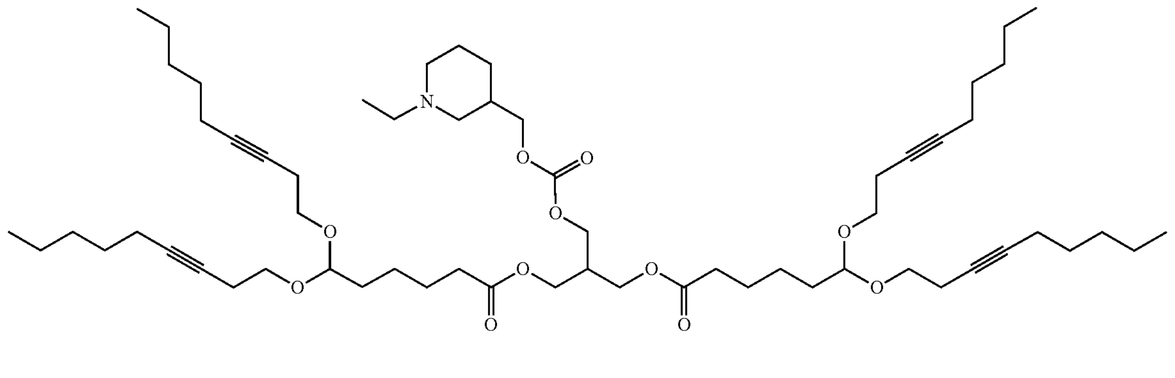

Example 4-46: 2-(((((1-ethylpiperidin-3-yl) methoxy)carbonyl)oxy)methyl)propane-1,3-diyl bis (6,6-bis(non-3-yn-1-yloxy)hexanoate)
UPLC-MS (Method A): Rt 2.25 min, m/z calculated [M+H]: 1024.74, found: 1025.2.
Example 4-47
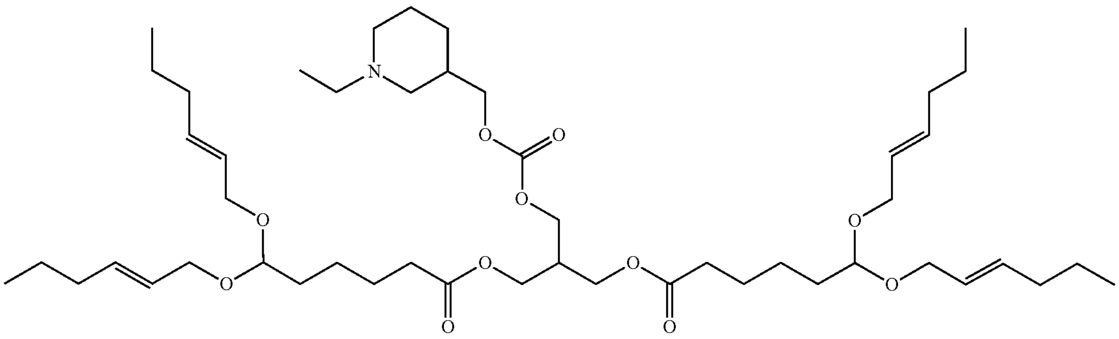
Example 4-47: 2-(((((1-ethylpiperidin-3-yl) methoxy)carbonyl)oxy)methyl)propane-1,3-diyl bis (6,6-bis(((E)-hex-2-en-1-yl)oxy)hexanoate)
UPLC-MS (Method A): Rt 2.01 min, m/z calculated [M+H]: 864.61, found: 864.6.
Example 4-48
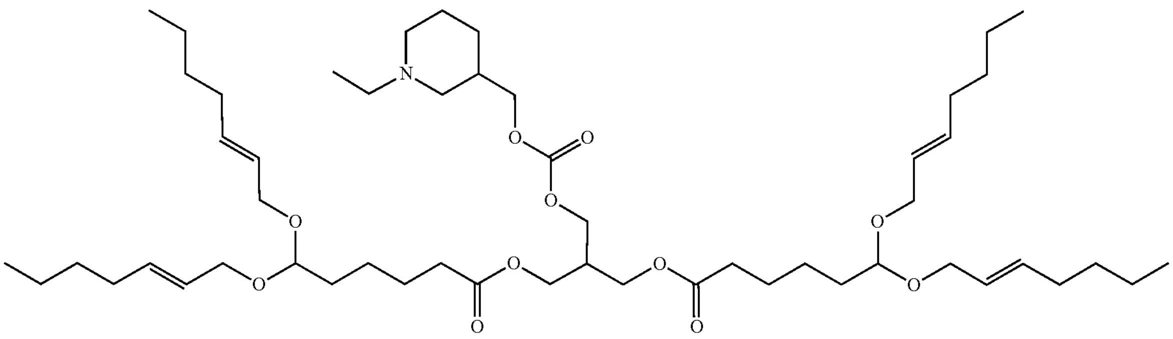

Example 4-48: 2-(((((1-ethylpiperidin-3-yl) methoxy)carbonyl)oxy)methyl)propane-1,3-diyl bis (6,6-bis(((E)-hept-2-en-1-yl)oxy)hexanoate)
UPLC-MS (Method A): Rt 2.28 min, m/z calculated [M+H]: 920.67, found: 921.1.
Example 4-49
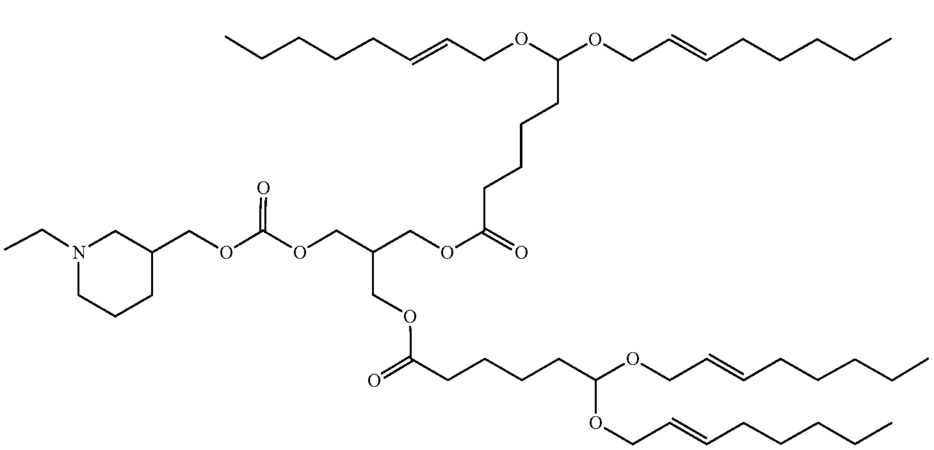
Example 4-49: 2-(((((1-ethylpiperidin-3-yl) methoxy)carbonyl)oxy)methyl)propane-1,3-diyl bis (6,6-bis(((E)-oct-2-en-1-yl)oxy)hexanoate)
UPLC-MS (Method A): Rt 2.32 min, m/z calculated [M+H]: 976.74, found: 977.4.
Example 4-50
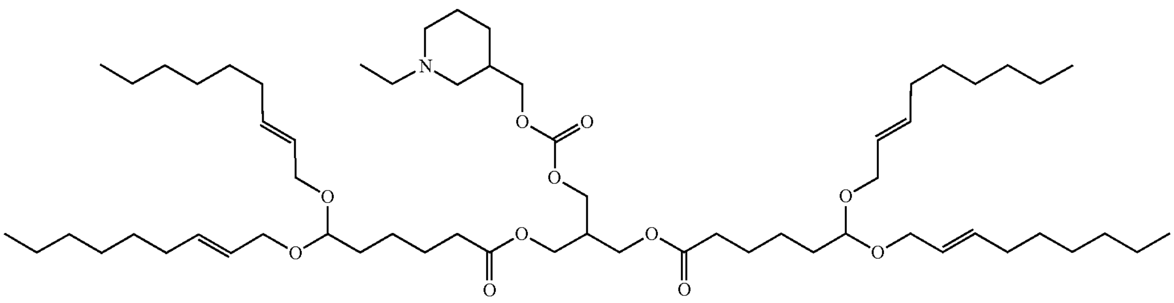

Example 4-50: 2-(((((1-ethylpiperidin-3-yl)methoxy)carbonyl)oxy)methyl)propane-1,3-diyl bis(6,6-bis(((E)-non-2-en-1-yl)oxy)hexanoate)
UPLC-MS (Method B): Rt 6.09 min, m/z calculated [M+H]: 1031.8, found: 1032.1.
Example 4-51
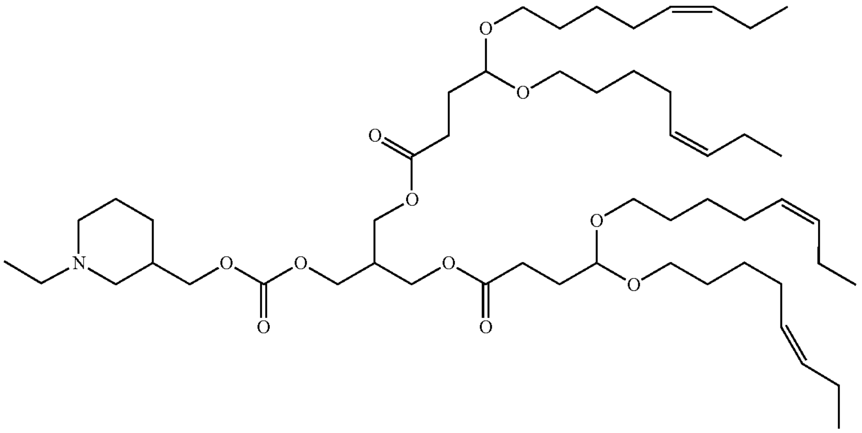
Example 4-51: 2-(((((1-ethylpiperidin-3-yl)methoxy)carbonyl)oxy)methyl)propane-1,3-diyl bis(4,4-bis(((Z)-oct-5-en-1-yl)oxy)butanoate)
UPLC-MS (Method C): Rt 3.69 min, m/z calculated [M+H]: 920.67, found: 920.78.
Example 4-52
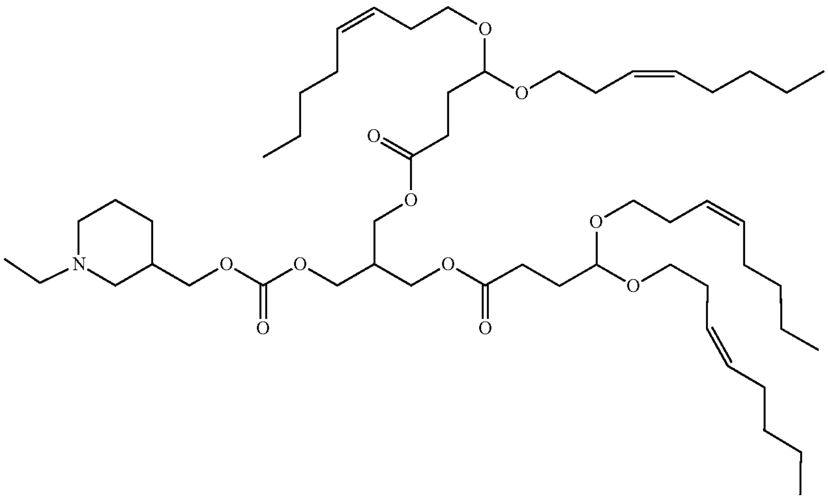

Example 4-52: 2-(((((1-ethylpiperidin-3-yl) methoxy)carbonyl)oxy)methyl)propane-1,3-diyl bis (4,4-bis(((Z)-oct-3-en-1-yl)oxy)butanoate)
UPLC-MS (Method C): Rt 3.88 min, m/z calculated [M+H]: 920.67, found: 920.68.
Example 4-53
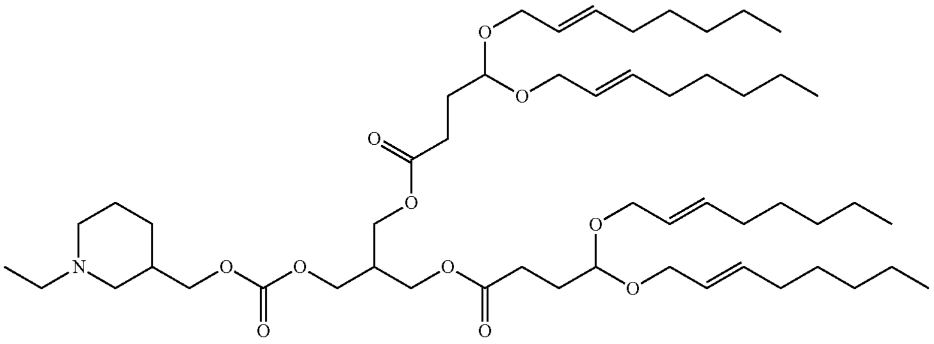
Example 4-53: 2-(((((1-ethylpiperidin-3-yl) methoxy)carbonyl)oxy)methyl)propane-1,3-diyl bis (4,4-bis(((E)-oct-2-en-1-yl)oxy)butanoate)
UPLC-MS (Method C): Rt 3.74 min, m/z calculated [M+H]: 920.67, found: 920.78.
Example 4-54
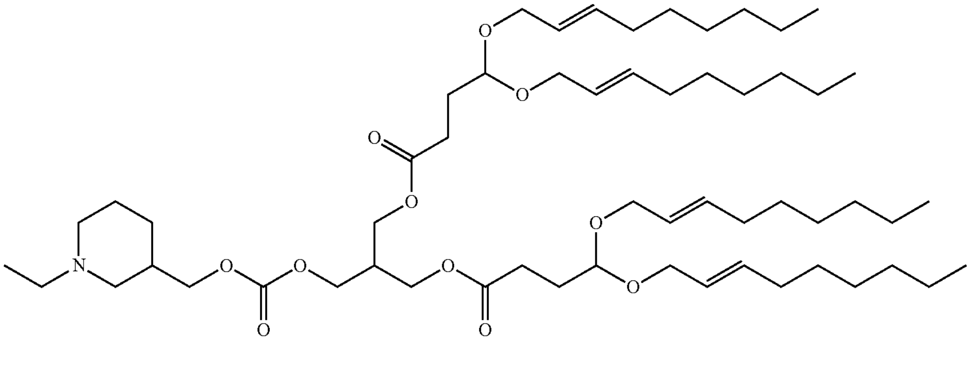

Example 4-54: 2-(((((1-ethylpiperidin-3-yl)methoxy)carbonyl)oxy)methyl)propane-1,3-diyl bis(4,4-bis(((E)-non-2-en-1-yl)oxy)butanoate)
UPLC-MS (Method C): Rt 4.29 min, m/z calculated [M+H]: 976.74, found: 976.78.
Example 4-55
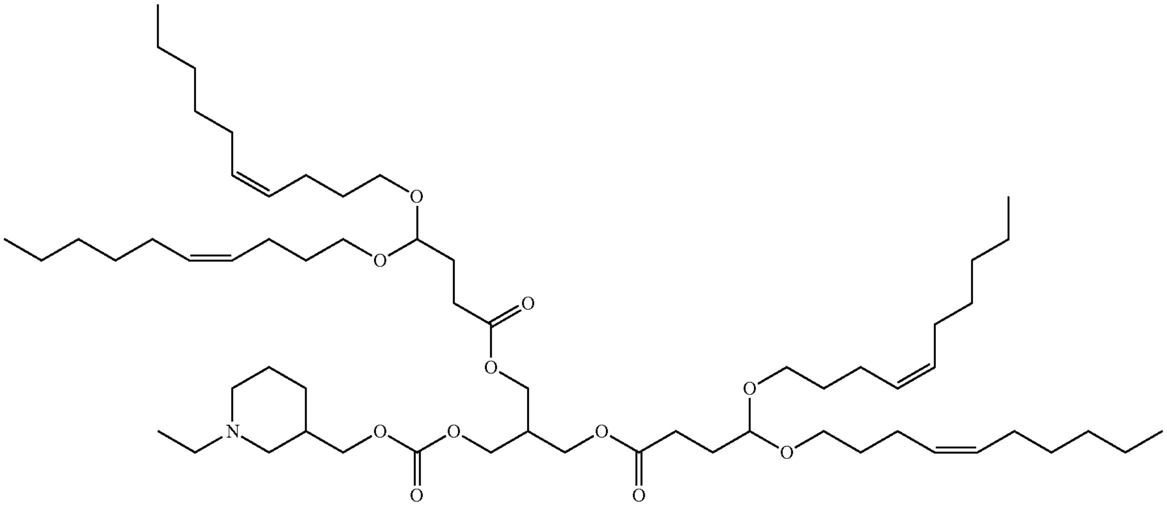
Example 4-55: 2-(((((1-ethylpiperidin-3-yl)methoxy)carbonyl)oxy)methyl)propane-1,3-diyl bis(4,4-bis(((Z)-dec-4-en-1-yl)oxy)butanoate)
UPLC-MS (Method C): Rt 4.73 min, m/z calculated [M+H]: 1032.80, found: 1032.87.
Example 4-56
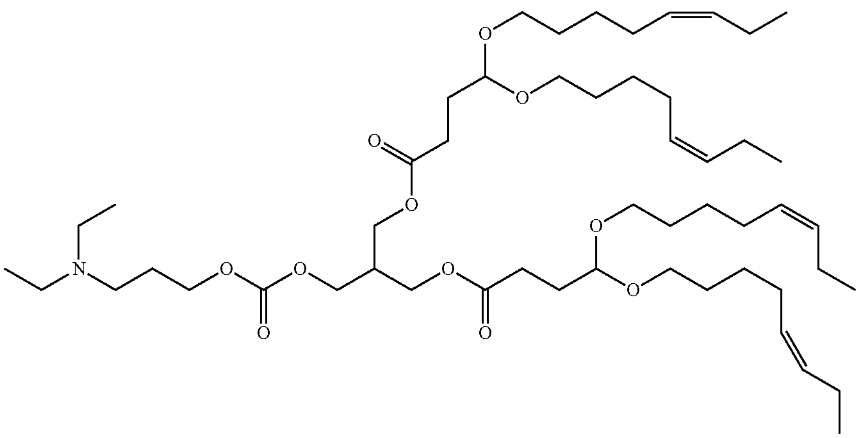

Example 4-56: 2-((((3-(diethylamino)propoxy)carbonyl)oxy)methyl)propane-1,3-diyl bis(4,4-bis(((Z)-oct-5-en-1-yl)oxy)butanoate)

UPLC-MS (Method C): Rt 3.66 min. m/z calculated [M+H]: 908.67. found: 908.88.

Example 4-57

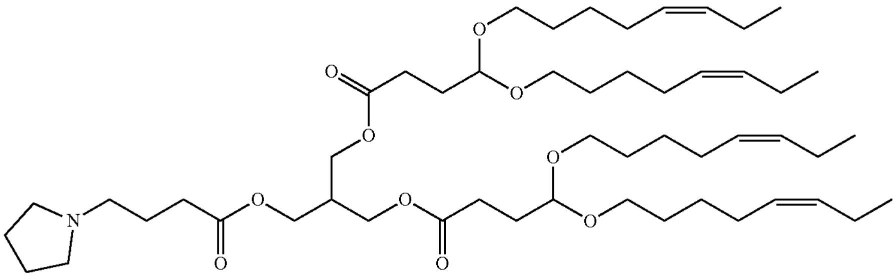

Example 4-57: 2-(((4-(pyrrolidin-1-yl)butanoyl)oxy)methyl)propane-1,3-diyl bis(4,4-bis(((Z)-oct-5-en-1-yl)oxy)butanoate)

UPLC-MS (Method C): Rt 3.63 min, m/z calculated [M+H]: 890.66, found: 890.79.

Example 4-58

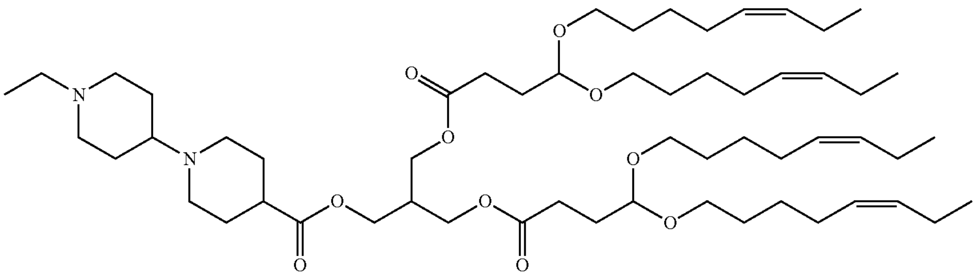

Example 4-58: 2-(((1'-ethyl-[1,4'-bipiperidine]-4-carbonyl)oxy)methyl)propane-1,3-diyl bis(4,4-bis(((Z)-oct-5-en-1-yl)oxy)butanoate)

UPLC-MS (Method C): Rt 3.20 min, m/z calculated [M+H]: 973.74, found: 973.88.

Example 4-59

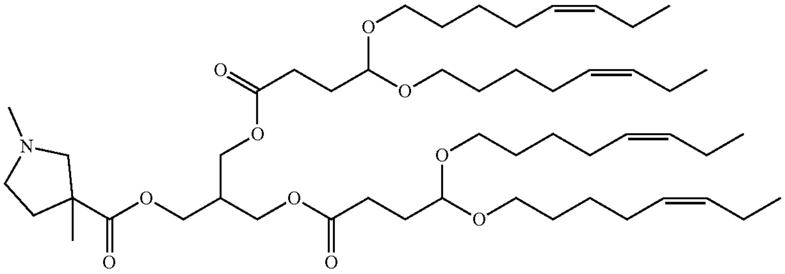

Example 4-59: 2-(((1,3-dimethylpyrrolidine-3-carbonyl)oxy)methyl)propane-1,3-diyl bis(4,4-bis(((Z)-oct-5-en-1-yl)oxy)butanoate)
UPLC-MS (Method C): Rt 3.58 min, m/z calculated [M+H]: 876.65, found: 876.79.
Example 4-60
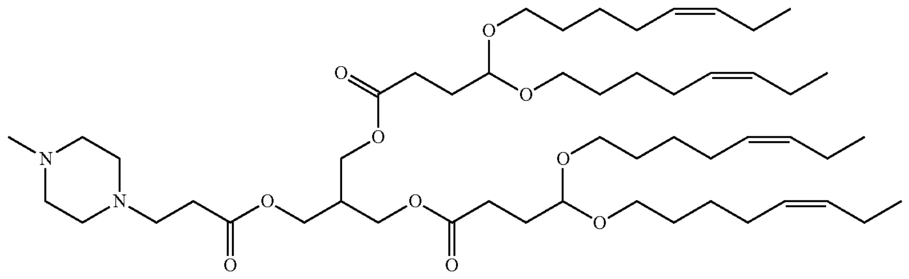
Example 4-60: 2-(((3-(4-methylpiperazin-1-yl)propanoyl)oxy)methyl)propane-1,3-diyl bis(4,4-bis(((Z)-oct-5-en-1-yl)oxy)butanoate)
UPLC-MS (Method C): Rt 3.64 min, m/z calculated [M+H]: 905.68, found: 905.78.
Example 4-61
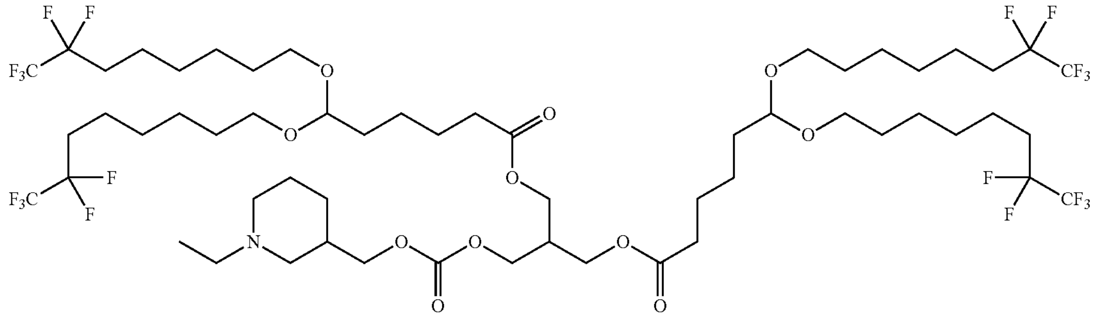

Example 4-61: 2-(((((1-ethylpiperidin-3-yl)methoxy)carbonyl)oxy)methyl)propane-1,3-diyl bis(6,6-bis((7,7,8,8,8-pentafluorooctyl)oxy)hexanoate)

UPLC-MS (Method A): Rt 2.19 min, m/z calculated [M+H]: 1344.6, found: 1344.8.

Example 4-62

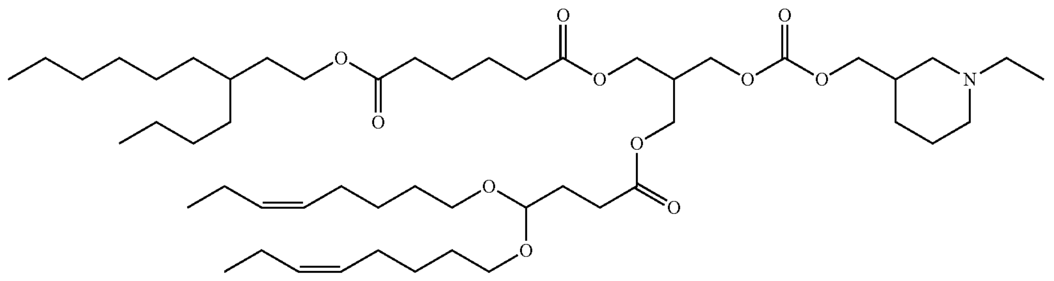

Example 4-62: 3-((4,4-bis(((Z)-oct-5-en-1-yl)oxy)butanoyl)oxy)-2-(((((1-ethylpiperidin-3-yl)methoxy)carbonyl)oxy)methyl)propyl (3-butylnonyl) adipate

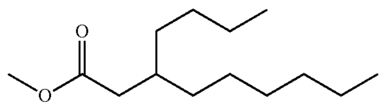 [SMILES: CCCCCCC(CCCC)CC(=O)OC]

Step 1: methyl 3-butylnonanoate

Copper (I) bromide (0.1 eqv) and lithium chloride (0.2 eqv) were added to a flame dried flask under argon atmosphere. Then was added dry THF (20 mL) and the mixture was stirred for 10 min during which time the solid dissolved. Reaction mixture was placed in an ice bath and stirred for 5 min. After that were added methyl (E)-non-2-enoate (1.0 eqv) and chlorotrimethylsilane (1.1 eqv) and was stirred for 15 min. Then, was added butylmagnesium bromide (18% w/v in THF) (1.4 eqv) drop wise and the reaction was stirred at 0° C. for another 1 h. The solution was poured into saturated $NH_4Cl$ solution (50 mL) and extracted with ethyl acetate (3×50 mL). The combined organic extracts were washed with brine (50 mL), dried over $Na_2SO_4$, filtered and concentrated under reduced pressure. Crude material thus obtained was purified by combiflash column chromatography, eluted with 1-2% ethyl acetate-hexane to afford methyl 3-butylnonanoate (1.3 g, 69%) as yellow oil. $^1H$ NMR (400 MHz, Chloroform-d) δ 0.73-1.01 (m, 9H), 1.08-1.43 (m, 13H), 1.81-1.86 (m, 1H), 2.22 (d, J=6.9 Hz, 2H), 3.65 (s, 3H).

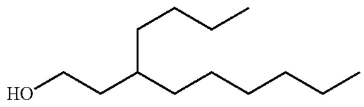

Step 2: 3-butylnonan-1-ol

To a stirred solution of methyl 3-butylnonanoate (1 eqv) in THF (10 mL) was added lithium aluminium hydride (2M in THF) (3.0 eqv) at 0° C. and stirred at 25° C. for 2 h. The reaction mass was quenched with sodium sulfate decahydrate at 0° C. and filtered through celite. The filtrate was concentrated under reduced pressure, purified by combiflash column chromatography, eluted by 3-5% ethyl acetate-hexane to afford 3-butylnonan-1-ol (540 mg, 67%) as colorless oil. $^1H$ NMR (400 MHz, Chloroform-d) δ 0.83-0.92 (m, 6H), 1.25 (s, 18H), 1.52 (q, J=6.9 Hz, 2H), 3.66 (t, J=6.9 Hz, 2H).

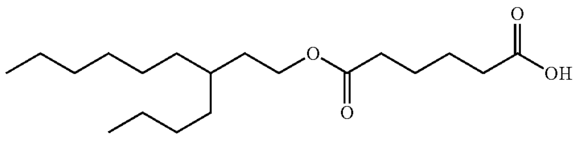 [SMILES: CCCCCCC(CCCC)CCOC(=O)CCCCC(=O)O]

Step 3: 6-((3-butylnonyl)oxy)-6-oxohexanoic acid

General Procedure G: To a stirred solution of adipic acid (3 eqv) in DCM (30 mL), were added DIPEA (3 eqv), EDC (1.5 eqv) and DMAP (0.5 eqv). The reaction mixture was stirred for 15 min and then was added 3-butylnonan-1-ol (1 eqv) and further was stirred at 25° C. for 17 h. Reaction mixture was diluted with DCM (200 mL) and washed with water (2×100 mL), brine (100 mL) and concentrated under reduced pressure. Crude material thus obtained was purified by combiflash chromatography, eluted with 40-60% EtOAc-hexane to afford 6-((3-butylnonyl)oxy)-6-oxohexanoic acid (980 mg, 66%) as colorless oil. $^1$H NMR (400 MHz, DMSO-$d_6$) δ 0.84-0.87 (m, 6H), 1.15-1.51 (m, 23H), 2.19 (t, J=6.9 Hz, 2H), 2.27 (t, J=6.6 Hz, 2H), 4.02 (t, J=6.7 Hz, 2H), 11.99 (s, 1H)

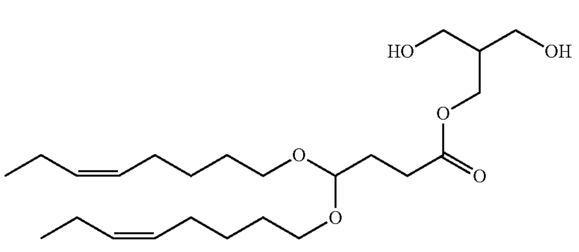 [SMILES: CC/C=C\CCCCOC(CCC(=O)OCC(CO)CO)OCCCC/C=C\CC]

Step 4: 3-hydroxy-2-(hydroxymethyl)propyl 4,4-bis(((Z)-oct-5-en-1-yl)oxy)butanoate To a stirred solution of 4,4-bis(((Z)-oct-5-en-1-yl)oxy)butanoic acid (3 g, 8.811 mmol) in DCM (50 mL) and DMF (5 mL), were added DIPEA (4.4 mL, 26.43 mmol), EDC (2.5 g, 13.216 mmol) and DMAP (538 mg, 4.405 mmol). The reaction mixture was stirred for 15 min and then was added 2-(hydroxymethyl)propane-1,3-diol (1.12 g, 10.573 mmol) and further was stirred at 25° C. for 17 h. Reaction mixture was diluted with DCM (350 mL) and washed with water (2×150 mL), brine (150 mL) and concentrated under reduce pressure. Crude material thus obtained was purified by combiflash chromatography, eluted with 50-60% EtOAc-hexane to afford 3-hydroxy-2-(hydroxymethyl)propyl 4,4-bis(((Z)-oct-5-en-1-yl)oxy)butanoate (1.8 g, 44%) as colorless oil. $^1$H NMR (400 MHz, Chloroform-d) δ 0.94 (t, J=7.5 Hz, 6H), 1.37-1.59 (m, 8H), 1.92-2.06 (m, 11H), 2.26-2.28 (m, 2H), 2.40 (t, J=7.5 Hz, 2H), 3.38-3.42 (m, 2H), 3.53-3.59 (m, 2H), 3.73-3.78 (m, 4H), 4.25 (d, J=6.3 Hz, 2H), 4.48 (t, J=5.5 Hz, 1H), 5.28-5.37 (m, 4H).

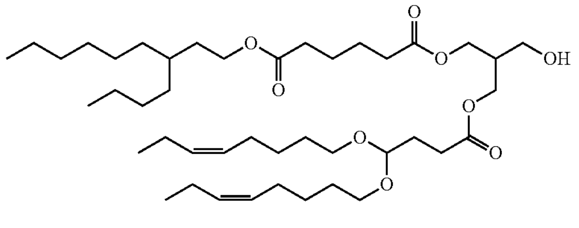 [SMILES: CC/C=C\CCCCOC(CCC(=O)OCC(CO)COC(=O)CCCCC(=O)OCCC(CCCC)CCCCCC)OCCCC/C=C\CC]

Step 5: 3-((4,4-bis(((Z)-oct-5-en-1-yl)oxy)butanoyl)oxy)-2-(hydroxymethyl)propyl (3-butylnonyl) adipate General Procedure H: To a stirred solution of 6-((3-butylnonyl)oxy)-6-oxohexanoic acid (1 eqv) in DCM (30 mL), were added DIPEA (3 eqv), EDC (1.5 eqv) and DMAP (0.5 eqv). The reaction mixture was stirred for 15 min and then was added 3-hydroxy-2-(hydroxymethyl)propyl 4,4-bis(((Z)-oct-5-en-1-yl)oxy)butanoate (1.1 eqv) and further was stirred at 25° C. for 17 h. Reaction mixture was diluted with DCM (200 mL) and washed with water (2×100 mL), brine (100 mL) and concentrated under reduce pressure. Crude material thus obtained was purified by combiflash chromatography, eluted with 10-20% EtOAc-hexane to afford 3-((4,4-bis(((Z)-oct-5-en-1-yl)oxy)butanoyl)oxy)-2-(hydroxymethyl)propyl (3-butylnonyl) adipate (185 mg, 48%) as colorless oil. $^1$H NMR (400 MHz, Chloroform-d) δ 0.83-0.91 (m, 6H), 0.93 (t, J=7.6 Hz, 6H), 1.18-1.31 (m, 15H), 1.33-1.46 (m, 5H), 1.53-1.61 (m, 4H), 1.65 (dd, J=3.5, 6.7 Hz, 4H), 1.87-1.98 (m, 3H), 1.97-2.09 (m, 9H), 2.14-2.27 (m, 2H), 2.26-2.51 (m, 6H), 3.34-3.45 (m, 2H), 3.51-3.65 (m, 5H), 4.07 (t, J=7.1 Hz, 2H), 4.11-4.25 (m, 4H), 4.48 (t, J=5.5 Hz, 1H), 5.13-5.51 (m, 4H).

Step 6: 3-((4,4-bis(((Z)-oct-5-en-1-yl)oxy)butanoyl)oxy)-2-(((((1-ethylpiperidin-3-yl)methoxy)carbonyl)oxy)methyl)propyl (3-butylnonyl) adipate (Example 4-62)

Prepared according to General Procedure F, substituting 3-((4,4-bis(((Z)-oct-5-en-1-yl)oxy)butanoyl)oxy)-2-(hydroxymethyl)propyl (3-butylnonyl) adipate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 70 mg, 41%. UPLC-MS (Method A): Rt 2.26 min, m/z calculated [M+H]: 908.7, found: 908.8. $^1$H NMR (400 MHz, DMSO-$d_6$) δ 0.81-0.95 (m, 12H), 0.96-1.05 (m, 4H), 1.18-1.30 (m, 15H), 1.35 (q, J=7.4 Hz, 4H), 1.41-1.56 (m, 11H), 1.62 (d, J=9.3 Hz, 1H), 1.77 (q, J=7.0 Hz, 2H), 1.81-1.93 (m, 1H), 1.93-2.05 (m, 8H), 2.23-2.42 (m, 8H), 3.44-3.54 (m, 2H), 4.07 (dd, J=2.4, 6.0 Hz, 4H), 3.90-4.10 (m, 4H), 4.13 (d, J=5.9 Hz, 2H), 4.44 (t, J=5.5 Hz, 1H), 5.23-5.40 (m, 4H).

Example 4-63

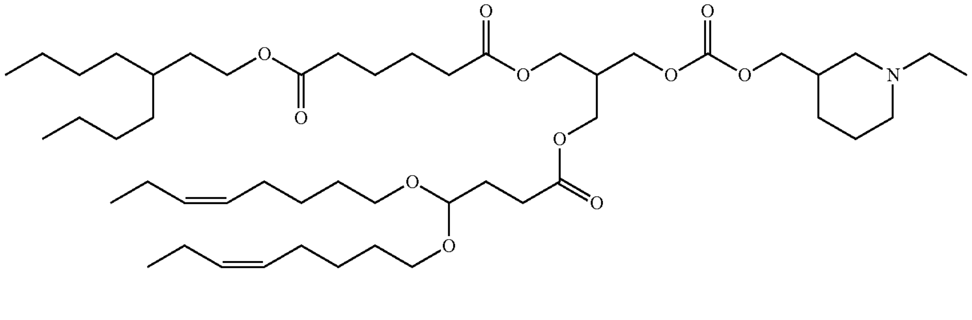

Example 4-63: 3-((4,4-bis(((Z)-oct-5-en-1-yl)oxy) butanoyl)oxy)-2-(((((1-ethylpiperidin-3-yl)methoxy) carbonyl)oxy)methyl)propyl (3-butylheptyl) adipate

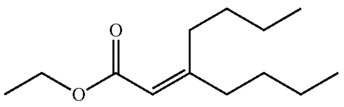

Step 1: ethyl 3-butylhept-2-enoate

To a stirred solution of triethyl phosphonoacetate (1.83 g, 9.15 mmol) in dry THF (10 mL) was added NaH (336 mg, 9.15 mmol) portion wise for period of 20 min and stirred for 30 min at 25° C. Reaction mixture was cooled to 0° C. and was added nonan-5-one (1 g, 7.04 mmol) in portion. The reaction mixture was gradually warmed to 25° C. and heated at 66° C. for 12 h. Upon completion, the reaction mixture was diluted with ethyl acetate (100 mL) and quenched with cold water. Then it was washed with water (2×15 mL) and brine (15 mL). Organic layer was dried over anhydrous $Na_2SO_4$ and concentrated under reduced pressure to afford ethyl 3-butylhept-2-enoate (1.6 g, crude) as a light yellow liquid which was used in the next step without any purification. $^1H$ NMR (400 MHz, Chloroform-d) δ 0.79-0.95 (m, 6H), 1.18-1.39 (m, 6H), 1.37-1.48 (m, 2H), 1.49-1.59 (m, 1H), 2.07-2.16 (m, 2H), 2.38 (t, J=7.5 Hz, 2H), 2.53-2.62 (m, 2H), 3.98-4.35 (m, 2H), 5.60 (s, 1H).

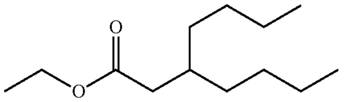

Step 2: ethyl 3-butylheptanoate

To a stirred solution of ethyl 3-butylhept-2-enoate (1 g, 4.7 mmol) in EtOH (10 mL), was added $Pd(OH)_2$ (20% w/w) (495 mg, 0.7 mmol). Reaction mixture was stirred at 25° C. for 2 h under $H_2$ atmosphere. After consumption of starting material, the reaction mixture was filtered through celite bed and concentrated under reduce pressure to afford ethyl 3-butylheptanoate (1.1 g, crude) as colorless liquid which was used directly for the next step. $^1H$ NMR (400 MHz, Chloroform-d) δ 0.88 (q, J=7.1 Hz, 6H), 1.18-1.38 (m, 14H), 1.46-1.65 (m, 1H), 1.75-1.91 (m. 1H). 2.21 (d, J=6.9 Hz, 1H), 2.38 (t, J=7.5 Hz, 1H), 3.90-4.42 (m, 2H).

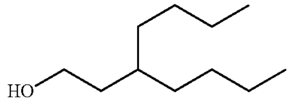

Step 3: 3-butylheptan-1-ol

To a stirred solution of ethyl 3-butylheptanoate (1.1 g, 5.14 mmol) in THF (10 mL) was added lithium aluminium hydride (2M in THF) (9.1 mL, 18.22 mmol) at 0° C. and stirred at 25° C. for 2 h. Then reaction mass was quenched with $Na_2SO_4.10H_2O$ at 0° C., and filtered and concentrated under reduced pressure. Crude residue was then purified by combiflash column chromatography, eluted with 2-5% ethyl acetate-hexane to afford 3-butylheptan-1-ol (600 mg, 68%) as colorless oil. $^1H$ NMR (400 MHz, Chloroform-d) δ 0.88 (t, J=6.8 Hz, 6H), 1.15 (s, 1H), 1.20-1.33 (m. 12H). 1.36-1.46 (m. 1H). 1.52 (q, J=6.8 Hz, 2H), 3.66 (t, J=7.1 Hz, 2H).

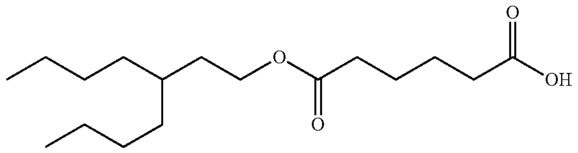 [SMILES: CCCCC(CCCC)CCOC(=O)CCCCC(=O)O]

Step 4: 6-((3-butylheptyl)oxy)-6-oxohexanoic acid

Prepared according to General Procedure G, substituting 3-butylheptan-1-ol for 3-butylnonan-1-ol. Isolated 790 mg, 50%. $^1H$ NMR (400 MHz, DMSO-$d_6$) δ 0.84-0.87 (m, 6H), 1.15-1.51 (m, 19H), 2.20 (t, J=6.9 Hz, 2H), 2.27 (t, J=6.5 Hz, 2H), 4.02 (t, J=6.8 Hz, 2H), 11.99 (s, 1H).

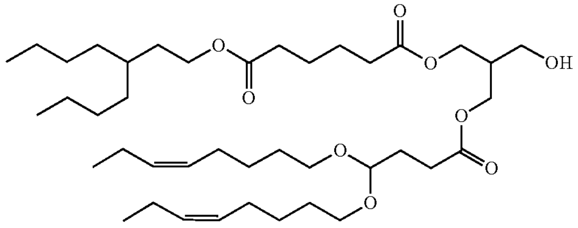 [SMILES: CC/C=C\CCCCOC(CCC(=O)OCC(CO)COC(=O)CCCCC(=O)OCCC(CCCC)CCCC)OCCCC/C=C\CC]

Step 5: 3-((4,4-bis(((Z)-oct-5-en-1-yl)oxy)butanoyl) oxy)-2-(hydroxymethyl)propyl (3-butylheptyl) adipate Prepared according to General Procedure H, substituting 6-((3-butylheptyl)oxy)-6-oxohexanoic acid for 6-((3-butylnonyl)oxy)-6-oxohexanoic acid. Isolated 170 mg, 46%. $^1H$ NMR (400 MHz, Chloroform-d) δ 0.88 (t, J=6.8 Hz, 6H), 0.94 (t, J=7.6 Hz, 6H), 1.17-1.33 (m, 19H), 1.32-1.47 (m, 5H), 1.59-1.73 (m, 4H), 1.85-2.11 (m, 10H), 2.12-2.27 (m, 1H), 2.28-2.44 (m, 6H), 3.40 (q, J=6.8 Hz, 2H), 3.49-3.68 (m, 4H), 4.07 (t, J=7.1 Hz, 2H), 4.12-4.24 (m, 4H), 4.48 (t, J=5.8 Hz, 1H), 5.27-5.37 (m, 4H).

Step 6: 3-((4,4-bis(((Z)-oct-5-en-1-yl)oxy)butanoyl) oxy)-2-(((((1-ethylpiperidin-3-yl)methoxy)carbonyl) oxy)methyl)propyl (3-butylheptyl) adipate (Example 4-63)

Prepared according to General Procedure F, substituting 3-((4,4-bis(((Z)-oct-5-en-1-yl)oxy)butanoyl)oxy)-2-(hydroxymethyl)propyl (3-butylheptyl) adipate for 3-((4,4-bis(((Z)-oct-5-en-1-yl)oxy)butanoyl)oxy)-2-(hydroxymethyl) propyl nonyl adipate and (1-ethylpiperidin-3-yl)methanol for 3-(diethylamino)propan-1-ol. Isolated 120 mg, 54%. UPLC-MS (Method A): Rt 2.12 min, m/z calculated [M+H]: 880.6, found: 880.8.

Example 4-64

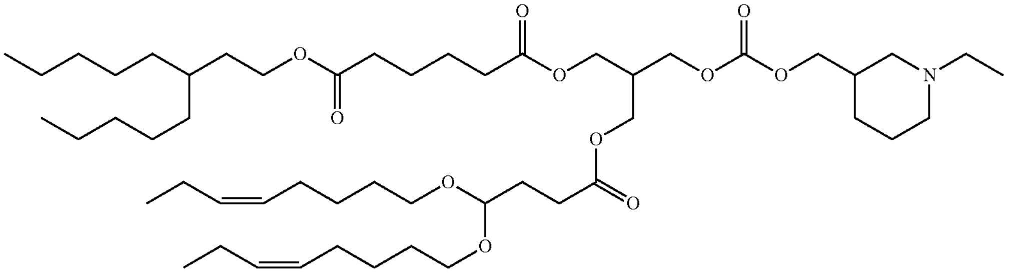

Example 4-64: 3-((4,4-bis(((Z)-oct-5-en-1-yl)oxy) butanoyl)oxy)-2-(((((1-ethylpiperidin-3-yl)methoxy) carbonyl)oxy)methyl)propyl (3-pentyloctyl) adipate

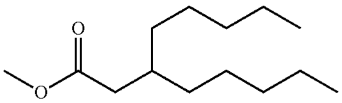 [SMILES: CCCCCC(CCCCC)CC(=O)OC]

Step 1: methyl 3-pentyloctanoate

Copper (I) bromide (0.1 eqv) and lithium chloride (0.2 eqv) were added to a flame dried flask under argon atmosphere. Then was added dry THF (20 mL) and the mixture was stirred for 10 min during which time the solid dissolved. Reaction mixture was placed in an ice bath and stirred for 5 min. After that, methyl (E)-oct-2-enoate (1.0 eqv) and chlorotrimethylsilane (1.1 eqv) were added and stirred for 15 min. Then, pentylmagnesium bromide (18% w/v in THF) (1.4 eqv) was added drop wise and the reaction was stirred at 0° C. for another 1 h. The solution was poured into saturated $NH_4C_1$ solution (50 mL) and extracted with ethyl acetate (3×50 mL). The combined organic extracts were washed with brine (50 mL), dried over $Na_2SO_4$, filtered and concentrated under reduced pressure. Crude material thus obtained was purified by combiflash column chromatography, eluted with 1-2% ethyl acetate-hexane to afford methyl 3-pentyloctanoate (1.0 g, 68%) as yellow oil. $^1$H NMR (400 MHz, Chloroform-d) δ 0.87 (t, J=6.8 Hz, 6H), 1.06-1.46 (m, 19H), 1.82 (s, 1H), 2.22 (d, J=6.9 Hz, 2H), 3.64 (s, 2H).

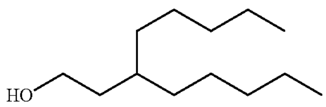

Step 2: 3-pentyloctan-1-ol

To a stirred solution of methyl 3-pentyloctanoate (1 eqv) in THF (10 mL) was added lithium aluminium hydride (2M in THF) (3.0 eqv) at 0° C. and stirred at 25° C. for 2 h. Then reaction mass was quenched with sodium sulfate decahydrate at 0° C. and filtered through celite. The filtrate was concentrated under reduced pressure, purified by combiflash column chromatography, eluted by 3-5% ethyl acetate-hexane to afford 3-pentyloctan-1-ol (580 mg, 65%) as colorless oil. $^1$H NMR (400 MHz, Chloroform-d) δ 0.87 (t, J=6.9 Hz, 6H), 1.13 (t, J=5.4 Hz, 1H), 1.17-1.35 (m, 15H), 1.38-1.44 (m, 1H), 1.51 (t, J=6.8 Hz, 2H), 3.65 (q, J=6.5 Hz, 2H), 5.29 (s, 1H).

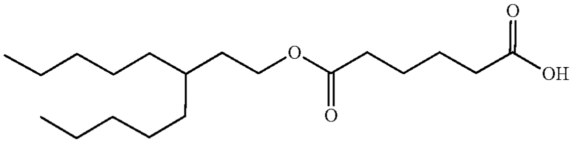 [SMILES: CCCCCC(CCCCC)CCOC(=O)CCCCC(=O)O]

Step 3: 6-oxo-6-((3-pentyloctyl)oxy)hexanoic acid

Prepared according to General Procedure G, substituting 3-pentyloctan-1-ol for 3-butylnonan-1-ol. Isolated 570 mg, 63%. $^1$H NMR (400 MHz, $CDCl_3$) δ 0.85-0.88 (m, 6H), 1.24-1.29 (m, 16H), 1.37-1.67 (m, 8H), 2.29-2.37 (m, 4H), 4.07 (t, J=7.1 Hz, 2H).

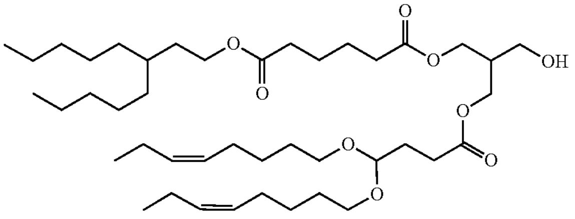 [SMILES: CC/C=C\CCCCOC(CCC(=O)OCC(CO)COC(=O)CCCCC(=O)OCCC(CCCCC)CCCCC)OCCCC/C=C\CC]

Step 4: 3-((4,4-bis(((Z)-oct-5-en-1-yl)oxy)butanoyl) oxy)-2-(hydroxymethyl)propyl (3-pentyloctyl) adipate Prepared according to General Procedure H, substituting 6-oxo-6-((3-pentyloctyl)oxy)hexanoic acid for 3-((4,4-bis(((Z)-oct-5-en-1-yl)oxy)butanoyl)oxy)-2-(hydroxymethyl) propyl (3-butylnonyl) adipate. Isolated 160 mg, 51%. $^1$H NMR (400 MHz, Chloroform-d) δ 0.87 (t, J=6.9 Hz, 6H), 0.94 (t, J=7.6 Hz, 6H), 1.16-1.34 (m, 14H), 1.35-1.45 (m, 4H), 1.47-1.73 (m, 14H), 1.87-1.97 (m, 2H), 2.02 (q, J=7.3 Hz, 8H), 2.11-2.25 (m, 1H), 2.28-2.44 (m, 6H), 3.40 (q, J=6.6 Hz, 2H), 3.52-3.66 (m, 4H), 4.07 (t, J=7.1 Hz, 2H), 4.12-4.22 (m, 4H), 4.48 (t, J=5.3 Hz, 1H), 5.21-5.46 (m, 4H).

Step 5: 3-((4,4-bis(((Z)-oct-5-en-1-yl)oxy)butanoyl) oxy)-2-(((((1-ethylpiperidin-3-yl)methoxy)carbonyl) oxy)methyl)propyl (3-pentyloctyl) adipate (Example 4-64)

Prepared according to General Procedure F, substituting 3-((4,4-bis(((Z)-oct-5-en-1-yl)oxy)butanoyl)oxy)-2-(hydroxymethyl)propyl (3-pentyloctyl) adipate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 120 mg, 54%. UPLC-MS (Method A): Rt 2.22 min, m/z calculated [M+H]: 908.7, found: 908.8. $^1$H NMR (400 MHz, DMSO-$d_6$) δ 0.81-0.95 (m, 12H), 0.95-1.08 (m, 4H), 1.12-1.25 (m, 18H), 1.24-1.40 (m, 5H), 1.42-1.58 (m, 11H), 1.56-1.69 (m, 2H), 1.77 (q, J=7.1 Hz, 3H), 1.81-1.92 (m, 1H), 1.93-2.05 (m, 8H), 2.22-2.41 (m, 9H), 2.68-2.88 (m, 1H), 3.31-3.40 (m, 2H), 3.44-3.54 (m, 2H), 3.90-4.10 (m, 8H), 4.13 (d, J=5.9 Hz, 2H), 4.44 (t, J=5.5 Hz, 1H), 5.23-5.40 (m, 4H).

Example 4-65

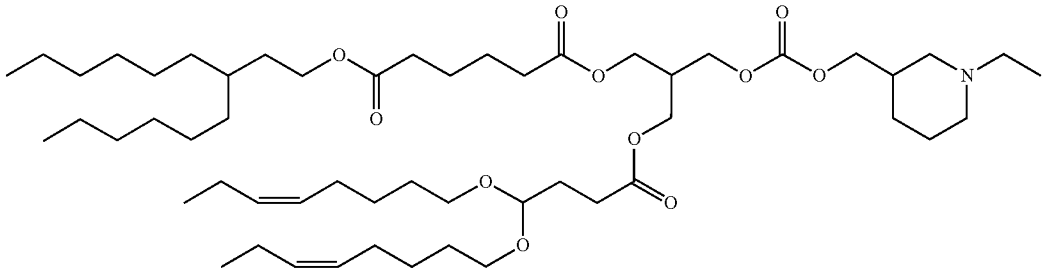

Example 4-65: 3-((4,4-bis(((Z)-oct-5-en-1-yl)oxy)butanoyl)oxy)-2-(((((1-ethylpiperidin-3-yl)methoxy)carbonyl)oxy)methyl)propyl (3-hexylnonyl) adipate

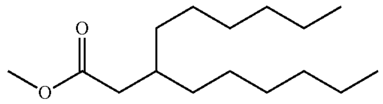 [SMILES: CCCCCCC(CCCCCC)CC(=O)OC]

Step 1: methyl 3-hexylnonanoate

Copper (I) bromide (0.1 eqv) and lithium chloride (0.2 eqv) were added to a flame dried flask under argon atmosphere. Then dry THF (20 mL) was added and the mixture was stirred for 10 min during which time the solid dissolved. Reaction mixture was placed in an ice bath and stirred for 5 min. After that, methyl (E)-non-2-enoate (1.0 eqv) and chlorotrimethylsilane (1.1 eqv) were added and stirred for 15 min. Then, pentylmagnesium bromide (18% w/v in THF) (1.4 eqv) was added drop wise and the reaction was stirred at 0° C. for another 1 h. The solution was poured into saturated $NH_4C_1$ solution (50 mL) and extracted with ethyl acetate (3×50 mL). The combined organic extracts were washed with brine (50 mL), dried over $Na_2SO_4$, filtered and concentrated under reduced pressure. Crude material thus obtained was purified by combiflash column chromatography, eluted with 1-2% ethyl acetate-hexane to afford methyl 3-hexylnonanoate (1.1 g, 67%) as yellow oil. $^1$H NMR (400 MHz, Chloroform-d) δ 0.81-0.91 (m, 6H), 1.13-1.37 (m, 20H), 1.82 (t, J=6.9 Hz, 1H), 2.22 (d, J=6.9 Hz, 2H), 3.65 (s, 3H).

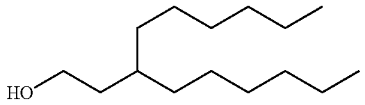 [SMILES: CCCCCCC(CCO)CCCCCC]

Step 2: 3-hexylnonan-1-ol

To a stirred solution of methyl 3-hexylnonanoate (1 eqv) in THF (10 mL) was added lithium aluminium hydride (2M in THF) (3.0 eqv) at 0° C. and stirred at 25° C. for 2 h. Then reaction mass was quenched with sodium sulfate decahydrate at 0° C. and filtered through celite. The filtrate was concentrated under reduced pressure, purified by combiflash column chromatography, eluted by 3-5% ethyl acetate-hexane to afford 3-hexylnonan-1-ol (540 mg, 61%) as colorless oil. $^1$H NMR (400 MHz, Chloroform-d) δ 0.87 (t, J=6.6 Hz, 6H), 1.12 (t, J=5.2 Hz, 1H), 1.16-1.34 (m, 20H), 1.35-1.45 (m, 1H), 1.51 (t, J=6.8 Hz, 2H), 3.65 (q, J=6.4 Hz, 2H).

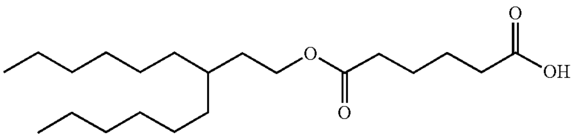 [SMILES: CCCCCCC(CCCCCC)CCOC(=O)CCCCC(=O)O]

Step 3: 6-((3-hexylnonyl)oxy)-6-oxohexanoic acid

Prepared according to General Procedure G, substituting 3-hexylnonan-1-ol for 3-butylnonan-1-ol. Isolated 680 mg, 58%. $^1$H NMR (400 MHz, DMSO-$d_6$) δ 0.83-0.86 (m, 6H), 1.12-1.50 (m, 27H), 2.19 (t, J=6.6 Hz, 2H), 2.25-2.32 (m, 2H), 4.02 (t, J=6.6 Hz, 2H), 11.99 (s, 1H).

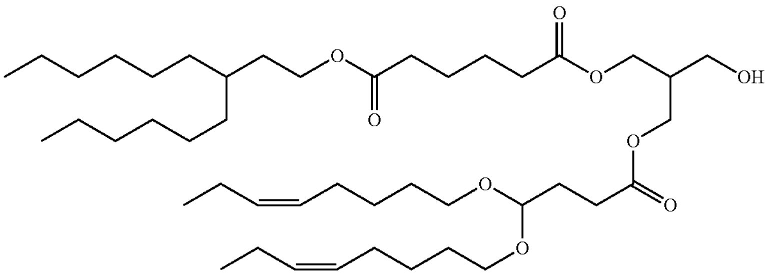 [SMILES: CC/C=C\CCCCOC(CCC(=O)OCC(CO)COC(=O)CCCCC(=O)OCCC(CCCCCC)CCCCCC)OCCCC/C=C\CC]

Step 4: 3-((4,4-bis(((Z)-oct-5-en-1-yl)oxy)butanoyl)oxy)-2-(hydroxymethyl)propyl (3-hexylnonyl) adipate Prepared according to General Procedure H, substituting 6-((3-hexylnonyl)oxy)-6-oxohexanoic acid for 6-((3-butylnonyl)oxy)-6-oxohexanoic acid. Isolated 175 mg, 54%. $^1$H NMR (400 MHz, Chloroform-d) δ 0.87 (t, J=6.6 Hz, 6H), 0.94 (t, J=7.5 Hz, 6H), 1.17-1.32 (m, 24H), 1.35-1.46 (m, 4H), 1.62-1.71 (m, 6H), 1.85-2.09 (m, 10H), 2.12-2.25 (m, 2H), 2.28-2.44 (m, 6H), 3.40 (q, J=7.0 Hz, 2H), 3.52-3.67 (m, 5H), 4.07 (t, J=6.9 Hz, 2H), 4.11-4.24 (m, 4H), 4.42-4.55 (m, 1H), 5.07-5.60 (m, 4H).

Step 5: 3-((4,4-bis(((Z)-oct-5-en-1-yl)oxy)butanoyl)oxy)-2-(((((1-ethylpiperidin-3-yl)methoxy)carbonyl)oxy)methyl)propyl (3-hexylnonyl) adipate Prepared according to General Procedure F, substituting 3-((4,4-bis(((Z)-oct-5-en-1-yl)oxy)butanoyl)oxy)-2-(hydroxymethyl)propyl (3-hexylnonyl) adipate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 52 mg, 37%. UPLC-MS (Method A): Rt 2.31 min, m/z calculated [M+H]: 936.7, found: 936.8. $^1$H NMR (400 MHz, DMSO-$d_6$) δ 0.81-0.95 (m, 12H), 0.95-1.11 (m, 3H), 1.15-1.30 (m, 29H), 1.35 (q, J=7.5 Hz, 5H), 1.42-1.57 (m, 10H), 1.57-1.70 (m, 2H), 1.77 (q, J=7.1 Hz, 2H), 1.95-2.04 (m, 7H), 2.20-2.45 (m, 8H), 3.32-3.40 (m, 2H), 3.44-3.54 (m, 2H), 3.93-4.10 (m, 8H), 4.14 (d, J=5.9 Hz, 2H), 4.44 (t, J=5.5 Hz, 1H), 5.23-5.40 (m, 4H).

Example 4-66

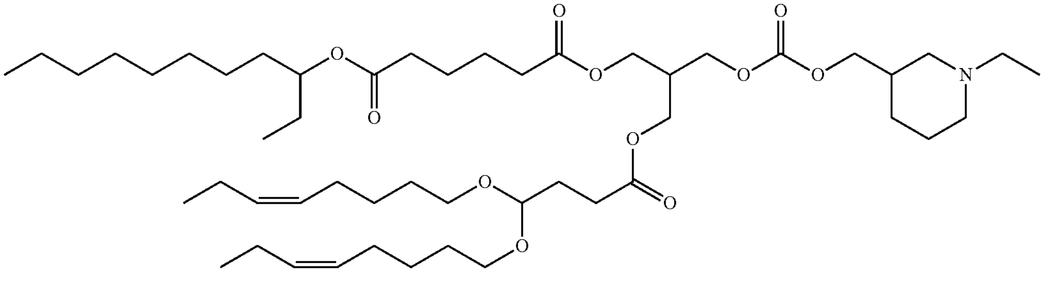

Example 4-66: 3-((4,4-bis(((Z)-oct-5-en-1-yl)oxy)butanoyl)oxy)-2-(((((1-ethylpiperidin-3-yl)methoxy)carbonyl)oxy)methyl)propyl undecan-3-yl adipate

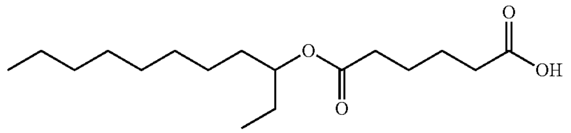 [SMILES: CCCCCCCCC(CC)OC(=O)CCCCC(=O)O]

Step 1: 6-oxo-6-(undecan-3-yloxy)hexanoic acid

Prepared according to General Procedure G, substituting undecan-3-ol for 3-butylnonan-1-ol. Isolated 1.1 g, 63%. $^1$H NMR (400 MHz, DMSO-$d_6$) δ 0.82-0.86 (m, 6H), 1.14-1.57 (m, 20H), 2.18-2.29 (m, 4H), 4.69-4.72 (m, 1H), 11.99 (s, 1H).

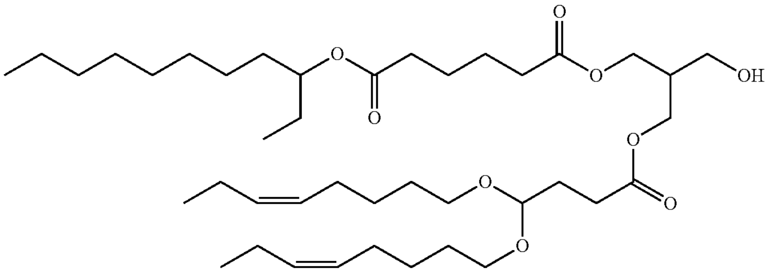 [SMILES: CC/C=C\CCCCOC(CCC(=O)OCC(CO)COC(=O)CCCCC(=O)OC(CC)CCCCCCCC)OCCCC/C=C\CC]

Step 2: 3-((4,4-bis(((Z)-oct-5-en-1-yl)oxy)butanoyl)oxy)-2-(hydroxymethyl)propyl undecan-3-yl adipate Prepared according to General Procedure H, substituting 6-oxo-6-(undecan-3-yloxy)hexanoic acid for 6-((3-butylnonyl)oxy)-6-oxohexanoic acid. Isolated 110 mg, 49%. $^1$H NMR (400 MHz, $CDCl_3$) δ 0.84-0.96 (m, 12H), 1.24-1.65 (m, 28H), 1.91-2.41 (m, 16H), 3.38-3.62 (m, 8H), 4.15-4.18 (m, 4H), 4.40-4.50 (m, 1H), 4.70-4.90 (m, 1H), 5.29-5.36 (m, 4H).

Step 3: 3-((4,4-bis(((Z)-oct-5-en-1-yl)oxy)butanoyl)oxy)-2-(((((1-ethylpiperidin-3-yl)methoxy)carbonyl)oxy)methyl)propyl undecan-3-yl adipate (Example 4-67)

Prepared according to General Procedure F, substituting 3-((4,4-bis(((Z)-oct-5-en-1-yl)oxy)butanoyl)oxy)-2-(hydroxymethyl)propyl undecan-3-yl adipate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 65 mg, 48%. UPLC-MS (Method A): Rt 2.09 min, m/z calculated [M+H]: 880.6, found: 880.8.

Example 4-67

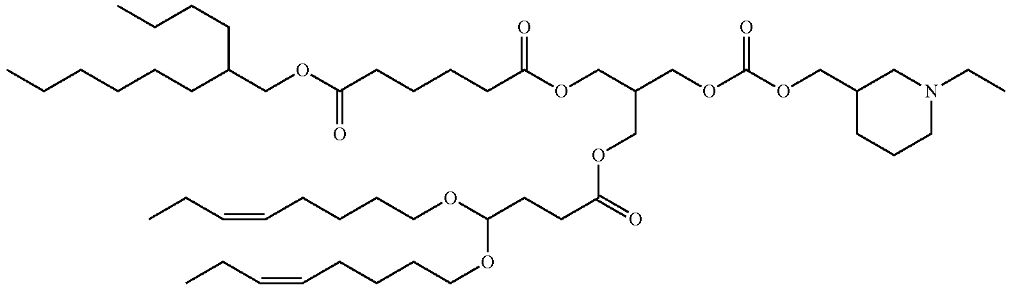

Example 4-67: 3-((4,4-bis(((Z)-oct-5-en-1-yl)oxy) butanoyl)oxy)-2-(((((1-ethylpiperidin-3-yl)methoxy) carbonyl)oxy)methyl)propyl (2-butyloctyl) adipate

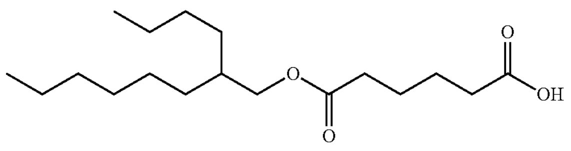 [SMILES: CCCCCCC(CCCC)COC(=O)CCCCC(=O)O]

Step 1: 6-((2-butyloctyl)oxy)-6-oxohexanoic acid

Prepared according to General Procedure G, substituting 2-butyloctan-1-ol for 3-butylnonan-1-ol. Isolated 550 mg, 51%. $^1$H NMR (400 MHz, DMSO-$d_6$) δ 0.84-0.85 (m, 6H), 1.17-1.30 (m, 16H), 1.50-1.60 (m, 5H), 2.18-2.30 (m, 4H), 3.92 (d, J=5.7 Hz, 2H), 11.99 (br s, 1H).

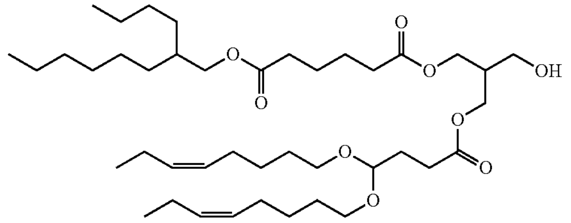 [SMILES: CC/C=C\CCCCOC(CCC(=O)OCC(CO)COC(=O)CCCCC(=O)OCC(CCCC)CCCCCC)OCCCC/C=C\CC]

Step 2: 3-((4,4-bis(((Z)-oct-5-en-1-yl)oxy)butanoyl) oxy)-2-(hydroxymethyl)propyl (2-butyloctyl) adipate Prepared according to General Procedure H, substituting 6-((2-butyloctyl)oxy)-6-oxohexanoic acid for 6-((3-butylnonyl)oxy)-6-oxohexanoic acid. Isolated 190 mg, 51%. $^1$H NMR (400 MHz, $CDCl_3$) δ 0.85-0.96 (m, 12H), 1.20-1.43 (m, 22H), 1.60-1.70 (m, 9H), 1.91-2.41 (m, 19H), 3.38-3.62 (m, 7H), 3.96 (d, J=5.8 Hz, 2H), 4.15-4.17 (m, 4H), 4.47 (t, J=5.4 Hz, 1H).

Step 3: 3-((4,4-bis(((Z)-oct-5-en-1-yl)oxy)butanoyl) oxy)-2-(((((1-ethylpiperidin-3-yl)methoxy)carbonyl) oxy)methyl)propyl (2-butyloctyl) adipate (Example 4-67)

Prepared according to General Procedure F, substituting 3-((4,4-bis(((Z)-oct-5-en-1-yl)oxy)butanoyl)oxy)-2-(hydroxymethyl)propyl (2-butyloctyl) adipate for 3-((4,4-bis(((Z)-oct-5-en-1-yl)oxy)butanoyl)oxy)-2-(hydroxymethyl) propyl nonyl adipate and (1-ethylpiperidin-3-yl)methanol for 3-(diethylamino)propan-1-ol. Isolated 110 mg, 47%. UPLC-MS (Method A): Rt 2.18 min, m/z calculated [M+H]: 894.7, found: 894.8.

Example 4-68

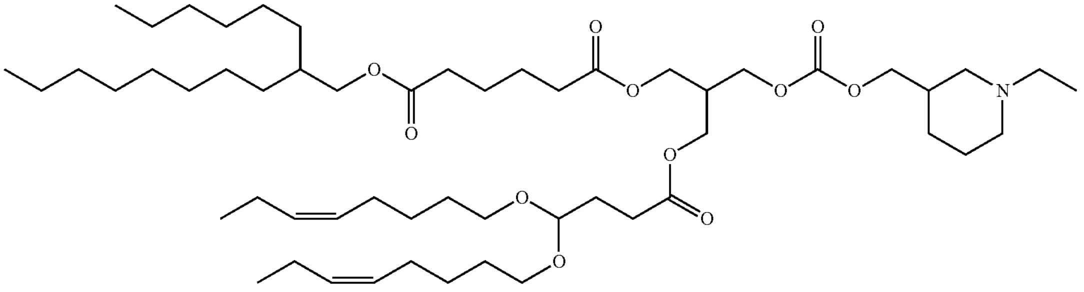

Example 4-68: 3-((4,4-bis(((Z)-oct-5-en-1-yl)oxy) butanoyl)oxy)-2-(((((1-ethylpiperidin-3-yl)methoxy) carbonyl)oxy)methyl)propyl (2-hexyldecyl) adipate

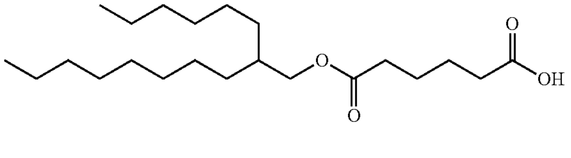 [SMILES: CCCCCCCCC(CCCCCC)COC(=O)CCCCC(=O)O]

Step 1: 6-((2-hexyldecyl)oxy)-6-oxohexanoic acid

Prepared according to General Procedure G, substituting 2-hexyldecan-1-ol for 3-butylnonan-1-ol. Isolated 590 mg, 46%. $^1$H NMR (400 MHz, DMSO-$d_6$) δ 0.83-0.86 (m, 6H), 1.20-1.40 (m, 24H), 1.51-1.60 (m, 5H), 2.20 (t, J=7.0 Hz, 2H), 2.29 (t, J=6.7 Hz, 2H), 3.92 (d, J=5.6 Hz, 2H), 11.98 (s, 1H).

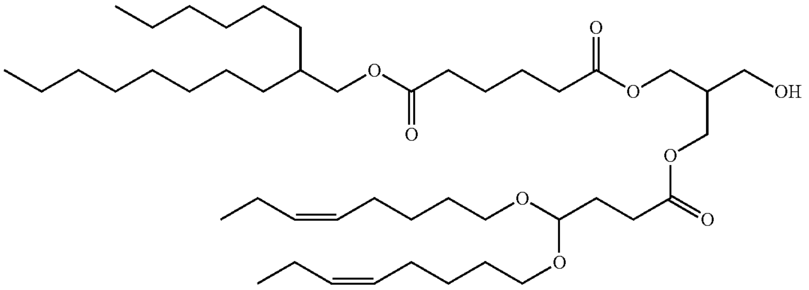 [SMILES: CC/C=C\CCCCOC(CCC(=O)OCC(CO)COC(=O)CCCCC(=O)OCC(CCCCCC)CCCCCCCC)OCCCC/C=C\CC]

Step 2: 3-((4,4-bis(((Z)-oct-5-en-1-yl)oxy)butanoyl)oxy)-2-(hydroxymethyl)propyl (2-hexyldecyl) adipate Prepared according to General Procedure H, substituting 6-((2-butyloctyl)oxy)-6-oxohexanoic acid for 6-((3-butylnonyl)oxy)-6-oxohexanoic acid. Isolated 180 mg, 49%. $^1$H NMR (400 MHz, $CDCl_3$) δ 0.85-0.96 (m, 12H), 1.20-1.65 (m, 36H), 1.89-2.41 (m, 17H), 3.36-3.62 (m, 6H), 3.96 (d, J=5.7 Hz, 2H), 4.12-4.20 (m, 4H), 4.47 (t, J=5.4 Hz, 1H).

Step 3: 3-((4,4-bis(((Z)-oct-5-en-1-yl)oxy)butanoyl)oxy)-2-(((((1-ethylpiperidin-3-yl)methoxy)carbonyl)oxy)methyl)propyl (2-hexyldecyl) adipate (Example 4-68)

Prepared according to General Procedure F, substituting 3-((4,4-bis(((Z)-oct-5-en-1-yl)oxy)butanoyl)oxy)-2-(hydroxymethyl)propyl (2-hexyldecyl) adipate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 110 mg, 45%. UPLC-MS (Method A): Rt 2.39 min, m/z calculated [M+H]: 950.7, found: 950.9.

Example 4-69

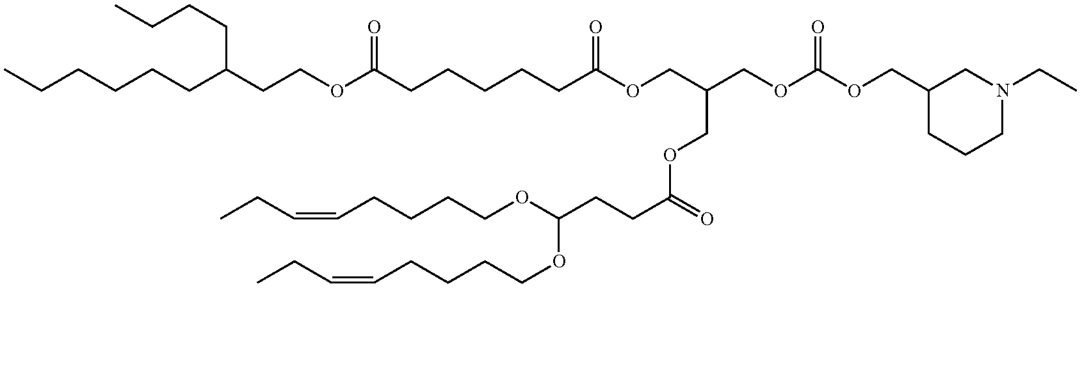

Example 4-69: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-butylnonyl) heptanedioate

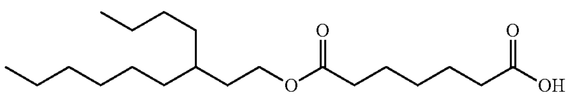 [SMILES: CCCCCCC(CCCC)CCOC(=O)CCCCCC(=O)O]

Step 1: 7-((3-butylnonyl)oxy)-7-oxoheptanoic acid

Prepared according to General Procedure G, substituting heptanedioic acid for adipic acid. Isolated 940 mg, 61%. $^1$H NMR (400 MHz, DMSO-$d_6$) δ 0.83-0.87 (m, 6H), 1.22-1.54 (m, 23H), 2.17 (t, J=7.4 Hz, 2H), 2.25 (t, J=7.3 Hz, 2H), 4.02 (t, J=6.7 Hz, 2H), 11.96 (s, 1H).

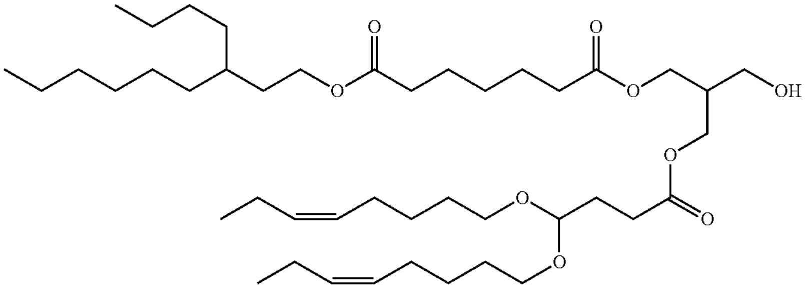 [SMILES: CC/C=C\CCCCOC(CCC(=O)OCC(CO)COC(=O)CCCCCC(=O)OCCC(CCCC)CCCCCC)OCCCC/C=C\CC]

Step 2: 1-(3-((4,4-bis(((Z)-oct-5-en-1-yl)oxy)butanoyl)oxy)-2-(hydroxymethyl)propyl) 7-(3-butylnonyl) heptanedioate Prepared according to General Procedure H, substituting 7-((3-butylnonyl)oxy)-7-oxoheptanoic acid for 6-((3-butylnonyl)oxy)-6-oxohexanoic acid. Isolated 150 mg, 52%. $^1$H NMR (400 MHz, Chloroform-d) δ 0.83-0.91 (m, 6H), 0.94 (t, J=7.5 Hz, 6H), 1.17-1.33 (m, 20H), 1.30-1.46 (m, 8H), 1.57-1.70 (m, 5H), 1.87-1.97 (m, 2H), 1.96-2.09 (m, 8H), 2.14-2.22 (m, 1H), 2.23-2.36 (m, 5H), 2.40 (t, J=7.5 Hz, 2H), 3.33-3.45 (m, 2H), 3.51-3.65 (m, 4H), 4.07 (t, J=7.0 Hz, 2H), 4.16 (t, J=5.9 Hz, 4H), 4.48 (t, J=5.5 Hz, 1H), 5.24-5.42 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-butylnonyl) heptanedioate (Example 4-69)

Prepared according to General Procedure F, substituting 1-(3-((4,4-bis(((Z)-oct-5-en-1-yl)oxy)butanoyl)oxy)-2-(hydroxymethyl)propyl) 7-(3-butylnonyl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 118 mg, 54%. UPLC-MS (Method A): Rt 2.24 min, m/z calculated [M+H]: 922.7, found: 922.8. $^1$H NMR (400 MHz, DMSO-$d_6$) δ 0.81-0.95 (m, 12H), 0.94-1.06 (m, 3H), 1.11-1.32 (m, 20H), 1.36 (q, J=7.6 Hz, 5H), 1.42-1.57 (m, 17H), 1.57-1.69 (m, 2H), 1.77 (q, J=7.1 Hz, 2H), 1.93-2.05 (m, 7H), 2.21-2.42 (m, 8H), 3.31-3.41 (m, 2H), 3.44-3.54 (m, 2H), 4.06 (dd, J=2.0, 6.0 Hz, 4H), 3.89-4.10 (m, 4H), 4.13 (d, J=5.9 Hz, 2H), 4.44 (t, J=5.5 Hz, 1H), 5.23-5.40 (m, 4H), 0.62-0.82 (m, 4H).

Example 4-70

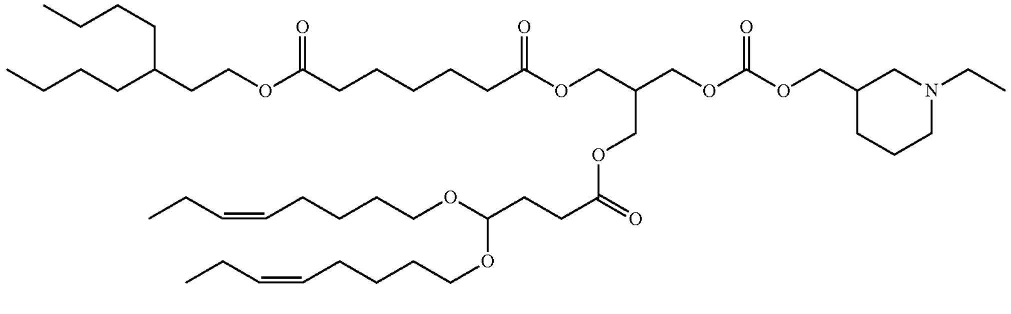

Example 4-70: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-butylheptyl) heptanedioate

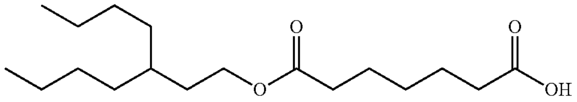 [SMILES: CCCCC(CCCC)CCOC(=O)CCCCCC(=O)O]

Step 1: 7-((3-butylheptyl)oxy)-7-oxoheptanoic acid

Prepared according to General Procedure G, substituting 3-butylheptan-1-ol for 3-butylnonan-1-ol and heptanedioic acid for adipic acid. Isolated 980 mg, 60%. $^1$H NMR (400 MHz, DMSO-$d_6$) δ 0.84-0.87 (m, 6H), 1.15-1.54 (m, 21H), 2.17 (t, J=7.3 Hz, 2H), 2.25 (t, J=7.3 Hz, 2H), 4.02 (t, J=6.8 Hz, 2H), 11.98 (s, 1H).

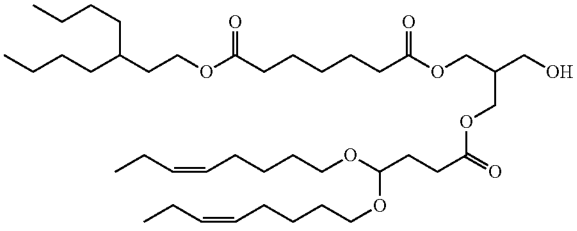 [SMILES: CC/C=C\CCCCOC(CCC(=O)OCC(CO)COC(=O)CCCCCC(=O)OCCC(CCCC)CCCC)OCCCC/C=C\CC]

Step 2: 1-(3-((4,4-bis(((Z)-oct-5-en-1-yl)oxy)butanoyl)oxy)-2-(hydroxymethyl)propyl) 7-(3-butylheptyl) heptanedioate Prepared according to General Procedure H, substituting 7-((3-butylheptyl)oxy)-7-oxoheptanoic acid for 6-((3-butylnonyl)oxy)-6-oxohexanoic acid. Isolated 145 mg, 48%. $^1$H NMR (400 MHz, Chloroform-d) δ 0.88 (t, J=6.7 Hz, 6H), 0.94 (t, J=7.5 Hz, 6H), 1.18-1.32 (m, 14H), 1.30-1.46 (m, 8H), 1.50-1.56 (m, 1H), 1.56-1.71 (m, 6H), 1.89-1.96 (m, 2H), 1.98-2.08 (m, 8H), 2.13-2.23 (m, 1H), 2.22-2.37 (m, 5H), 2.40 (t, J=7.4 Hz, 2H), 3.34-3.45 (m, 2H), 3.51-3.65 (m, 4H), 4.07 (t, J=7.1 Hz, 2H), 4.16 (t, J=6.0 Hz, 4H), 4.48 (t, J=5.5 Hz, 1H), 5.24-5.42 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-butylheptyl) heptanedioate (Example 4-70)

Prepared according to General Procedure F, substituting 1-(3-((4,4-bis(((Z)-oct-5-en-1-yl)oxy)butanoyl)oxy)-2-(hydroxymethyl)propyl) 7-(3-butylnonyl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 112 mg, 52%. UPLC-MS (Method A): Rt 2.15 min, m/z calculated [M+H]: 894.7, found: 894.8.

Example 4-71

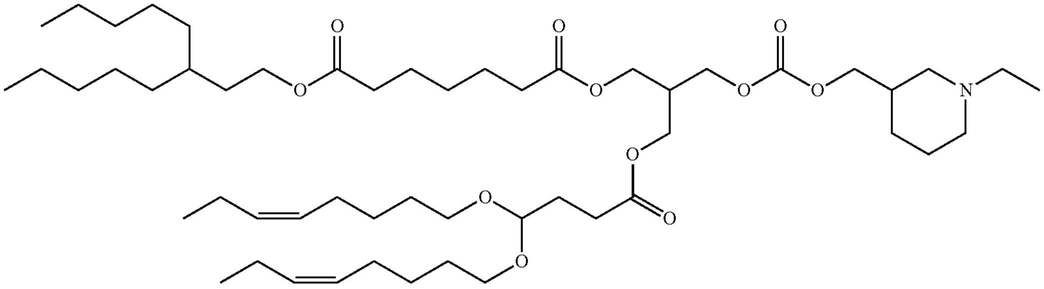

Example 4-71: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-pentyloctyl) heptanedioate

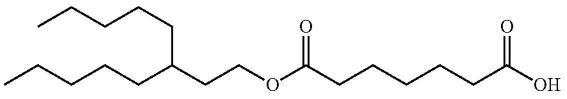 [SMILES: CCCCCC(CCCCC)CCOC(=O)CCCCCC(=O)O]

Step 1: 7-oxo-7-((3-pentyloctyl)oxy)heptanoic acid

Prepared according to General Procedure G, substituting 3-pentyloctan-1-ol for 3-butylnonan-1-ol and heptanedioic acid for adipic acid. Isolated 580 mg, 37%. $^1$H NMR (400 MHz, DMSO-$d_6$) δ 0.86 (t, J=7.0 Hz, 6H), 1.13-1.34

(m,18H), 1.33-1.41 (m, 1H), 1.42-1.58 (m, 6H), 2.18 (t, J=7.4 Hz, 2H), 2.26 (t, J=7.3 Hz, 2H), 4.01 (t, J=6.8 Hz, 2H), 11.96 (s, 1H).

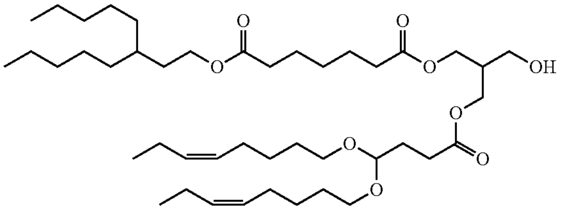 [SMILES: CC/C=C\CCCCOC(CCC(=O)OCC(CO)COC(=O)CCCCCC(=O)OCCC(CCCCC)CCCCC)OCCCC/C=C\CC]

Step 2: 1-(3-((4,4-bis(((Z)-oct-5-en-1-yl)oxy)butanoyl)oxy)-2-(hydroxymethyl)propyl) 7-(3-pentyloctyl) heptanedioate Prepared according to General Procedure H, substituting 7-oxo-7-((3-pentyloctyl)oxy)heptanoic acid for 6-((3-butylnonyl)oxy)-6-oxohexanoic acid. Isolated 150 mg, 49%. $^{1}$H NMR (400 MHz, Chloroform-d) δ 0.87 (t, J=6.9 Hz, 6H), 0.94 (t, J=7.5 Hz, 6H), 1.15-1.35 (m, 19H), 1.35-1.46 (m, 6H), 1.56-1.70 (m, 7H), 1.82-2.01 (m, 3H), 1.98-2.09 (m, 7H), 2.14-2.36 (m, 6H), 2.40 (t, J=7.5 Hz, 2H), 3.34-3.45 (m, 2H), 3.51-3.65 (m, 4H), 3.67-3.81 (m, 1H), 4.06 (t, J=7.0 Hz, 2H), 4.11-4.24 (m, 4H), 4.48 (t, J=5.5 Hz, 1H), 5.24-5.42 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-pentyloctyl) heptanedioate (Example 4-71)

Prepared according to General Procedure F, substituting 1-(3-((4,4-bis(((Z)-oct-5-en-1-yl)oxy)butanoyl)oxy)-2-(hydroxymethyl)propyl) 7-(3-pentyloctyl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 90 mg, 49%. UPLC-MS (Method A): Rt 2.34 min, m/z calculated [M+H]: 922.7, found: 922.8.

Example 4-72

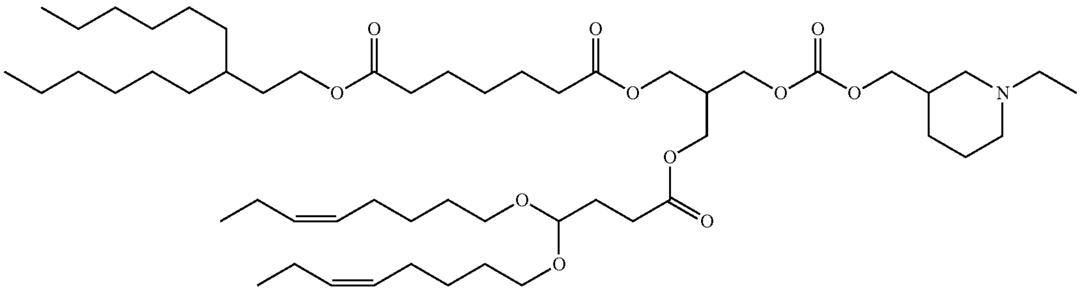

Example 4-72: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-hexylnonyl) heptanedioate

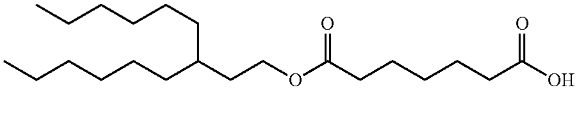 [SMILES: CCCCCCC(CCCCCC)CCOC(=O)CCCCCC(=O)O]

Step 1: 7-((3-hexylnonyl)oxy)-7-oxoheptanoic acid

Prepared according to General Procedure G, substituting 3-hexylnonan-1-ol for 3-butylnonan-1-ol and heptanedioic acid for adipic acid. Isolated 790 mg, 65%. $^1$H NMR (400 MHz, DMSO-$d_6$) δ 0.83-0.86 (m, 6H), 1.07-1.54 (m, 29H), 2.17 (t, J=7.3 Hz, 2H), 2.25 (t, J=7.2 Hz, 2H), 4.01 (t, J=6.7 Hz, 2H), 11.97 (s, 1H).

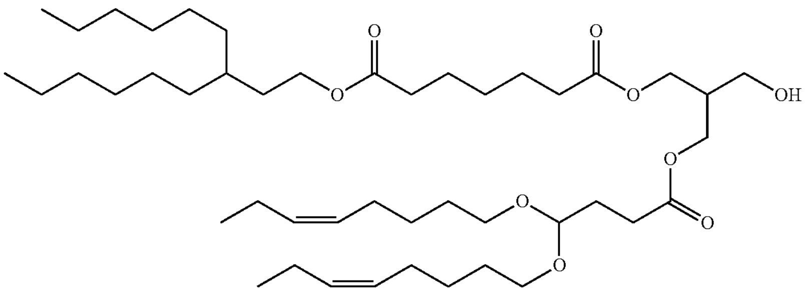 [SMILES: CC/C=C\CCCCOC(CCC(=O)OCC(CO)COC(=O)CCCCCC(=O)OCCC(CCCCCC)CCCCCC)OCCCC/C=C\CC]

Step 2: 1-(3-((4,4-bis(((Z)-oct-5-en-1-yl)oxy)butanoyl)oxy)-2-(hydroxymethyl)propyl) 7-(3-hexylnonyl) heptanedioate Prepared according to General Procedure H, substituting 7-((3-hexylnonyl)oxy)-7-oxoheptanoic acid for 6-((3-butylnonyl)oxy)-6-oxohexanoic acid. Isolated 140 mg, 53%. $^1$H NMR (400 MHz, Chloroform-d) δ 0.87 (t, J=6.7 Hz, 6H), 0.94 (t, J=7.5 Hz, 6H), 1.17-1.32 (m, 34H), 1.32-1.45 (m, 4H), 1.57-1.73 (m, 3H), 1.84-2.10 (m, 8H), 2.11-2.50 (m, 7H), 3.41 (t, J=6.8 Hz, 2H), 3.51-3.65 (m, 4H), 4.07 (t, J=7.1 Hz, 2H), 4.16 (t, J=5.5 Hz, 3H), 4.48 (t, J=5.4 Hz, 1H), 5.26-5.41 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(3-hexylnonyl) heptanedioate (Example 4-72)

Prepared according to General Procedure F, substituting 1-(3-((4,4-bis(((Z)-oct-5-en-1-yl)oxy)butanoyl)oxy)-2-(hydroxymethyl)propyl) 7-(3-hexylnonyl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 88 mg, 40%. UPLC-MS (Method A): Rt 2.35 min, m/z calculated [M+H]: 950.7, found: 950.8.

Example 4-73

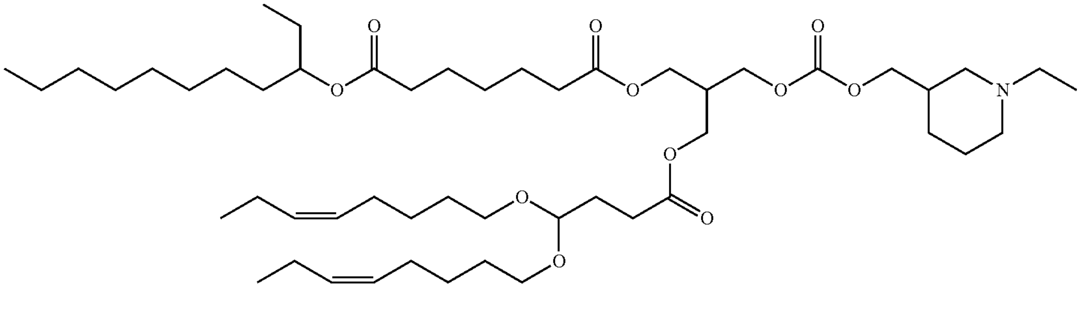

Example 4-73: 1-(3-((4,4-bis(((Z)-oct-5-en-1-yl) oxy)butanoyl)oxy)-2-(((((1-ethylpiperidin-3-yl) methoxy)carbonyl)oxy)methyl)propyl) 7-(undecan-3-yl) heptanedioate

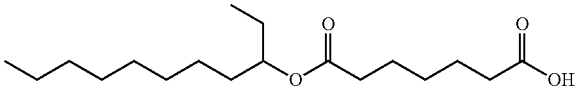 [SMILES: CCCCCCCCC(CC)OC(=O)CCCCCC(=O)O]

Step 1: 7-oxo-7-(undecan-3-yloxy)heptanoic acid

Prepared according to General Procedure G, substituting undecan-3-ol for 3-butylnonan-1-ol and heptanedioic acid for adipic acid. Isolated 910 mg, 50%. $^1H$ NMR (400 MHz, DMSO-$d_6$) δ 0.70-0.90 (m, 6H), 1.20-1.60 (m, 22H), 2.17 (t, J=7.4 Hz, 2H), 2.24-2.33 (m, 2H), 4.68-4.74 (m, 1H), 11.96 (s, 1H).

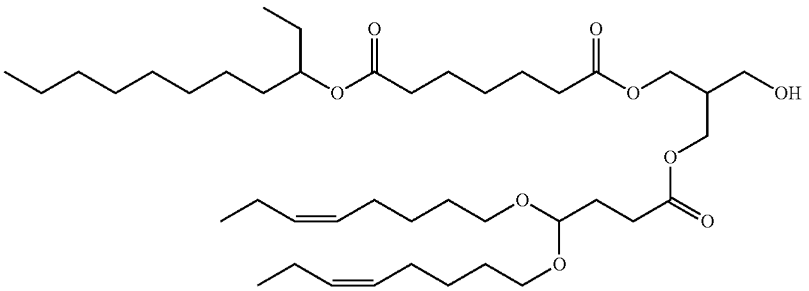 [SMILES: CC/C=C\CCCCOC(CCC(=O)OCC(CO)COC(=O)CCCCCC(=O)OC(CC)CCCCCCCC)OCCCC/C=C\CC]

Step 2: 1-(3-((4,4-bis(((Z)-oct-5-en-1-yl)oxy)butanoyl)oxy)-2-(hydroxymethyl)propyl) 7-(undecan-3-yl) heptanedioate Prepared according to General Procedure H, substituting 7-oxo-7-(undecan-3-yloxy)heptanoic acid for 6-((3-butylnonyl)oxy)-6-oxohexanoic acid. Isolated 150 mg, 48%. $^1H$ NMR (400 MHz, $CDCl_3$) δ 0.80-0.96 (m, 12H), 1.10-1.63 (m, 25H), 1.91-2.41 (m, 19H), 3.38-3.62 (m, 8H), 4.14-4.17 (m, 5H), 4.40-4.50 (m, 1H), 4.70-4.90 (m, 1H), 5.31-5.34 (m, 4H).

Step 3: 1-(3-((4,4-bis(((Z)-oct-5-en-1-yl) oxy)butanoyl)oxy)-2-(((((1-ethylpiperidin-3-yl)methoxy) carbonyl)oxy)methyl)propyl) 7-(undecan-3-yl) heptanedioate (Example 4-73)

Prepared according to General Procedure F, substituting 1-(3-((4,4-bis(((Z)-oct-5-en-1-yl)oxy)butanoyl)oxy)-2-(hydroxymethyl)propyl) 7-(undecan-3-yl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 82 mg, 44%. UPLC-MS (Method A): Rt 2.18 min, m/z calculated [M+H]: 894.7, found: 894.7.

Example 4-74

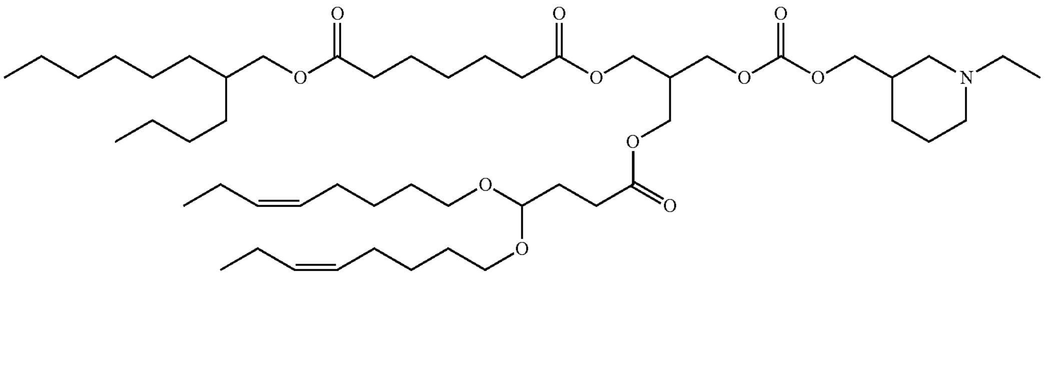

Example 4-74: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(2-butyloctyl) heptanedioate

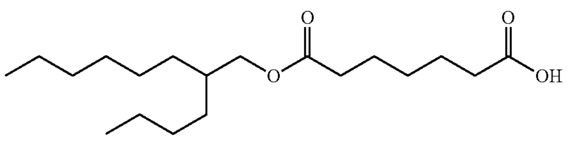 [SMILES: CCCCCCC(CCCC)COC(=O)CCCCCC(=O)O]

Step 1: 7-((2-butyloctyl)oxy)-7-oxoheptanoic acid

Prepared according to General Procedure G, substituting 2-butyloctan-1-ol for 3-butylnonan-1-ol and heptanedioic acid for adipic acid. Isolated 960 mg, 54%. $^1H$ NMR (400 MHz, DMSO-$d_6$) δ 0.80-0.90 (m, 6H), 1.44-1.55 (m, 5H), 2.17 (t, J=7.3 Hz, 2H), 2.27 (t, J=7.2 Hz, 2H), 3.92 (d, J=5.7 Hz, 2H), 11.97 (s, 1H).

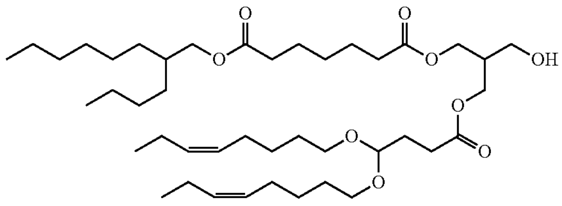 [SMILES: CC/C=C\CCCCOC(CCC(=O)OCC(CO)COC(=O)CCCCCC(=O)OCC(CCCC)CCCCCC)OCCCC/C=C\CC]

Step 2: 1-(3-((4,4-bis(((Z)-oct-5-en-1-yl)oxy)butanoyl)oxy)-2-(hydroxymethyl)propyl) 7-(2-butyloctyl) heptanedioate Prepared according to General Procedure H, substituting 7-((2-butyloctyl)oxy)-7-oxoheptanoic acid for 6-((3-butylnonyl)oxy)-6-oxohexanoic acid. Isolated 145 mg, 46%. $^1H$ NMR (400 MHz, $CDCl_3$) δ 0.70-1.00 (m, 12H), 1.10-1.70 (m, 30H), 1.80-2.50 (m, 18H), 3.38-3.62 (m, 6H), 3.94-4.17 (m, 6H), 4.40-4.50 (m, 1H), 5.00-5.40 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 7-(2-butyloctyl) heptanedioate (Example 4-74)

Prepared according to General Procedure F, substituting 1-(3-((4,4-bis(((Z)-oct-5-en-1-yl)oxy)butanoyl)oxy)-2-(hydroxymethyl)propyl) 7-(2-butyloctyl) heptanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 102 mg, 51%. UPLC-MS (Method A): Rt 2.30 min, m/z calculated [M+H]: 908.7, found: 908.7.

Example 4-75

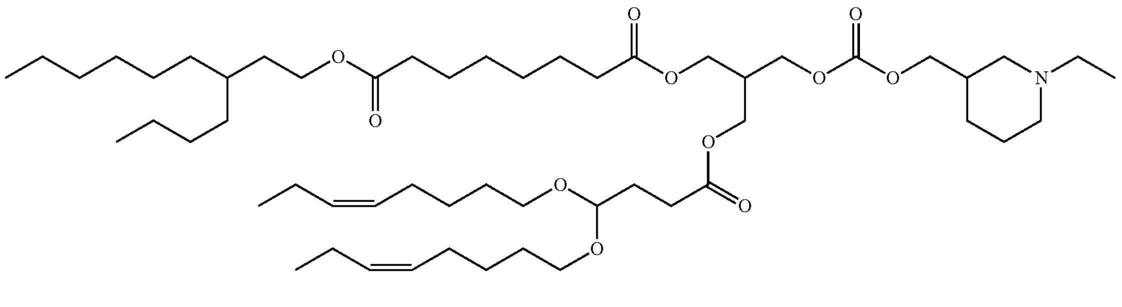

Example 4-75: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-butylnonyl) octanedioate

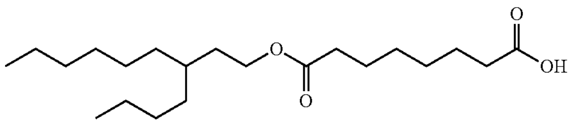 [SMILES: CCCCCCC(CCCC)CCOC(=O)CCCCCCC(=O)O]

Step 1: 8-((3-butylnonyl)oxy)-8-oxooctanoic acid

Prepared according to General Procedure G, substituting octanedioic acid for adipic acid. Isolated 765 mg, 72%. $^1H$ NMR (400 MHz, Chloroform-d) δ 0.85-0.88 (m, 6H), 1.24-1.35 (m, 21H), 1.53-1.65 (m, 6H), 2.25-2.44 (m, 4H), 4.07 (t, J=7.1 Hz, 2H).

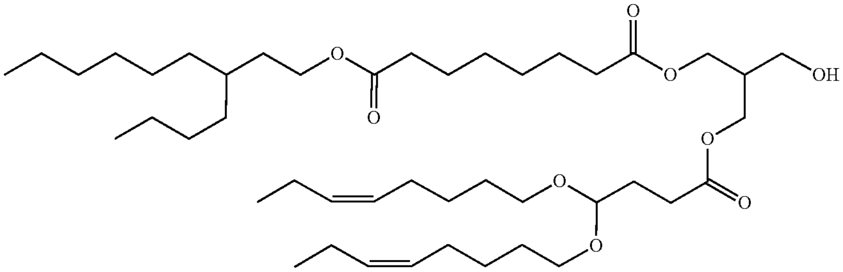 [SMILES: CC/C=C\CCCCOC(CCC(=O)OCC(CO)COC(=O)CCCCCCC(=O)OCCC(CCCC)CCCCCC)OCCCC/C=C\CC]

Step 2: 1-(3-((4,4-bis(((Z)-oct-5-en-1-yl)oxy)butanoyl)oxy)-2-(hydroxymethyl)propyl) 8-(3-butylnonyl) octanedioate Prepared according to General Procedure H, substituting 8-((3-butylnonyl)oxy)-8-oxooctanoic acid for 6-((3-butylnonyl)oxy)-6-oxohexanoic acid. Isolated 150 mg, 70%. $^1$H NMR (400 MHz, Chloroform-d) δ 0.85-0.95 (m, 12H), 1.23-1.70 (m, 34H), 1.91-2.40 (m, 18H), 3.38-3.62 (m, 6H), 4.04-4.17 (m, 6H), 4.40-4.50 (m, 1H), 5.31-5.34 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-butylnonyl) octanedioate (Example 4-75)

Prepared according to General Procedure F, substituting 1-(3-((4,4-bis(((Z)-oct-5-en-1-yl)oxy)butanoyl)oxy)-2-(hydroxymethyl)propyl) 8-(3-butylnonyl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 50 mg, 51%. UPLC-MS (Method A): Rt 2.30 min, m/z calculated [M+H]: 936.7, found: 936.8.

Example 4-76

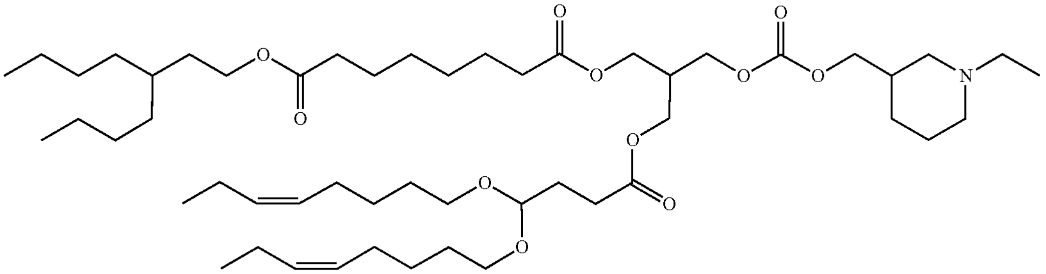

Example 4-76: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-butylheptyl) octanedioate

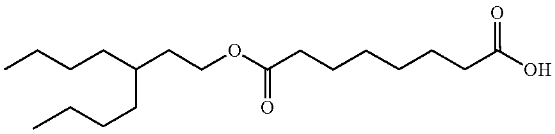 [SMILES: CCCCC(CCCC)CCOC(=O)CCCCCCC(=O)O]

Step 1: 8-((3-butylheptyl)oxy)-8-oxooctanoic acid

Prepared according to General Procedure G, substituting 3-butylheptan-1-ol for 3-butylnonan-1-ol and octanedioic acid for adipic acid. Isolated 175 mg, 71%. $^1$H NMR (400 MHz, Chloroform-d) δ 0.80-0.89 (m, 6H), 1.14-1.78 (m, 23H), 2.27 (t, J=7.4 Hz, 2H), 2.33 (t, J=7.4 Hz, 2H), 4.07 (t, J=7.1 Hz, 2H).

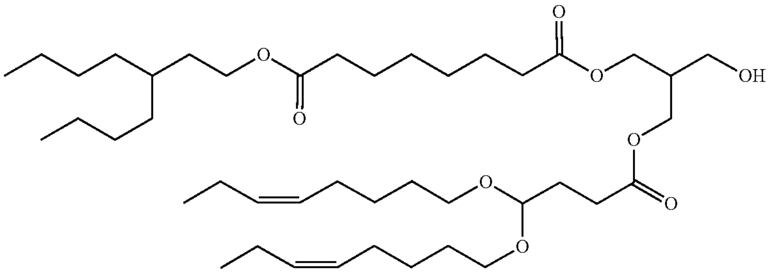 [SMILES: CC/C=C\CCCCOC(CCC(=O)OCC(CO)COC(=O)CCCCCCC(=O)OCCC(CCCC)CCCC)OCCCC/C=C\CC]

Step 2: 1-(3-((4,4-bis(((Z)-oct-5-en-1-yl)oxy)butanoyl)oxy)-2-(hydroxymethyl)propyl) 8-(3-butylheptyl) octanedioate Prepared according to General Procedure H, substituting 8-((3-butylheptyl)oxy)-8-oxooctanoic acid for 6-((3-butylnonyl)oxy)-6-oxohexanoic acid. Isolated 115 mg, 51%. $^1$H NMR (400 MHz, Chloroform-d) δ 0.86-1.71 (m, 42H), 1.91-2.41 (m, 18H), 3.38-3.62 (m, 6H), 4.06 (t, J=6.9 Hz, 2H), 4.14-4.20 (m, 4H), 4.40-4.50 (m, 1H), 5.20-5.30 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-butylheptyl) octanedioate (Example 4-76)

Prepared according to General Procedure F, substituting 1-(3-((4,4-bis(((Z)-oct-5-en-1-yl)oxy)butanoyl)oxy)-2-(hydroxymethyl)propyl) 8-(3-butylheptyl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 40 mg, 37%. UPLC-MS (Method A): Rt 2.23 min, m/z calculated [M+H]: 908.7, found: 908.8. $^1$H NMR (400 MHz, Chloroform-d) δ 0.88 (t, J=6.8 Hz, 6H), 0.94 (t, J=7.4 Hz, 6H), 1.12-1.46 (m, 37H), 1.58-1.69 (m, 6H), 1.76-1.87 (m, 2H), 1.86-2.09 (m, 11H), 2.23-2.34 (m, 5H), 2.35-2.47 (m, 3H), 3.34-3.44 (m, 2H), 3.50-3.64 (m, 2H), 4.07 (t, J=7.0 Hz, 2H), 4.13 (d, J=5.8 Hz, 4H), 4.18 (d, J=5.9 Hz, 2H), 4.47 (t, J=5.5 Hz, 1H), 5.24-5.42 (m, 4H).

Example 4-77

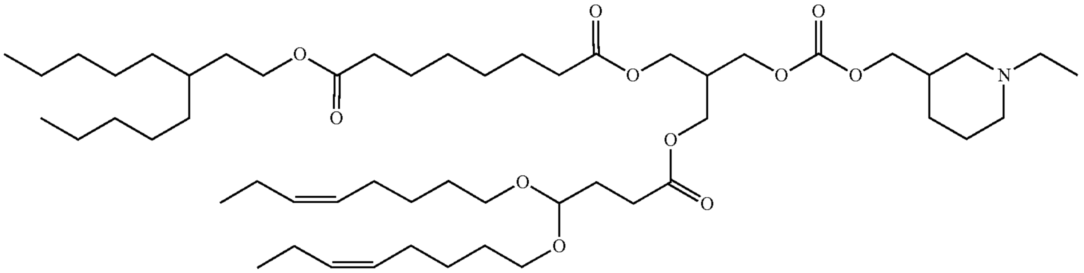

Example 4-77: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-pentyloctyl) octanedioate

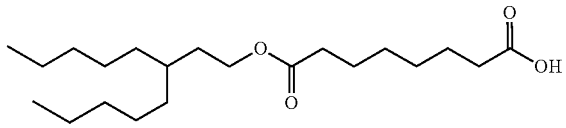 [SMILES: CCCCCC(CCCCC)CCOC(=O)CCCCCCC(=O)O]

Step 1: 8-oxo-8-((3-pentyloctyl)oxy)octanoic acid

Prepared according to General Procedure G, substituting 3-pentyloctan-1-ol for 3-butylnonan-1-ol and octanedioic acid for adipic acid. Isolated 560 mg, 63%. $^1$H NMR (400 MHz, Chloroform-d) δ 0.87 (t, J=6.8 Hz, 6H), 1.24-1.65 (m, 27H), 2.27 (t, J=7.4 Hz, 2H), 2.34 (t, J=7.5 Hz, 2H), 4.06 (t, J=7.1 Hz, 2H).

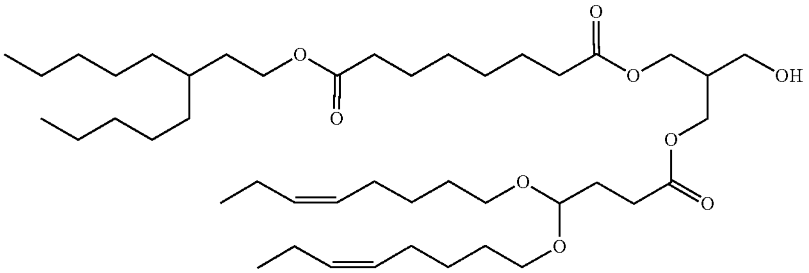 [SMILES: CC/C=C\CCCCOC(CCC(=O)OCC(CO)COC(=O)CCCCCCC(=O)OCCC(CCCCC)CCCCC)OCCCC/C=C\CC]

Step 2: 1-(3-((4,4-bis(((Z)-oct-5-en-1-yl)oxy)butanoyl)oxy)-2-(hydroxymethyl)propyl) 8-(3-pentyloctyl) octanedioate Prepared according to General Procedure H, substituting 8-oxo-8-((3-pentyloctyl)oxy)octanoic acid for 6-((3-butylnonyl)oxy)-6-oxohexanoic acid. Isolated 150 mg, 70%. $^1$H NMR (400 MHz, Chloroform-d) δ 0.80-1.0 (m, 12H), 1.10-1.60 (m, 36H), 1.91-2.32 (m, 15H), 2.39 (t, J=7.4 Hz, 2H), 3.30-3.62 (m, 6H), 4.06 (t, J=7.1 Hz, 2H), 4.14-4.17 (m, 4H), 4.40-4.50 (m, 1H), 5.30-5.40 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-pentyloctyl) octanedioate (Example 4-77)

Prepared according to General Procedure F, substituting 1-(3-((4,4-bis(((Z)-oct-5-en-1-yl)oxy)butanoyl)oxy)-2-(hydroxymethyl)propyl) 8-(3-pentyloctyl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 70 mg, 57%. UPLC-MS (Method A): Rt 2.37 min, m/z calculated [M+H]: 936.7, found: 936.9.

Example 4-78

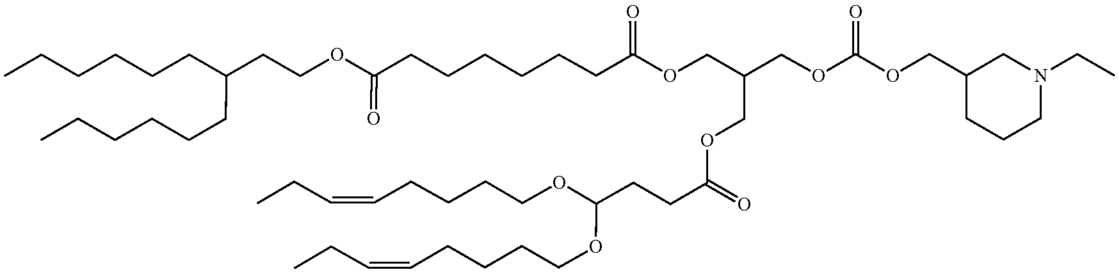

Example 4-78: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-hexylnonyl) octanedioate

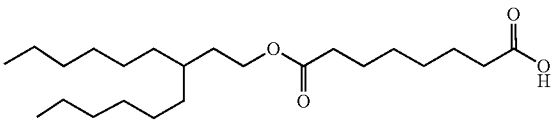

Step 1: 8-((3-hexylnonyl)oxy)-8-oxooctanoic acid

Prepared according to General Procedure G, substituting 3-hexylnonan-1-ol for 3-butylnonan-1-ol and octanedioic acid for adipic acid. Isolated 1.35 g, 80%. $^1$H NMR (400 MHz, Chloroform-d) δ 0.85-0.88 (m, 6H), 1.24-1.41 (m, 23H), 1.61-1.70 (m, 8H), 2.25-2.35 (m, 4H), 4.06 (t, J=7.1 Hz, 2H).

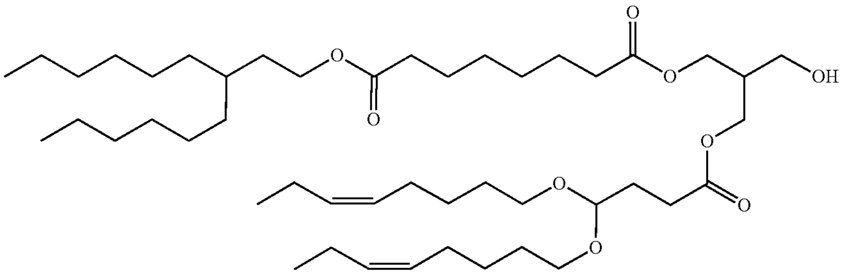 [SMILES: CC/C=C\CCCCOC(CCC(=O)OCC(CO)COC(=O)CCCCCCC(=O)OCCC(CCCCCC)CCCCCC)OCCCC/C=C\CC]

Step 2: 1-(3-((4,4-bis(((Z)-oct-5-en-1-yl)oxy)butanoyl)oxy)-2-(hydroxymethyl)propyl) 8-(3-hexylnonyl) octanedioate Prepared according to General Procedure H, substituting 8-oxo-8-((3-pentyloctyl)oxy)octanoic acid for 6-((3-butylnonyl)oxy)-6-oxohexanoic acid. Isolated 150 mg, 73%. $^1$H NMR (400 MHz, $CDCl_3$) δ 0.85-0.96 (m, 12H), 1.23-1.70 (m, 32H), 1.90-2.50 (m, 18H), 3.40-3.70 (m, 6H), 4.00-4.20 (m, 6H), 4.40-4.47 (m, 1H), 5.28-5.34 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(3-hexylnonyl) octanedioate (Example 4-78)

Prepared according to General Procedure F, substituting 1-(3-((4,4-bis(((Z)-oct-5-en-1-yl)oxy)butanoyl)oxy)-2-(hydroxymethyl)propyl) 8-(3-hexylnonyl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 75 mg, 62%. UPLC-MS (Method A): Rt 2.46 min, m/z calculated [M+H]: 964.7, found: 964.9.

Example 4-79

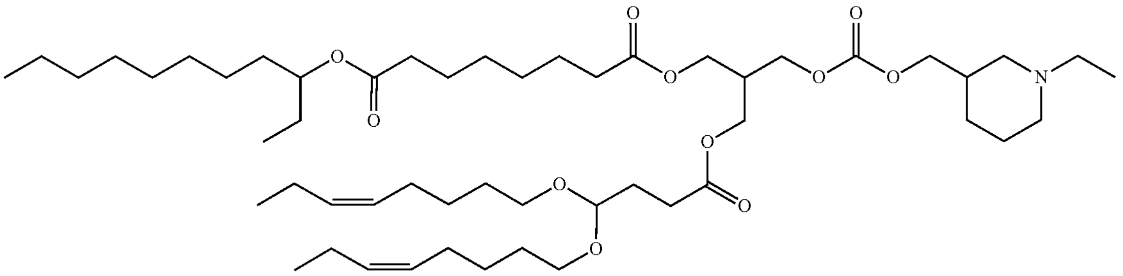

Example 4-79: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(undecan-3-yl) octanedioate

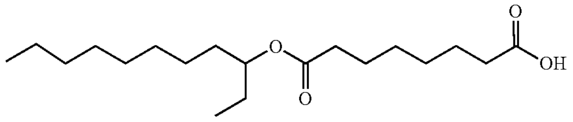 [SMILES: CCCCCCCCC(CC)OC(=O)CCCCCCC(=O)O]

Step 1: 8-oxo-8-(undecan-3-yloxy)octanoic acid

Prepared according to General Procedure G, substituting undecan-3-ol for 3-butylnonan-1-ol and octanedioic acid for adipic acid. Isolated 2.5 g, 87%. $^1$H NMR (400 MHz, Chloroform-d) δ 0.83-0.87 (m, 6H), 1.17-1.63 (m, 24H), 2.26-2.35 (m, 4H), 4.76-4.83 (m, 1H).

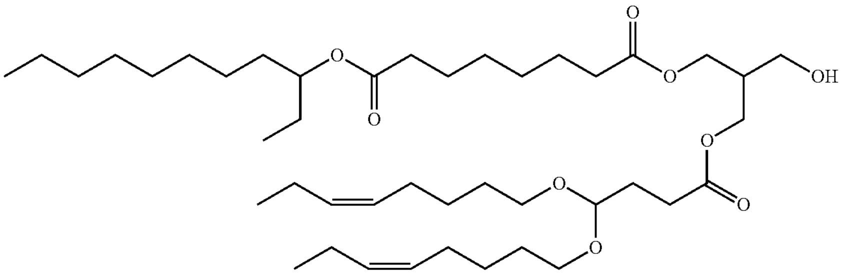 [SMILES: CC/C=C\CCCCOC(CCC(=O)OCC(CO)COC(=O)CCCCCCC(=O)OC(CC)CCCCCCCC)OCCCC/C=C\CC]

Step 2: 1-(3-((4,4-bis(((Z)-oct-5-en-1-yl)oxy)butanoyl)oxy)-2-(hydroxymethyl)propyl) 8-(undecan-3-yl) octanedioate Prepared according to General Procedure H, substituting 8-oxo-8-(undecan-3-yloxy)octanoic acid for 6-((3-butylnonyl)oxy)-6-oxohexanoic acid. Isolated 110 mg, 49%. $^{1}H$ NMR (400 MHz, $CDCl_3$) δ 0.83-0.96 (m, 12H), 1.24-1.61 (m, 33H), 1.80-2.50 (m, 17H), 3.30-3.60 (m, 6H), 4.14-4.17 (m, 4H), 4.40-4.50 (m, 1H), 4.70-4.80 (m, 1H), 5.20-5.40 (m, 4H).

Step 3: 1-(3-((4,4-bis(((Z)-oct-5-en-1-yl)oxy)butanoyl)oxy)-2-(((((1-ethylpiperidin-3-yl)methoxy)carbonyl)oxy)methyl)propyl) 8-(undecan-3-yl) octanedioate (Example 4-79)

Prepared according to General Procedure F, substituting 1-(3-((4,4-bis(((Z)-oct-5-en-1-yl)oxy)butanoyl)oxy)-2-(hydroxymethyl)propyl) 8-(undecan-3-yl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 35 mg, 29%. UPLC-MS (Method A): Rt 2.36 min, m/z calculated [M+H]: 908.7, found: 908.8. $^{1}H$ NMR (400 MHz, Chloroform-d) δ 0.82-0.91 (m, 9H), 0.94 (t, J=7.4 Hz, 9H), 1.14-1.70 (m, 23H), 1.84-2.02 (m, 6H), 1.98-2.09 (m, 4H), 2.23-2.35 (m, 4H), 2.35-2.59 (m, 4H), 3.01-3.18 (m, 4H), 3.34-3.45 (m, 4H), 3.50-3.62 (m, 4H), 4.10-4.22 (m, 12H), 4.47 (t, J=5.5 Hz, 2H), 4.72-4.90 (m, 2H), 5.24-5.42 (m, 6H).

Example 4-80

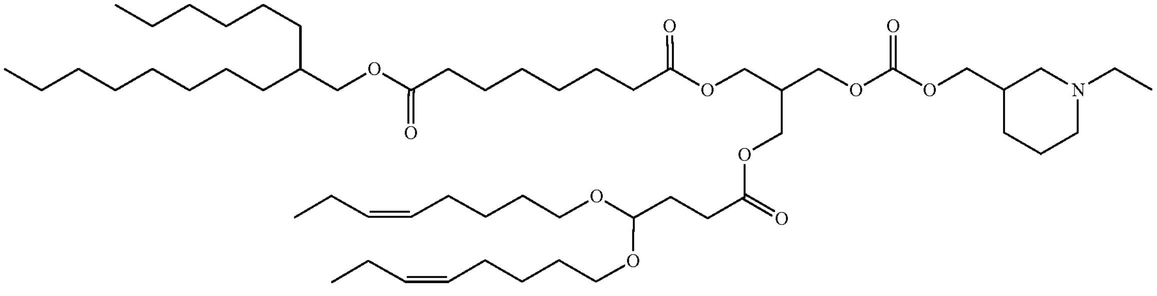

Example 4-80: 1-(3-((4,4-bis(((Z)-oct-5-en-1-yl) oxy)butanoyl)oxy)-2-(((((1-ethylpiperidin-3-yl) methoxy)carbonyl)oxy)methyl)propyl) 8-(2-hexyl-decyl) octanedioate

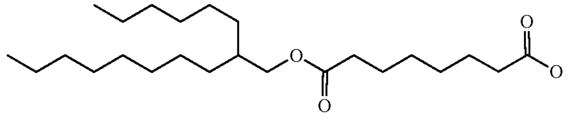 [SMILES: CCCCCCCCC(CCCCCC)COC(=O)CCCCCCC(=O)O]

Step 1: 8-((2-hexyldecyl)oxy)-8-oxooctanoic acid

Prepared according to General Procedure G, substituting 2-hexyldecan-1-ol for 3-butylnonan-1-ol and octanedioic acid for adipic acid. Isolated 400 mg, 49%. $^1$H NMR (400 MHz, Chloroform-d) δ 0.85-0.88 (m, 6H), 1.18-1.34 (m, 24H), 1.49-1.80 (m, 8H), 2.27-2.34 (m, 4H), 3.96 (d, J=5.7 Hz, 2H).

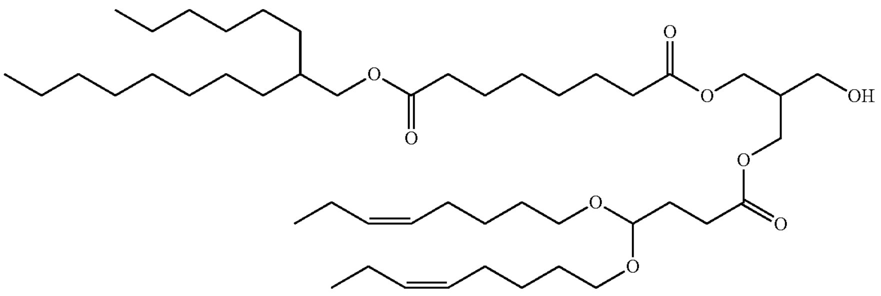 [SMILES: CC/C=C\CCCCOC(CCC(=O)OCC(CO)COC(=O)CCCCCCC(=O)OCC(CCCCCC)CCCCCCCC)OCCCC/C=C\CC]

Step 2: 1-(3-((4,4-bis(((Z)-oct-5-en-1-yl)oxy)butanoyl)oxy)-2-(hydroxymethyl)propyl) 8-(2-hexyl-decyl) octanedioate Prepared according to General Procedure H, substituting 8-((2-hexyldecyl)oxy)-8-oxooctanoic acid for 6-((3-butylnonyl)oxy)-6-oxohexanoic acid. Isolated 100 mg, 49%. $^1$H NMR (400 MHz, $CDCl_3$) δ 0.85-0.96 (m, 12H), 1.25-1.63 (m, 40H), 1.91-2.41 (m, 18H), 3.38-3.62 (m, 6H), 3.95 (d, J=5.8 Hz, 2H), 4.14-4.17 (m, 4H), 4.46-4.47 (m, 1H), 5.28-5.37 (m, 4H).

Step 3: 1-(3-((4,4-bis(((Z)-oct-5-en-1-yl)oxy)butanoyl)oxy)-2-(((((1-ethylpiperidin-3-yl)methoxy) carbonyl)oxy)methyl)propyl) 8-(2-hexyldecyl) octanedioate (Example 4-80)

Prepared according to General Procedure F, substituting 1-(3-((4,4-bis(((Z)-oct-5-en-1-yl)oxy)butanoyl)oxy)-2-(hydroxymethyl)propyl) 8-(2-hexyldecyl) octanedioate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 75 mg, 41%. UPLC-MS (Method A): Rt 2.44 min, m/z calculated [M+H]: 978.7, found: 978.9. $^1$H NMR (400 MHz, Chloroform-d) δ 0.87 (t, J=6.9 Hz, 6H), 0.94 (t, J=7.5 Hz, 6H), 1.13-1.18 (m, 4H), 1.18-1.38 (m, 31H), 1.38-1.46 (m, 4H), 1.50-1.67 (m, 9H), 1.70-1.82 (m, 2H), 1.91 (q, J=7.0 Hz, 2H), 1.98-2.09 (m, 8H), 2.24-2.34 (m, 4H), 2.34-2.46 (m, 4H), 2.47-2.70 (m, 2H), 2.85-3.24 (m, 2H), 3.34-3.45 (m, 2H), 3.49-3.64 (m, 2H), 3.92-4.11 (m, 4H), 4.16 (dd, J=5.9, 19.4 Hz, 6H), 4.47 (t, J=5.5 Hz, 1H), 5.24-5.42 (m, 4H).

Example 4-81

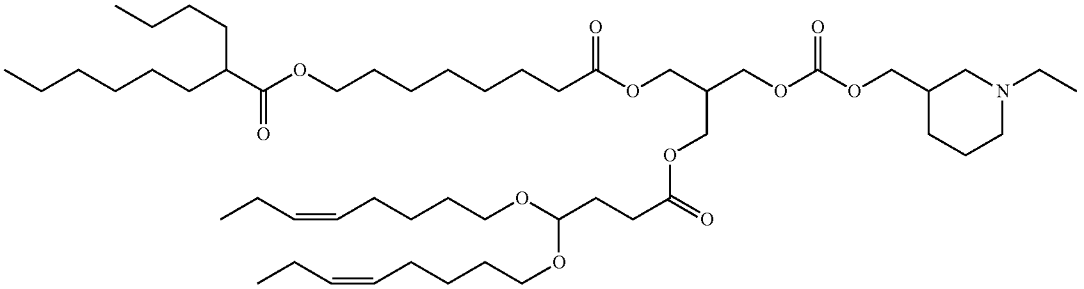

Example 4-81: 8-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-8-oxooctyl 2-butyloctanoate

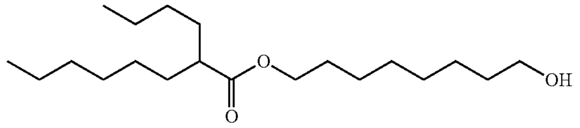 [SMILES: CCCCCCC(CCCC)C(=O)OCCCCCCCCO]

Step 1: 8-hydroxyoctyl 2-butyloctanoate

General Procedure J: To a stirred solution of 2-butyloctanoic acid (500 mg, 2.5 mmol, 1 eqv) in DCM (30 mL), were added DIPEA (970 mg, 7.5 mmol, 3 eqv), EDC (719 mg, 3.75 mmol, 1.5 eqv) and DMAP (153 mg, 1.25 mmol, 0.5 eqv). The reaction mixture was stirred for 15 min and then was added octane-1,8-diol (1.1 g, 7.5 mmol, 3.0 eqv) and further was stirred at 25° C. for 17 h. Reaction mixture was diluted with DCM (200 mL) and washed with water (2×100 mL), brine (100 mL) and concentrated under reduce pressure. Crude material thus obtained was purified by combiflash chromatography, eluted with 15-20% EtOAc-hexane to afford 6-hydroxyhexyl 2-butyloctanoate as colorless oil (500 mg, 61%). $^1$H NMR (400 MHz, Chloroform-d) δ 0.80-0.87 (m, 6H), 1.00-1.62 (m, 29H), 2.25-2.32 (m, 1H), 3.61-3.62 (m, 2H), 4.04 (t, J=6.6 Hz, 2H).

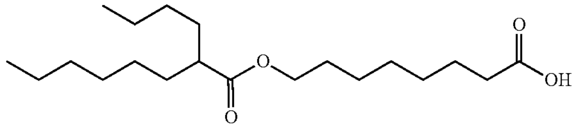 [SMILES: CCCCCCC(CCCC)C(=O)OCCCCCCCC(=O)O]

Step 2: 8-((2-butyloctanoyl)oxy)octanoic acid

General Procedure K: To a stirred solution of 6-hydroxyhexyl 2-butyloctanoate (1.0 g, 3.1 mmol, 1.0 eqv) in acetone (20 mL) was added Jones reagent (2M $CrO_3$ in $H_2SO_4$, 1.86 mL, 3.72 mmol, 1.2 eqv) dropwise under ice cold condition. The cooling bath was then removed, and the mixture was stirred at 25° C. for 16 h. Upon completion, isopropanol (1 mL) was added to the reaction mixture followed by filtration. The filtrate was dried under reduced pressure. The residue was diluted with water and heptane. The heptane layer was separated and discarded, and the aqueous phase was washed with EtOAc, which was discarded. The pH of the aqueous layer was adjusted to 6 and the mixture was extracted with 5% MeOH/DCM (5×40 ml). The organic extracts were dried over anhydrous sodium sulfate and filtered. The filtrate was concentrated under reduced pressure to afford 8-((2-butyloctanoyl)oxy)octanoic acid (900 mg, 86%) as colorless oil which was used in the next step without further purification. $^1$H NMR (400 MHz, DMSO-$d_6$) δ 0.80-0.90 (m, 6H), 1.19-1.60 (m, 26H), 2.17 (t, J=7.3 Hz, 2H), 2.23-2.30 (m, 1H), 4.00 (t, J=6.3 Hz, 2H), 11.95 (s, 1H).

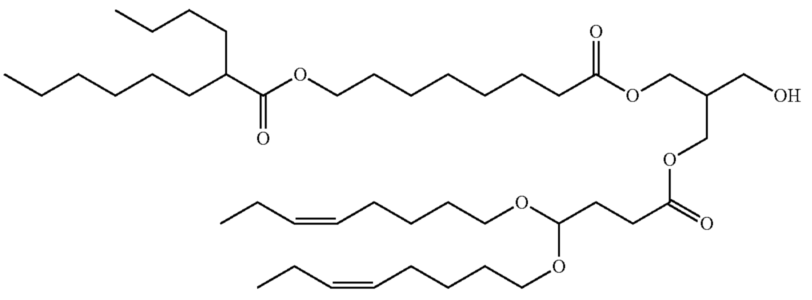 [SMILES: CC/C=C\CCCCOC(CCC(=O)OCC(CO)COC(=O)CCCCCCCOC(=O)C(CCCC)CCCCCC)OCCCC/C=C\CC]

Step 3: 8-(3-((4,4-bis(((Z)-oct-5-en-1-yl)oxy)butanoyl)oxy)-2-(hydroxymethyl)propoxy)-8-oxooctyl 2-butyloctanoate Prepared according to General Procedure H, substituting 8-((2-butyloctanoyl)oxy)octanoic acid for 6-((3-butylnonyl)oxy)-6-oxohexanoic acid. Isolated 170 mg, 55%. $^1$H NMR (400 MHz, Chloroform-d) δ 0.82-0.91 (m, 6H), 0.94 (t, J=7.5 Hz, 6H), 1.15-1.49 (m, 27H), 1.60 (t, J=8.4 Hz, 7H), 1.87-1.96 (m, 2H), 1.96-2.09 (m, 8H), 2.13-2.26 (m, 2H), 2.28-2.35 (m, 3H), 2.40 (t, J=7.5 Hz, 2H), 3.34-3.44 (m, 2H), 3.50-3.66 (m, 4H), 4.04 (t, J=6.7 Hz, 2H), 4.11-4.23 (m, 4H), 4.48 (t, J=5.5 Hz, 1H), 5.24-5.42 (m, 4H).

Step 4: 8-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-8-oxooctyl 2-butyloctanoate (Example 4-81)

Prepared according to General Procedure F, substituting 8-(3-((4,4-bis(((Z)-oct-5-en-1-yl)oxy)butanoyl)oxy)-2-(hydroxymethyl)propoxy)-8-oxooctyl 2-butyloctanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 95 mg, 50%. UPLC-MS (Method A): Rt 2.32 min, m/z calculated [M+H]: 922.7, found: 922.8. $^1$H NMR (400 MHz, DMSO-$d_6$) δ 0.79-0.95 (m, 12H), 0.94-1.08 (m, 3H), 1.10-1.42 (m, 28H), 1.42-1.58 (m, 11H), 1.57-1.68 (m, 2H), 1.77 (q, J=7.0 Hz, 2H), 1.81-1.92 (m, 2H), 1.93-2.05 (m, 8H), 2.21-2.42 (m, 8H), 3.31-3.40 (m, 2H), 3.44-3.54 (m, 2H), 3.91-4.11 (m, 8H), 4.13 (d, J=5.9 Hz, 2H), 4.44 (t, J=5.5 Hz, 1H), 5.23-5.40 (m, 4H).

Example 4-82

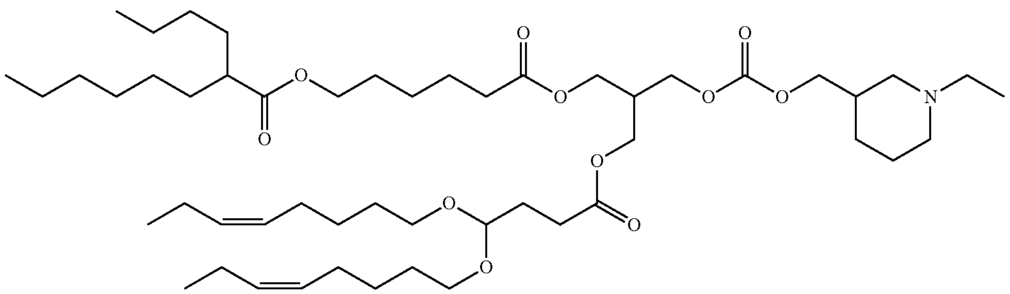

Example 4-82: 6-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-6-oxohexyl 2-butyloctanoate

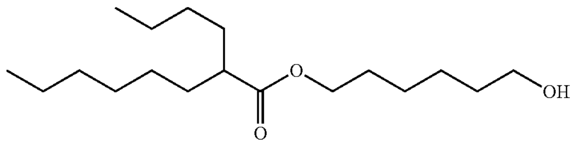 [SMILES: CCCCCCC(CCCC)C(=O)OCCCCCCO]

Step 1: 6-hydroxyhexyl 2-butyloctanoate

Prepared according to General Procedure J, substituting hexane-1,6-diol for octane-1,8-diol. Isolated 320 mg, used crude in the next step.

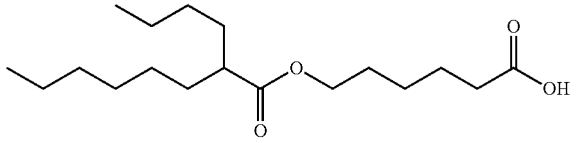 [SMILES: CCCCCCC(CCCC)C(=O)OCCCCCC(=O)O]

Step 2: 6-((2-butyloctanoyl)oxy)hexanoic acid

Prepared according to General Procedure K, substituting 6-hydroxyhexyl 2-butyloctanoate for 8-hydroxyoctyl 2-butyloctanoate. Isolated 285 mg, used crude in the next step.

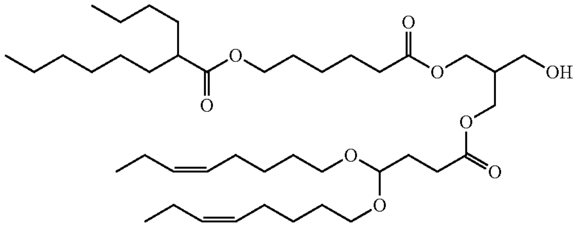 [SMILES: CC/C=C\CCCCOC(CCC(=O)OCC(CO)COC(=O)CCCCCOC(=O)C(CCCC)CCCCCC)OCCCC/C=C\CC]

Step 3: 6-(3-((4,4-bis(((Z)-oct-5-en-1-yl)oxy)butanoyl)oxy)-2-(hydroxymethyl)propoxy)-6-oxohexyl 2-butyloctanoate Prepared according to General Procedure H, substituting 6-((2-butyloctanoyl)oxy)hexanoic acid for 6-((3-butylnonyl)oxy)-6-oxohexanoic acid. Isolated 140 mg, 45%. $^1$H NMR (400 MHz, Chloroform-d) δ 0.82-0.99 (m, 12H), 1.15-1.35 (m, 14H), 1.33-1.49 (m, 8H), 1.49-1.57 (m, 3H), 1.56-1.72 (m, 5H), 1.89-1.96 (m, 2H), 1.97-2.08 (m, 8H), 2.13-2.26 (m, 2H), 2.25-2.36 (m, 3H), 2.40 (t, J=7.5 Hz, 2H), 3.34-3.45 (m, 2H), 3.51-3.65 (m, 4H), 4.05 (t, J=6.6 Hz, 2H), 4.11-4.22 (m, 4H), 4.48 (t, J=5.5 Hz, 1H), 5.24-5.42 (m, 4H).

Step 4: 6-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-6-oxohexyl 2-butyloctanoate (Example 4-82)

Prepared according to General Procedure F, substituting 6-(3-((4,4-bis(((Z)-oct-5-en-1-yl)oxy)butanoyl)oxy)-2-(hydroxymethyl)propoxy)-6-oxohexyl 2-butyloctanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 90 mg, 50%. UPLC-MS (Method A): Rt 2.24 min, m/z calculated [M+H]: 894.7, found: 894.8.

Example 4-83

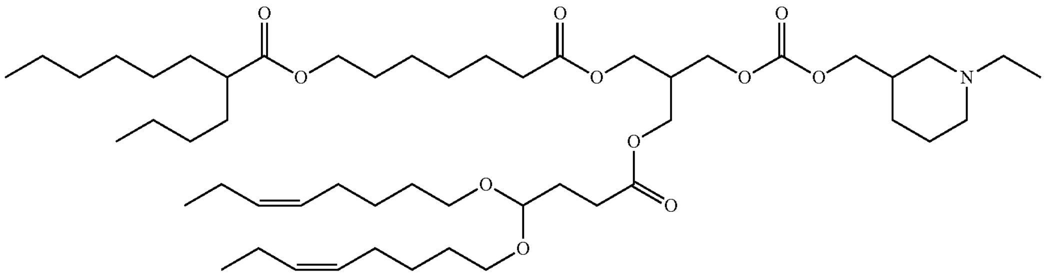

Example 4-83: 7-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-7-oxoheptyl 2-butyloctanoate

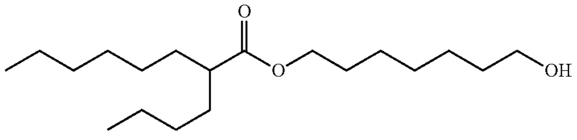 [SMILES: CCCCCCC(CCCC)C(=O)OCCCCCCCO]

Step 1: 7-hydroxyheptyl 2-butyloctanoate

Prepared according to General Procedure J, substituting heptane-1,7-diol for octane-1,8-diol. Isolated 280 mg, used crude in the next step.

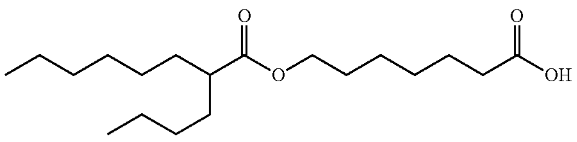 [SMILES: CCCCCCC(CCCC)C(=O)OCCCCCCC(=O)O]

Step 2: 7-((2-butyloctanoyl)oxy)heptanoic acid

Prepared according to General Procedure K, substituting 7-hydroxyheptyl 2-butyloctanoate for 8-hydroxyoctyl 2-butyloctanoate. Isolated 246 mg, used crude in the next step.

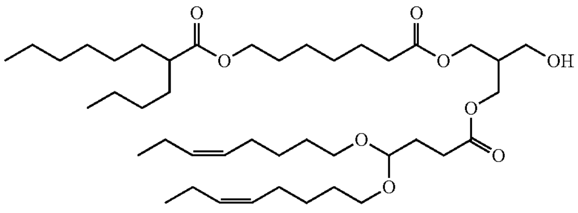 [SMILES: CC/C=C\CCCCOC(CCC(=O)OCC(CO)COC(=O)CCCCCCOC(=O)C(CCCC)CCCCCC)OCCCC/C=C\CC]

Step 3: 7-(3-((4,4-bis(((Z)-oct-5-en-1-yl)oxy)butanoyl)oxy)-2-(hydroxymethyl)propoxy)-7-oxoheptyl 2-butyloctanoate Prepared according to General Procedure H, substituting 7-((2-butyloctanoyl)oxy)heptanoic acid for 6-((3-butylnonyl)oxy)-6-oxohexanoic acid. Isolated 155 mg, 49%. $^1$H NMR (400 MHz, Chloroform-d) δ 0.82-0.91 (m, 6H), 0.94 (t, J=7.5 Hz, 6H), 1.15-1.48 (m, 25H), 1.54-1.70 (m, 7H), 1.92 (q, J=7.2 Hz, 2H), 1.97-2.08 (m, 8H), 2.13-2.25 (m, 2H), 2.25-2.34 (m, 3H), 2.40 (t, J=7.5 Hz, 2H), 3.34-3.46 (m, 2H), 3.51-3.65 (m, 4H), 4.05 (t, J=6.5 Hz, 2H), 4.10-4.23 (m, 4H), 4.48 (t, J=5.5 Hz, 1H), 5.24-5.42 (m, 4H).

Step 4: 7-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-7-oxoheptyl 2-butyloctanoate (Example 4-83)

Prepared according to General Procedure F, substituting 7-(3-((4,4-bis(((Z)-oct-5-en-1-yl)oxy)butanoyl)oxy)-2-(hydroxymethyl)propoxy)-7-oxoheptyl 2-butyloctanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 85 mg, 46%. UPLC-MS (Method A): Rt 2.28 min, m/z calculated [M+H]: 908.7, found: 908.8.

Example 4-84

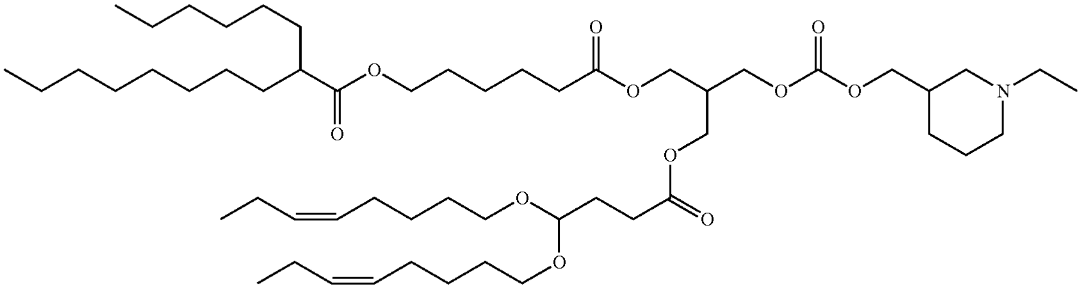

Example 4-84: 6-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-6-oxohexyl 2-hexyldecanoate

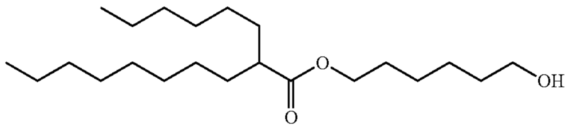 [SMILES: CCCCCCCCC(CCCCCC)C(=O)OCCCCCCO]

Step 1: 6-hydroxyhexyl 2-hexyldecanoate

Prepared according to General Procedure J, substituting hexane-1,6-diol for octane-1,8-diol and 2-hexyldecanoic acid for 2-butyloctanoic acid. Isolated 480 mg, 69%. $^{1}H$ NMR (400 MHz, Chloroform-d) δ 0.84-0.87 (m, 6H), 1.23-1.64 (m, 32H), 2.25-2.32 (m, 1H), 3.60-3.70 (m, 2H), 4.05 (t, J=6.6 Hz, 2H).

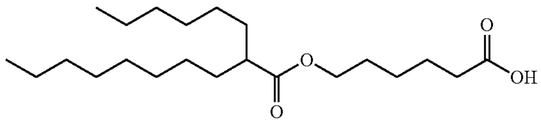 [SMILES: CCCCCCCCC(CCCCCC)C(=O)OCCCCCC(=O)O]

Step 2: 6-((2-hexyldecanoyl)oxy)hexanoic acid

Prepared according to General Procedure K, substituting 6-hydroxyhexyl 2-hexyldecanoate for 8-hydroxyoctyl 2-butyloctanoate. Isolated 900 mg, 96%. $^{1}H$ NMR (400 MHz, Chloroform-d) δ 0.82-0.85 (m, 6H), 1.13-1.58 (m, 30H), 2.18 (t, J=7.3 Hz, 2H), 2.23-2.30 (m, 1H), 4.0 (t, J=6.4 Hz, 2H), 11.98 (s, 1H).

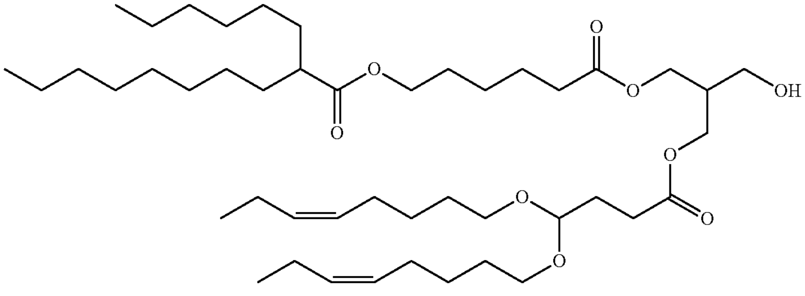 [SMILES: CC/C=C\CCCCOC(CCC(=O)OCC(CO)COC(=O)CCCCCOC(=O)C(CCCCCC)CCCCCCCC)OCCCC/C=C\CC]

Step 3: 6-(3-((4,4-bis(((Z)-oct-5-en-1-yl)oxy)butanoyl)oxy)-2-(hydroxymethyl)propoxy)-6-oxohexyl 2-hexyldecanoate Prepared according to General Procedure H, substituting 6-((2-hexyldecanoyl)oxy)hexanoic acid for 6-((3-butylnonyl)oxy)-6-oxohexanoic acid. Isolated 145 mg, 47%. $^{1}H$ NMR (400 MHz, Chloroform-d) δ 0.86 (t, J=6.7 Hz, 9H), 0.90-0.99 (m, 6H), 1.14-1.34 (m, 23H), 1.33-1.48 (m, 9H), 1.56-1.72 (m, 6H), 1.87-1.97 (m, 1H), 1.97-2.11 (m, 8H), 2.14-2.25 (m, 1H), 2.24-2.45 (m, 4H), 2.63 (t, J=6.4 Hz, 1H), 2.81 (t, J=6.5 Hz, 1H), 3.34-3.45 (m, 1H), 3.58-3.68 (m, 4H), 4.06 (t, J=6.6 Hz, 2H), 4.10-4.25 (m, 4H), 5.27-5.41 (m, 4H).

Step 4: 6-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-6-oxohexyl 2-hexyldecanoate (Example 4-84)

Prepared according to General Procedure F, substituting 6-(3-((4,4-bis(((Z)-oct-5-en-1-yl)oxy)butanoyl)oxy)-2-(hydroxymethyl)propoxy)-6-oxohexyl 2-hexyldecanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 94 mg, 55%. UPLC-MS (Method A): Rt 2.44 min, m/z calculated [M+H]: 950.7, found: 950.8. $^1$H NMR (400 MHz, DMSO-$d_6$) δ 0.79-0.86 (m, 6H), 0.90 (t, J=7.4 Hz, 6H), 1.09-1.31 (m, 35H), 1.28-1.43 (m, 8H), 1.42-1.61 (m, 10H), 1.77 (q, J=6.9 Hz, 2H), 1.91-2.07 (m, 8H), 2.20-2.42 (m, 6H), 3.31-3.40 (m, 2H), 3.41-3.54 (m, 2H), 4.00 (t, J=6.3 Hz, 3H), 4.07 (dd, J=2.2, 6.1 Hz, 4H), 4.13 (d, J=6.0 Hz, 2H), 4.45 (t, J=5.5 Hz, 1H), 5.23-5.40 (m, 4H).

Example 4-85

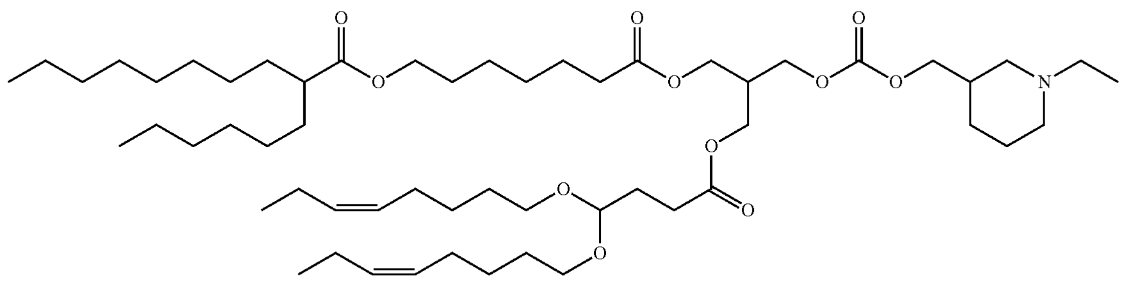

Example 4-85: 7-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-7-oxoheptyl 2-hexyldecanoate

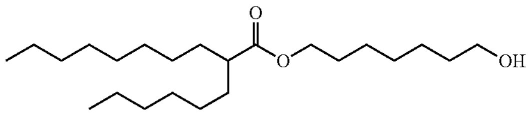 [SMILES: CCCCCCCCC(CCCCCC)C(=O)OCCCCCCCO]

Step 1: 7-hydroxyheptyl 2-hexyldecanoate

Prepared according to General Procedure J, substituting heptane-1,7-diol for octane-1,8-diol and 2-hexyldecanoic acid for 2-butyloctanoic acid. Isolated 1.1 g, 76%. $^1$H NMR (400 MHz, Chloroform-d) δ 0.83-0.87 (m, 6H), 1.23-1.64 (m, 35H), 2.25-2.32 (m, 1H), 3.62 (t, J=6.3 Hz, 2H), 4.04 (t, J=6.6 Hz, 2H).

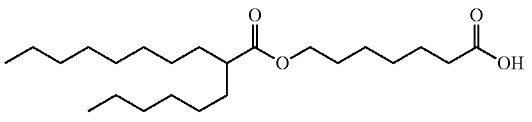 [SMILES: CCCCCCCCC(CCCCCC)C(=O)OCCCCCCC(=O)O]

Step 2: 7-((2-hexyldecanoyl)oxy)heptanoic acid

Prepared according to General Procedure K, substituting 7-hydroxyheptyl 2-hexyldecanoate for 8-hydroxyoctyl 2-butyloctanoate. Isolated 980 mg, 94%. $^1$H NMR (400 MHz, Chloroform-d) δ 0.82-0.86 (m, 6H), 1.20-1.55 (m, 32H), 2.17 (t, J=7.3 Hz, 2H), 2.24-2.31 (m, 1H), 4.0 (t, J=6.3 Hz, 2H), 11.96 (s, 1H).

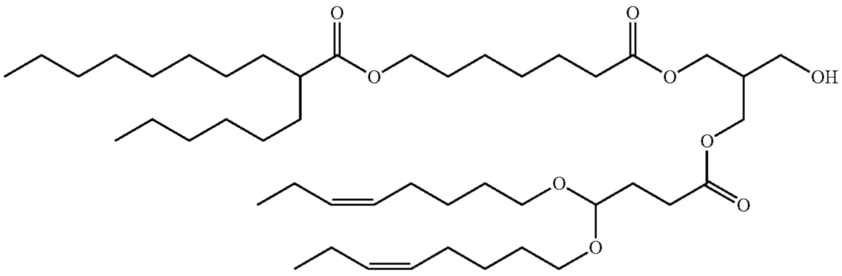 [SMILES: CC/C=C\CCCCOC(CCC(=O)OCC(CO)COC(=O)CCCCCCOC(=O)C(CCCCCC)CCCCCCCC)OCCCC/C=C\CC]

Step 3: 7-(3-((4,4-bis(((Z)-oct-5-en-1-yl)oxy)butanoyl)oxy)-2-(hydroxymethyl)propoxy)-7-oxoheptyl 2-hexyldecanoate Prepared according to General Procedure H, substituting 7-((2-hexyldecanoyl)oxy)heptanoic acid for 6-((3-butylnonyl)oxy)-6-oxohexanoic acid. Isolated 160 mg, 53%. $^1$H NMR (400 MHz, Chloroform-d) δ 0.86 (t, J=7.0 Hz, 6H), 0.90-0.99 (m, 6H), 1.17-1.32 (m, 22H), 1.31-1.48 (m, 6H), 1.48-1.69 (m, 12H), 1.87-1.96 (m, 1H), 1.97-2.12 (m, 8H), 2.19 (h, J=5.7 Hz, 1H), 2.24-2.37 (m, 4H), 2.40 (t, J=7.5 Hz, 1H), 2.63 (t, J=6.5 Hz, 1H), 2.81 (t, J=6.5 Hz, 1H), 3.34-3.45 (m, 1H), 3.50-3.73 (m, 5H), 4.04 (t, J=6.6 Hz, 2H), 4.10-4.25 (m, 4H), 4.48 (t, J=5.4 Hz, 1H), 5.26-5.43 (m, 4H).

Step 4: 7-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-7-oxoheptyl 2-hexyldecanoate (Example 4-85)

Prepared according to General Procedure F, substituting 7-(3-((4,4-bis(((Z)-oct-5-en-1-yl)oxy)butanoyl)oxy)-2-(hydroxymethyl)propoxy)-7-oxoheptyl 2-hexyldecanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 106 mg, 56%. UPLC-MS (Method A): Rt 2.38 min, m/z calculated [M+H]: 964.7, found: 964.8.

Example 4-86

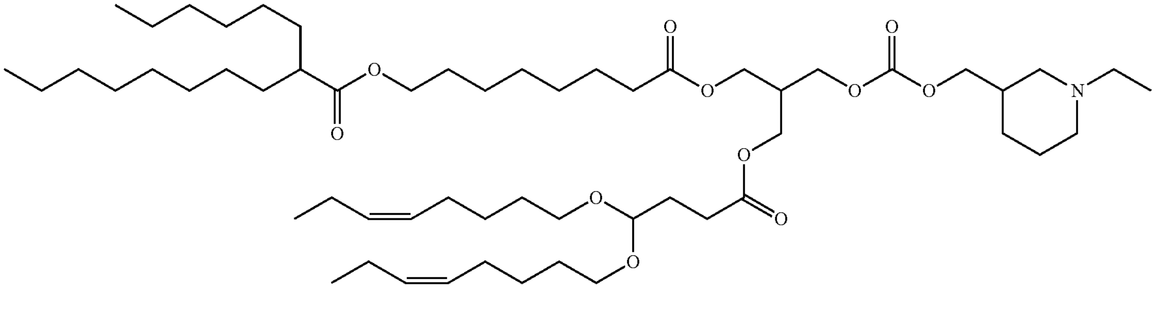

Example 4-86: 8-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-8-oxooctyl 2-hexyldecanoate

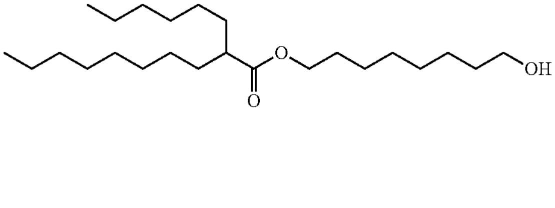 [SMILES: CCCCCCCCC(CCCCCC)C(=O)OCCCCCCCCO]

Step 1: 8-hydroxyoctyl 2-hexyldecanoate

Prepared according to General Procedure J, substituting 2-hexyldecanoic acid for 2-butyloctanoic acid. Isolated 1.1 g, 73%. $^1$H NMR (400 MHz, Chloroform-d) δ 0.84-0.87 (m, 6H), 0.99-1.02 (m, 1H), 1.23-1.70 (m, 36H), 2.25-2.32 (m, 1H), 3.60-3.70 (m, 2H), 4.05 (t, J=6.6 Hz, 2H).

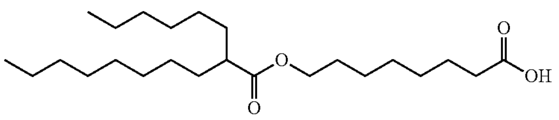 [SMILES: CCCCCCCCC(CCCCCC)C(=O)OCCCCCCCC(=O)O]

Step 2: 8-((2-hexyldecanoyl)oxy)octanoic acid

Prepared according to General Procedure K, substituting 8-hydroxyoctyl 2-hexyldecanoate for 8-hydroxyoctyl 2-butyloctanoate. Isolated 1.0 g, 95%. $^1$H NMR (400 MHz, DMSO-$d_6$) δ 0.77-0.86 (m, 6H), 1.0-1.60 (m, 34H), 2.17 (t, J=7.3 Hz, 2H), 2.23-2.30 (m, 1H), 4.00 (t, J=6.3 Hz, 2H), 11.94 (s, 1H).

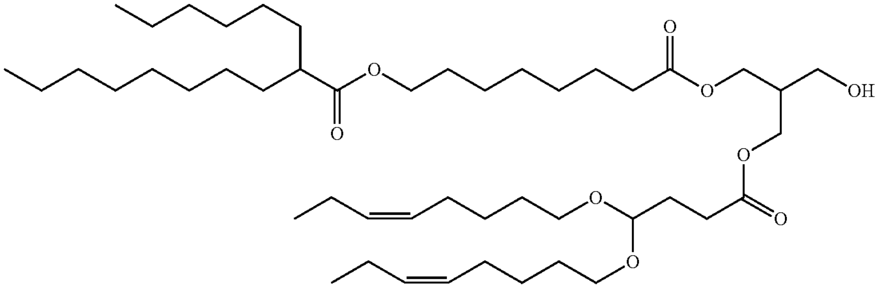 [SMILES: CC/C=C\CCCCOC(CCC(=O)OCC(CO)COC(=O)CCCCCCCOC(=O)C(CCCCCC)CCCCCCCC)OCCCC/C=C\CC]

Step 3: 8-(3-((4,4-bis(((Z)-oct-5-en-1-yl)oxy)butanoyl)oxy)-2-(hydroxymethyl)propoxy)-8-oxooctyl 2-hexyldecanoate Prepared according to General Procedure H, substituting 8-((2-hexyldecanoyl)oxy)octanoic acid for 6-((3-butylnonyl)oxy)-6-oxohexanoic acid. Isolated 170 mg, 56%. $^1$H NMR (400 MHz, Chloroform-d) δ 0.83-0.89 (m, 6H), 0.91-0.99 (m, 5H), 1.17-1.36 (m, 22H), 1.35-1.47 (m, 6H), 1.57-1.70 (m, 9H), 1.87-1.97 (m, 2H), 1.98-2.11 (m, 8H), 2.13-2.25 (m, 2H), 2.23-2.36 (m, 4H), 2.40 (t, J=7.5 Hz, 2H), 2.63 (t, J=6.5 Hz, 1H), 2.81 (t, J=6.5 Hz, 1H), 3.34-3.45 (m, 2H), 3.51-3.68 (m, 6H), 4.05 (t, J=6.6 Hz, 2H), 4.10-4.25 (m, 4H), 4.48 (t, J=5.5 Hz, 1H), 5.24-5.42 (m, 4H).

Step 4: 8-(3-((4,4-bis(((Z)-oct-5-en-1-yl)oxy)butanoyl)oxy)-2-(((((1-ethylpiperidin-3-yl)methoxy)carbonyl)oxy)methyl)propoxy)-8-oxooctyl 2-hexyldecanoate (Example 4-86)

Prepared according to General Procedure F, substituting 8-(3-((4,4-bis(((Z)-oct-5-en-1-yl)oxy)butanoyl)oxy)-2-(hydroxymethyl)propoxy)-8-oxooctyl 2-hexyldecanoate for 3-((4,4-bis(((Z)-oct-5-en-1-yl)oxy)butanoyl)oxy)-2-(hydroxymethyl)propyl nonyl adipate and (1-ethylpiperidin-3-yl)methanol for 3-(diethylamino)propan-1-ol. Isolated 31 mg, 28%. UPLC-MS (Method A): Rt 2.42 min, m/z calculated [M+H]: 978.8, found: 978.9.

Example 5: LNP Preparations for mRNA Delivery to Liver and Spleen

The present Example provides exemplary LNP compositions, preparations, nanoparticles, and/or nanomaterials that deliver mRNA to liver and spleen.

LNP preparations (Exemplary Lipids 12-23, which are exemplary compounds of Formula I and exemplary compounds of provided compounds 4-1 through 4-86) were selected to determine each preparation's ability to intravenously deliver functional mRNA in C57BL6/j mice. Each LNP preparation contained Trilink Fluc mRNA and was administered at a dose of 0.3 mg/kg. Six hours post injection, several tissue, including liver and spleen, were isolated and luminescence was measured using standard luminescence assays as described herein (see FIGS. 7-8).

Figure 7:
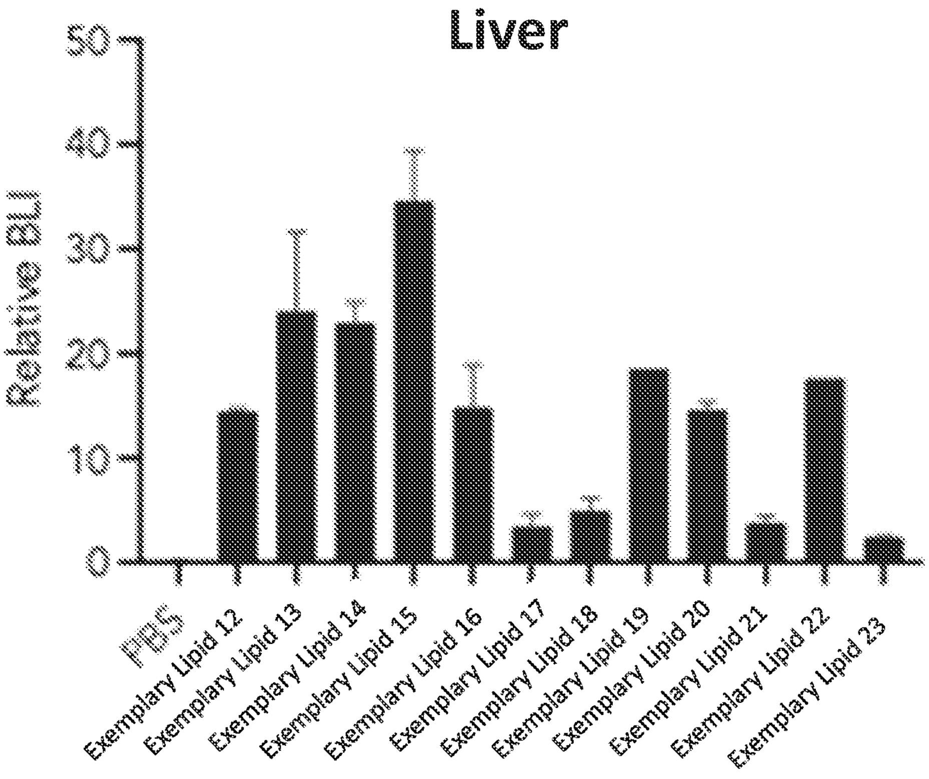
FIG. 7 depicts a bar graph that shows potent delivery of exemplary LNP preparations (Exemplary Lipid 12, Exemplary Lipid 13, Exemplary Lipid 14, Exemplary Lipid 15, Exemplary Lipid 16, Exemplary Lipid 17, Exemplary Lipid 18, Exemplary Lipid 19, Exemplary Lipid 20, Exemplary Lipid 21, Exemplary Lipid 22, Exemplary Lipid 23) to the liver.
Figure 8:
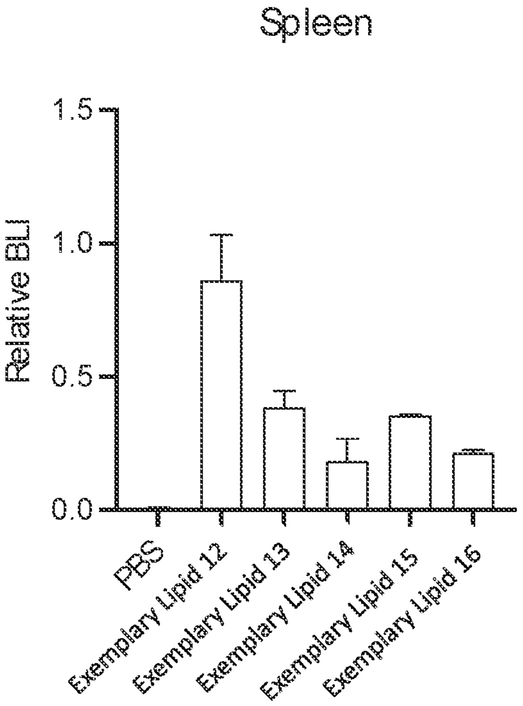
FIG. 8 depicts a bar graph that shows potent delivery of exemplary LNP preparations (Exemplary Lipid 12, Exemplary Lipid 13, Exemplary Lipid 14, Exemplary Lipid 15, Exemplary Lipid 16) to the spleen.

Unexpectedly, representative data in FIGS. 7-8 show that screening platforms described herein can identify several highly potent LNP preparations to determine what type of LNP preparation would be most potent for a particular cell type. Accordingly, in some embodiments, the present example demonstrates that lipids characterized by having a degradable tail feature show potent delivery across various cell types, including liver cells and spleen cells.

Example 6: Utilization of LNP Preparations for Base Editing in Liver

The present Example provides exemplary LNP compositions, preparations, nanoparticles, and/or nanomaterials that confer gene editing (e.g., using base editors) in a variety of cell types.

Methods

Seven exemplary LNP preparations (Exemplary Lipid 13, Exemplary Lipid 14, Exemplary Lipid 15, Exemplary Lipid 16, Exemplary Lipid 20, Exemplary Lipid 12, which are exemplary compounds of Formula I and exemplary compounds of provided compounds 4-1 through 4-86, and Comparative Lipid 24), were selected to determine each preparation's ability to perform base editing in a Balb/C mouse model as described herein. Comparative Lipid 24 does not comprise a degradable tail feature (i.e., is a lipid described by WO/2021141969).

Lipid nanoparticle components were dissolved in 100% ethanol at specified lipid component molar ratios. mRNA encoding an adenine base editor and a chemically-modified sgRNA was dissolved at a mass ratio of 1:1 in 10 mM citrate, 100 mM NaCl, pH 4.0, resulting in a concentration of NA cargo of approximately 0.22 mg/mL. LNP preparations were formulated with molar ratios of 47.5% Ionizable Lipid: 40% Cholesterol: 2.5% PEG2000-DMG: 10% DSPC total lipid to NA mass ratio of 11.7 to 40. LNP preparations were formed by microfluidic mixing of lipid and NA solutions using a Precision Nanosystems NanoAssemblr Spark or Benchtop series Instruments, according to the manufacturers protocol. A 3:1 ratio of aqueous to organic solvent was maintained during mixing using differential flow rates. After mixing, LNP preparations were collected, diluted in PBS (approximately 2:1 v/v), and further buffer exchange was conducted using dialysis in PBS at 4° C. for 8 to 24 hours against a 20 kDa filter. After this initial dialysis, each individual LNP preparation was characterized via dynamic light scattering (DLS) to measure size and polydispersity. pKa of a subpopulation of LNP preparations was measured via TNS assay. After dialysis, LNP preparations were sterile filtered using 0.22 micron sterile filter and stored at 4° C. for further use. In some embodiments, LNP preparations may be concentrated using 100 kDa Amicon filters per manufacturers protocol.

LNP Characterization

DLS—LNP preparation hydrodynamic diameter and polydispersity index (PDI) was measured using high throughput dynamic light scattering (DLS) (DynaPro plate reader II, Wyatt). LNP preparations were diluted 1× PBS to an appropriate concentration and analyzed.

Concentration & Encapsulation Efficiency

Concentration of NA was determined by Qubit microRNA kit (for siRNA) or HS RNA kit (for mRNA) per manufacturer's instructions. Encapsulation efficiency was determined by measuring unlysed and lysed LNPs.

LNP Administration

Male Balc/C mice aged approximately 8-12 weeks were used in the experiments described herein. Each mouse is temporarily restrained, and LNP preparations are administered IV via tail vein injection. Age-matched mice are also used to administer vehicle (1× PBS) via tail vein injection as a control. Four to six days post-dose, tissues including liver, spleen, and bone marrow were collected. Genomic DNA was isolated and fragmented and adapter-ligated using a Nextera DNA Flex Library Prep Kit (Illumina) using a 96-well plate Nextera indexing primers (Illumina), according to the manufacturer's instructions. Library size and concentration was confirmed by Fragment Analyzer (Agilent) and sent to Novogene for whole genome sequencing using an Illumina HiSeq.

Base Editing

For base editing, mRNA encoding an adenine base editor (ABE) and a guide RNA (sgRNA) targeting ALAS1 at 1:1 (mass ratio) were coencapsulated in LNP preparations as described herein. LNP preparations were administrated into Balb/c mice through tail vein injections at 0.3 mg/kg total RNA. At 4 days after dosing, mice were euthanized and liver, spleen and bone barrow were harvested. Base editing was determined by performing targeted deep sequencing analysis at an ALAS1 target site using extracted genomic DNA.

Results

Figure 9:
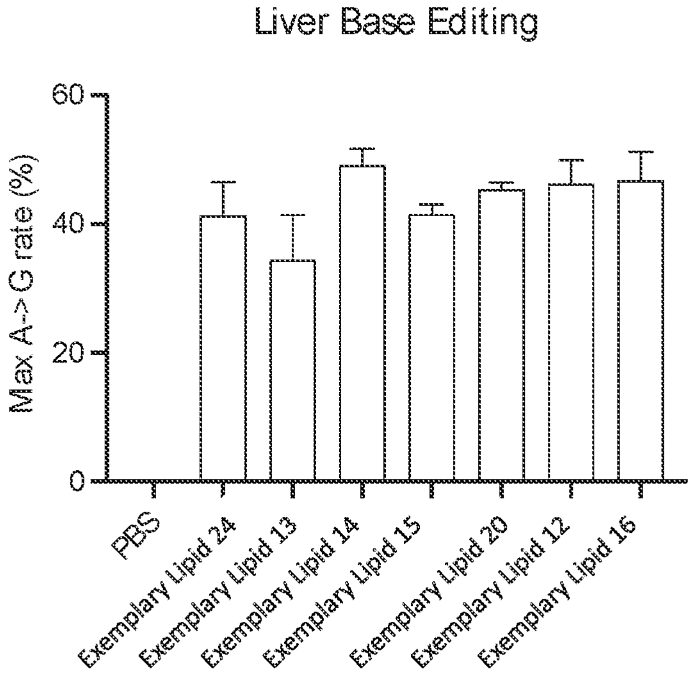
FIG. 9 depicts a bar graph that shows base editing in liver cells after delivery of exemplary LNP preparations (Comparative Lipid 24, Exemplary Lipid 13, Exemplary Lipid 14, Exemplary Lipid 15, Exemplary Lipid 20, Exemplary Lipid 12, Exemplary Lipid 16) to the liver.

FIG. 9 shows a bar graph depicting base editing in liver cells using a variety of LNP preparations containing different exemplary lipids described herein. Results are also shown in Table 2.

TABLE 2

| Group | Treatment | Dose (mg/kg) | mRNA: sgRNA | Route | N | Necropsy Date |
|---|---|---|---|---|---|---|
| 1 | PBS | — | — | IV | 2 | 4 days |
| 2-8 | Exemplary Lipid, N/P = 6 | 0.3 | 1:1 | IV | 3 | 4 days |

Unexpectedly, representative data in FIG. 9 show that screening platforms described herein can identify several highly potent LNP preparations for base editing in particular cell types. Accordingly, in some embodiments, the present example demonstrates that lipids characterized by having a degradable tail feature can be used for base editing across various cell types, including liver cells.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A compound of Formula (IIIA):

(IIIA)

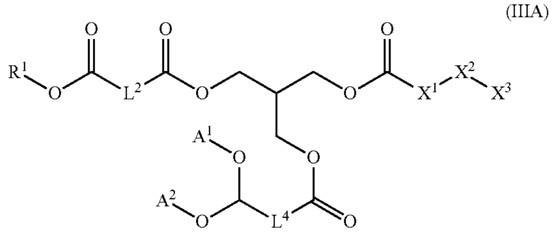

or a pharmaceutically acceptable salt thereof, wherein:

$L^2$ is a covalent bond, an optionally substituted bivalent saturated or unsaturated, straight or branched $C_1$-$C_{12}$ hydrocarbon chain, or

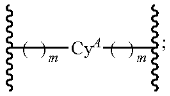;

Cy^A is an optionally substituted ring selected from phenylene and 3- to 7-membered saturated or partially unsaturated carbocyclene;

each m is independently 0, 1, or 2;

$R^1$ is a saturated, branched $C_3$-$C_{20}$ hydrocarbon chain;

each $L^4$ is independently a bivalent saturated or unsaturated, straight or branched $C_1$-$C_6$ hydrocarbon chain;

each $A^1$ and $A^2$ is independently $C_2$-$C_{20}$ alkenyl;

$X^1$ is a covalent bond, —O—, or —NR—;

—$X^2$—$X^3$ is selected from:

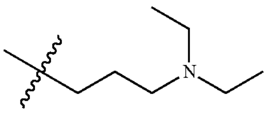,
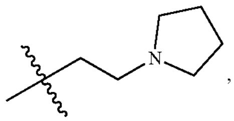,
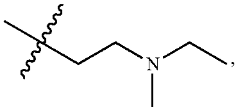,
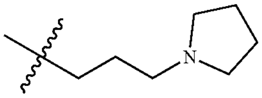,
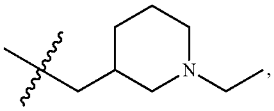,
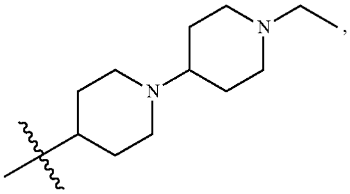, and
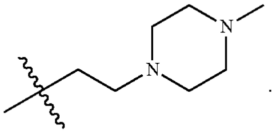.

2. The compound of claim 1, wherein the compound of Formula (IIIA) is a compound of Formula (VI):

(VI)

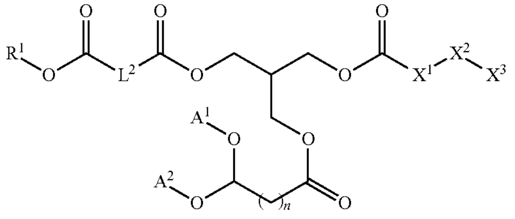

or a pharmaceutically acceptable salt thereof, wherein n is 1, 2, 3 or 4.

3. The compound of claim 1, wherein the compound of Formula (IIIA) is a compound of Formula (VIA):

(VIA)

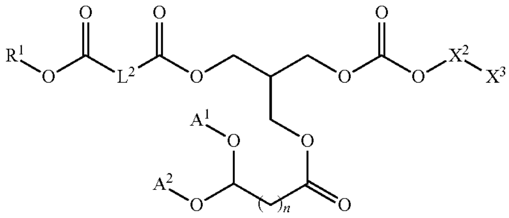

or a pharmaceutically acceptable salt thereof, wherein n is 1, 2, 3 or 4.

4. The compound of claim 1, wherein R' is selected from:

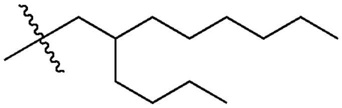,
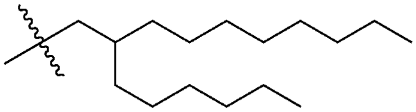,
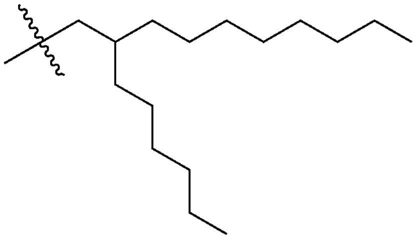,
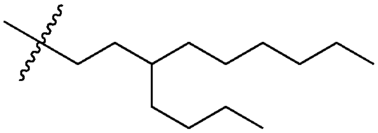,
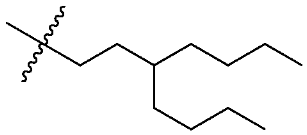,
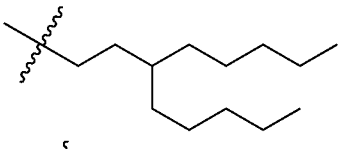, and
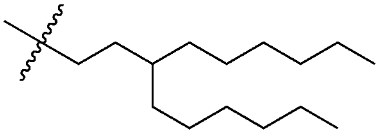.

5. The compound of claim 1, wherein each of A1 and A2 is independently selected from:
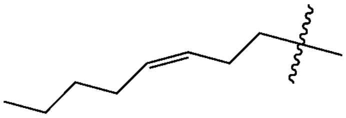
,
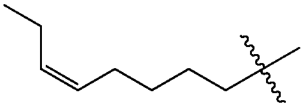
,
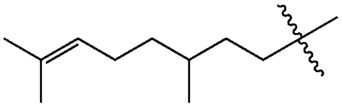
,
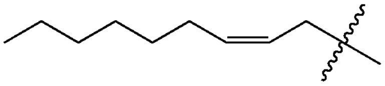
,
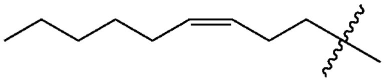
,
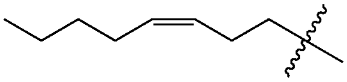
,
-continued
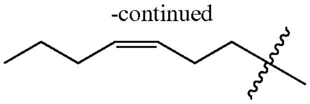
,
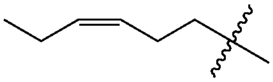
,
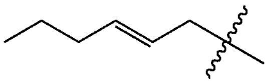
,
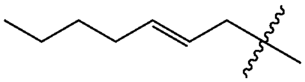
,
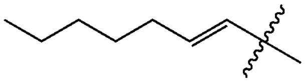
,
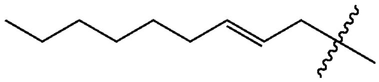
, and
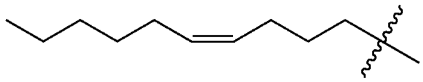
.
6. The compound of claim 1, wherein the compound is selected from
Example 4-6
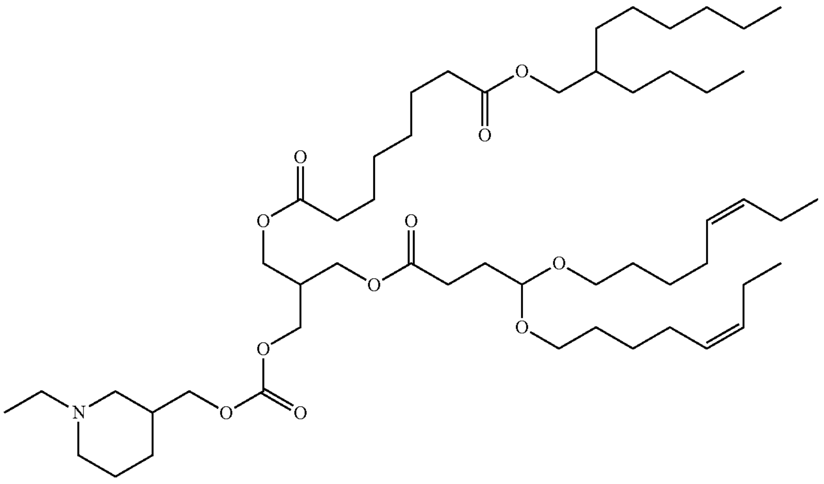
Example 4-30
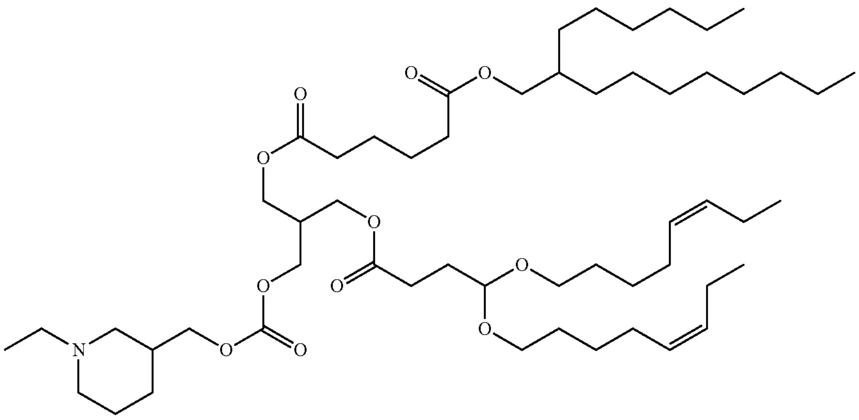

-continued
Example 4-31
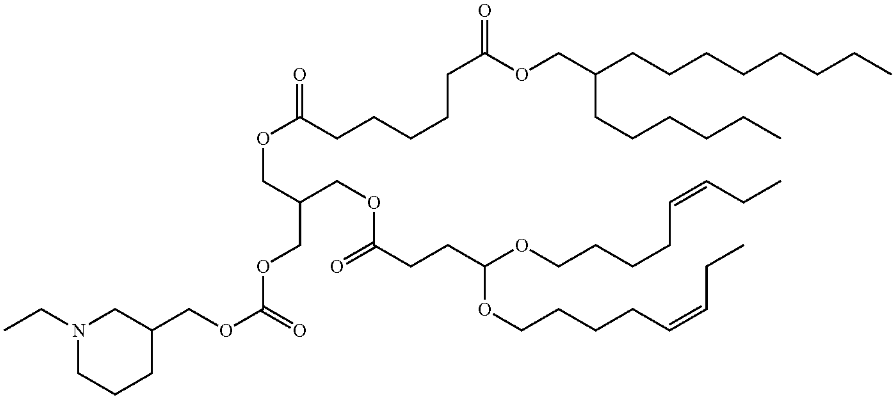
Example 4-62
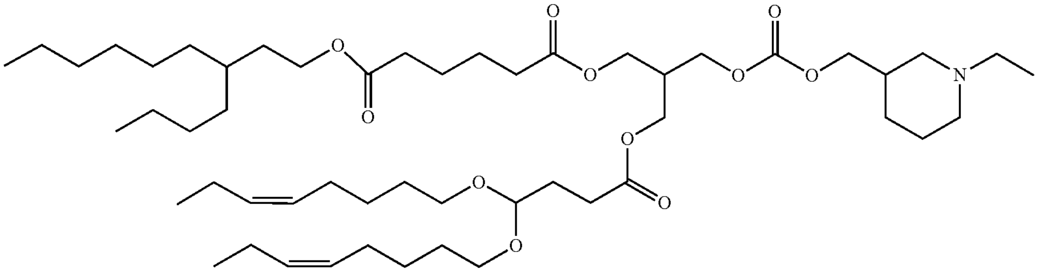
Example 4-63
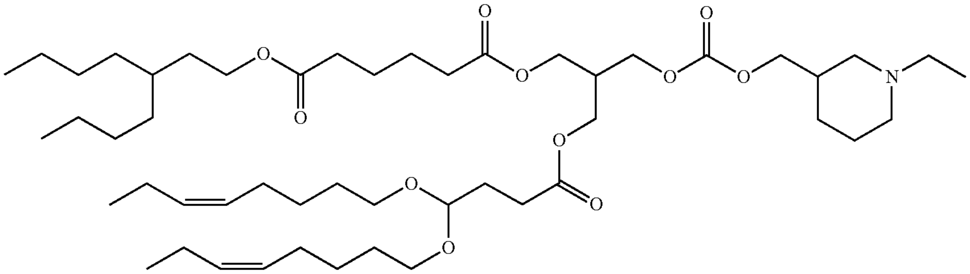
Example 4-64
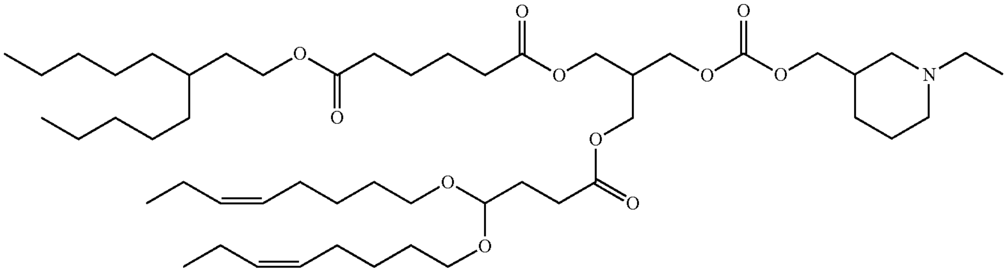
Example 4-65
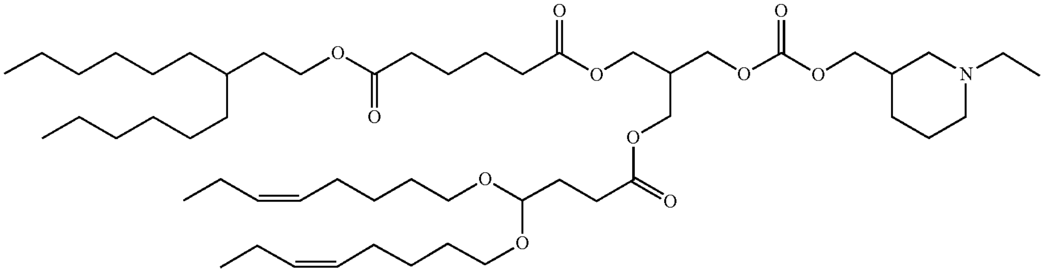

-continued
Example 4-67
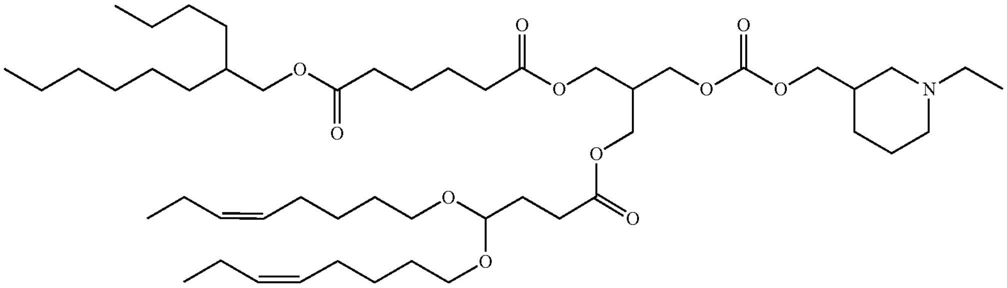
Example 4-68
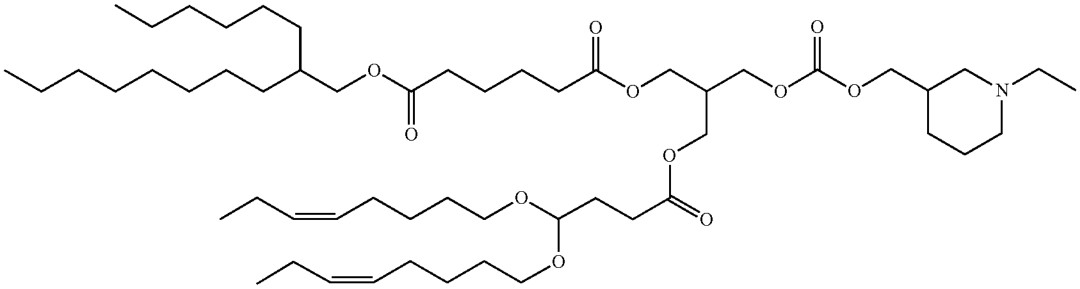
Example 4-69
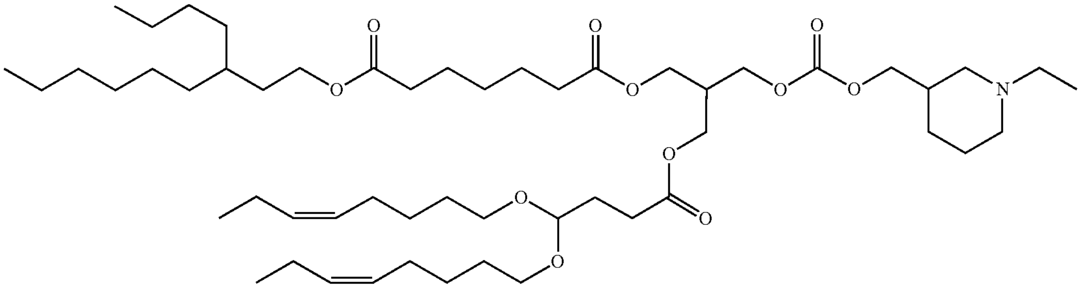
Example 4-70
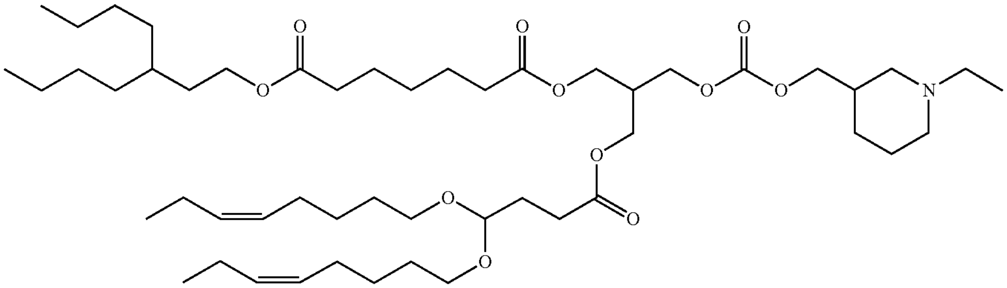
Example 4-71
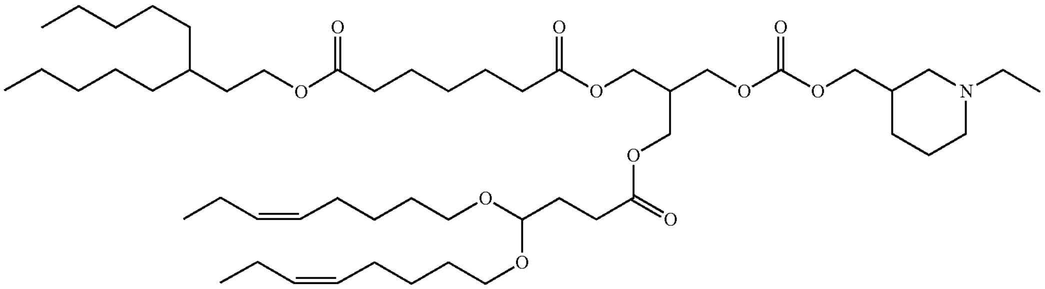

-continued
Example 4-72
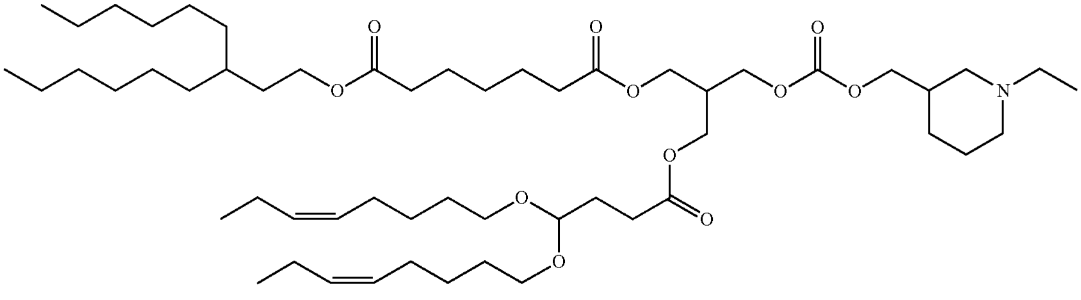
Example 4-74
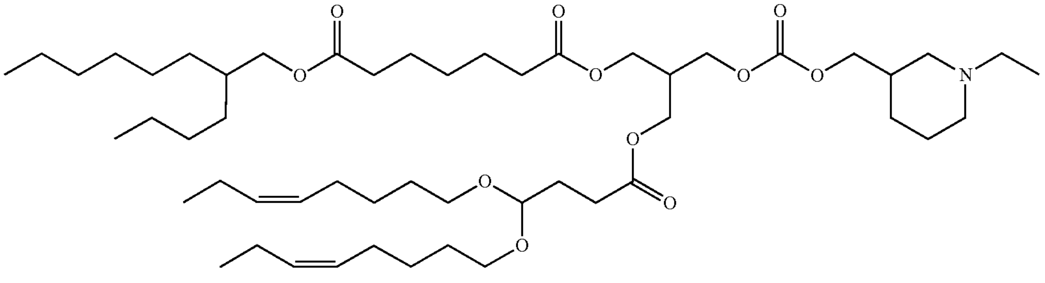
Example 4-75
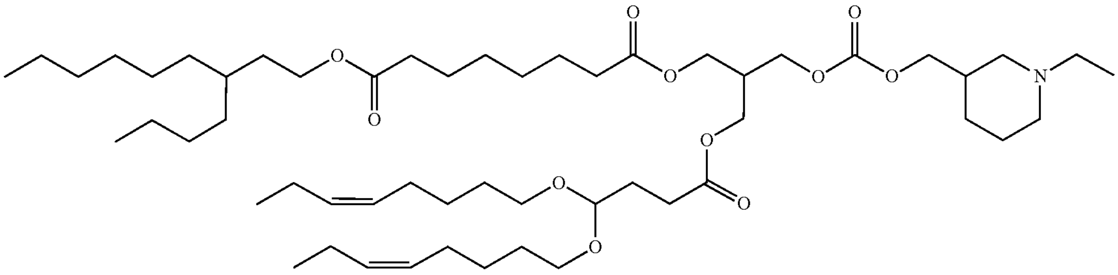
Example 4-76
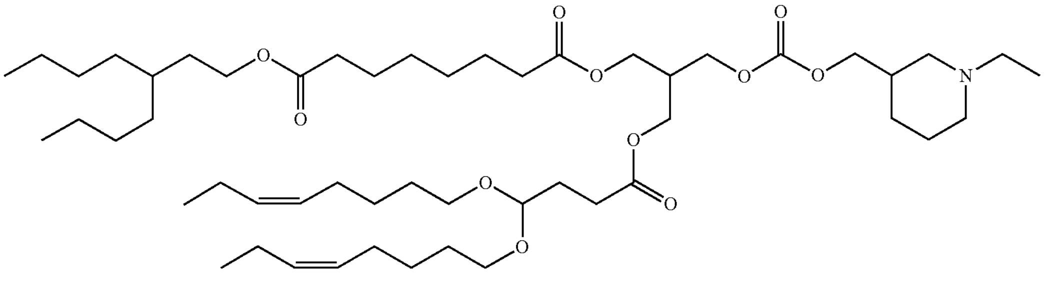
Example 4-77
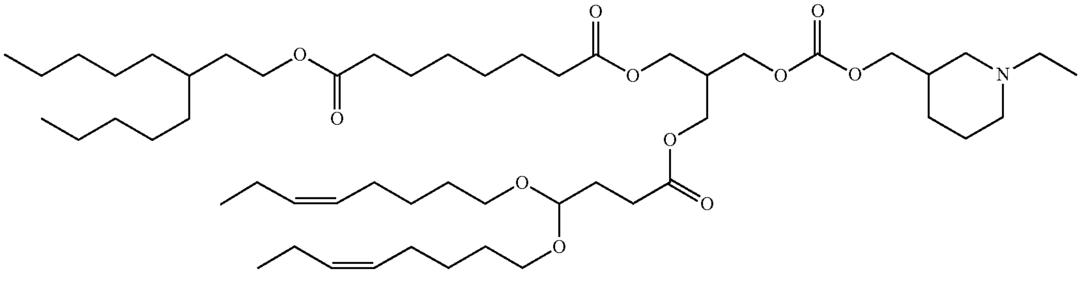

-continued

Example 4-78

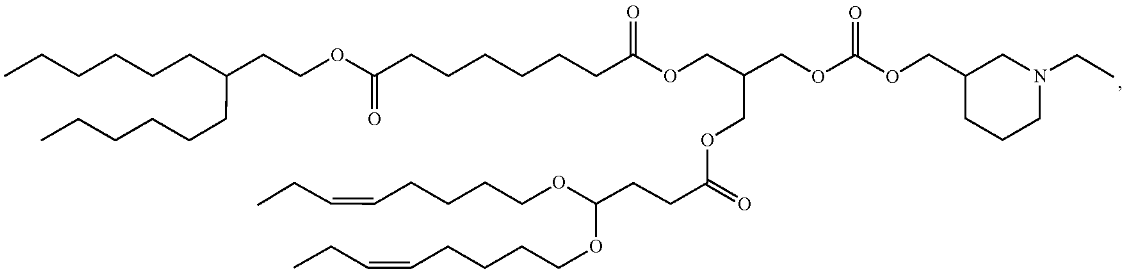

, and

Example 4-80

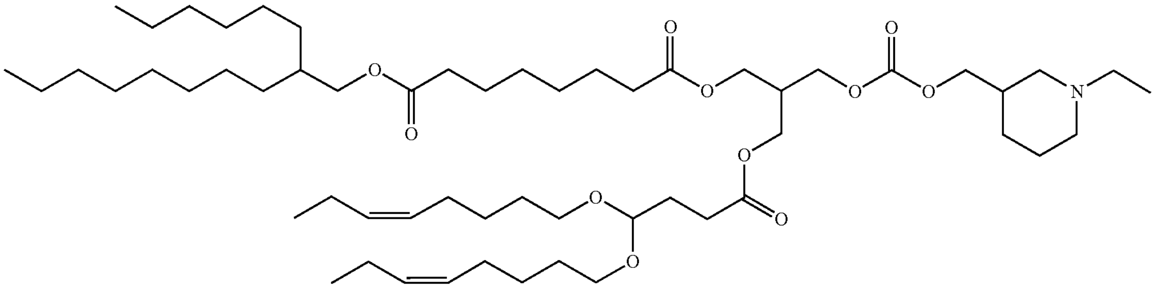

or a pharmaceutically acceptable salt thereof.

7. A lipid nanoparticle (LNP) preparation comprising the compound according to claim 1.

8. A pharmaceutical composition comprising the LNP preparation of claim 7 and a pharmaceutically acceptable excipient.

9. A compound having the following structure:

Example 4-65

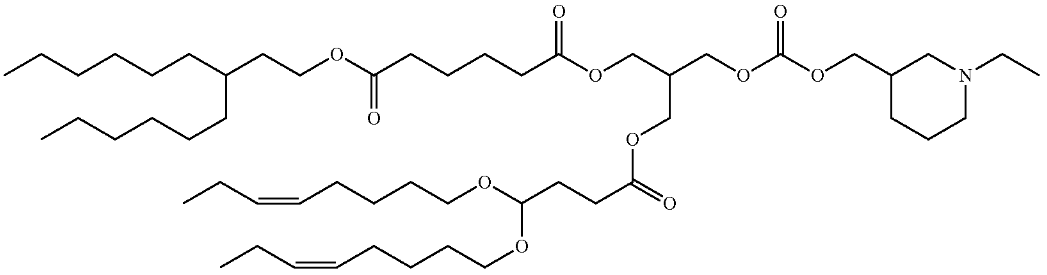

or a pharmaceutically acceptable salt thereof.

10. A lipid nanoparticle (LNP) preparation comprising the compound according to claim 9.

11. A pharmaceutical composition comprising the LNP preparation of claim 10 and a pharmaceutically acceptable excipient.

12. A compound having the following structure:
Example 4-71
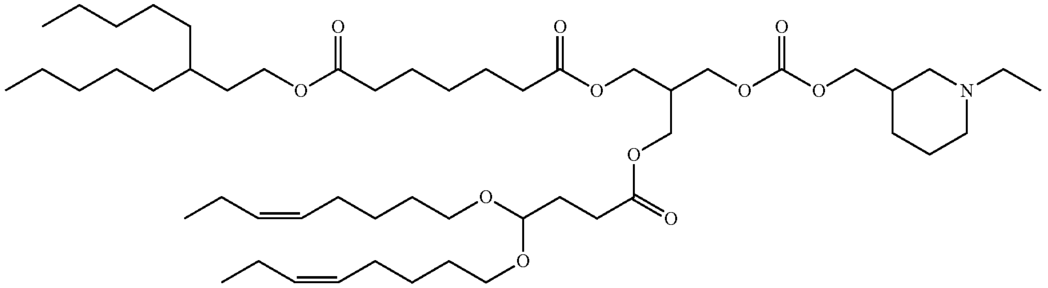
or a pharmaceutically acceptable salt thereof.
13. A lipid nanoparticle (LNP) preparation comprising the compound according to claim 12.
14. A pharmaceutical composition comprising the LNP preparation of claim 13 and a pharmaceutically acceptable excipient.
* * * * *

UNITED STATES PATENT AND TRADEMARK OFFICE

CERTIFICATE OF CORRECTION

PATENT NO. : 12,268,753 B2
APPLICATION NO. : 17/579150
DATED : April 8, 2025
INVENTOR(S) : Shehata et al.

It is certified that error appears in the above-identified patent and that said Letters Patent is hereby corrected as shown below:

In the Specification

Column 32, Lines 5-15:

Delete the structure " 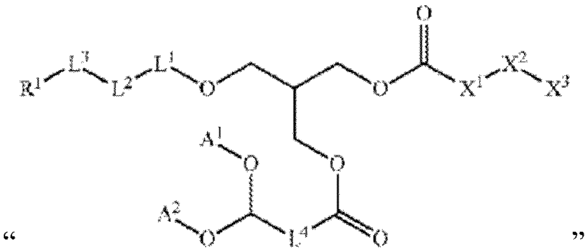 "

And replace with: -- 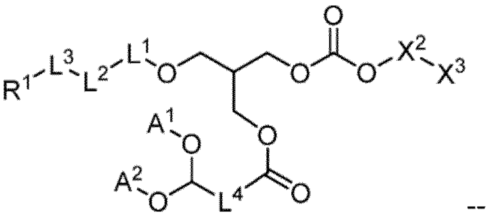 --

Signed and Sealed this
Second Day of December, 2025

John A. Squires
*Director of the United States Patent and Trademark Office*

Columns 171-172, Lines 60-65:
Delete the structure "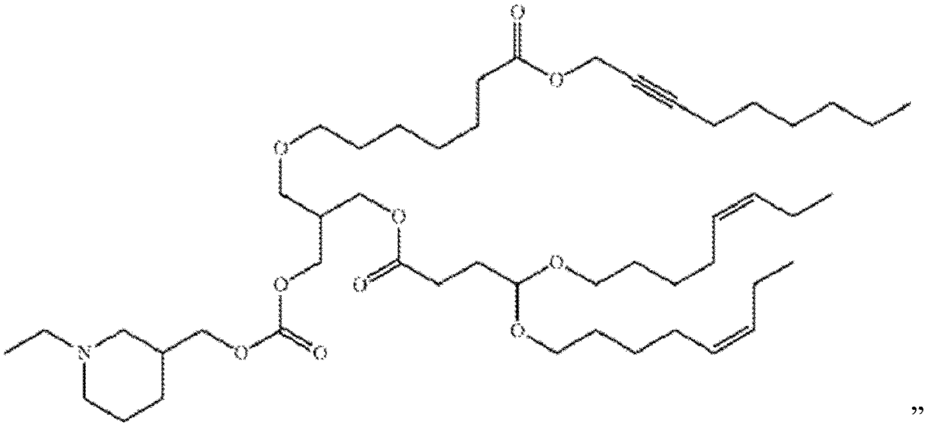"
And replace with: --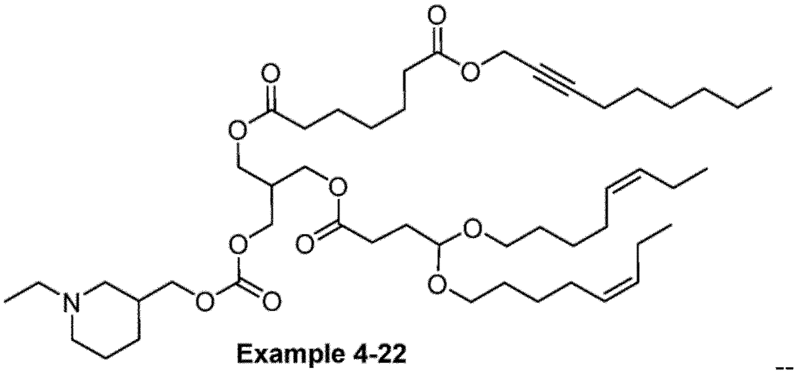
Example 4-22 --
Columns 185-186, Lines 13-30:
Delete the structure
"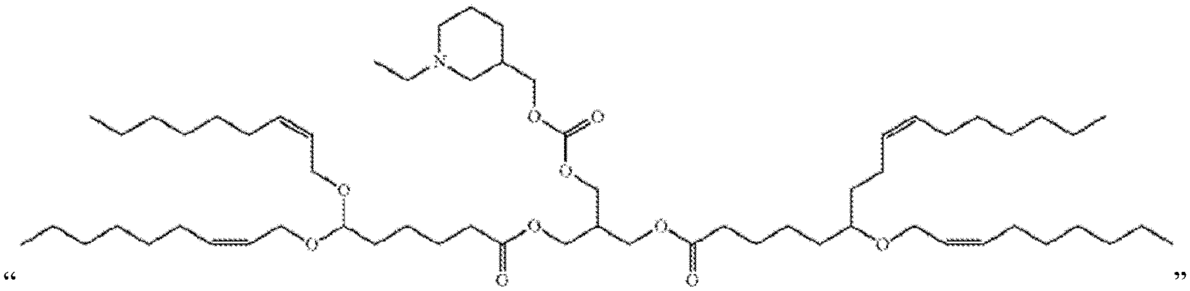"
And replace with:
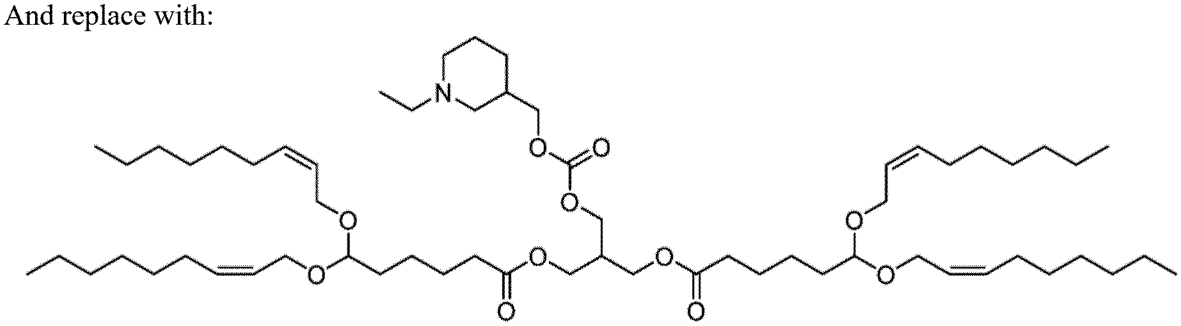
-- Example 4-35 --

Columns 187-188, Lines 20-30:
Delete the structure
“ 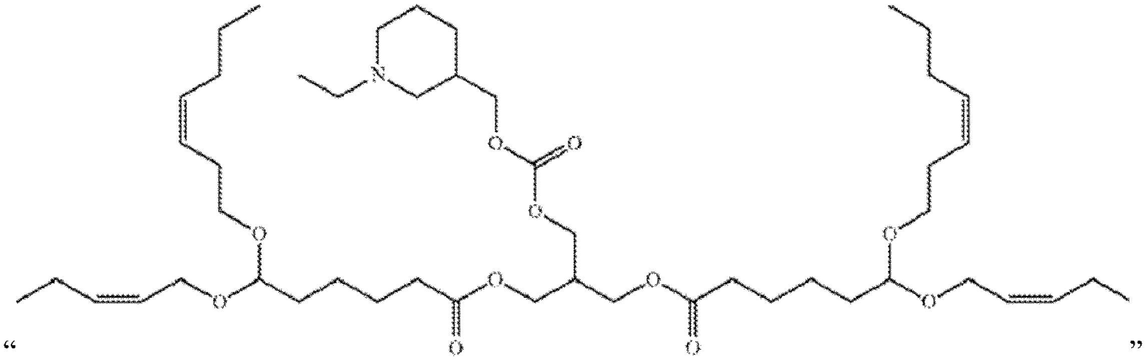 ”
And replace with:
-- 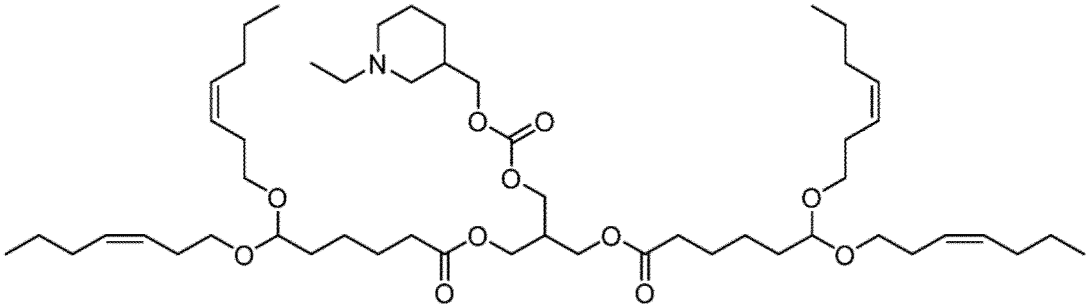
Example 4-37 --
In the Claims
Claim 5, Column 271, Line 1:
Delete “wherein each of A1 and A2”
Replace with: -- wherein each of $A^1$ and $A^2$ --
Claim 5, Column 272, Lines 14-16:
Delete the structure “ 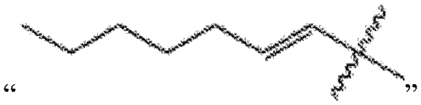 ”
And replace with: -- 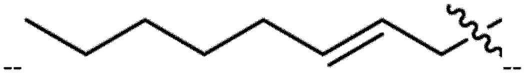 --